United States Patent
Wu et al.

(10) Patent No.: US 11,192,886 B2
(45) Date of Patent: Dec. 7, 2021

(54) S1P1 AGONIST AND APPLICATION THEREOF

(71) Applicant: MEDSHINE DISCOVERY INC., Jiangsu (CN)

(72) Inventors: Lingyun Wu, Shanghai (CN); Peng Zhang, Shanghai (CN); Jian Li, Shanghai (CN); Shuhui Chen, Shanghai (CN)

(73) Assignee: MEDSHINE DISCOVERY INC., Nanjing (CN)

( * ) Notice: Subject to any disclaimer, the term of this patent is extended or adjusted under 35 U.S.C. 154(b) by 374 days.

(21) Appl. No.: 16/319,491

(22) PCT Filed: Jul. 21, 2017

(86) PCT No.: PCT/CN2017/093808
§ 371 (c)(1),
(2) Date: Mar. 11, 2019

(87) PCT Pub. No.: WO2018/014862
PCT Pub. Date: Jan. 25, 2018

(65) Prior Publication Data
US 2021/0300908 A1 Sep. 30, 2021

(30) Foreign Application Priority Data

Jul. 22, 2016 (CN) .......................... 201610583286.X

(51) Int. Cl.
| | | |
|---|---|---|
| *C07D 413/04* | (2006.01) |
| *C07D 413/14* | (2006.01) |
| *C07D 417/04* | (2006.01) |
| *C07D 471/04* | (2006.01) |
| *C07D 409/04* | (2006.01) |
| *C07D 513/04* | (2006.01) |
| *C07D 487/04* | (2006.01) |
| *C07D 209/58* | (2006.01) |
| *C07D 417/14* | (2006.01) |

(52) U.S. Cl.
CPC ......... *C07D 413/04* (2013.01); *C07D 209/58* (2013.01); *C07D 409/04* (2013.01); *C07D 413/14* (2013.01); *C07D 417/04* (2013.01); *C07D 417/14* (2013.01); *C07D 471/04* (2013.01); *C07D 487/04* (2013.01); *C07D 513/04* (2013.01)

(58) Field of Classification Search
CPC .. C07D 487/04; C07D 513/04; C07D 413/14; C07D 417/14; C07D 413/04; C07D 409/04; C07D 209/58

USPC ...................................................... 514/259.1
See application file for complete search history.

(56) References Cited

FOREIGN PATENT DOCUMENTS

| | | |
|---|---|---|
| CN | 101622234 A | 1/2010 |
| CN | 102099333 A | 6/2011 |
| CN | 102762100 A | 10/2012 |
| CN | 103298807 A | 9/2013 |
| CN | 103380112 A | 10/2013 |
| WO | 2008107436 A1 | 9/2008 |
| WO | 2009088531 A1 | 7/2009 |
| WO | 2011005290 A1 | 1/2011 |
| WO | 2011060392 A1 | 5/2011 |
| WO | 2011082732 A1 | 7/2011 |
| WO | 2012061459 A1 | 5/2012 |
| WO | 2012071184 A1 | 5/2012 |
| WO | 2012158550 A2 | 11/2012 |

OTHER PUBLICATIONS

International Search Report and Written Opinion of PCT/CN2017/093808 dated Oct. 26, 2017.
1st Office Action issued in the counterpart Russian application No. 2019104953 dated Jun. 23, 2020.
1st Office Action issued in the counterpart Indian application No. 201927006726 dated Sep. 24, 2020.
Extended European Search Report issued in the counterpart European application No. 17830496.0 dated Feb. 3, 2020.

*Primary Examiner* — Kahsay Habte
(74) *Attorney, Agent, or Firm* — SZDC Law P.C.

(57) ABSTRACT

The present invention relates to a class of tricyclic compounds and an application thereof as a sphingosine 1-phosphate type 1 (S1P1) receptor agonist. The invention specifically relates to a compound represented by formula (II), and a tautomer and pharmaceutically acceptable salt of same.

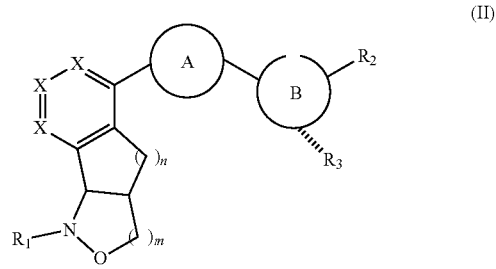

(II)

45 Claims, No Drawings

S1P1 AGONIST AND APPLICATION THEREOF

This application is the National Stage Application of PCT/CN2017/093808, filed on Jul. 21, 2017, which claims priority to Chinese Patent Application No.: 201610583286.X, filed on Jul. 22, 2016, which is incorporated by reference for all purposes as if fully set forth herein.

FIELD OF INVENTION

The present invention relates to a class of tricyclic compounds and an application thereof as a sphingosine 1-phosphate type 1 (S1P1) receptor agonist. The invention specifically relates to a compound represented by formula (II), a tautomer or a pharmaceutically acceptable salt of the same.

PRIOR ARTS

Sphingosine 1-phosphate (S1P) is a multi-effect lipid mediator, which has broad-spectrum physiological activity, including cell proliferation, survival, lymphocyte migration, cytoskeletal modeling and morphogenesis. Sphingosine is released from ceramide under the catalysis of enzyme ceramide. Sphingosine is phosphorylated under the catalysis of sphingosine kinase thereby producing sphingosine 1-phosphate (S1P) and interacts with sphingosine 1-phosphate receptor (S1PR) to exhibit physiological activity.

Sphingosine 1-phosphate receptor 1 (S1PR1) also known as endothelial cell differentiation gene 1 (EDG1) is a G-protein-coupled receptor belonging to the endothelial cell differentiation gene (EDG) receptor family, which is a protein encoded by an S1PR1 gene. The sphingosine 1-phosphate receptor 1 comprises five subtypes (S1PR1-5), wherein the 1-phosphosphingohol receptor 1 (S1PR1) is abundantly distributed on the endothelial cells membrane. Like other G-protein-coupled receptors, S1PR1 detects the ligands extracellular and activates the intracellular signal pathways that lead to cellular responses.

Sphingosine 1-phosphate (S1P) is very important to human and is responsible for regulating the vascular system and immune system. Small molecule S1P1 agonists and inhibitors imitate the mechanism of sphingosine 1-phosphate (S1P) binding to receptors, which has been shown to play important physiological roles in their signaling systems. Sphingosine 1-phosphate receptor 1 (S1PR1) activation disrupts lymphocyte migration, isolating lymphocytes in lymph nodes and other secondary lymphoid organs, resulting in rapidly reversible lymphopenia. Clinical studies have shown that lymphocyte isolation reduces inflammation or autoimmune disease responses and is critical for immune regulation.

Currently, in vivo pharmaceutical studies of sphingosine 1-phosphate receptor 1 (S1PR1) agonists are disclosed to be used in treating or preventing autoimmune diseases. The development and application of sphingosine 1-phosphate receptor 1 (S1PR1) agonists have promising prospects.

CONTENT OF THE PRESENT INVENTION

The present invention provides a compound represented by formula (II), or a pharmaceutically acceptable salt of the same,

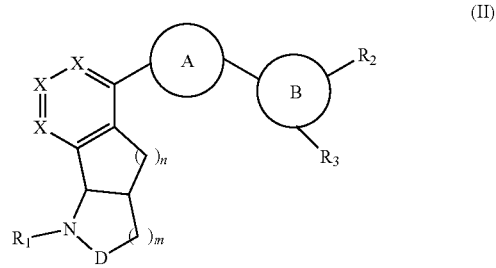

(II)

wherein,

X is independently N or CH;

m is 0, 1 or 2;

n is 1 or 2;

D is —C(=O)—, —C(=O)O—, —CH$_2$—;

R$_1$ is C$_{1-6}$ alkyl, C$_{1-6}$ heteroalkyl or C$_{3-6}$ cycloalkyl, which is optionally substituted by one, two or three R;

each of R$_2$ and R$_3$ is independently H, halogen, OH, NH$_2$, CN or R$_4$-L-, or is selected from the group consisting of C$_{1-6}$ alkyl, C$_{1-6}$ heteroalkyl, phenyl and 5-6 membered heteroaryl, each of which is optionally substituted by one, two or three R;

R$_4$ is C$_{3-6}$ cycloalkyl, 3-6 membered heterocyclic alkyl, phenyl or 5-6 membered heteroaryl, each of which is optionally substituted by one, two or three R;

L is —(CRR)$_{1-3}$— or —O—(CRR)$_{0-3}$—;

ring A is 5 membered heteroaryl;

ring B is phenyl or 5-9 membered heteroaryl;

R is H, F, Cl, Br, I, CN, OH, NH$_2$, COOH,

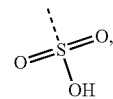

or selected from the group consisting of C$_{1-6}$ alkyl and C$_{1-6}$ heteroalkyl, which is optionally substituted by one, two or three R';

R' is H, F, Cl, Br, I, OH, CN, NH$_2$, COOH, Me, Et, CF$_3$, CHF$_2$, CH$_2$F, NHCH$_3$, N(CH$_3$)$_2$;

"hetero" represents a heteroatom or a heteroatom group, selected from the group consisting of —C(=O)N(R)—, —N(R)—, —C(=NR)—, —S(=O)$_2$N(R)—, —S(=O)N(R)—, —O—, —S—, =O, =S, —O—N=, —C(=O)O—, —C(=O)—, —C(=S)—, —S(=O)—, —S(=O)$_2$— and —N(R)C(=O)N(R)—;

in any one of the above cases, the number of the heteroatom or heteroatom group is independently selected from one, two or three.

The present invention provides a compound represented by formula (I), or a pharmaceutically acceptable salt of the same,

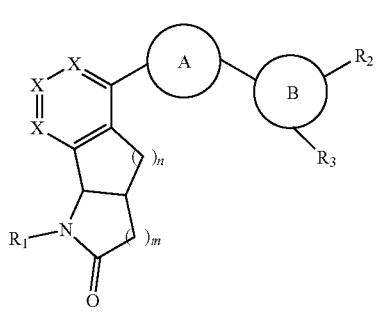

wherein
X is N or CH;
each of m and n is one or two;
$R_1$ is selected from the group consisting of $C_{1-6}$ alkyl and $C_{1-6}$ heteroalkyl, which is optionally substituted by one, two or three R;
each of $R_2$ and $R_3$ is H, halogen, OH, $NH_2$, CN or $R_4$-L-, or selected from the group consisting of $C_{1-6}$ alkyl, $C_{1-6}$ heteroalkyl, phenyl and 5-6 membered heteroaryl, each of which is optionally substituted by one, two or three R;
$R_4$ is selected from the group consisting of $C_{3-6}$ cycloalkyl, 3-6 membered heterocyclic alkyl, phenyl and 5-6 membered heteroaryl, each of which is optionally substituted by one, two or three R.
L is —$(CRR)_{1-3}$— or —O—$(CRR)_{0-3}$—;
ring A is 5 membered heteroaryl;
ring B is phenyl or 5-9 membered heteroaryl;
R is H, F, Cl, Br, I, CN, OH, $NH_2$ or COOH, or selected from the group consisting of $C_{1-6}$ alkyl and $C_{1-6}$ heteroalkyl, which is optionally substituted by one, two or three R';
R' is H, F, Cl, Br, I, OH, CN, $NH_2$, COOH, Me, Et, $CF_3$, $CHF_2$, $CH_2F$, $NHCH_3$ or $N(CH_3)_2$;
"hetero" represents a heteroatom or a heteroatom group, selected from the group consisting of —C(=O)N(R)—, —N(R)—, —C(=NR)—, —S(=O)$_2$N(R)—, —S(=O)N(R)—, —O—, —S—, =O, =S, —O—N=, —C(=O)O—, —C(=O)—, —C(=S)—, —S(=O)—, —S(=O)$_2$— and —N(R)C(=O)N(R)—;
in any one of the above cases, the number of the heteroatom or heteroatom group is independently selected from one, two or three.

In some embodiments of the present invention, R is H, F, Cl, Br, I, CN, OH, $NH_2$ or COOH, or selected from the group consisting of $C_{1-3}$ alkyl, $C_{1-3}$ alkoxy, $C_{1-3}$ alkylthiol, $C_{1-3}$ alkylamino, N,N'-di($C_{1-2}$ alkyl))amino, $C_{1-3}$ alkyl-S(=O)— and $C_{1-3}$ alkyl-S(=O)$_2$—, each of which is optionally substituted by one, two or three R'.

In some embodiments of the present invention, R is selected from the group consisting of H, F, Cl, Br, I, CN, OH, $NH_2$, COOH, Me, Et, $CF_3$,

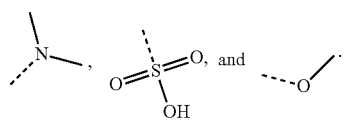

In some embodiments of the present invention, $R_1$ is selected from the group consisting of $C_{1-6}$ alkyl, $C_{1-3}$ alkyl-S(=O)$_2$—$C_{1-3}$ alkyl-, $C_{1-3}$ alkyl-S(=O)—$C_{1-3}$ alkyl- and $C_{1-3}$ alkyl-NH—C(=O)$_2$—$C_{1-3}$ alkyl-, each of which is optionally substituted by one, two or three R.

In some embodiments of the present invention, $R_1$ is selected from

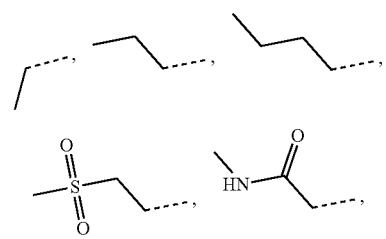

each of which is optionally substituted by one, two or three R.

In some embodiments of the present invention, $R_1$ is selected from the group consisting of

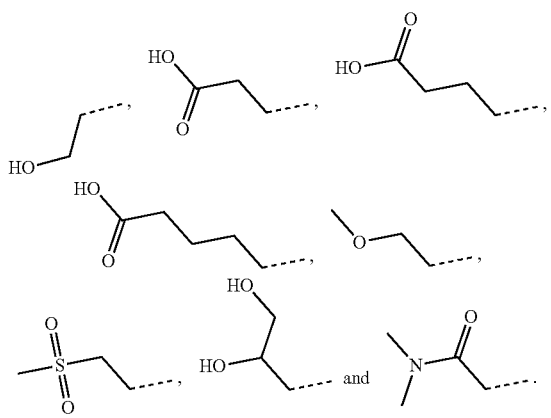

In some embodiments of the present invention, L is —$(CH_2)_{1-3}$— or —O—$(CH_2)_{0-3}$—.

In some embodiments of the present invention, L is selected from the group consisting of —$CH_2$—, —$CH_2CH_2$—, —$CH_2CH_2CH_2$—, —O—, —O—$CH_2$—, —O—$CH_2CH_2$— and —O—$CH_2CH_2CH_2$—.

In some embodiments of the present invention, $R_4$ is selected from the group consisting of

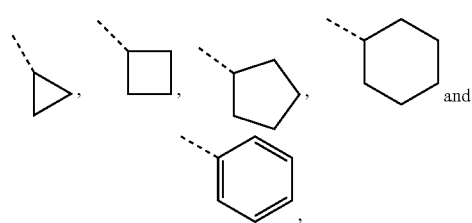

each of which is optionally substituted by one, two or three R.

In some embodiments of the present invention, R₄ is

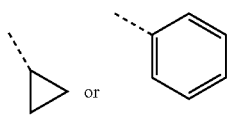

In some embodiments of the present invention, R₄-L- is

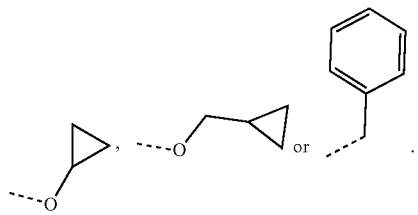

In some embodiments of the present invention, each of R₂ and R₃ is H, F, Cl, Br, I, OH, NH₂, CN or R₄-L-, or optionally selected from the group consisting of $C_{1-3}$ alkyl, $C_{1-3}$ alkoxy, $C_{1-3}$ alkylthiol, $C_{1-3}$ alkyl-S(=O)—, $C_{1-3}$ alkyl-S(=O)₂—, phenyl, thiazolyl, isothiazolyl, oxazolyl and isoxazolyl, which is optionally substituted by one, two or three R.

In some embodiments of the present invention, each of R₂ and R₃ is H, F, Cl, Br, I, OH, NH₂, CN, R₄-L-, or selected from the group consisting of Me, Et,

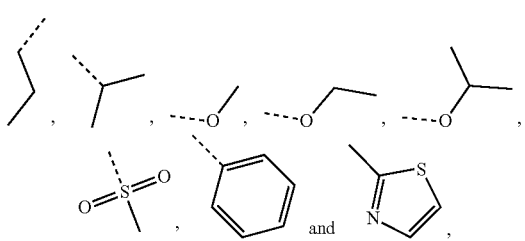

each of which is optionally substituted by one, two or three R.

In some embodiments of the present invention, each of R₂ and R₃ is H, F, Cl, Br, I, OH, NH₂, CN, Me,

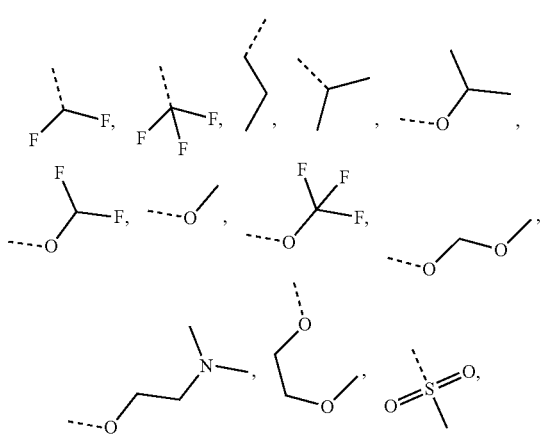

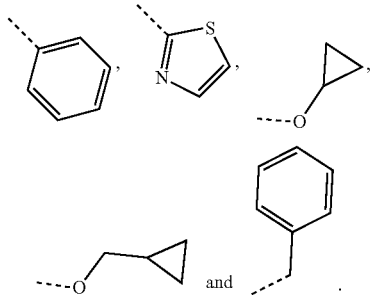

In some embodiments of the present invention, ring A is selected from the group consisting of 1,3,4-oxadiazolyl, 1,3,4-thiadiazolyl, 1,2,4-oxadiazolyl, 1,2,4-thiadiazolyl, thiazolyl, isothiazolyl, oxazolyl, isoxazolyl and thienyl.

In some embodiments of the present invention, ring A is selected from the group consisting of

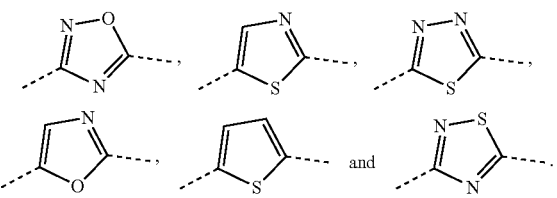

In some embodiments of the present invention, ring B is selected from the group consisting of phenyl, oxazolyl, isoxazolyl, thiazolyl, isothiazolyl, 1,2,3-thiadiazolyl, imidazo[1,2-a]pyridyl, imidazo[1,2-a]pyrimidinyl, 4,5,6,7-tetrahydro[5,4-c]pyridyl, 5,6,7,8-tetrahydroimidazo[1,2-a]pyridyl, 4,5,6,7-tetrahydrothiazolo[5,4-c]pyridyl and 1,2,3-triazolyl.

In some embodiments of the present invention, ring B is selected from the group consisting of

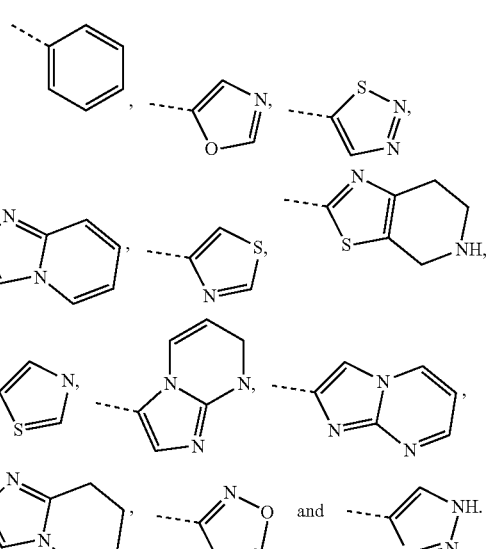

In some embodiments of the present invention, the structure unit

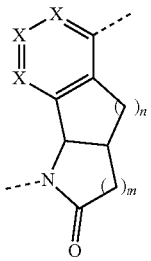

is selected from the group consisting of

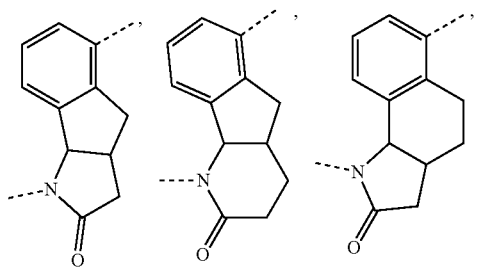

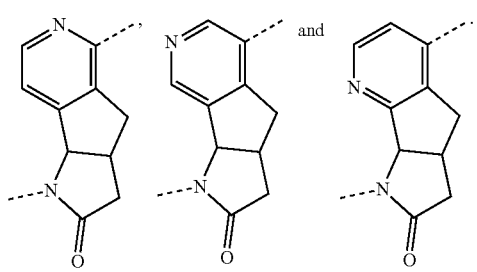

In some embodiments of the present invention, R is H, F, Cl, Br, I, CN, OH, NH$_2$, COOH or

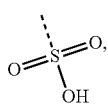

or selected from the group consisting of C$_{1-3}$ alkyl, C$_{1-3}$ alkoxy, C$_{1-3}$ alkylthiol, C$_{1-3}$ alkylamino, N,N'-di(C$_{1-2}$ alkyl)amino, C$_{1-3}$ alkyl-S(=O)— and C$_{1-3}$ alkyl-S(=O)$_2$—, each of which is optionally substituted by one, two or three R' as defined in the present invention.

In some embodiments of the present invention, R is H, F, Cl, Br, I, CN, OH, NH$_2$, COOH, Me, Et, CF$_3$,

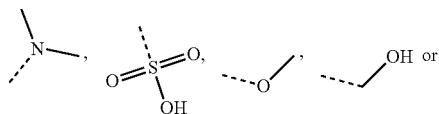

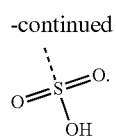

In some embodiments of the present invention, R$_1$ is C$_{1-6}$ alkyl, C$_{1-3}$ alkyl-S(=O)$_2$—C$_{1-3}$ alkyl-, C$_{1-3}$ alkyl-S(=O)—C$_{1-3}$ alkyl-, C$_{1-3}$ alkyl-NH—C(=O)—C$_{1-3}$ alkyl- and C$_{3-6}$ cycloalkyl, each of which is optionally substituted by one, two or three R as defined in the present invention.

In some embodiments of the present invention, R$_1$ is Me, each of which is optionally substituted by one, two or three R as defined in the present invention.

In some embodiments of the present invention, R$_1$ is

In some embodiments of the present invention, L is —(CH$_2$)$_{1-3}$— or —O—(CH$_2$)$_{0-3}$—.

In some embodiments of the present invention, L is —CH$_2$—, —CH$_2$CH$_2$—, —CH$_2$CH$_2$CH$_2$—, —O—, —O—CH$_2$—, —O—CH$_2$CH$_2$— or —O—CH$_2$CH$_2$CH$_2$—.

In some embodiments of the present invention, R₄ is selected from the group consisting of

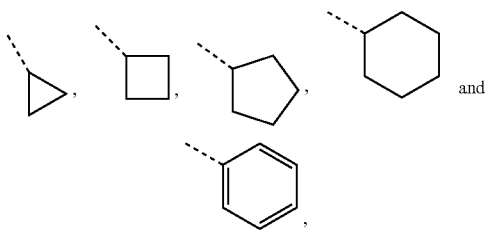

each of which is optionally substituted by one, two or three R as defined in the present invention.

In some embodiments of the present invention, R₄ is

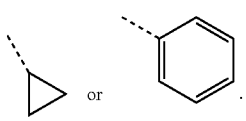

In some embodiments of the present invention, R₄-L- is selected from

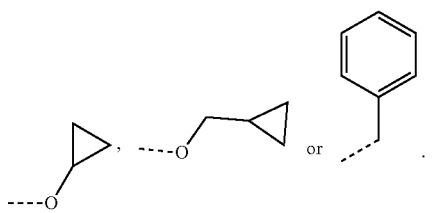

In some embodiments of the present invention, each of R₂ and R₃ is independently H, F, Cl, Br, I, OH, NH₂, CN or R₄-L-, or selected from the group consisting of C$_{1-3}$ alkyl, C$_{1-3}$ alkoxy, C$_{1-3}$ alkylthiol, C$_{1-3}$ alkyl-S(=O)—, C$_{1-3}$ alkyl-S(=O)₂—, phenyl, thiazolyl, isothiazolyl, oxazolyl and isoxazolyl, each of which is optionally substituted by one, two or three R as defined in the present invention.

In some embodiments of the present invention, each of R₂ and R₃ is H, F, Cl, Br, I, OH, NH₂, CN or R₄-L-, or selected from the group consisting of Me, Et,

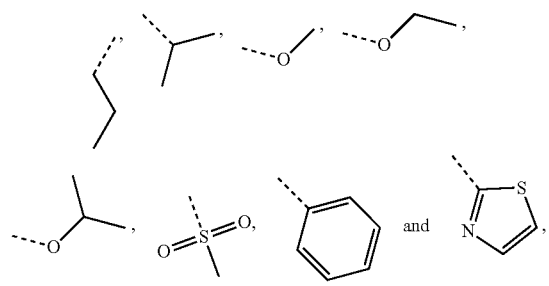

each of which is optionally substituted by one, two or three R as defined in the present invention.

In some embodiments of the present invention, each of R₂ and R₃ is H, F, Cl, Br, I, OH, NH₂, CN, Me,

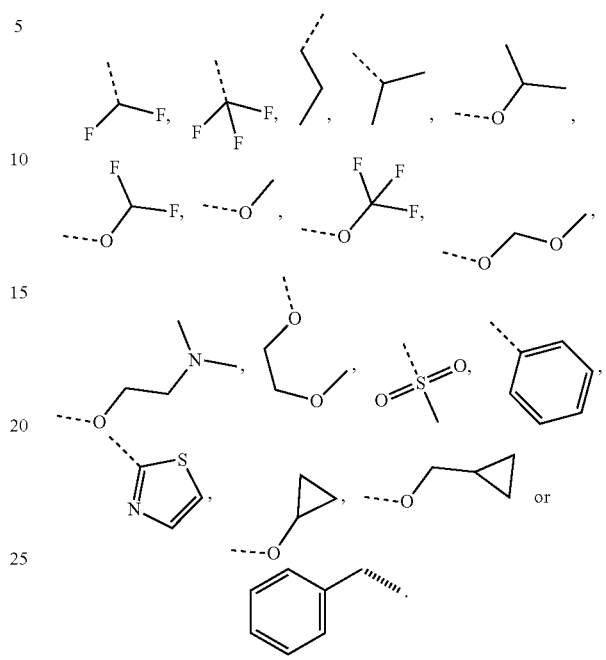

In some embodiments of the present invention, the ring A is selected from the group consisting of 1,3,4-oxadiazolyl, 1,3,4-thiadiazolyl, 1,2,4-oxadiazolyl, 1,3,4-oxadiazolyl, 1,2,4-triazolyl, 1,2,4-thiadiazolyl, thiazolyl, isothiazolyl, oxazolyl, isoxazolyl and thienyl.

In some embodiments of the present invention, the ring A is

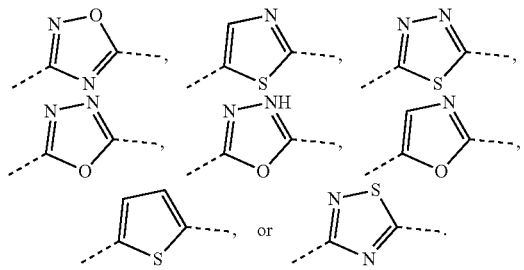

In some embodiments of the present invention, the ring B is selected from the group consisting of phenyl, oxazolyl, isoxazolyl, thiazolyl, isothiazolyl, 1,2,3-thiadiazolyl, imidazo[1,2-a]pyridyl, imidazo[1,2-a]pyrimidinyl, 4,5,6,7-tetrahydro[5,4-c]pyridyl, 5,6,7,8-tetrahydroimidazo[1,2-a]pyridyl, 4,5,6,7-tetrahydrothiazolo[5,4-c]pyridyl and 1,2,3-triazolyl.

In some embodiments of the present invention, the ring B is

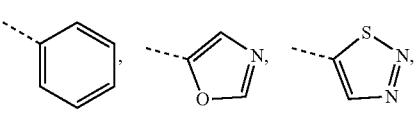

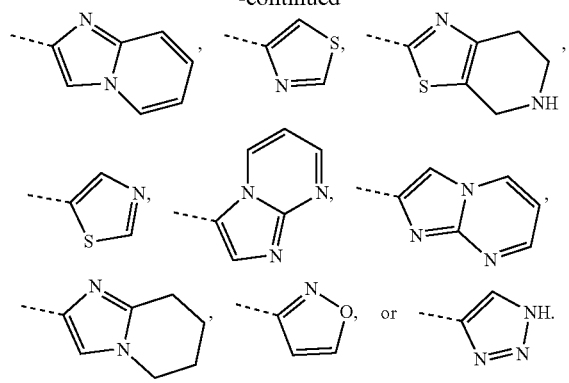
In some embodiments of the present invention, the structure unit
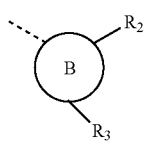
is selected from the group consisting of
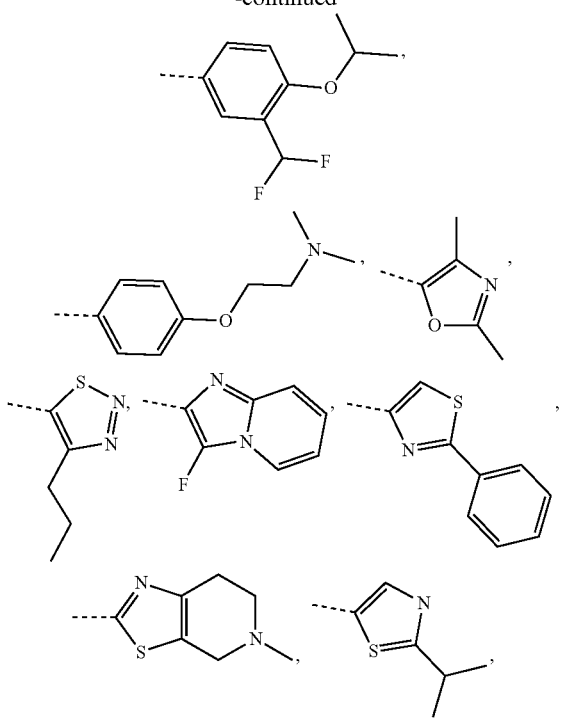
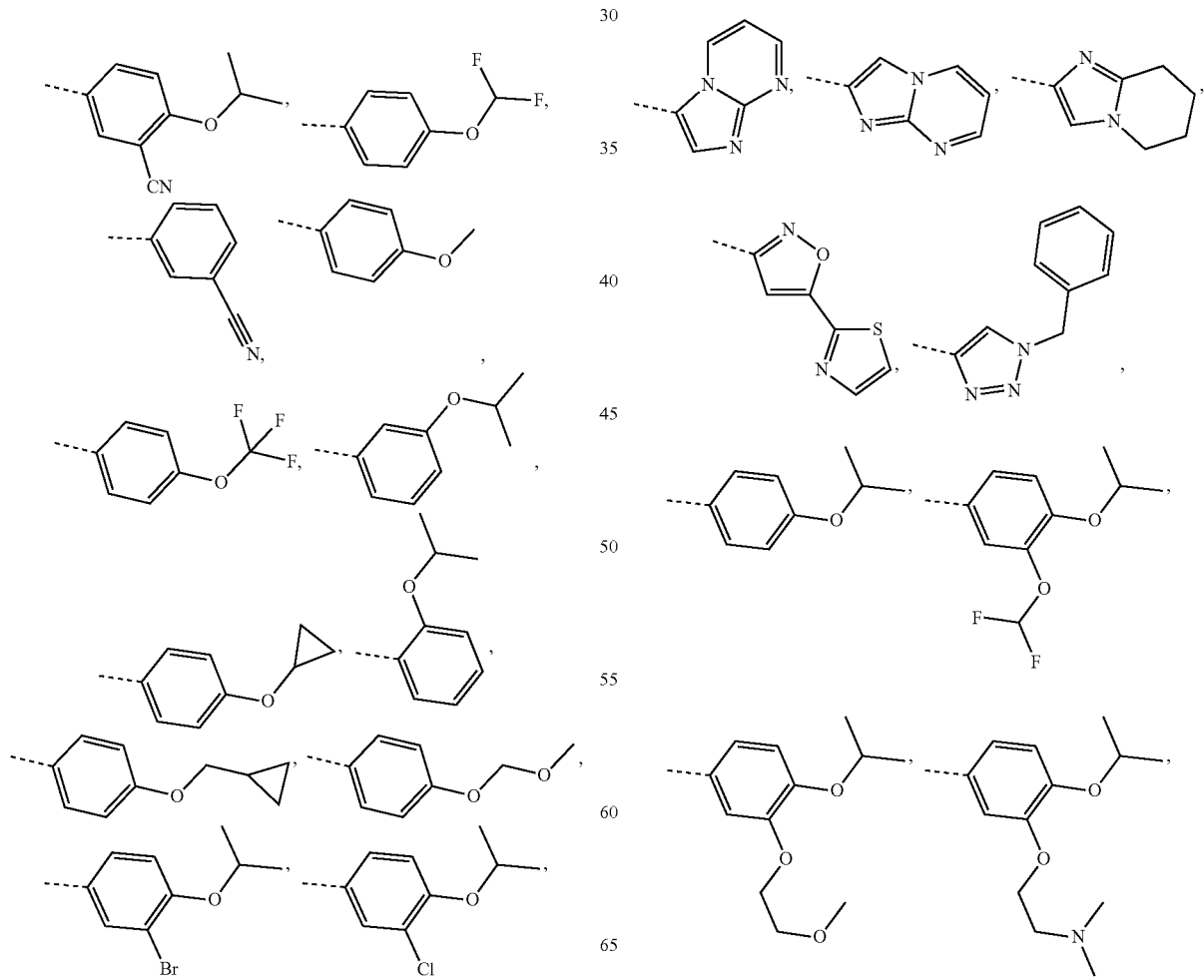

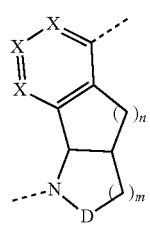

In some embodiments of the present invention, the structure unit

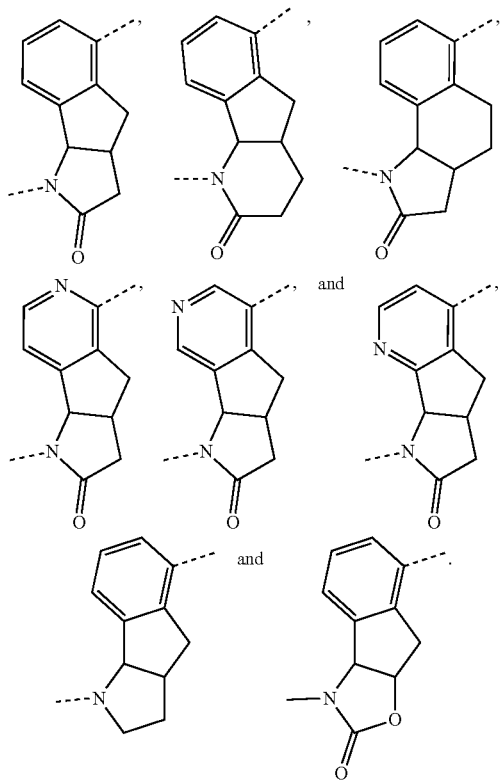

is selected from the group consisting of

In some embodiments of the present invention, R is H, F, Cl, Br, I, CN, OH, NH₂ or COOH, or selected from the group consisting of $C_{1-3}$ alkyl, $C_{1-3}$ alkoxy, $C_{1-3}$ alkylthiol, $C_{1-3}$ alkylamino, N,N'-di($C_{1-2}$ alkyl)amino, $C_{1-3}$ alkyl-S(=O)— and $C_{1-3}$ alkyl-S(=O)₂—, each of which is optionally substituted by one, two or three R', wherein other variables are as defined above.

In some embodiments of the present invention, R is H, F, Cl, Br, I, CN, OH, NH₂, COOH, Me, Et, CF₃,

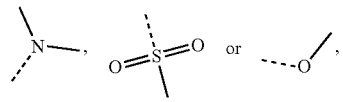

wherein other variables are as defined above.

In some embodiments of the present invention, $R_1$ is selected from the group consisting of $C_{1-6}$ alkyl, $C_{1-3}$ alkyl-S(=O)₂—$C_{1-3}$ alkyl-, $C_{1-3}$ alkyl-S(=O)—$C_{1-3}$ alkyl- and $C_{1-3}$ alkyl-NH—C(=O)₂—$C_{1-3}$ alkyl-, each of which is optionally substituted by one, two or three R, wherein other variables are as defined above.

In some embodiments of the present invention, $R_1$ is selected from the group consisting of

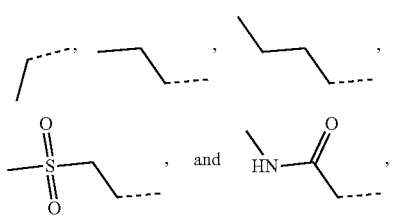

each of which is optionally substituted by one, two or three R, wherein other variables are as defined above.

In some embodiments of the present invention, $R_1$ is selected from the group consisting of

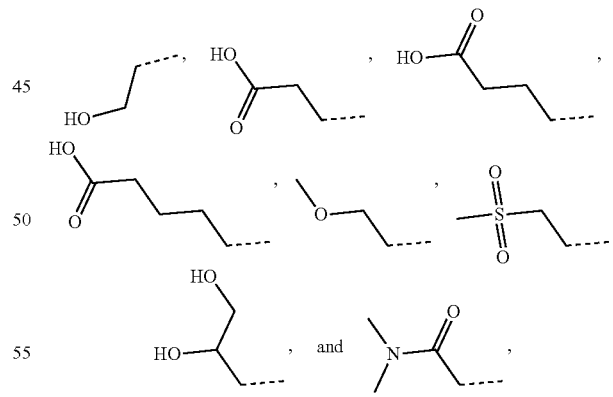

wherein other variables are as defined above.

In some embodiments of the present invention, L is —(CH₂)₁₋₃— or —O—(CH₂)₀₋₃—, wherein other variables are as defined above.

In some embodiments of the present invention, L is —CH₂—, —CH₂CH₂—, —CH₂CH₂CH₂—, —O—, —O—CH₂—, —O—CH₂CH₂— or —O—CH₂CH₂CH₂—, wherein other variables are as defined above.

In some embodiments of the present invention, $R_4$ is

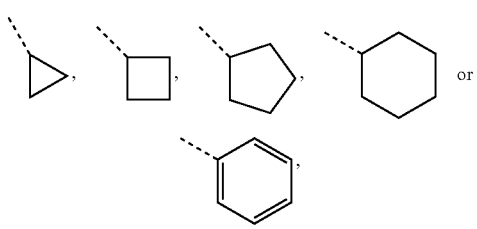

each of which is optionally substituted by one, two or three R, wherein other variables are as defined above.

In some embodiments of the present invention, $R_4$ is

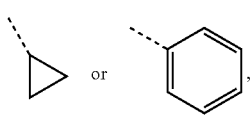

wherein other variables are as defined above.

In some embodiments of the present invention, $R_4$-L- is selected from the group consisting of

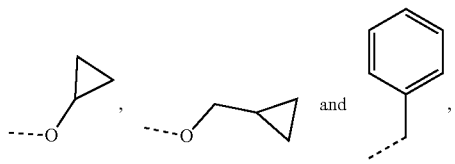

wherein other variables are as defined above.

In some embodiments of the present invention, each of $R_2$ and $R_3$ is H, F, Cl, Br, I, OH, $NH_2$, CN, $R_4$-L-, or selected from the group consisting of $C_{1-3}$ alkyl, $C_{1-3}$ alkoxy, $C_{1-3}$ alkylthiol, $C_{1-3}$ alkyl-S(=O)—, $C_{1-3}$ alkyl-S(=O)$_2$—, phenyl, thiazolyl, isothiazolyl, oxazolyl and isoxazolyl, each of which is optionally substituted by one, two or three R as defined in the present invention, wherein other variables are as defined above.

In some embodiments of the present invention, each of $R_2$ and $R_3$ is H, F, Cl, Br, I, OH, $NH_2$, CN or $R_4$-L-, or selected from the group consisting of Me, Et,

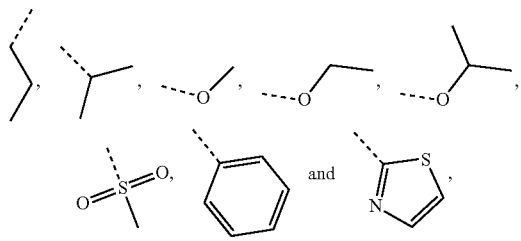

each of which is optionally substituted by one, two or three R as defined in the present invention, wherein other variables are as defined above.

In some embodiments of the present invention, each of $R_2$ and $R_3$ is H, F, Cl, Br, I, OH, $NH_2$, CN, Me,

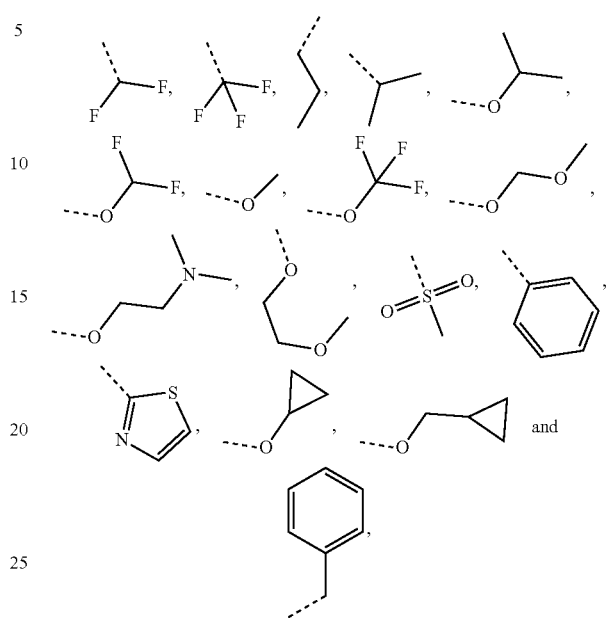

wherein other variables are as defined above.

In some embodiments of the present invention, the ring A is selected from the group consisting of 1,3,4-oxadiazolyl, 1,3,4-thiadiazolyl, 1,2,4-oxadiazolyl, 1,2,4-thiadiazolyl, thiazolyl, isothiazolyl, oxazolyl, isoxazolyl and thienyl, wherein other variables are as defined above.

In some embodiments of the present invention, the ring A is

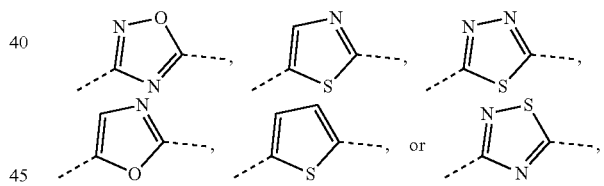

wherein other variables are as defined above.

In some embodiments of the present invention, the ring B is selected from the group consisting of phenyl, oxazolyl, isoxazolyl, thiazolyl, isothiazolyl, 1,2,3-thiadiazolyl, imidazo[1,2-a]pyridyl, imidazo[1,2-a]pyrimidinyl, 4,5,6,7-tetrahydro[5,4-c]pyridyl, 5,6,7,8-tetrahydroimidazo[1,2-a]pyridyl, 4,5,6,7-tetrahydrothiazolo[5,4-c]pyridyl and 1,2,3-triazolyl, wherein other variables are as defined above.

In some embodiments of the present invention, the ring B is selected from the group consisting of

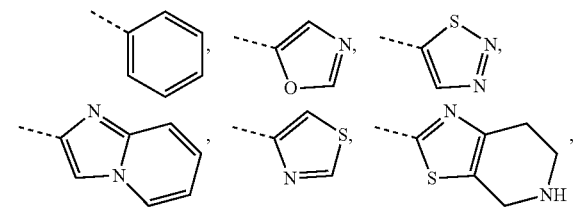

-continued

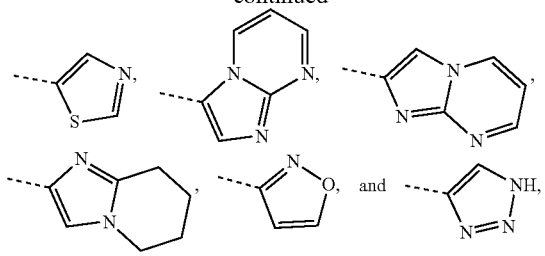

wherein other variables are as defined above.

In some embodiments of the present invention, the structure unit

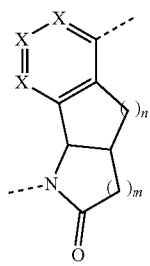

is selected from the group consisting of

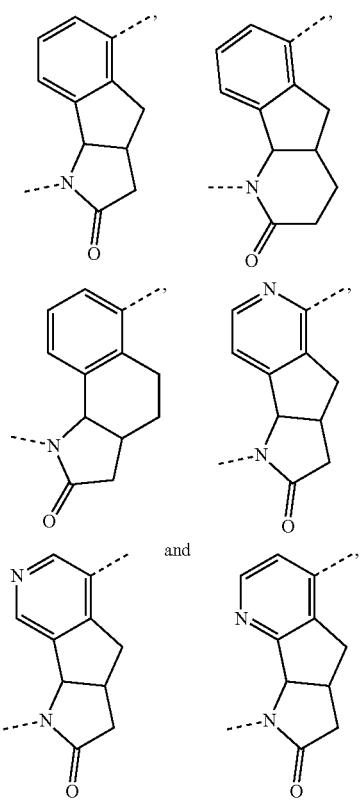

wherein other variables are as defined above.

In some embodiments of the present invention, R is H, F, Cl, Br, I, CN, OH, NH$_2$, COOH or

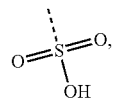

or selected from the group consisting of C$_{1-3}$ alkyl, C$_{1-3}$ alkoxy, C$_{1-3}$ alkylthiol, C$_{1-3}$ alkylamino, N,N'-di(C$_{1-2}$ alkyl) amino, C$_{1-3}$ alkyl-S(=O)—, C$_{1-3}$ alkyl-S(=O)$_2$—, each of which is optionally substituted by one, two or three R' as defined in the present invention, wherein other variables are as defined above.

In some embodiments of the present invention, R is selected from the group consisting of H, F, Cl, Br, I, CN, OH, NH$_2$, COOH, Me, Et, CF$_3$,

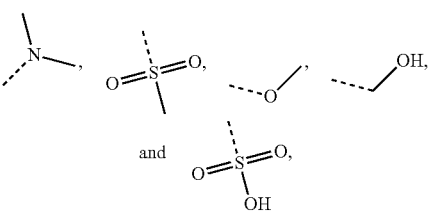

wherein other variables are as defined above.

In some embodiments of the present invention, R$_1$ is selected from the group consisting of C$_{1-6}$ alkyl, C$_{1-3}$ alkyl-S(=O)$_2$—C$_{1-3}$ alkyl-, C$_{1-3}$ alkyl-S(=O)—C$_{1-3}$ alkyl-, C$_{1-3}$ alkyl-NH—C(=O)—C$_{1-3}$ alkyl- and C$_{3-6}$ cycloalkyl, each of which is optionally substituted by one, two or three R as defined in the present invention, wherein other variables are as defined above.

In some embodiments of the present invention, R$_1$ is

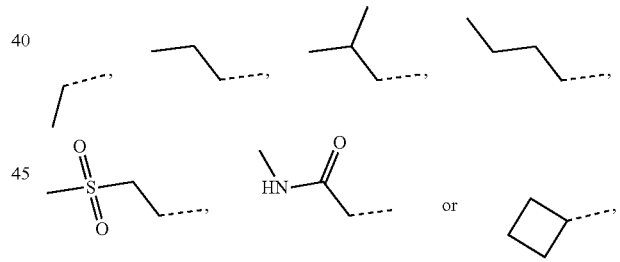

each of which is optionally substituted by one, two or three R as defined in the present invention, wherein other variables are as defined above.

In some embodiments of the present invention, R$_1$ is selected from the group consisting of

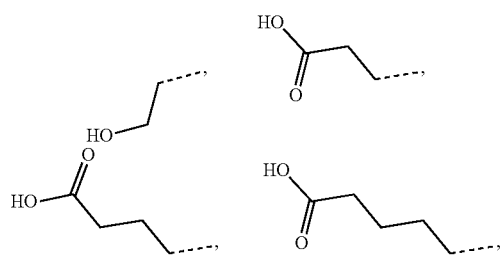

-continued

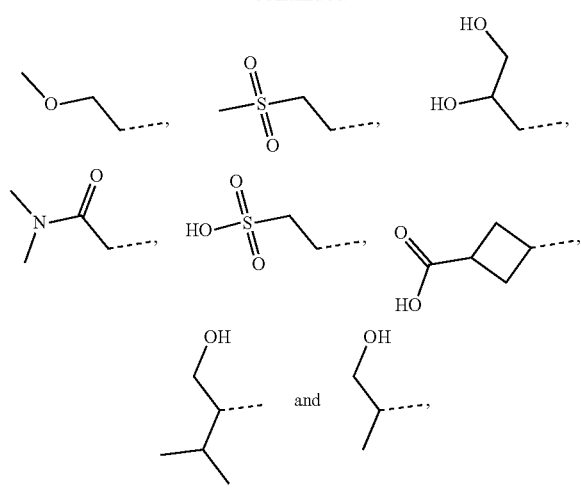

wherein other variables are as defined above.

In some embodiments of the present invention, L is —(CH$_2$)$_{1-3}$— or —O—(CH$_2$)$_{0-3}$—, wherein other variables are as defined above.

In some embodiments of the present invention, L is —CH$_2$—, —CH$_2$CH$_2$—, —CH$_2$CH$_2$CH$_2$—, —O—, —O—CH$_2$—, —O—CH$_2$CH$_2$— or —O—CH$_2$CH$_2$CH$_2$—, wherein other variables are as defined above.

In some embodiments of the present invention, R$_4$ is selected from the group consisting of

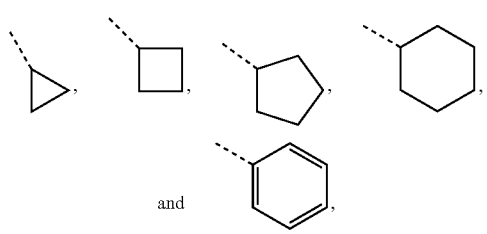

each of which is optionally substituted by one, two or three R, wherein other variables are as defined above.

In some aspects of the present invention, R$_4$ is selected from

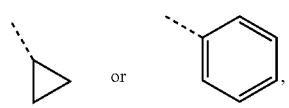

wherein other variables are as defined above.

In some embodiments of the present invention, R$_4$-L- is selected from the group consisting of

-continued

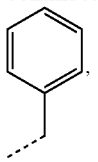

wherein other variables are as defined above.

In some embodiments of the present invention, each of R$_2$ and R$_3$ is H, F, Cl, Br, I, OH, NH$_2$, CN or R$_4$-L-, or selected from the group consisting of C$_{1-3}$ alkyl, C$_{1-3}$ alkoxy, C$_{1-3}$ alkylthiol, C$_{1-3}$ alkyl-S(=O)—, C$_{1-3}$ alkyl-S(=O)$_2$—, phenyl, thiazolyl, isothiazolyl, oxazolyl and isoxazolyl, each of which is optionally substituted by one, two or three R, wherein other variables are as defined above.

In some embodiments of the present invention, each of R$_2$ and R$_3$ is H, F, Cl, Br, I, OH, NH$_2$, CN or R$_4$-L-, or selected from the group consisting of Me, Et,

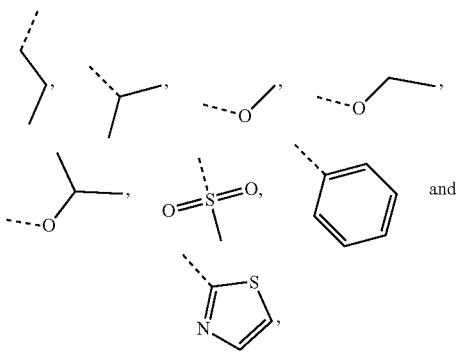

each of which is optionally substituted by one, two or three R, wherein other variables are as defined above.

In some embodiments of the present invention, each of R$_2$ and R$_3$ is H, F, Cl, Br, I, OH, NH$_2$, CN, Me,

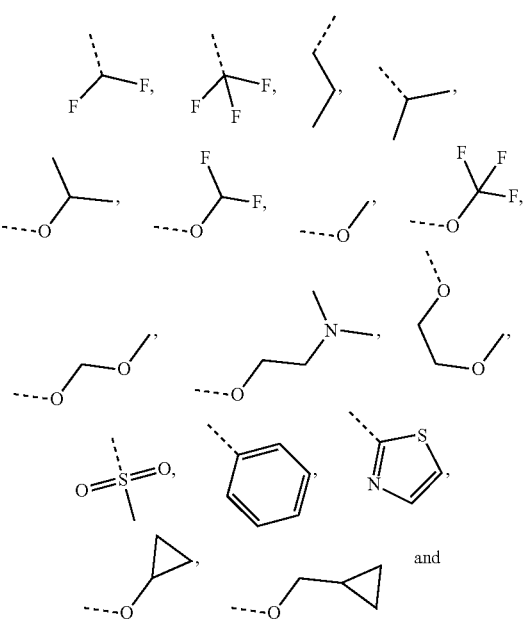

-continued

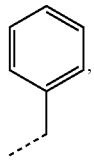

wherein other variables are as defined above.

In some embodiments of the present invention, the ring A is selected from the group consisting of 1,3,4-oxadiazolyl, 1,3,4-thiadiazolyl, 1,2,4-oxadiazolyl, 1,3,4-oxadiazolyl, 1,2,4-triazolyl, 1,2,4-thiadiazolyl, thiazolyl, isothiazolyl, oxazolyl, isoxazolyl and thienyl, wherein other variables are as defined above.

In some embodiments of the present invention, the ring A is selected from the group consisting of

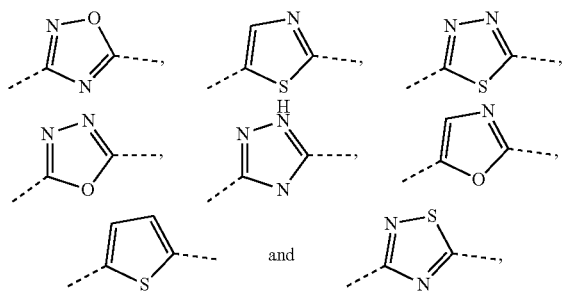

wherein other variables are as defined above.

In some embodiments of the present invention, the ring B is selected from the group consisting of phenyl, oxazolyl, isoxazolyl, thiazolyl, isothiazolyl, 1,2,3-thiadiazolyl, imidazo[1,2-a]pyridyl, imidazo[1,2-a]pyrimidinyl, 4,5,6,7-tetrahydro[5,4-c]pyridyl, 5,6,7,8-tetrahydroimidazo[1,2-a]pyridyl, 4,5,6,7-tetrahydrothiazolo[5,4-c]pyridyl and 1,2,3-triazolyl, wherein other variables are as defined above.

In some embodiments of the present invention, the ring B is selected from the group consisting of

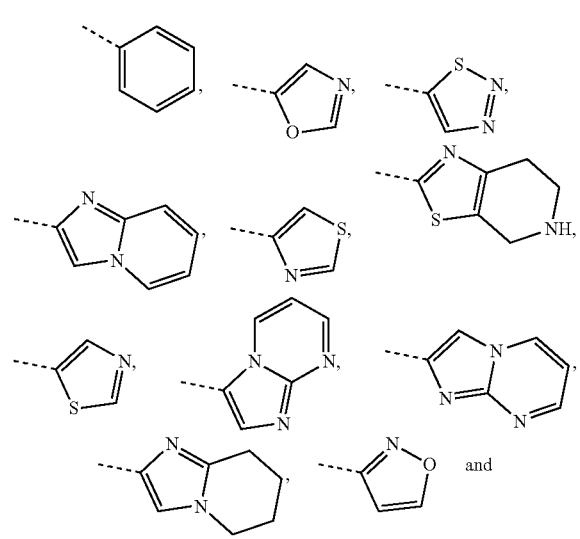

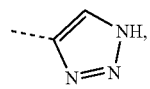

wherein other variables are as defined above.

In some embodiments of the present invention, the structure unit

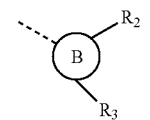

is selected from the group consisting of

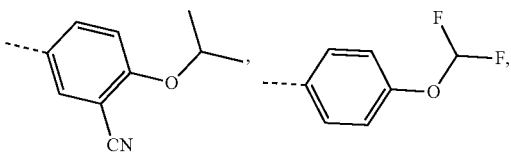

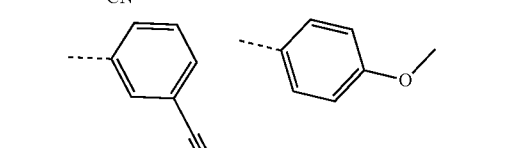

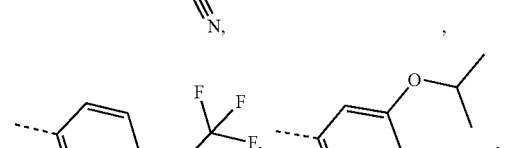

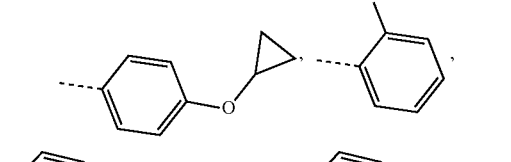

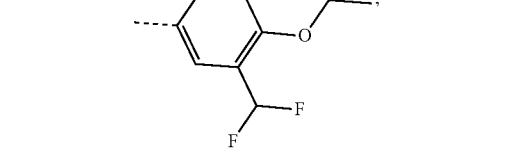

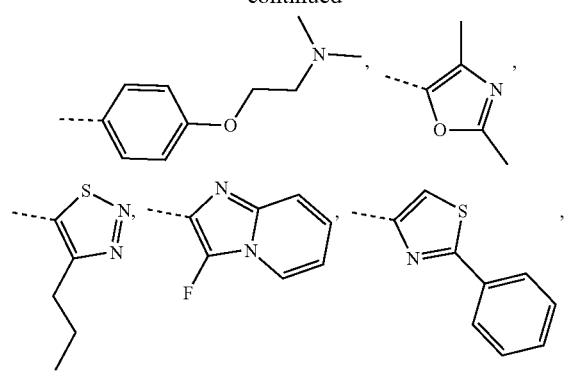
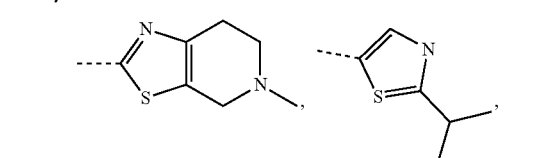
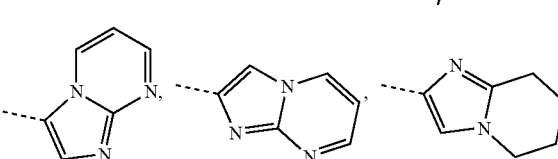
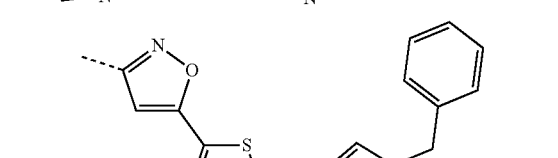
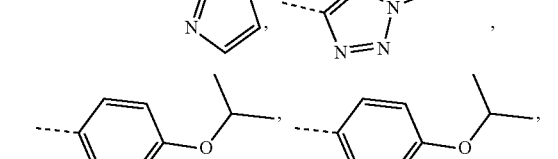
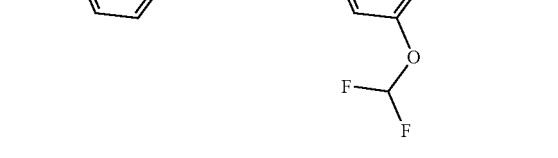
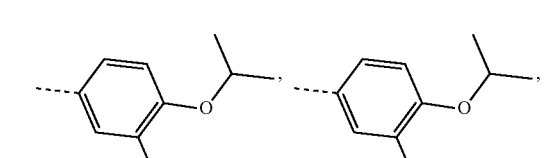
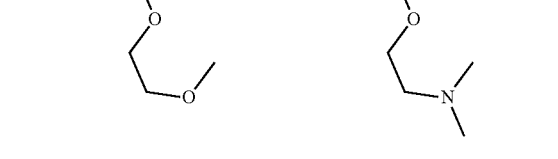
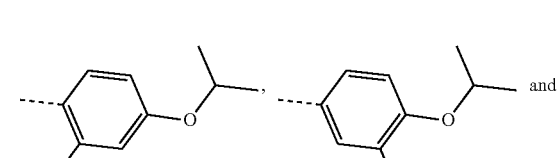
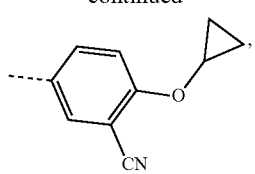
wherein other variables are as defined above.
In some embodiments of the present invention, the structure unit
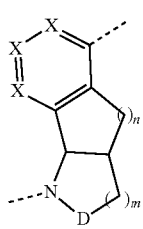
is selected from the group consisting of
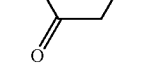
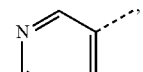
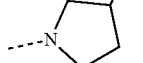
wherein other variables are as defined above.

In some embodiments of the present invention, the compound or the pharmaceutically acceptable salt of the same is

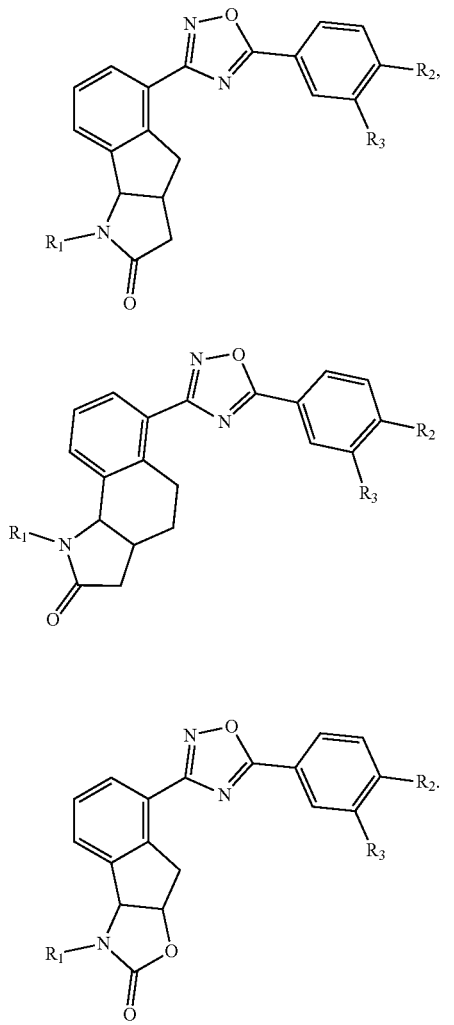

(II-1)

(II-2) or (II-3)

wherein,

R₁, R₂ and R₃ are as defined above.

In some embodiments of the present invention, the compound or the pharmaceutically acceptable salt of the same is selected from the group consisting of

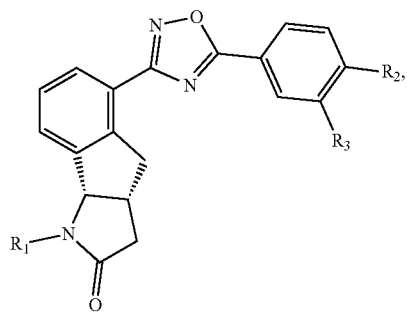

(II-1A)

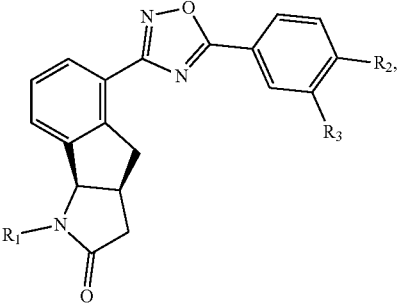

(II-1B)

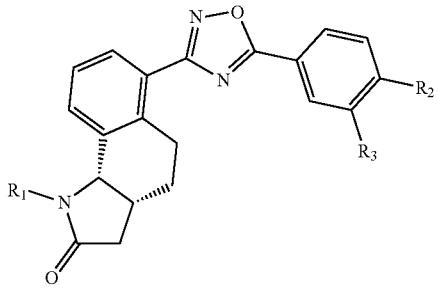

(II-2A)

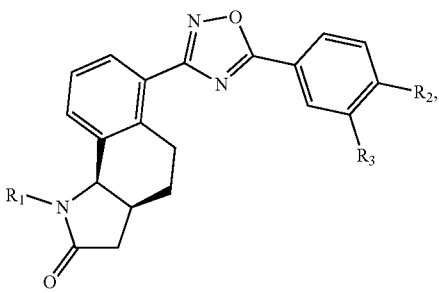

(II-2B)

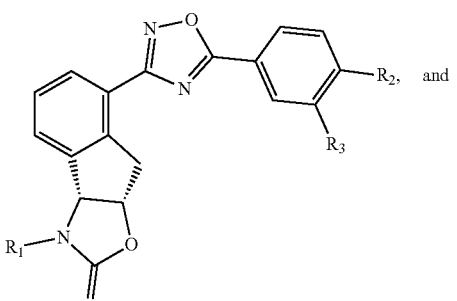

(II-3A), and

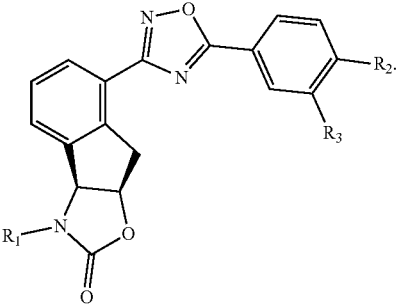

(II-3B)

wherein,

R₁, R₂ and R₃ are as defined above.

The present invention also provides some embodiments which are obtained by randomly combinations of the parameters above.
The present invention also provides the compound or the pharmaceutically acceptable salt of the same, which is selected from the group consisting of
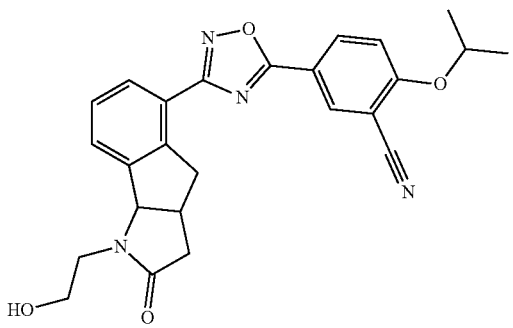
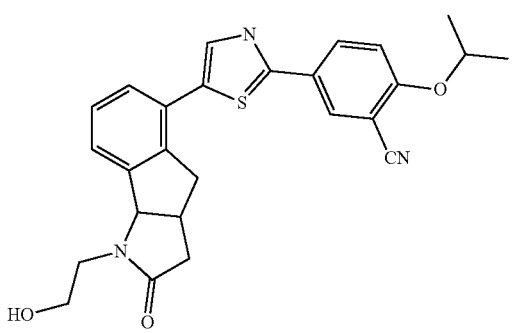
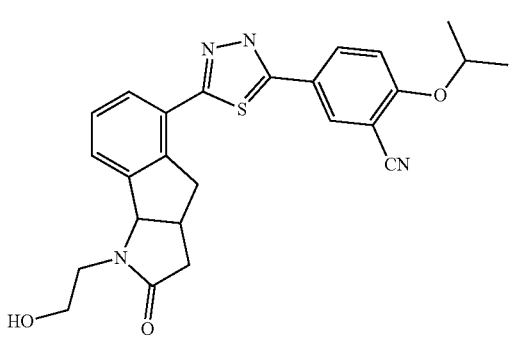
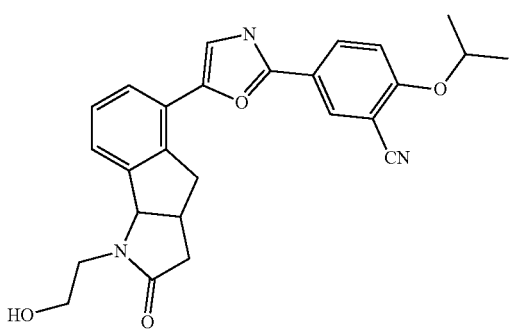
-continued
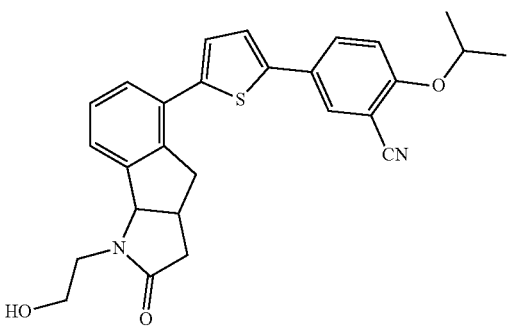
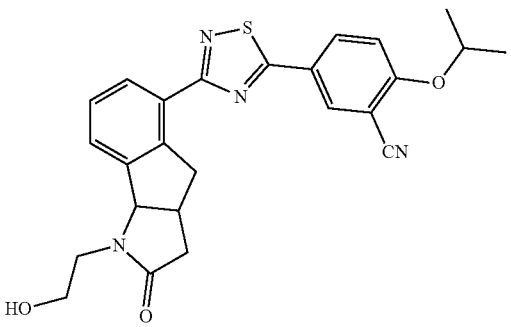
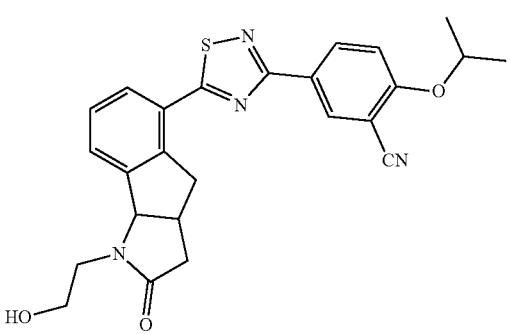
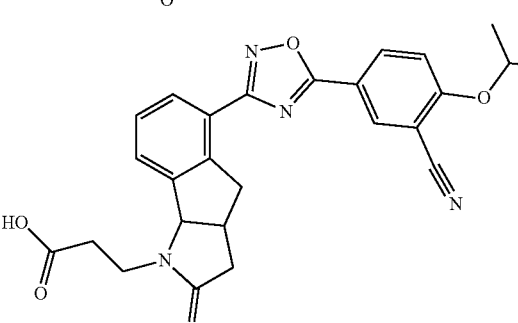
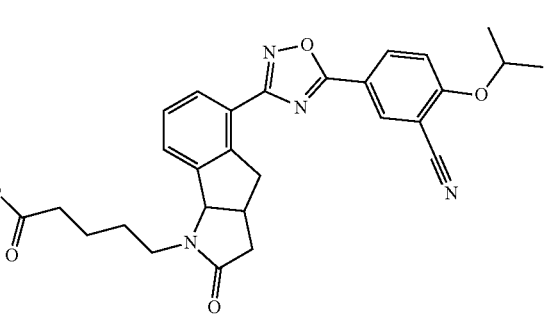

| 29 -continued | 30 -continued |
|---|---|
| 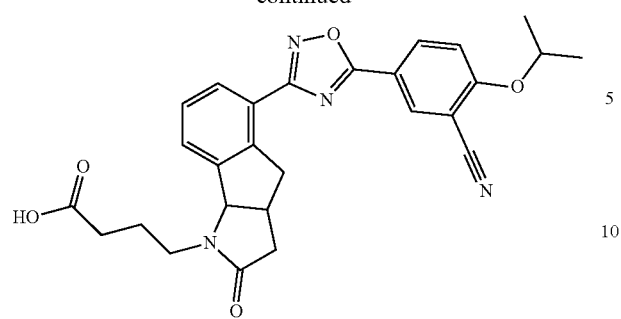 | 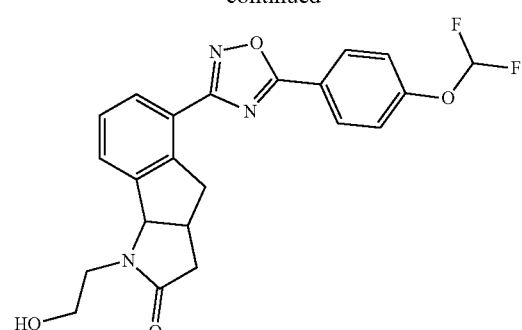 |
| 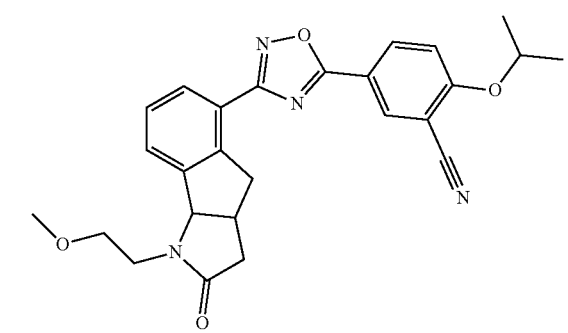 | 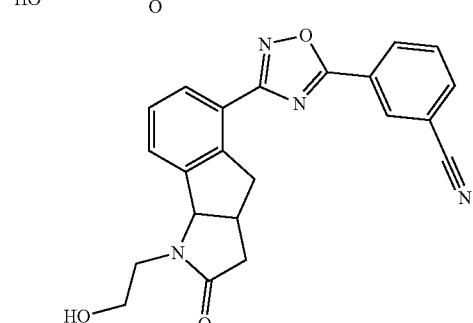 |
| 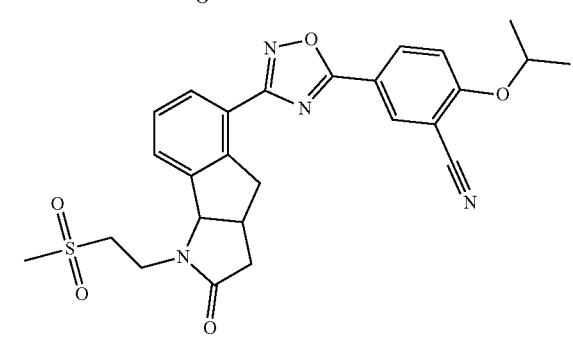 | 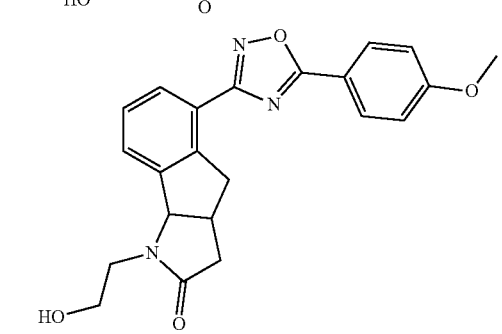 |
| 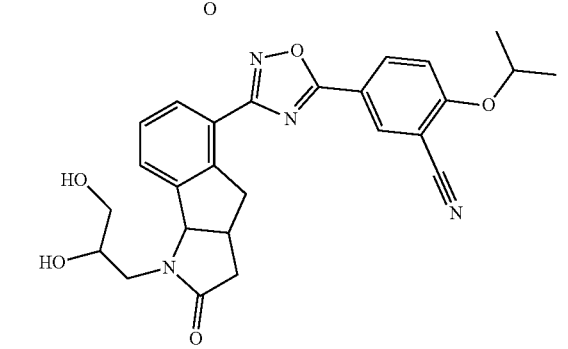 | 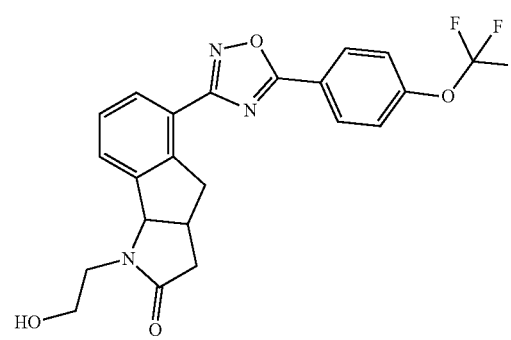 |

31
-continued
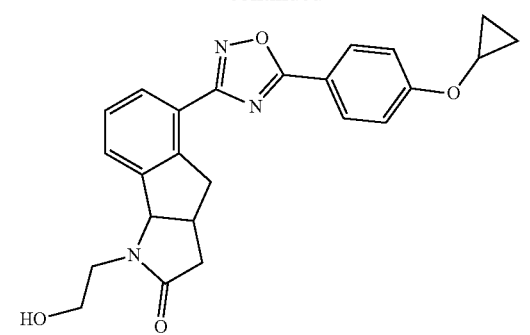
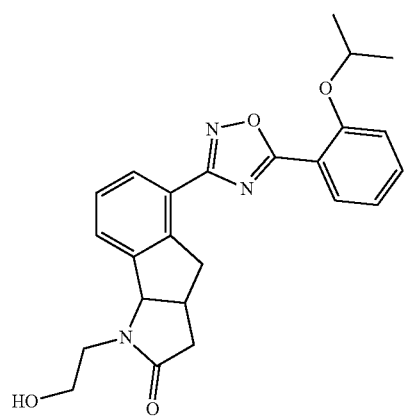
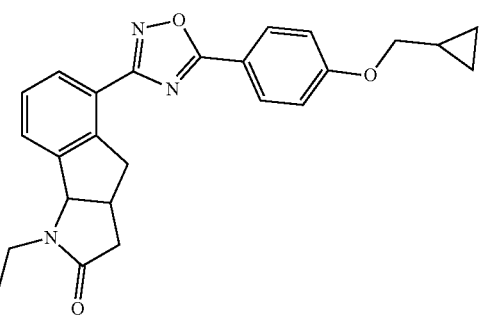
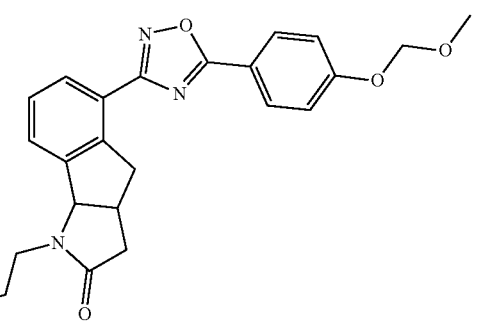
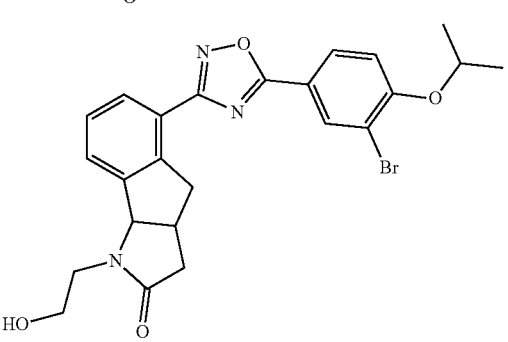
32
-continued
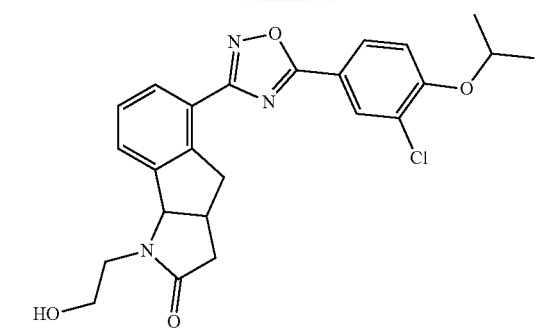
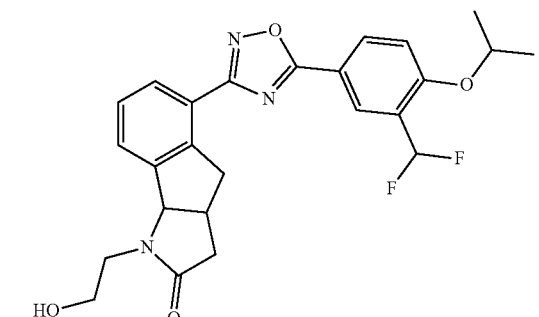
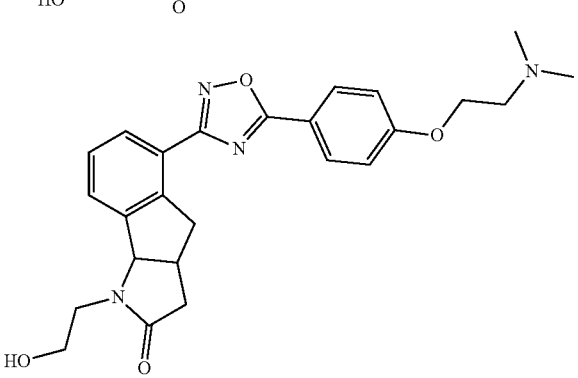
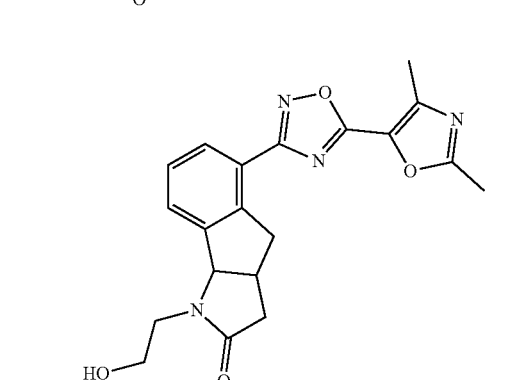
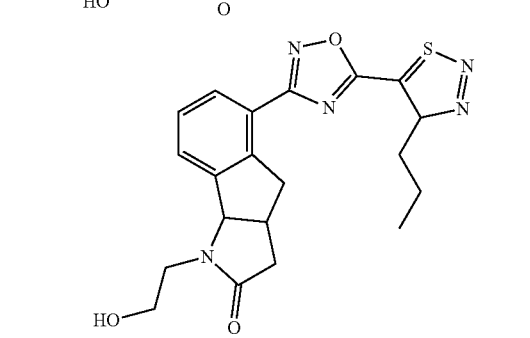

33
-continued
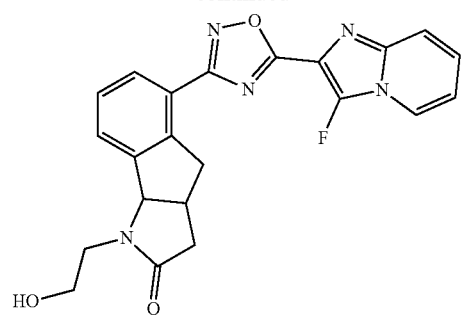
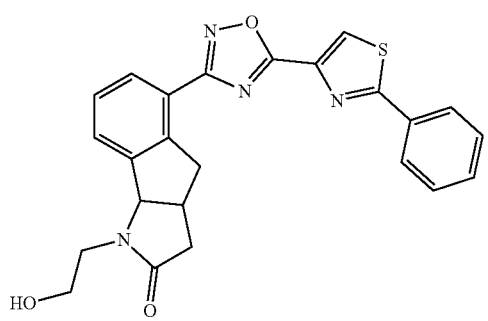
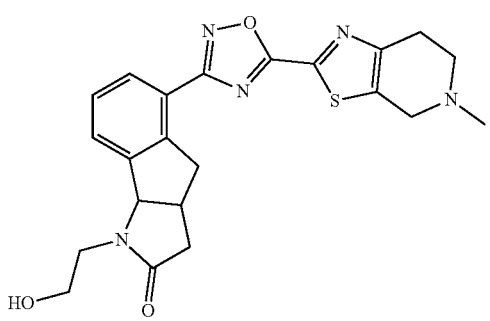
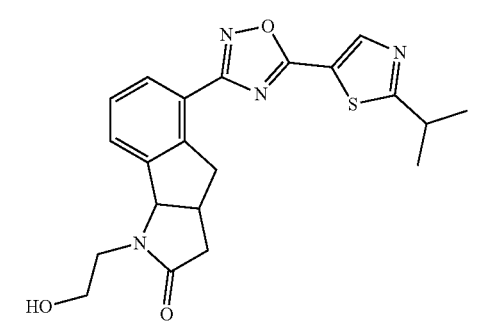
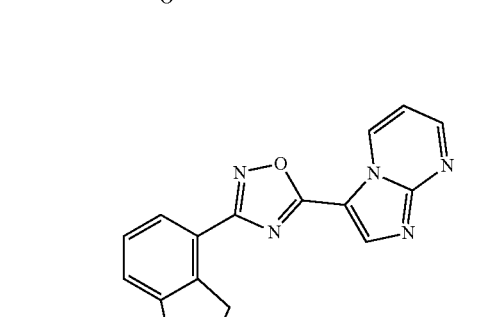
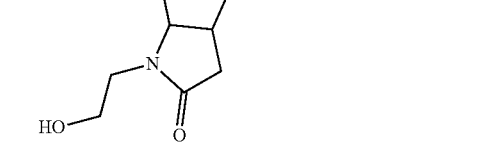
34
-continued
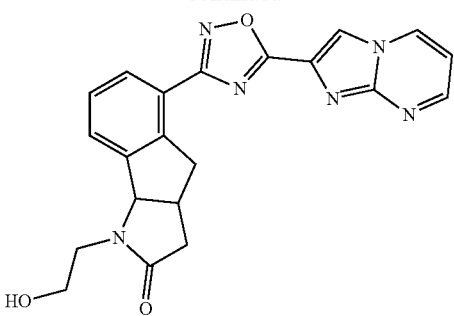
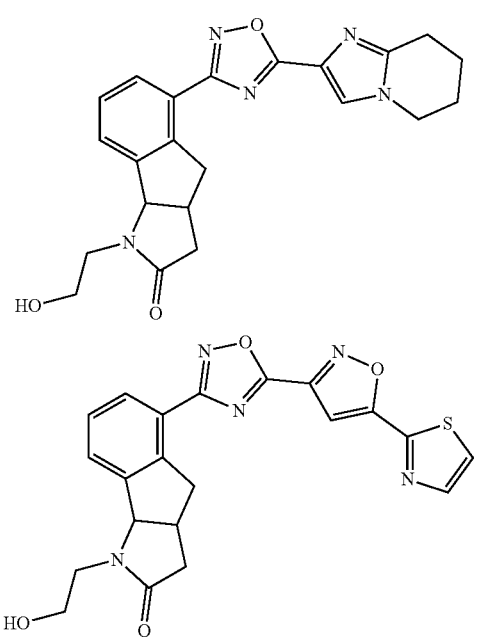
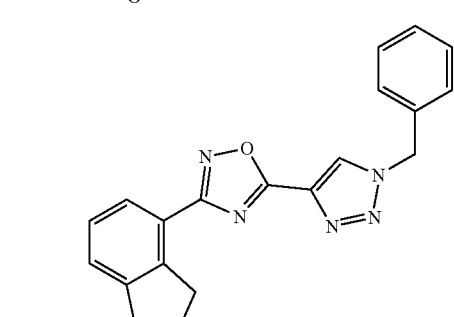
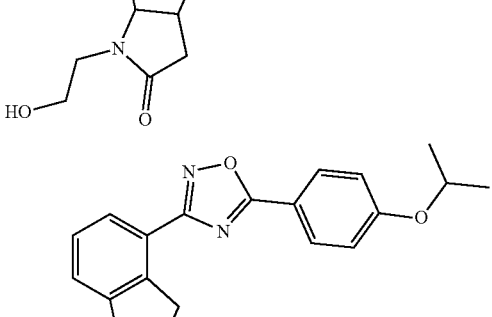
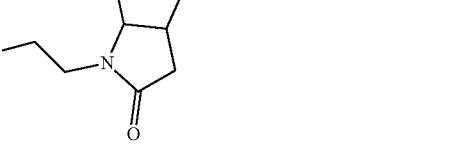

35
-continued
36
-continued
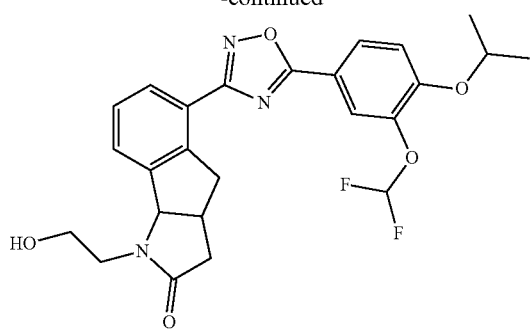
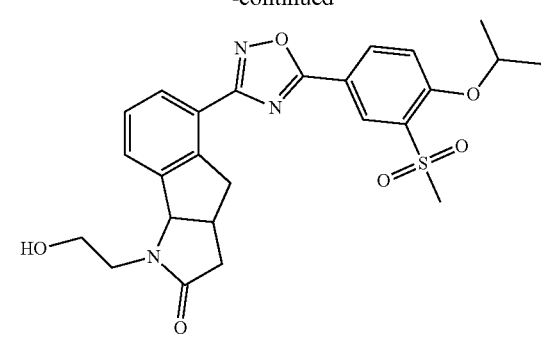

37
-continued
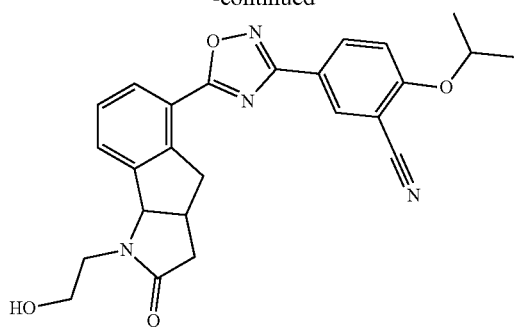
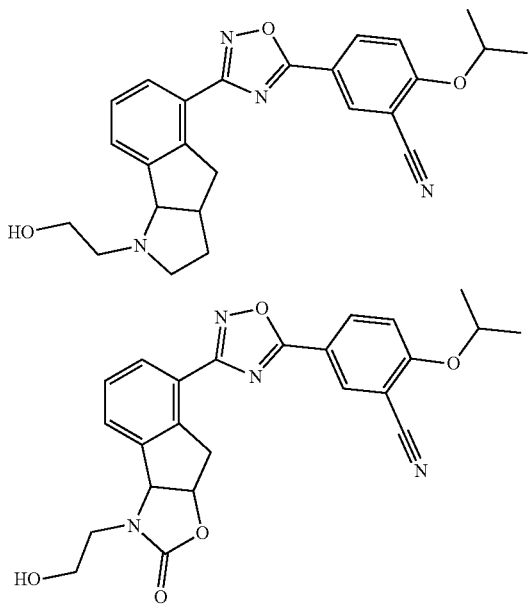
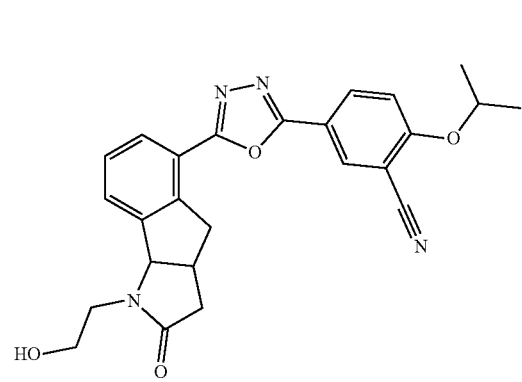
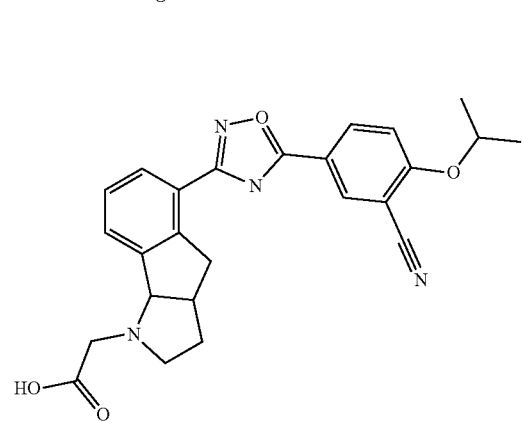
38
-continued
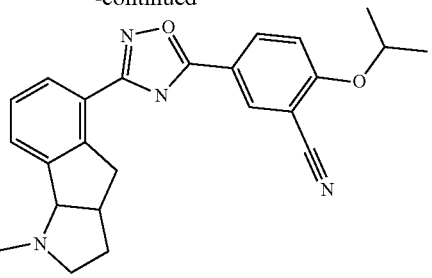
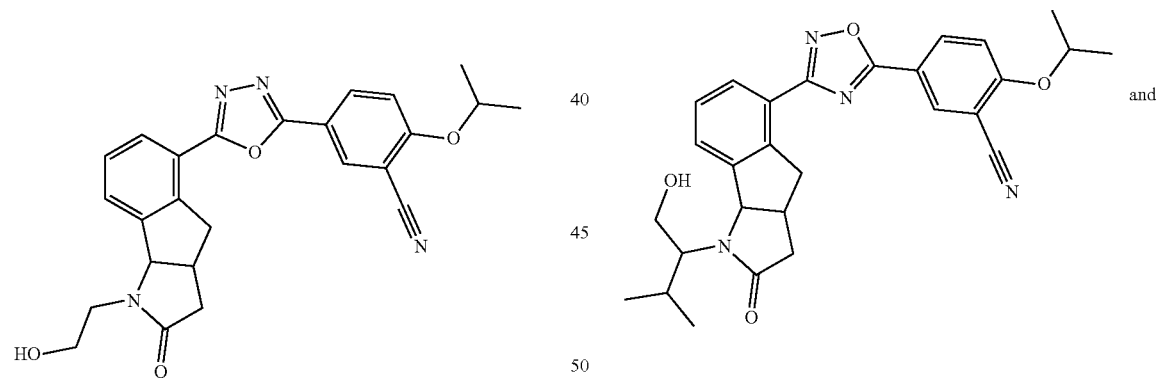
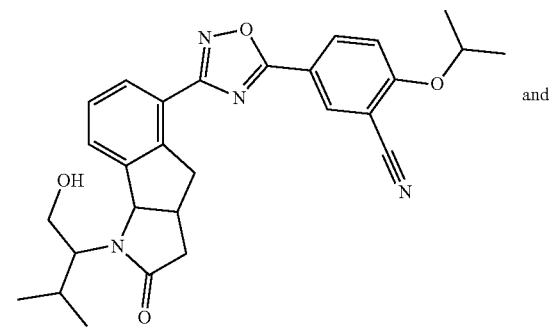 and
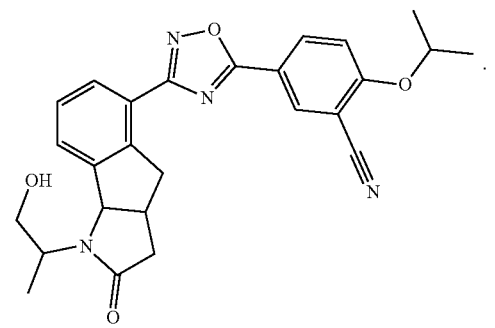

In some embodiments of the present invention, the compound or the pharmaceutically acceptable salt of the same is selected from the group consisting of
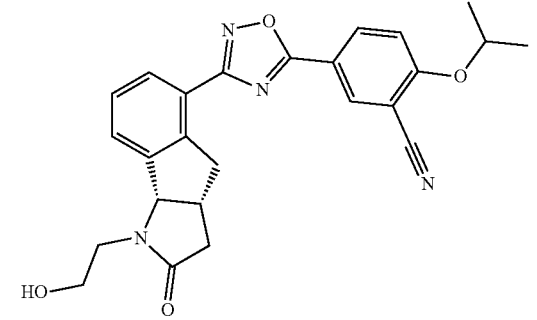
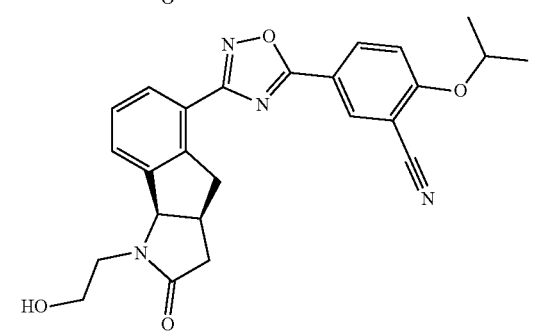
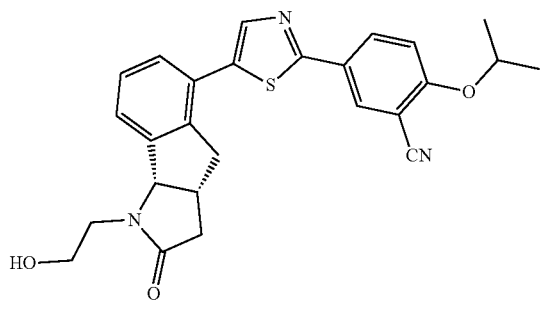
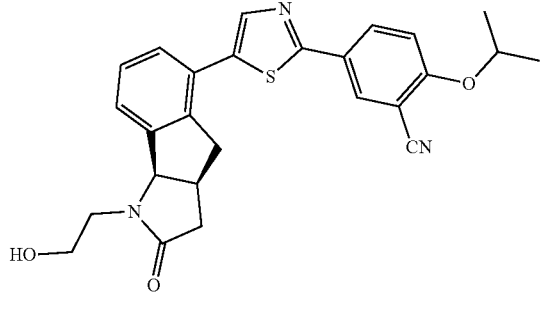
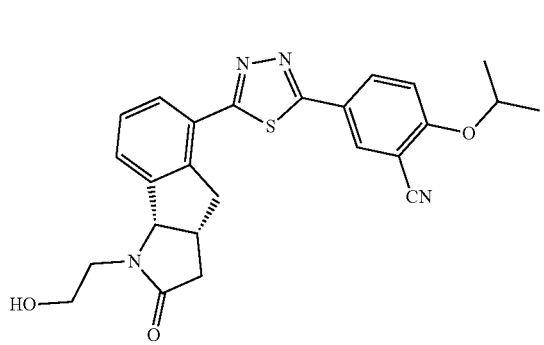
-continued
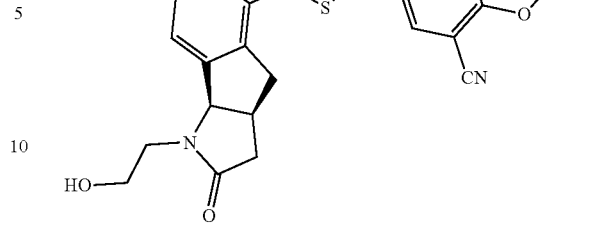
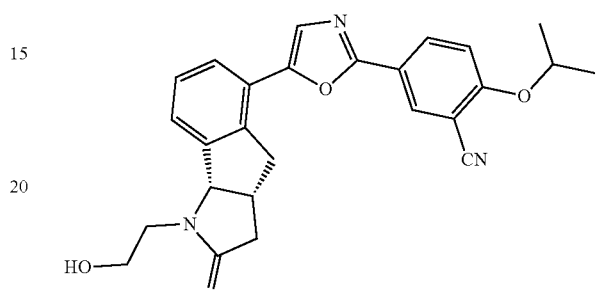
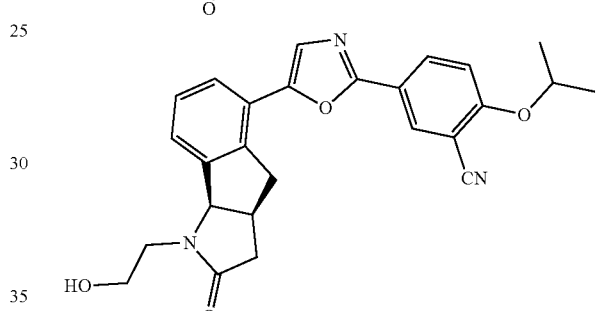
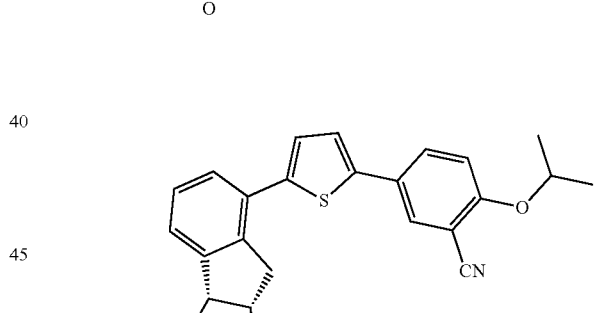
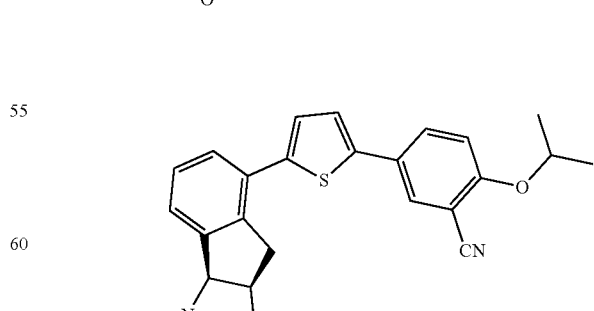

41
-continued
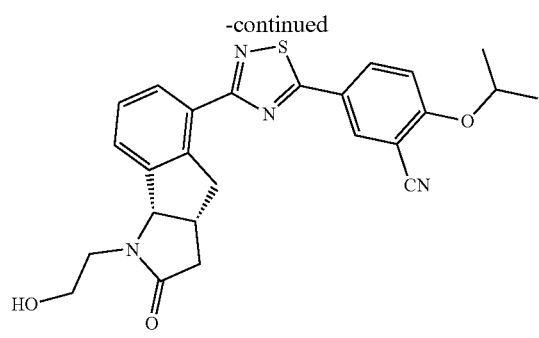
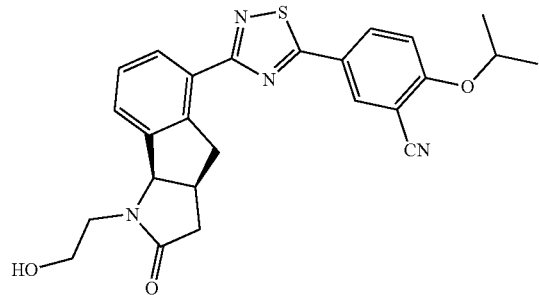
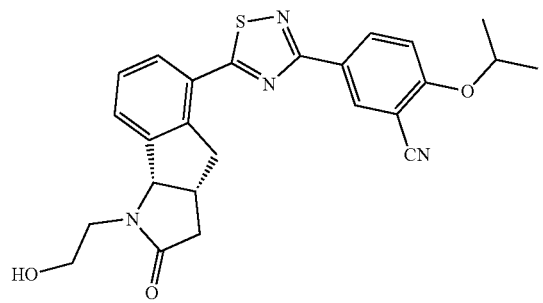
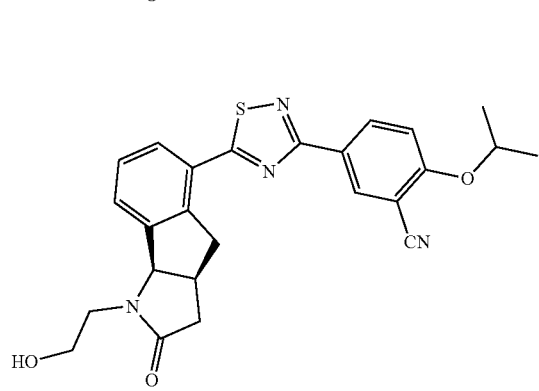
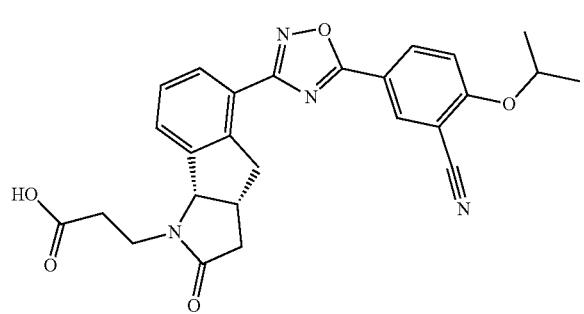
42
-continued
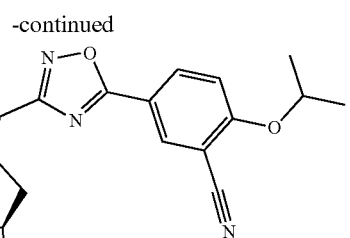
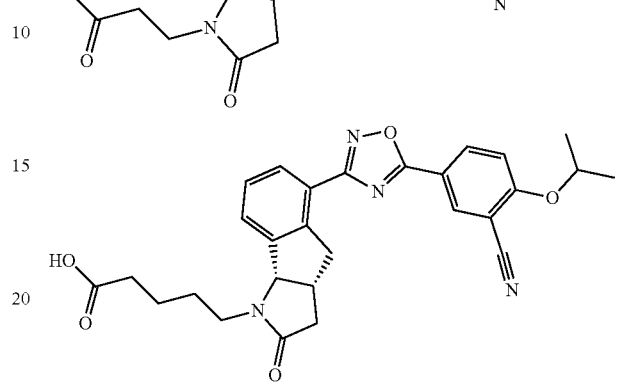
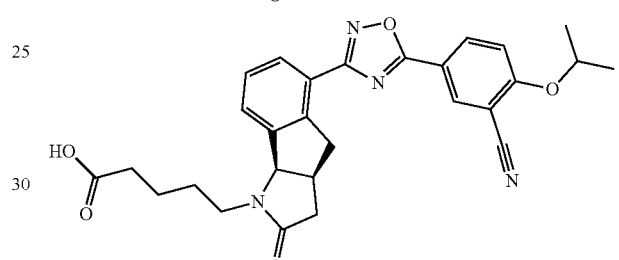
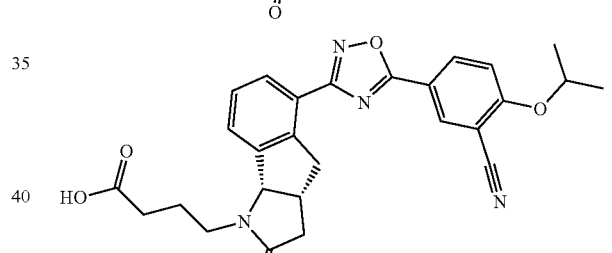
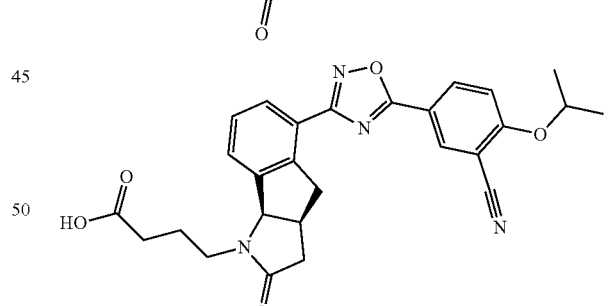
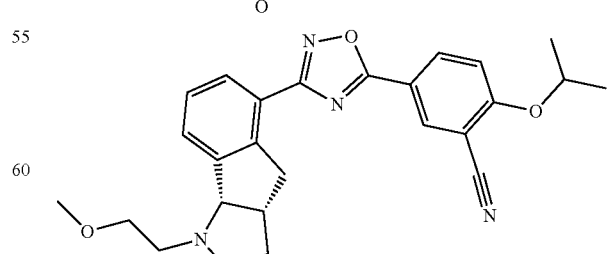

43
-continued
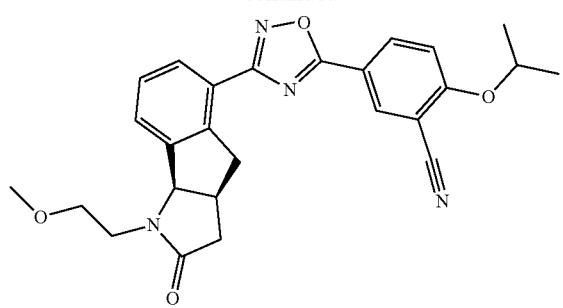
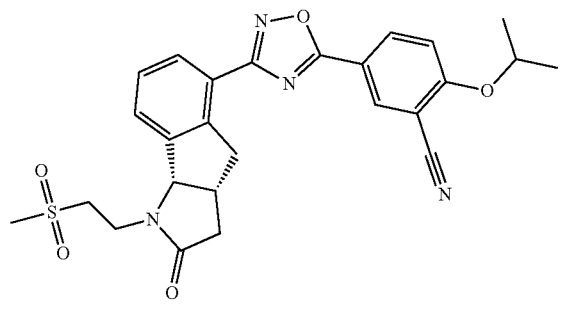
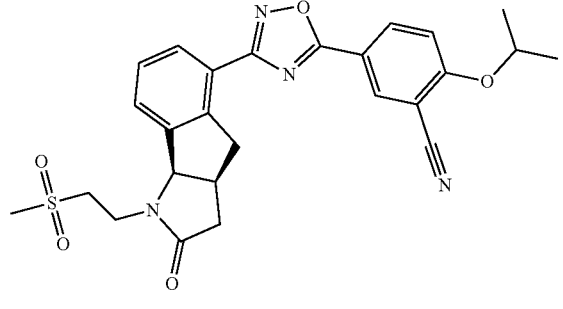
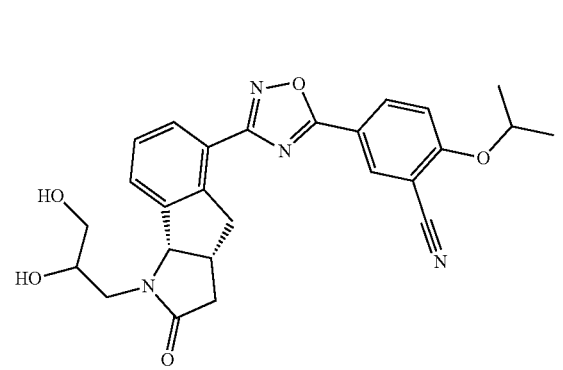
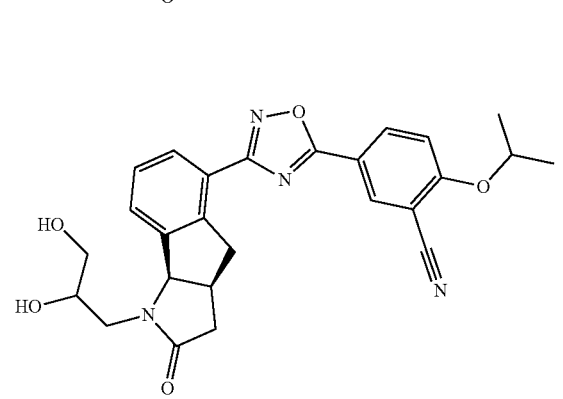
44
-continued
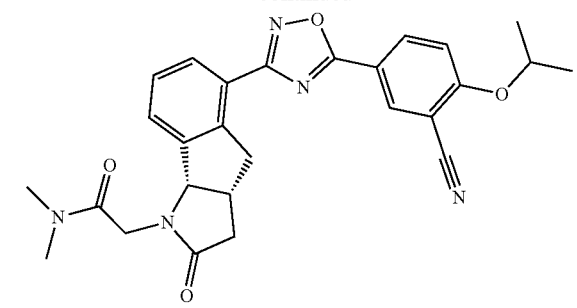
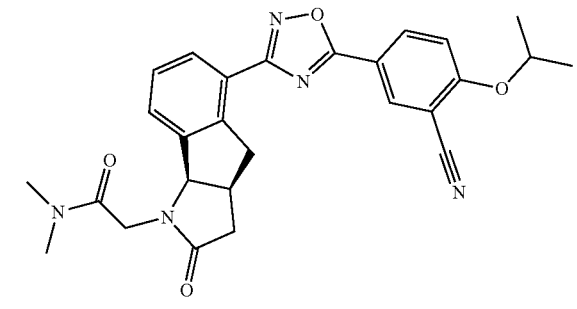
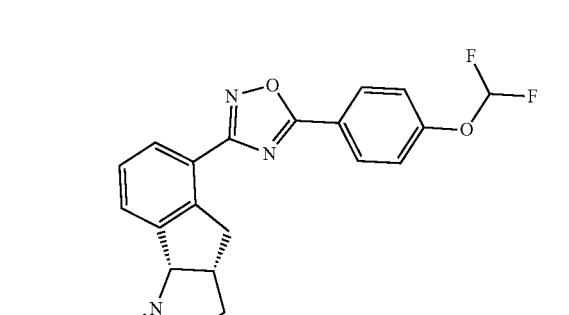
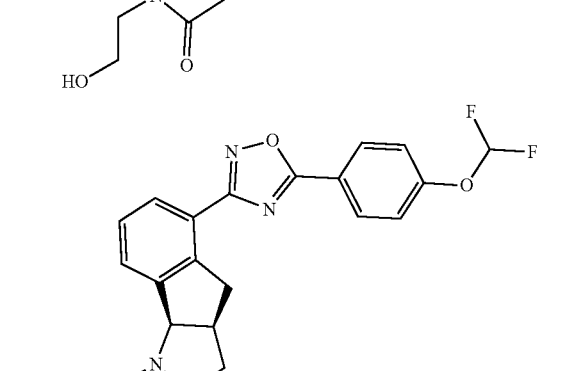
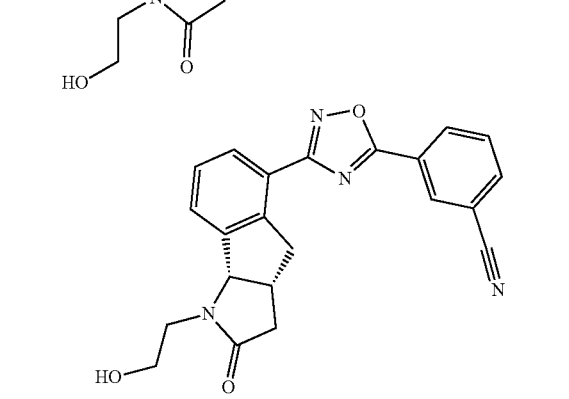

45
-continued
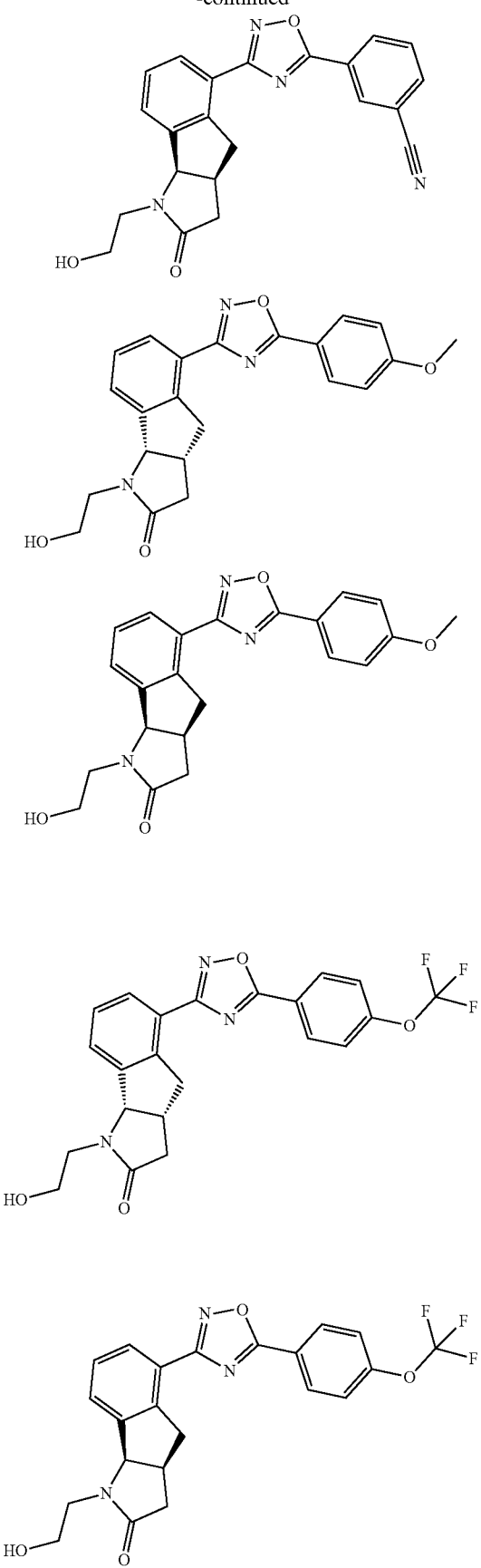
46
-continued
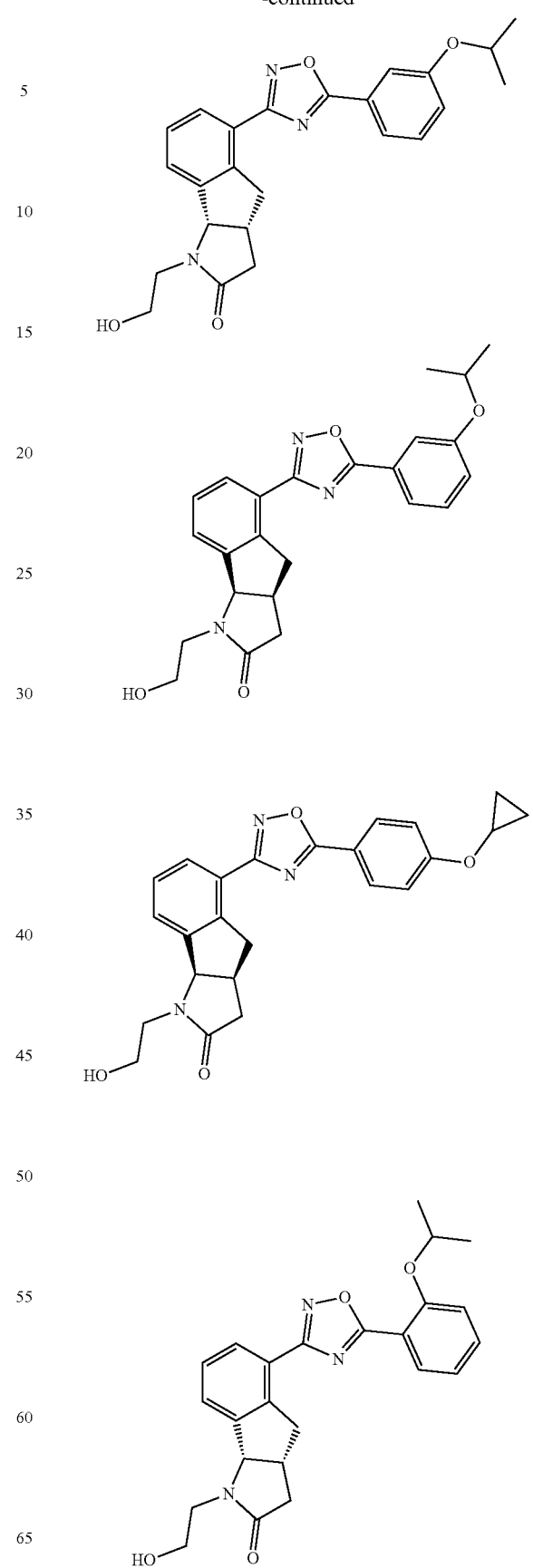

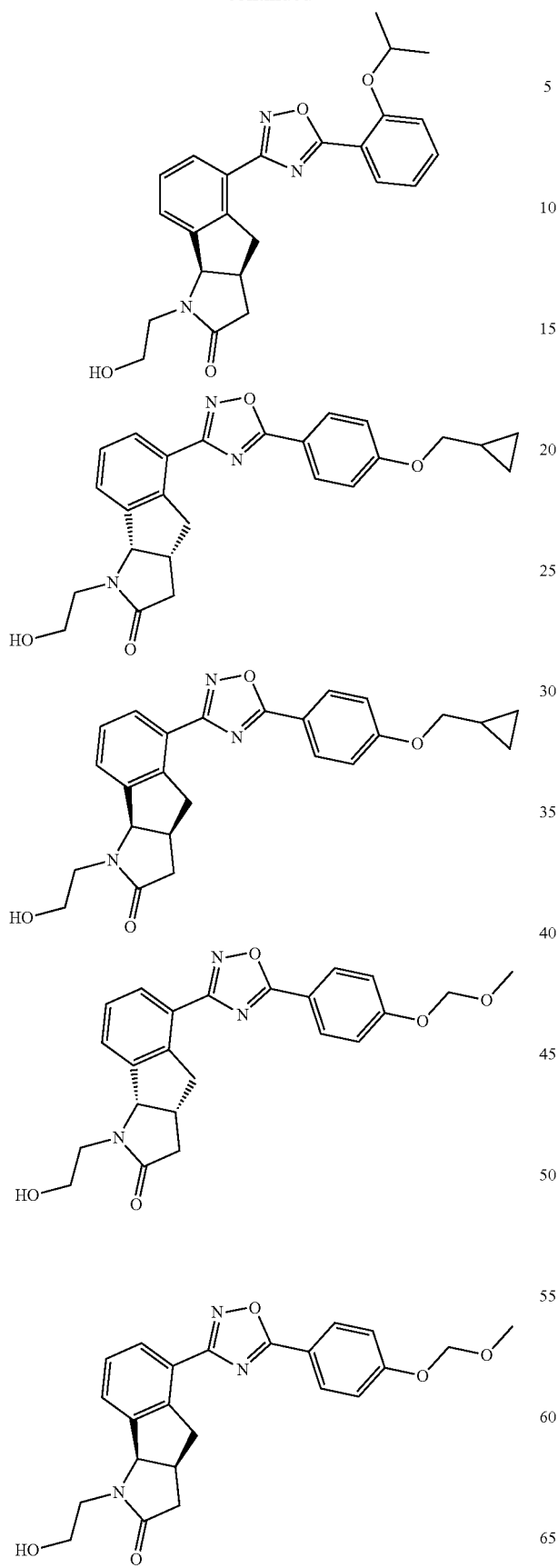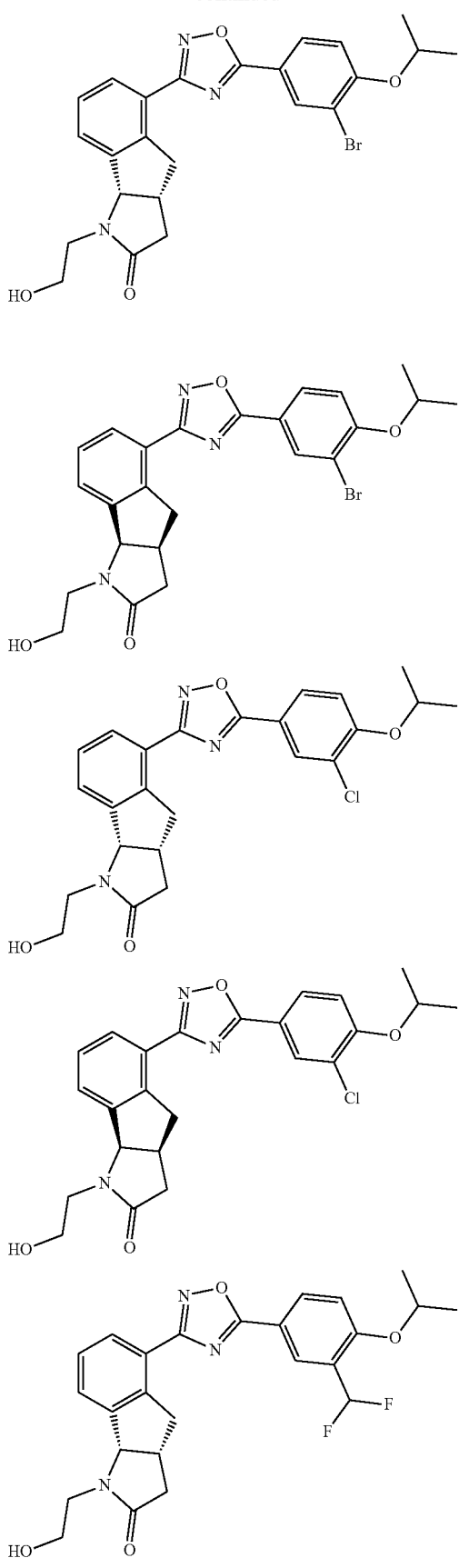

49
-continued
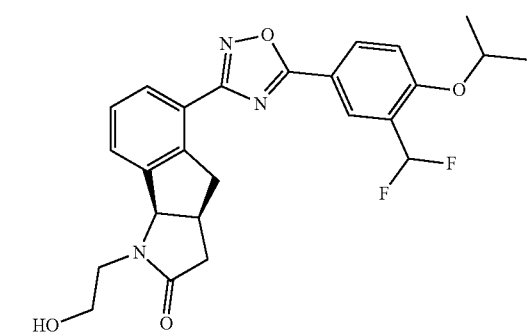
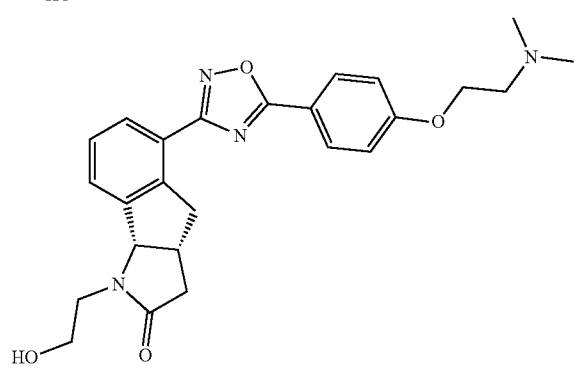
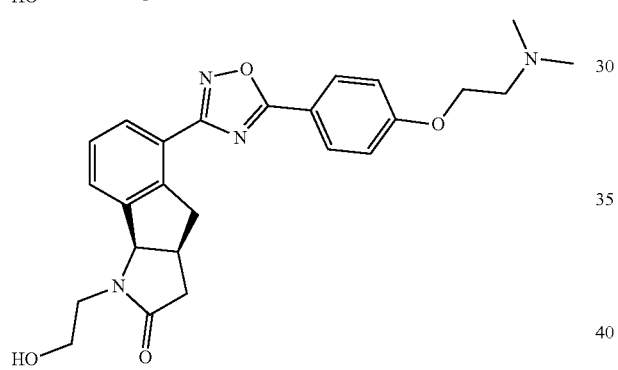
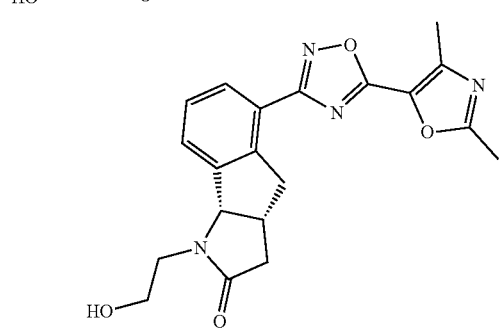
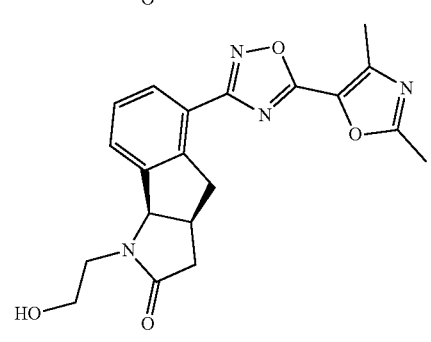
50
-continued
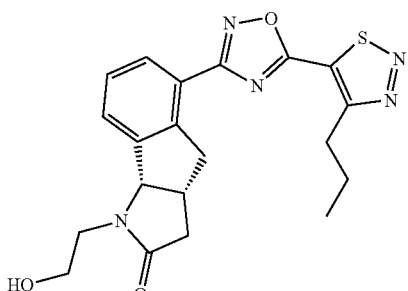
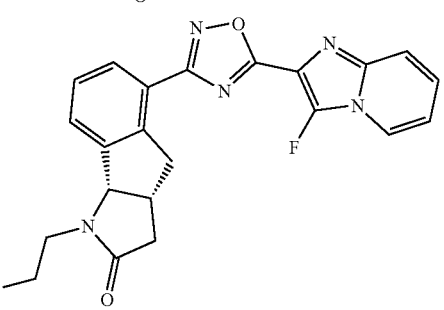
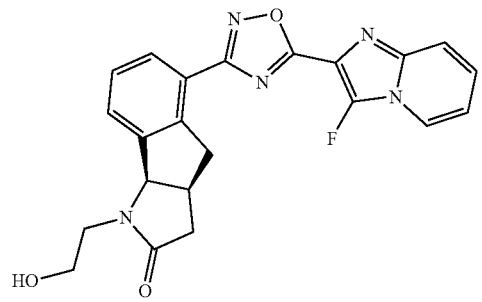
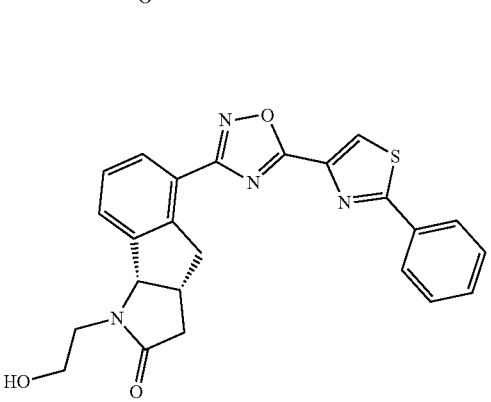

51
-continued
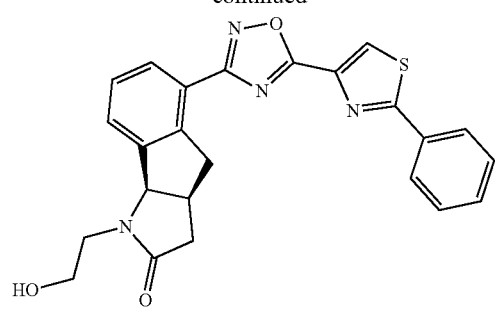
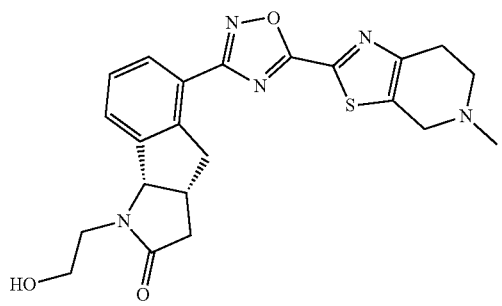
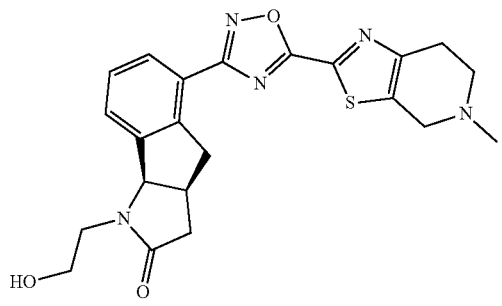
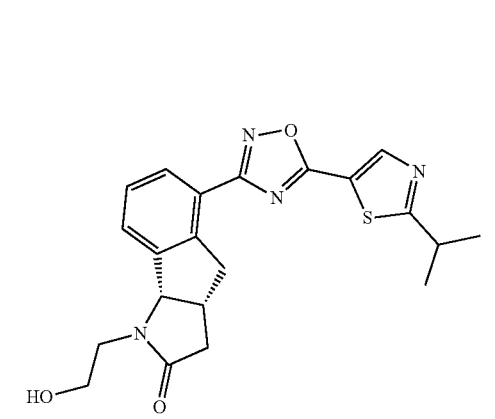
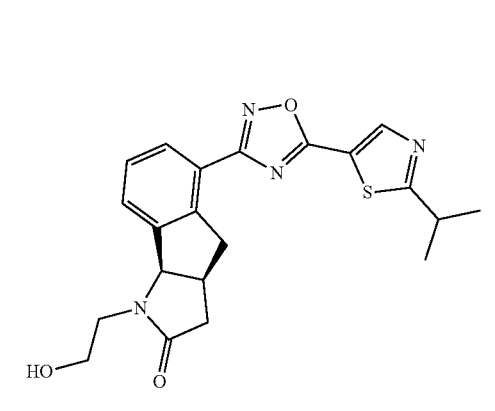
52
-continued
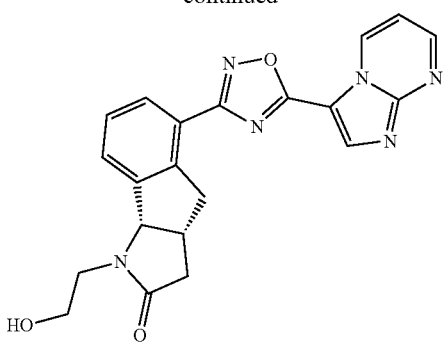
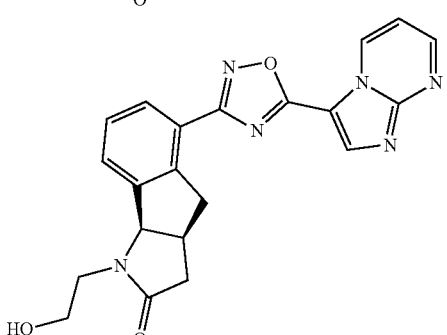
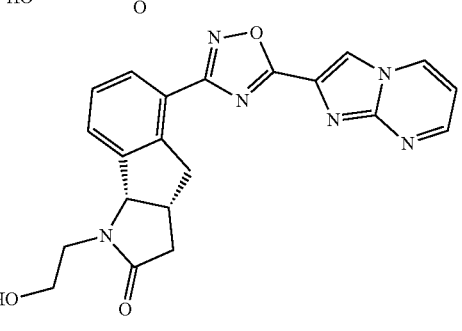
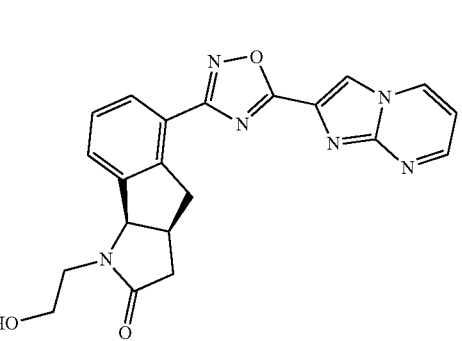
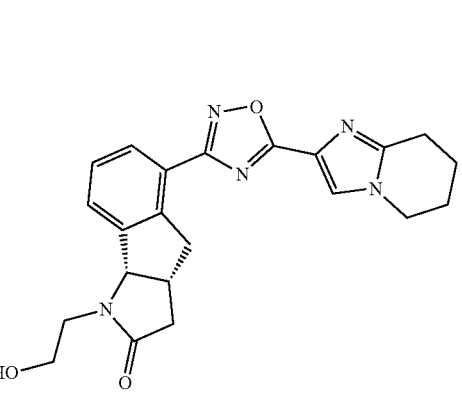

53
-continued
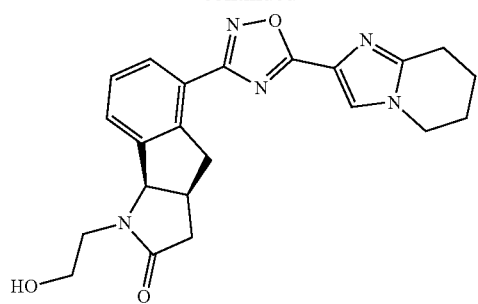
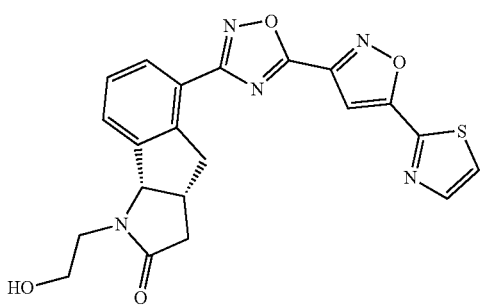
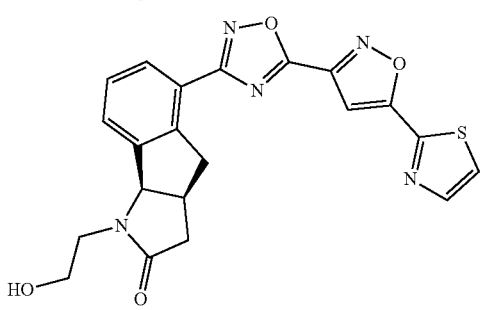
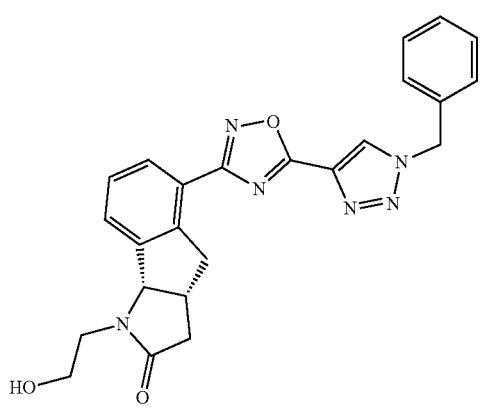
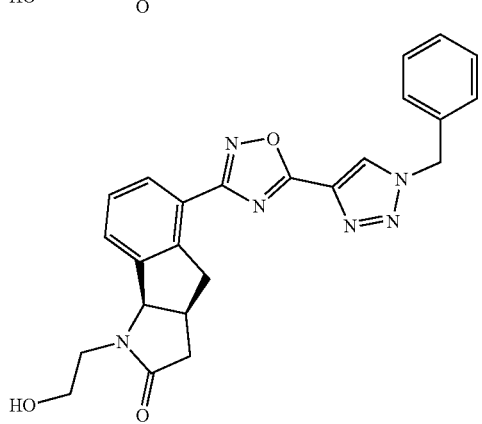
54
-continued
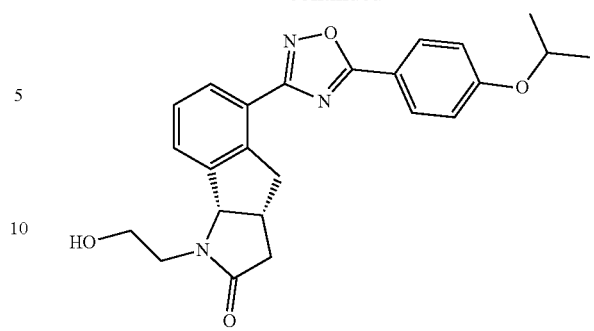
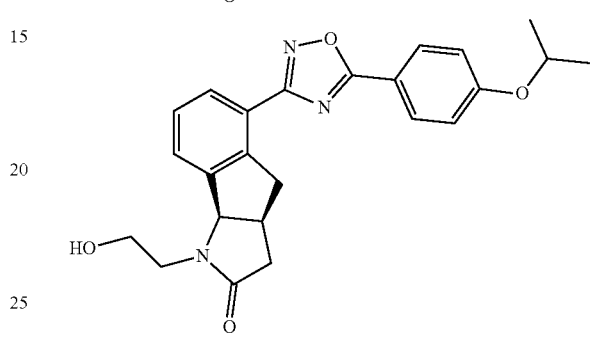
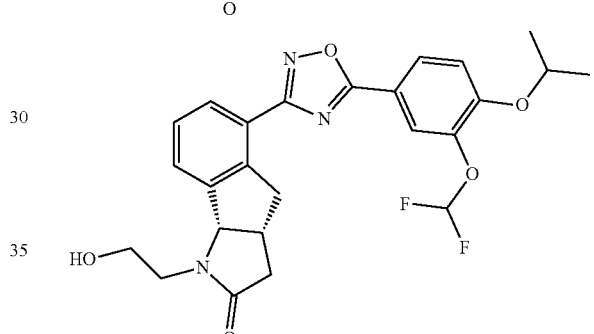
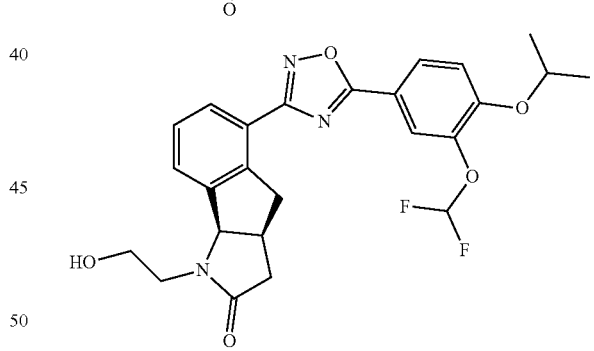
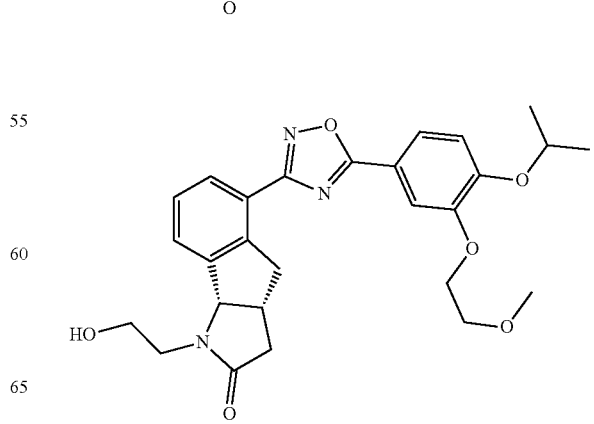

55 -continued
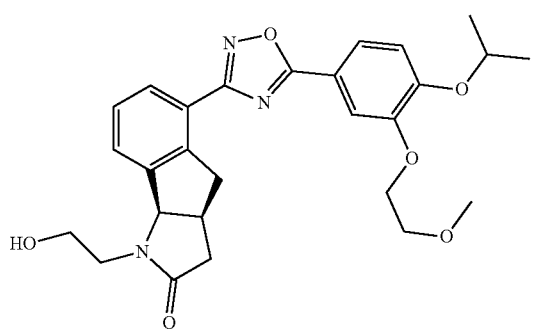
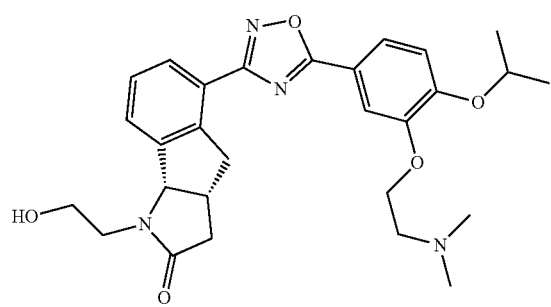
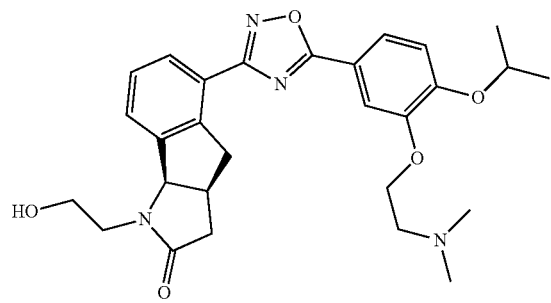
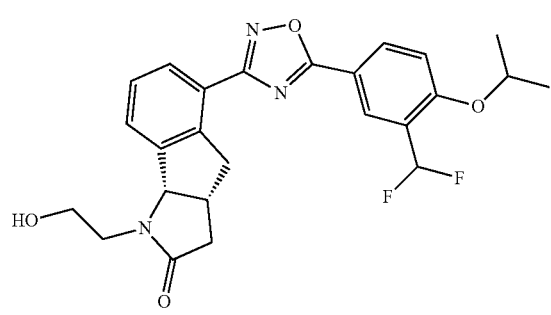
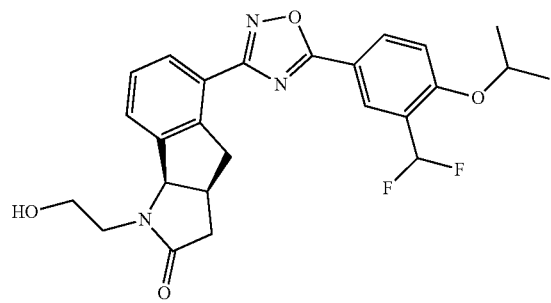
56 -continued
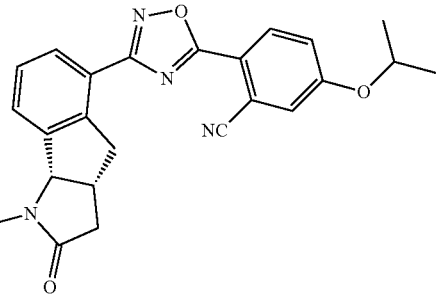
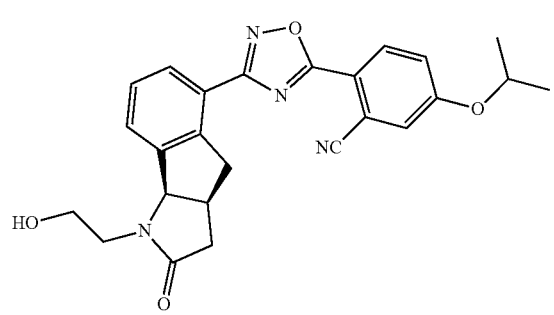
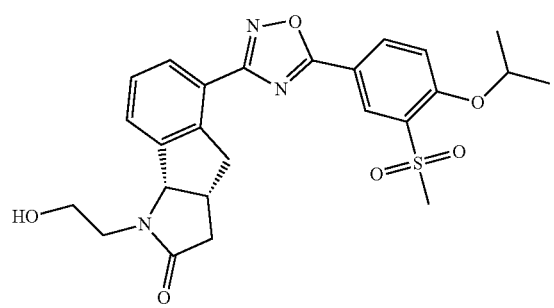
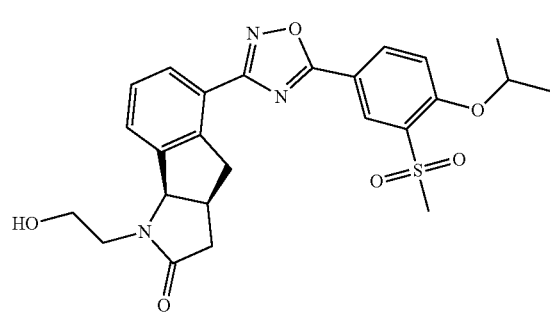
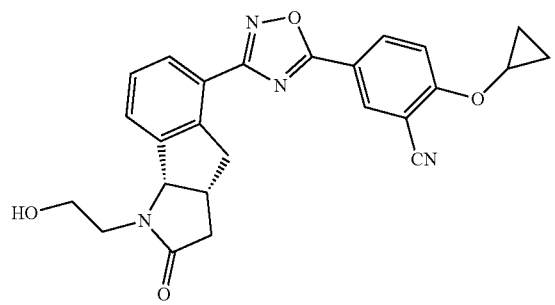

57
-continued
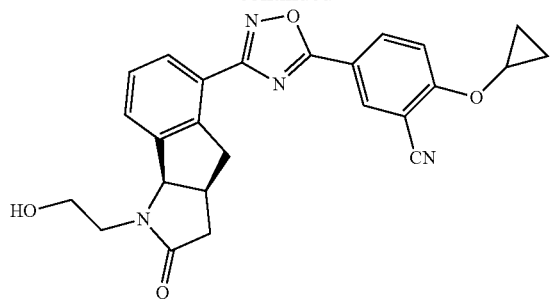
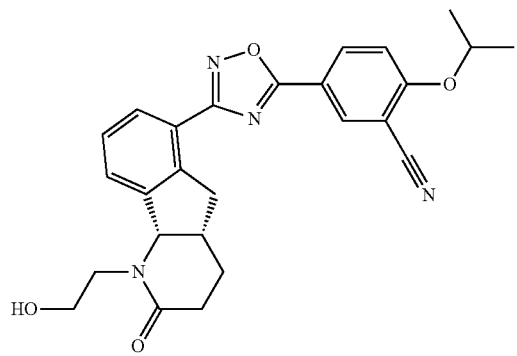
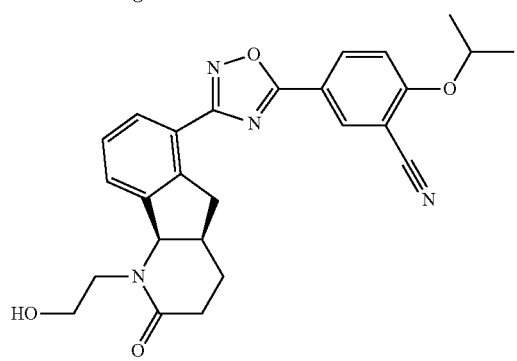
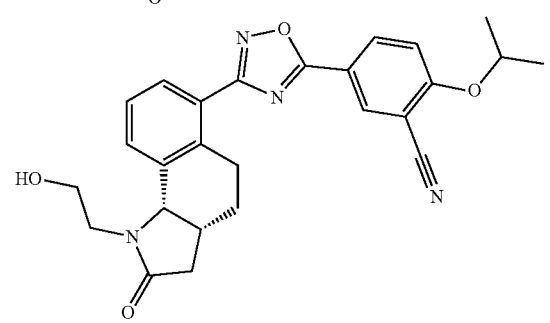
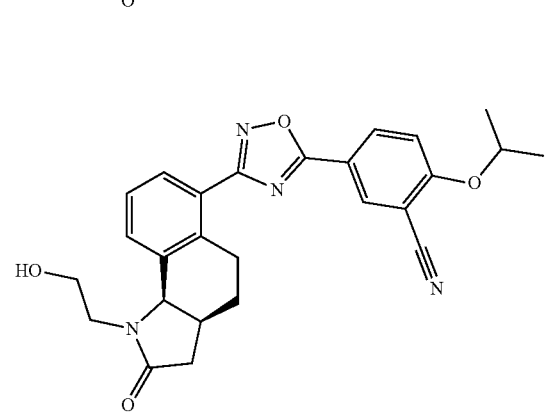
58
-continued
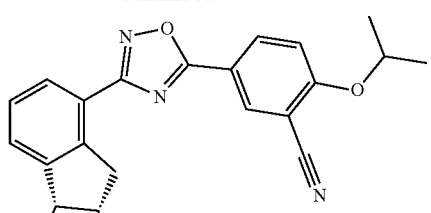
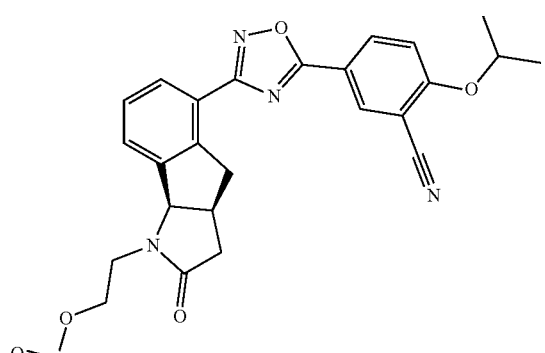
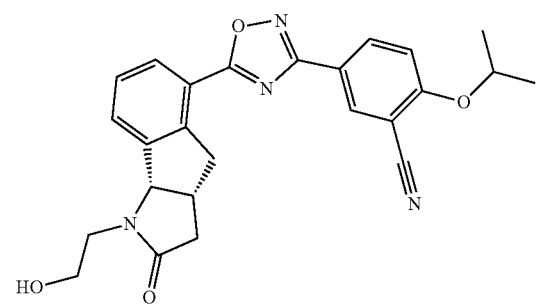
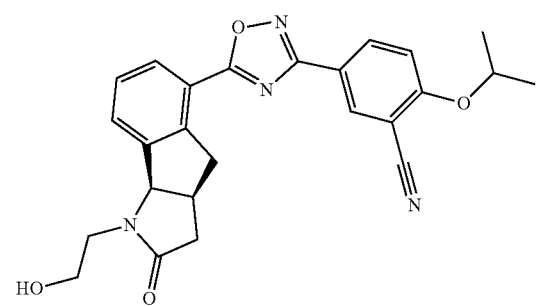
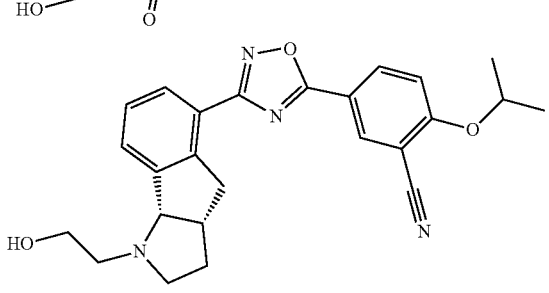

59
-continued
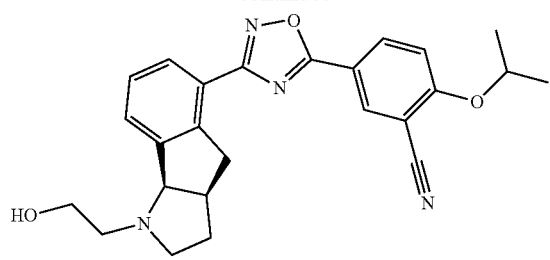
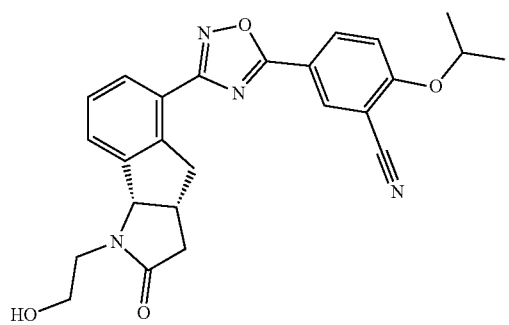
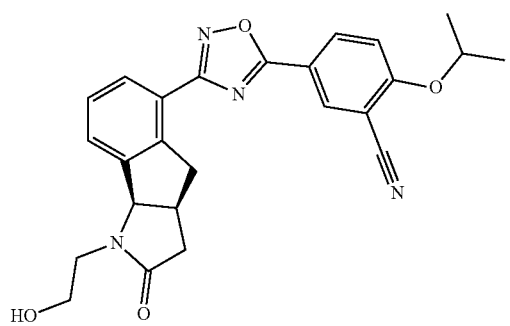
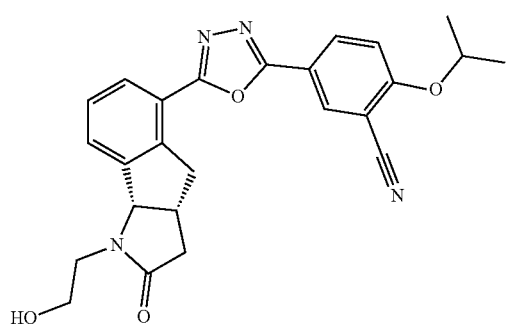
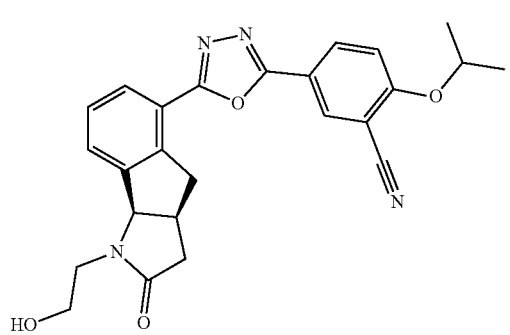
60
-continued
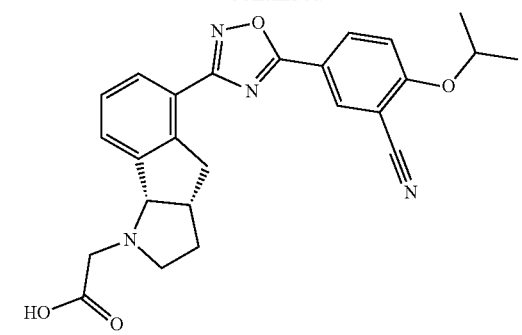
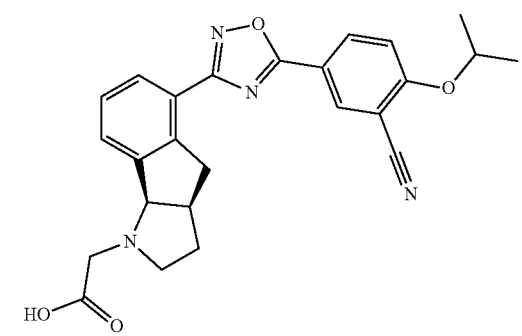
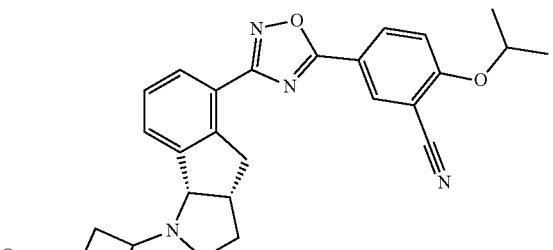
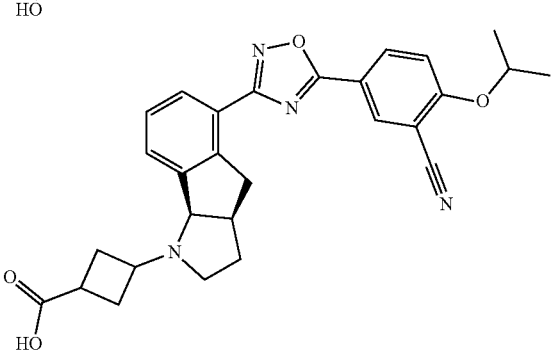
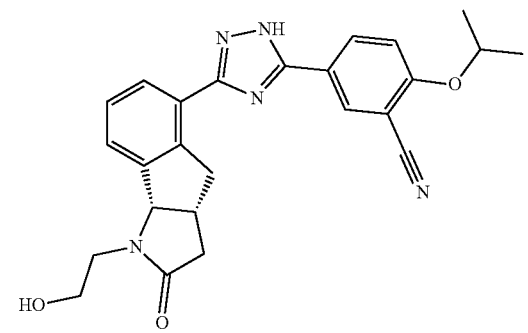

-continued

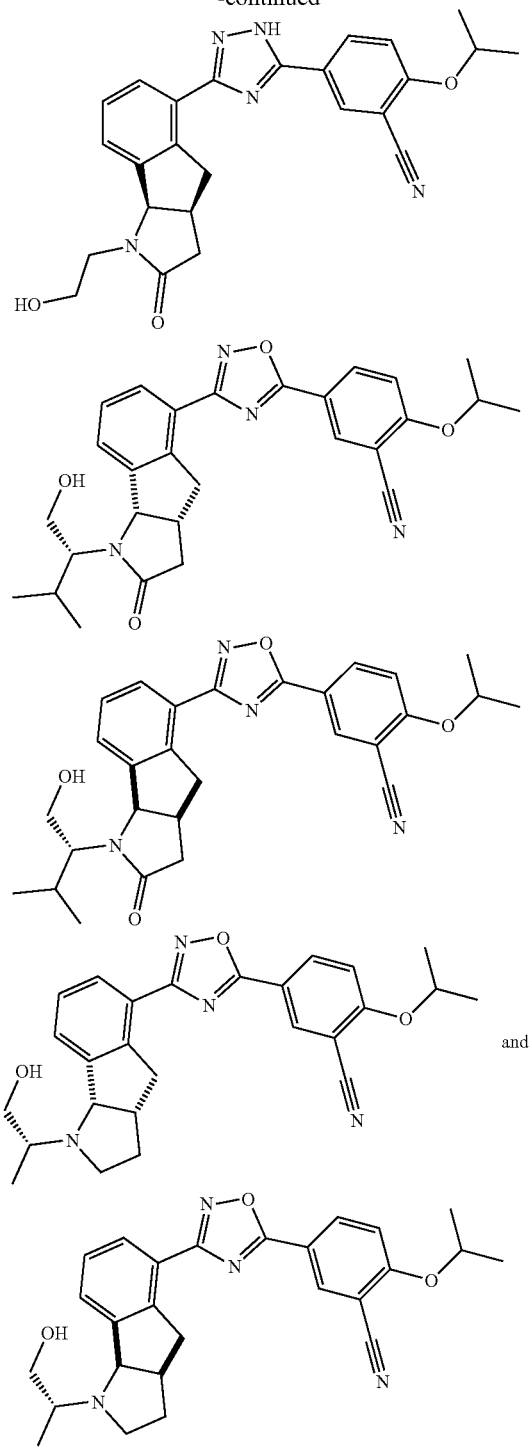

and

Technical Effect

The present invention provides a series of novel S1P1 receptor agonists for the treatment of autoimmune diseases such as multiple sclerosis, inflammatory bowel disease, systemic lupus erythematosus, psoriasis, etc. The compound of the present invention has better activity, better pharmacokinetics, and is advantageous for formulations.

Definition and Instruction

Unless otherwise specified, the following terms and phrases as used herein are intended to reflect the following meanings. A particular term or phrase should be understood as ordinary meaning if it is not specifically defined, instead of being considered undefined or unclear. When a commodity name appears in this document, it is intended to refer to its corresponding commodity or its active ingredient. The term "pharmaceutically acceptable" as used herein is intended to mean that those compounds, materials, compositions and/or dosage forms are suitable for using in contact with human and animal tissues without excessive toxicity, irritation, allergic reactions or other problems or complications and commensurate with a reasonable risk-benefit ratio within the scope of sound medical judgment.

The term "pharmaceutically acceptable salt" refers to a salt of the compound of the invention prepared from a compound with specific substituents disclosed by the present invention and a relatively non-toxic acid or alkali. When the compound disclosed by the invention contains relatively acidic functional groups, an alkali addition salt can be provided in a manner that a sufficient amount of an alkali is in contact with the neutral form of said compound in a pure solution or an appropriate inert solvent. Pharmaceutically acceptable alkali addition salts comprise sodium, potassium, calcium, ammonium, organic ammonia, magnesium salts, etc. When the compound disclosed by the invention contains relatively alkaline functional groups, the acid addition salt can be provided in a manner that a sufficient amount of acid is in contact with the neutral form of the compound in a pure solution or an appropriate inert solvent. Pharmaceutically acceptable acid addition salts comprise inorganic acid salts, organic acid salts, salts of amino acids (such as arginine, etc.) and salts of organic acids such as glucuronic acid (see Berge et al., "Pharmaceutical Salts", Journal of Pharmaceutical Science 66: 1-19 (1977)), wherein said inorganic acid comprises, for example, hydrochloric acid, hydrobromic acid, nitric acid, carbonic acid, hydrogencarbonate, phosphoric acid, monohydrogen phosphate, dihydrogen phosphate, sulfuric acid, hydrogen sulfate, hydroiodic acid, phosphorous acid, etc.; wherein said organic acid comprises acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, etc. Some specific compounds of the present invention which contains both alkaline and acidic functional groups can be converted into any alkali or acid addition salt.

Preferably, the salt is contacted with alkali or acid in a conventional manner, and then the parent compound is separated, thereby regenerating the neutral form of the compound. The parent form of the compound is different from the form of various salts thereof in certain physical properties, for example, the solubility in a polar solvent.

As used herein, "pharmaceutically acceptable salts" belong to derivatives of the compounds of the present invention, wherein the parent compound is modified by salifying from acid and alkali. The examples of pharmaceutically acceptable salts comprise, but are not limited to, an alkaline group such as an inorganic acid or an organic acid salt of an amine, an alkali metal or an organic salt of a carboxylic acid, etc. The pharmaceutically acceptable salt comprises a conventional non-toxic salt or a quaternary ammonium salt of a parent compound, such as a non-toxic inorganic or organic acid salt. Conventional non-toxic salts comprise, but are not limited to, those derived from inorganic acids and organic acids, wherein said inorganic acids or organic acids are selected from 2-acetoxybenzoic acid, 2-hydroxyethanesulfonic acid, acetic acid, ascorbic acid, benzenesulfonic acid, benzoic acid, hydrogencarbonate, carbonic acid, citric acid, edetic acid, ethane disulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionethane, lactic acid, lactose, dodecylsulfonic acid, maleic acid, malic acid, mandelic acid, methanesulfonic acid, nitric acid, oxalic acid, Pamoic acid, pantothenic acid, phenylacetic acid, phosphoric acid, polygalacturon, propionic acid, salicylic acid, stearic acid, acrylic acid, succinic acid, sulfamic acid, p-aminobenzenesulfonic acid, sulfuric acid, tannin, Tartaric acid and p-toluenesulfonic acid.

The pharmaceutically acceptable salts of the present invention can be synthesized from the parent compound with an acid group or an alkali group through conventional chemical methods. In general, such salts are prepared by reacting these compounds in free acid or alkali form with a stoichiometric amount of a suitable base or acid in water or an organic solvent or a mixture of both. Generally, a nonaqueous medium such as ether, ethyl acetate, ethanol, isopropanol or acetonitrile is preferred.

Besides the form of the salt, the compounds provided herein also exist in the form of prodrugs. Prodrugs of said compounds are readily chemically altered under physiological conditions to convert to the compounds of the present invention. Furthermore, prodrugs can be converted to the compounds of the invention through chemical or biochemical methods within the body.

Certain compounds of the invention may exist in unsolvated as well as solvated forms, including hydrated forms. In general, the solvated forms are equivalent to the unsolvated forms and are included within the scope of the present invention.

Certain compounds of the invention may have asymmetric carbon atoms (optical centers) or double bonds. Racemates, diastereomers, geometric isomers and individual isomers are included within the scope of the invention.

Unless otherwise specified, a wedge bond and a dashed bond (  ) are used to indicate the absolute configuration of a stereocenter and  are used to indicate the relative configuration of a stereocenter. The compounds described herein contain olefinic double bonds or other several asymmetric centers, unless stated otherwise, which comprises an E and Z geometric isomer. Likewise, all of the tautomer forms are included within the scope of the present invention.

The compounds of the present invention can exist in specific geometric or stereoisomeric forms. The present invention contemplates all such compounds, including the cis and trans isomers, the (−)- and (+)-p-enantiomers, the (R)- and (S)-enantiomers, and the diastereomeric configuration, a (D)-isomer, a (L)-isomer, and a racemic mixture thereof, and other mixtures, such as enantiomerically or diastereomeric enriched mixtures, all of which are within the scope of the present invention. An additional asymmetric carbon atom may be present in the substituents such as alkyl groups. All of these isomers, as well as mixtures thereof, are included within the scope of the invention.

The optically active (R)- and (S)-isomers as well as the D and L isomers can be prepared by chiral synthesis or chiral reagents or other conventional techniques. If an enantiomer of a compound of the present invention is desired, it can be prepared by asymmetric synthesis or by derivatization with a chiral auxiliary wherein the mixture of diastereomers is separated and the auxiliary group is cleaved to provide the pure desired enantiomer. Alternatively, when a molecule contains an alkaline functional group (e.g., an amino group) or an acidic functional group (e.g., a carboxyl group), a diastereomeric salt is formed with an appropriate optically active acid or alkali, followed by the resolution of enantiomers via conventional methods known in the field, wherein, the pure enantiomer is recovered. Furthermore, the separation of enantiomers and diastereomers is generally accomplished by chromatography adopting a chiral stationary phase, optionally combined with chemical derivatization method (e.g., formation of a carbamate from an amine).

The compounds of the present invention can contain unnatural proportions of atomic isotopes at one or more of the atoms that constitute such compounds. For example, a compound can be labeled with a radioisotope such as hydrazine ($^3$H), iodine-125 ($^{125}$I) or C-14 ($^{14}$C). All isotopic compositional changes of the compounds of the invention, whether radioactive or not, are included within the scope of the invention.

The term "pharmaceutically acceptable carrier" refers to any preparation or carrier medium that is capable of delivering an effective amount of the active substance of the present invention, which does not interfere with the biological activity of the active substance, and has no toxic side effects to the host or patient. Representative carriers include water, oil, vegetables and minerals, cream bases, lotion bases, ointment bases, etc. These bases include suspending agents, tackifiers, transdermal enhancers, and the like. Their preparations are well known to those skilled in the cosmetic or topical pharmaceutical art. With regard to other information of the carrier, reference can be made to the following: the Science and Practice of Pharmacy, 21st Ed., Gilincott, Williams elamp, Wilkins (2005), the contents of which are incorporated herein by reference.

The term "excipient" generally refers to a carrier, a diluent and/or a medium required to prepare an effective pharmaceutical composition.

The term "effective amount" or "therapeutically effective amount" with respect to a pharmaceutical or pharmacologically active agent refers to a sufficient amount of a drug or agent that is non-toxic but that achieves the desired effect. For oral dosage forms in the present invention, an "effective amount" of an active substance in a composition refers to the amount required to achieve the desired effect when used in combination with another active substance in the composition. The determination of the effective amount varies from person to person, depending on the age and general condition of the recipient, and also on the particular active substance, and the appropriate effective amount of an individual case can be determined by one skilled in the art according to routine experimentation.

The term "active ingredient", "therapeutic agent", "active substance" or "active agent" refers to a chemical entity that is effective in treating a target disorder, disease or condition.

"Optional" or "optionally" refers to the event or condition described subsequently may, but not necessarily, occur. Such description includes the situations in which the event or condition occurs and the situations in which the event or condition does not occur.

The term "substituted" refers to any one or more hydrogen atoms on a specific atom substituted by substituents, which can comprise variants of heavy hydrogen and hydrogen, as long as the valence state of a specific atom is normal and the substituted compound is stable. It is indicated that two hydrogen atoms are substituted when the substituent is a keto group (=O). Ketone substitution does not occur on an aromatic group. The term "optionally substituted" means that it can or cannot be substituted, and unless otherwise specified, the kind and number of substituents can be arbitrary on the basis of chemically achievable.

When any variable (e.g., R) occurs more than once in the composition or structure of the compound, its definition in each condition is independent. Thus, for example, if one group is substituted by 0-2 R, said group can optionally be substituted by at most two R, and has an independent option in each case. Furthermore, combinations of substituents and/or variants thereof are permissible only if such combinations result in stable compounds.

When the number of a linking group is 0, such as —(CRR)$_0$—, it indicates that the linking group is a single bond.

It is indicated that the two groups to which it is attached are directly linked when one of the variables is selected from a single bond. For example, when L represents a single bond in A-L-Z, the structure is actually A-Z.

It is indicated that the substituent is absent when a substituent is vacant. For example, when X is vacant in A-X, the structure is actually A. When a bond of a substituent can be cross-linked to two atoms on a ring, the substituent can be bonded to any atoms on the ring. When the recited substituents do not indicate which atom is attached to a compound included in the chemical structural formula including but not specifically mentioned, such a substituent may be bonded through any of its atoms. Combinations of substituents and/or variants thereof are permissible only if such combinations result in stable compounds. For example, a structural unit

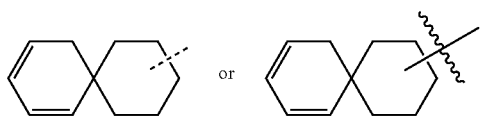

indicates that it can be substituted at any position on a cyclohexyl group or a cyclohexadiene.

Unless otherwise specified, the term "hetero" refers to hetero atom or hetero atomic group (i.e., a radical containing a hetero atom), including atoms other than carbon (C) and hydrogen (H), and radicals containing such heteroatoms, including, for example, oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, "ring" refers to substituted or unsubstituted cycloalkyl, heterocycloalkyl, cycloalkenyl, heterocycloalkenyl, cycloalkynyl, heterocycloalkynyl, aryl or heteroaryl. Said rings include single rings, interlocking rings, spiral rings, parallel rings or bridge rings. The number of atoms on the ring is usually defined as the number of elements of the ring. For example, "5-7 membered ring" means 5-7 atoms arranged in a circle. Unless otherwise specified, the ring optionally contains from 1 to 3 heteroatoms. Thus, "5-7 membered ring" includes, for example, phenyl, pyridine, and piperidinyl; on the other hand, the term "5-7 membered heterocycloalkyl ring" includes pyridyl and piperidinyl, instead of phenyl. The term "ring" also includes ring systems comprising at least one ring, wherein each of "ring" independently conforms to the above definition.

Unless otherwise specified, the term "heterocycle" or "heterocyclic" refers to a stable monocyclic, bicyclic or tricyclic ring containing a hetero atom or a heteroatom group which can be saturated, partially unsaturated or unsaturated (Aromatic), wherein said rings comprise a carbon atom and 1, 2, 3 or 4 ring heteroatoms independently selected from N, O and S, wherein any of the above heterocycles can be fused to a phenyl ring to form a bicyclic ring. The nitrogen and sulfur heteroatoms can be optionally oxidized (i.e., NO and S(O)$_p$, p is 1 or 2). The nitrogen atom can be substituted or unsubstituted (i.e., N or NR, wherein R is H or other substituents as defined herein). The heterocyclic ring can be attached to the pendant groups of any hetero atom or carbon atom to form a stable structure. If the resulting compound is stable, the heterocycles described herein can undergo substitutions at the carbon or nitrogen sites. The nitrogen atom in the heterocycle is optionally quaternized. A preferred embodiment is that when the total number of S and O atoms in the heterocycle exceeds 1, these heteroatoms are not adjacent to each other. Another preferred embodiment is that the total number of S and O atoms in the heterocycle does not exceed one. The term "aromatic heterocyclic group" or "heteroaryl" as used herein means a stable 5, 6, or 7 membered monocyclic or bicyclic or aromatic ring of a 7, 8, 9 or 10 membered bicyclic heterocyclic group. It contains carbon atoms and 1, 2, 3 or 4 ring heteroatoms independently selected from N, O and S. The nitrogen atom can be substituted or unsubstituted (i.e., N or NR, wherein R is H or other substituents as already defined herein). The nitrogen and sulfur heteroatoms can be optionally oxidized (i.e., NO and S(O)$_p$, p is 1 or 2). Surprisingly, a bridge always converts a single ring into a three ring. In the bridged ring, a substituent on the ring can also be present on the bridge.

Examples of heterocyclic compounds include, but are not limited to, acridinyl, anthracycline, benzimidazolyl, benzofuranyl, benzofuranylfuranyl, benzindenylphenyl, benzoxazolyl, benzimidin Oxazolinyl, benzothiazolyl, benzotriazolyl, benzotetrazolyl, benzisoxazolyl, benzisothiazolyl, benzimidazolyl, oxazolyl, 4aH-carbazolyl, Porphyrin, chroman, chromene, porphyrin-decahydroquinolinyl, 2H, 6H-1,5,2-dithiazinyl, dihydrofuro[2,3-b] Tetrahydrofuranyl, furyl, furfuryl, imidazolidinyl, imidazolinyl, imidazolyl, 1H-carbazolyl, nonenyl, indanyl, indolizinyl, fluorenyl, 3H-indole Mercapto, isobenzofuranyl, isodecyl, isoindoline, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxymethyl, pyrimidinyl, phenanthryl, phenanthroline, phenazine, phenothiazine, benzoxanthyl, phenoloxazinyl, pyridazinyl, piperazinyl, piperidinyl, piperidinone, 4-piperidinone, piperonyl, pteridinyl, fluorenyl, pyranyl, Pyrazinyl, pyrazolidinyl, pyrazolinyl, pyrazolyl, pyridazinyl, pyridooxazole, pyridoimidazole, pyridothiazole, pyridyl, pyrrolidinyl, pyrrolinyl, 2H-pyrrolyl, pyrrolyl, quinazolinyl, quinolyl, 4H-quinazinyl, quinoxalinyl, quinuclidinyl, tetrahydrofuranyl, tetrahydroisoquinolinyl, tetrahydroquinolyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thiazolidine, thiazolyl, isothiazolylthiophenyl, thienooxazolyl, thienothiazolyl, thienoimidazolyl, thienyl, triazinyl, 1,2,3-triazole Base, 1,2,4-triazolyl, 1,2,5-triazolyl, 1,3,4-triazolyl, xanthene, fused ring and spiro compounds.

Unless otherwise specified, the term "hydrocarbyl" or its subordinate concept (e.g., alkyl, alkenyl, alkynyl, aryl, etc.)

by itself or as part of another substituent refers to straight-chain, branched or cyclic hydrocarbon atom group or a combination thereof, which can be fully saturated (e.g., an alkyl group), monounsaturated or polyunsaturated (e.g. an alkenyl group, an alkynyl group, an aryl group), monosubstituted or polysubstituted, and can be monovalent (e.g., Methyl), divalent (e.g., methylene) or polyvalent (e.g., methine), including divalent or multivalent radicals with a specified number of carbon atoms (e.g., $C_1$-$C_{12}$ represents 1 to 12 carbons, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$, $C_{3-12}$ is selected from $C_3$, $C_4$, $C_5$, $C_6$, $C_7$, $C_8$, $C_9$, $C_{10}$, $C_{11}$ and $C_{12}$). "Hydrocarbyl" includes, but is not limited to, aliphatic and aromatic hydrocarbyl groups. Said aliphatic hydrocarbyl groups are chained and cyclic, including but not limited to alkyl, alkenyl, alkynyl groups. Said aromatic hydrocarbyl groups include, but not limited to, 6-12 members, such as benzene, naphthalene, etc. In some embodiments, the term "hydrocarbyl" refers to a straight or branched chain radical or a combination thereof, which can be fully saturated, unitary or polyunsaturated, and can include divalent and multivalent radicals. Examples of saturated hydrocarbon radicals include, but are not limited to, methyl, ethyl, n-propyl, isopropyl, n-butyl, t-butyl, isobutyl, sec-butyl, isobutyl, (cyclohexyl) methyl, cyclopropylmethyl and the homologs or isomers of n-pentyl, n-hexyl, n-heptyl or n-octyl. The unsaturated hydrocarbon group has one or more double or triple bonds, and examples thereof include, but are not limited to, a vinyl group, a 2-propenyl group, a butenyl group, a crotyl group, a 2-isopentenyl group, and a 2-(butadienyl group), 2,4-pentadienyl, 3-(1,4-pentadienyl), ethynyl, 1- and 3-propynyl, 3-butynyl, and higher homologs and isomers.

Unless otherwise specified, the term "heterohydrocarbyl" or its subordinate concept (e.g., heteroalkyl, heteroalkenyl, heteroalkynyl, heteroaryl, etc.), by itself or in conjunction with another term, refers to a stable straight chain, branched chain or cyclic hydrocarbon radical or a combination thereof, comprising a number of carbon atoms and at least one heteroatom. In some embodiments, the term "heteroalkyl" by itself or in conjunction with another term refers to a stable straight chain, branched hydrocarbon radical or combination thereof, comprising a number of carbon atoms and at least one heteroatom. In a typical embodiment, the heteroatoms are selected from B, O, N, and S, wherein the nitrogen and sulfur atoms are optionally oxidized, and the nitrogen heteroatoms are optionally quaternized. The heteroatom or heteroatom group can be located at any internal position of the heterohydrocarbyl group, including where the hydrocarbyl group is attached to the rest of the molecule. However, the terms "alkoxy", "alkylamino" and "alkylthio" (or thioalkoxy) belonging to customary expression, refer to those alkyl groups which are attached to the remainder of the molecule through an oxygen atom, an amino group or a sulfur atom, respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two heteroatoms can be continuous, such as —$CH_2$—NH—$OCH_3$.

Unless otherwise specified, the term "cycloalkyl", "heterocycloalkyl" or its subordinate concept (e.g., aryl, heteroaryl, cycloalkyl, heterocycloalkyl, cycloalkenyl, heterocycloalkenyl, cycloalkynyl, heterocyclic alkyne), by themselves or in conjunction with other terms, refers to cyclized "hydrocarbyl" or "heterohydrocarbyl", respectively. Furthermore, with respect to a heterohydrocarbyl group or a heterocycloalkyl group (e.g., a heteroalkyl group or a heterocycloalkyl group), a hetero atom may occupy a position at which the hetero ring is attached to the rest of the molecule. Examples of cycloalkyl groups include, but are not limited to, cyclopentyl, cyclohexyl, 1-cyclohexenyl, 3-cyclohexenyl, cycloheptyl, etc. Examples of heterocyclic groups include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothiophen-2-yl, tetrahydrothiophen-3-yl, 1-piperazinyl and 2-piperazinyl.

Unless otherwise specified, the term "alkyl" refers to a straight or branched saturated hydrocarbon group, which can be monosubstituted (e.g., —$CH_2F$) or polysubstituted (e.g., —$CF_3$), and can be monovalent (e.g., methyl), divalent (e.g., methylene) or polyvalent (e.g., methine). Examples of the alkyl group include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl), etc.

Unless otherwise specified, the term "alkenyl" refers to an alkyl group with one or more carbon-carbon double bonds at any position of the chain, which can be monosubstituted or polysubstituted, and can be monovalent, divalent or multivalent. Examples of the alkenyl group include a vinyl group, a propenyl group, a butenyl group, a pentenyl group, a hexenyl group, a butadienyl group, a pentadienyl group, a hexadienyl group, etc.

Unless otherwise specified, the term "alkynyl" refers to an alkyl group with one or more carbon-carbon triple bonds at any position of the chain, which can be monosubstituted or polysubstituted, and can be monovalent, divalent or multivalent. Examples of alkynyl groups include ethynyl, propynyl, butynyl, pentynyl, etc.

Unless otherwise specified, a cycloalkyl group includes any stable cyclic or polycyclic hydrocarbon group and any carbon atom which is saturated, which can be monosubstituted or polysubstituted, and can be monovalent, divalent or multivalent. Examples of such cycloalkyl groups include, but are not limited to, cyclopropyl, norbornyl, [2.2.2]bicyclooctane, [4.4.0]bicyclononane, etc.

Unless otherwise specified, a cycloalkenyl group includes any stable cyclic or polycyclic hydrocarbon group with one or more unsaturated carbon-carbon double bonds at any position of the ring, which can be monosubstituted or polysubstituted, and can be monovalent, divalent or multivalent. Examples of such cycloalkenyl groups include, but are not limited to, cyclopentenyl, cyclohexenyl, etc.

Unless otherwise specified, a cycloalkynyl group includes any stable cyclic or polycyclic hydrocarbon group which contains one or more carbon-carbon triple bonds at any position of the ring, which can be monosubstituted or polysubstituted, and can be monovalent, divalent or multivalent.

Unless otherwise specified, the term "halo" or "halogen" by itself or as part of another substituent refers to a fluorine, chlorine, bromine or iodine atom. Furthermore, the term "haloalkyl" includes both monohaloalkyl and polyhaloalkyl. For example, the term "halo($C_1$-$C_4$)alkyl" includes, but is not limited to, trifluoromethyl, 2,2,2-trifluoroethyl, 4-chlorobutyl, 3-bromopropyl, etc. Unless otherwise specified, examples of haloalkyl include, but are not limited to, trifluoromethyl, trichloromethyl, pentafluoroethyl, and pentachloroethyl.

"Alkoxy" refers to said alkyl group with a specified number of carbon atoms attached through an oxygen bridge. Unless otherwise specified, $C_{1-6}$ alkoxy includes $C_1$, $C_2$, $C_3$, C₄, C₅ and C₆ alkoxy group. Examples of alkoxy groups include, but are not limited to, methoxy, ethoxy, n-propoxy, isopropoxy, n-butoxy, sec-butoxy, tert-butoxy, n-pentyloxy and S-Pentyloxy. Unless otherwise specified, the term "aryl" refers to a polyunsaturated, aromatic hydrocarbon substituent which can be monosubstituted or polysubstituted, and can be monovalent, divalent or polyvalent, and can be monocyclic or polycyclic (e.g., 1 to 3 rings; at least one of which is aromatic). They are fused together or covalently linked. The term "heteroaryl" refers to an aryl (or ring) with one to four heteroatoms. In an embodiment, the heteroatoms are selected from the group consisting of B, N, O, and S, wherein the nitrogen and sulfur atoms are optionally oxidized, and the nitrogen atom is optionally quaternized. A heteroaryl group can be attached to the remainder of the molecule through a heteroatom. Non-limiting embodiments of aryl or heteroaryl groups include phenyl, 1-naphthyl, 2-naphthyl, 4-biphenyl, 1-pyrrolyl, 2-pyrrolyl, 3-pyrrolyl, 3-pyridyl Azyl, 2-imidazolyl, 4-imidazolyl, pyrazinyl, 2-oxazolyl, 4-oxazolyl, 2-phenyl-4-oxazolyl, 5-oxazolyl, 3-isoxan Azyl, 4-isoxazolyl, 5-isoxazolyl, 2-thiazolyl, 4-thiazolyl, 5-thiazolyl, 2-furyl, 3-furyl, 2-thienyl, 3-thiophene, 2-pyridyl, 3-pyridyl, 4-pyridyl, 2-pyrimidinyl, 4-pyrimidinyl, 5-benzothiazolyl, indolyl, 2-benzimidazolyl, 5-indenyl, 1-isoquinolyl, 5-isoquinolinyl, 2-quinoxalinyl, 5-quinoxalinyl, 3-quinolyl and 6-quinolinyl. The substituents of any said aryl and said heteroaryl ring systems are selected from the acceptable substituents described below.

Unless otherwise specified, aryl groups, when used in conjunction with other terms (e.g, aryloxy, arylthio, aralkyl), include aryl and heteroaryl rings as defined above. Thus, the term "aralkyl" includes those radicals of which the aryl group is attached to the alkyl group (e.g., benzyl, phenethyl, pyridylmethyl, etc.), wherein including those alkyl groups of which the carbon atom (e.g., methylene) is substituted by an oxygen atom, such as phenoxymethyl, 2-pyridyloxymethyl 3-(1-naphthyl oxy)propyl, etc.

The term "leaving group" refers to a functional group or atom which can be substituted by another functional group or atom through a substitution reaction such as an affinity substitution reaction. For example, representative leaving groups include triflate; chlorine, bromine, iodine; sulfonate groups such as mesylate, tosylate, p-bromobenzenesulfonate, p-toluenesulfonate, etc.; acyloxy groups such as acetoxy, trifluoroacetoxy, etc.

The term "protecting group" includes, but is not limited to, "amino protecting group", "hydroxy protecting group" or "thiol protecting group". The term "amino protecting group" refers to a protecting group for preventing side reactions at the amino nitrogen position. Representative amino protecting groups include, but are not limited to formyl; acyl, such as alkanoyl (e.g., acetyl, trichloroacetyl or trifluoroacetyl); alkoxycarbonyl, such as tert-butoxycarbonyl (Boc); Arylmethoxycarbonyl, such as benzyloxycarbonyl (Cbz) and 9-fluorenylmethoxycarbonyl (Fmoc); arylmethyl, such as benzyl (Bn), trityl (Tr), 1,1-di-(4'-methoxyphenyl)methyl; silyl groups such as trimethylsilyl (TMS) and tert-butyldimethylsilyl (TBS), etc. The term "hydroxy protecting group" refers to a protecting group for preventing the side reaction of a hydroxyl group. Representative hydroxy protecting groups include, but are not limited to, alkyl groups such as methyl, ethyl and t-butyl groups; acyl groups such as alkanoyl groups (e.g., acetyl); arylmethyl groups such as benzyl (Bn), Oxybenzyl (PMB), 9-fluorenylmethyl (Fm) and diphenylmethyl (diphenylmethyl, DPM); silyl groups such as trimethylsilyl (TMS) and tert-butyl Dimethylsilyl (TBS), etc.

The compounds of the present invention can be prepared by a variety of synthetic methods well known to those skilled in the art, including the embodiments listed below, combinations thereof with other chemical synthesis methods, and equivalent alternatives known to those skilled in the art. Preferred embodiments include, but are not limited to, the embodiments of the invention.

The solvent used in the present invention is commercially available. The present invention employs the following abbreviations: aq stands for water; HATU stands for 0-(7-azabenzotriazol-1-yl)-N,N,N',N'-tetramethyluronium hexafluorophosphate; EDC stands for N-(3-dimethylaminopropyl)-N'-ethyl carbodiimide hydrochloride; m-CPBA stands for 3-chloroperoxybenzoic acid; eq stands for equivalent; CDI stands for Carbonyldiimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc stands for ethyl acetate; EtOH stands for ethanol; MeOH stands for methanol; CBz stands for benzyloxycarbonyl, an amine protecting group; BOC stands for that t-butylcarbonyl is an amine protecting group; HOAc for acetic acid; NaCNBH₃ for sodium cyanoborohydride; r.t. stands for room temperature; 0/N stands for overnight; THE stands for tetrahydrofuran; Boc₂O stands for di-tert-butyl dicarbonate; TFA stands for trifluoroacetic acid; DIPEA stands for diisopropylethylamine; SOCl₂ stands for thionyl chloride; CS₂ stands for carbon disulfide; TsOH stands for p-toluenesulfonic acid; NFSI stands for N-fluoro-N-(phenyl sulfonyl)benzenesulfonamide; NC S stands for 1-chloropyrrolidine-2,5-di one; n-Bu₄NF stands for tetrabutylammonium fluoride; iPrOH represents 2-propanol; mp stands for melting point; LDA stands for lithium diisopropylamide; SEMCI stands for 2-(trimethylsilyl)-ethoxymethyl chloride.

Compounds are named by hand or by software ChemDraw®, and commercially available compounds are listed in the supplier's catalogue.

EXAMPLES

The invention is described in detail below by means of examples, but it is not intended to limit the invention. The present invention and the embodiments thereof are disclosed herein in detail. It is apparent to those skilled in the art that various changes and modifications can be made to the embodiments of the invention.

EMBODIMENTS

The invention is described in detail below by means of examples, but it is not intended to limit the invention.

Example 1

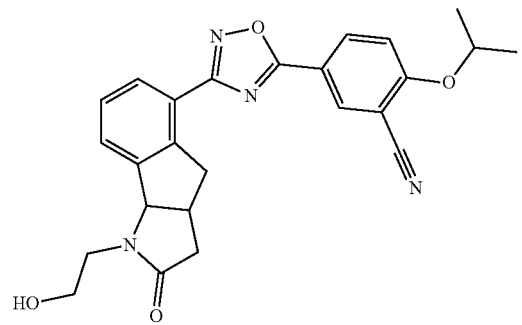

71
-continued
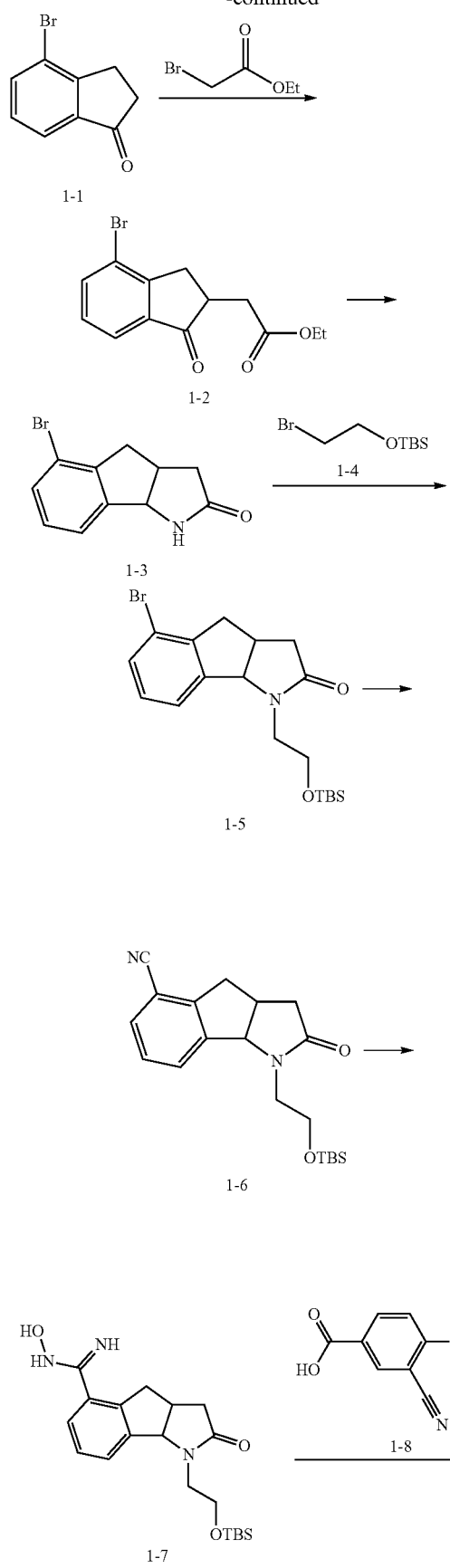
72
-continued
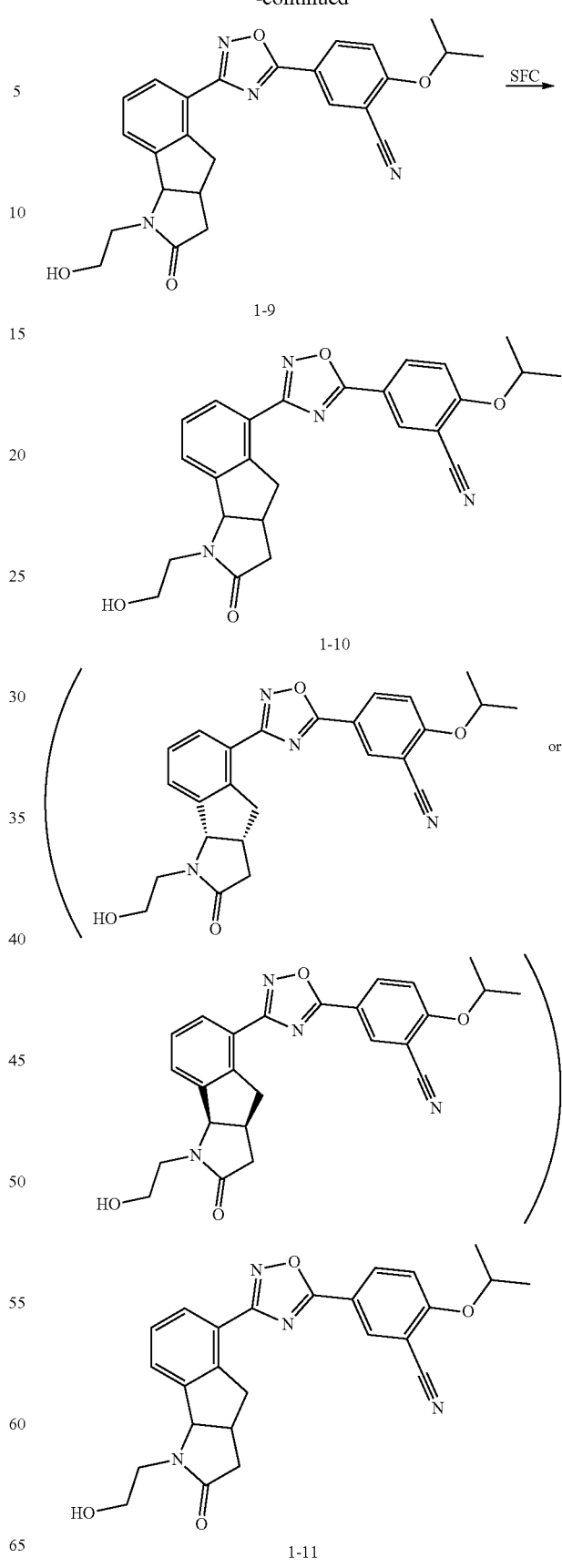

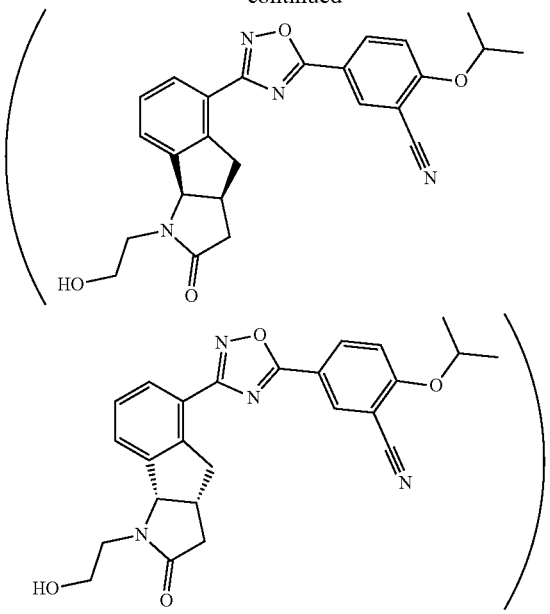

Step 1

Compound 1-1 (20.0 g, 94.8 mmol) was dissolved in anhydrous tetrahydrofuran (200 mL), and bis(trimethylsilyl)amide lithium (1M in tetrahydrofuran, 113 mL) was added dropwise at −78° C. The reaction mixture was stirred at this temperature for 30 minutes. Then, ethyl bromoacetate (17.4 g, 104 mmol) was added to the reaction mixture, and the mixture was stirred at 25° C. for 2 hours. Water (200 mL) was added to the reaction mixture, and the mixture was extracted with ethyl acetate (200 mL×3). The organic layers were combined and washed with saturated brine (300 mL×2), dried over anhydrous sodium sulfate, filtered and the filtrate was concentrated with reduced pressure. The residue was isolated and purified by silica gel column chromatography (10:1 petroleum ether/ethyl acetate, $R_f$=0.7) to give compound 1-2 (15.0 g, pale yellow oil); yield 53%.

$^1$H NMR: (400 MHz, CDCl$_3$) δ 7.87 (d, J=8.0 Hz, 1H), 7.71 (d, J=8.0 Hz, 1H), 7.38 (t, J=8.0 Hz, 1H), 4.11 (q, J=6.8 Hz, 2H), 3.33-3.10 (m, 1H), 2.96-2.87 (m, 2H), 2.69-2.65 (m, 2H), 1.19 (t, J=6.8 Hz, 3H). MS-ESI: calculated value [M+H]$^+$: 297 and 299; measured value: 297 and 299.

Step 2

Compound 1-2 (25.0 g, 84.1 mmol) was dissolved in anhydrous ethanol (300 mL), and ammonium acetate (64.9 g, 841 mmol) was added at 25° C. The reaction was stirred at this temperature for 1 hour. Then, sodium cyanoborohydride (15.9 g, 252 mmol) was added to the reaction mixture, and the mixture was stirred at 80° C. for 12 hours. Water (300 mL) was added to the reaction mixture, and the mixture was extracted with ethyl acetate (400 mL×3). The organic layers were combined and washed with saturated brine (300 mL×2), dried over anhydrous sodium sulfate, filtered and the filtrate was concentrated with reduced pressure. The residue was isolated and purified by silica gel column chromatography (10:1 ethyl acetate/methanol, $R_f$=0.4) to give compound 1-3 (10.0 g, pale yellow oil); yield 47%. MS-ESI [M+H]$^+$ calculated value: 252 and 254; measured value: 252 and 254.

Step 3

Compound 1-3 (10.0 g, 39.7 mmol) was dissolved in N,N-dimethylformamide (80 mL), and sodium hydride (2.38 g, 59.5 mmol, 60% purity) was added in portions at 0° C. The reaction was stirred at this temperature for 30 minutes. Then, compound 1-4 (9.49 g, 39.7 mmol) was added to the reaction mixture, and the mixture was stirred at 25° C. for 2 hours. Water (200 mL) was added to the reaction mixture, and the mixture was extracted with ethyl acetate (200 mL×3). The organic layers were combined and washed with saturated brine (300 mL×2), dried over anhydrous sodium sulfate, filtered and the filtrate was concentrated with reduced pressure. The residue was isolated and purified by silica gel column chromatography (1:1 petroleum ether/ethyl acetate, $R_f$=0.5) to give compound 1-5 (5.0 g, colorless oil); yield 31%.

$^1$H NMR: (400 MHz, Methonal-d$_4$) δ 7.46-7.42 (m, 2H), 7.12 (d, J=8.0 Hz, 1H), 5.17 (d, J=7.2 Hz, 1H), 3.70-3.67 (m, 3H), 3.24-3.23 (m, 1H), 3.18-3.16 (m, 2H), 2.70-2.68 (m, 2H), 2.34-2.33 (m, 1H), 0.84 (s, 9H), 0.01 (s, 6H). MS-ESI [M+H]$^+$: calculated value: 410 and 412; measured value: 410 and 412.

Step 4

Compound 1-5 (5.0 g, 12.2 mmol) was dissolved in N,N-dimethylformamide (8 mL), and zinc cyanide (2.86 g, 24.4 mmol) and tetratriphenylphosphine palladium (1.41 g, 1.22 mmol) were added to the mixture. The reaction was stirred for 16 hours at 100° C. under nitrogen atmosphere. Water (30 mL) was added after the mixture was cooled to room temperature, and the mixture was extracted with ethyl acetate (50 mL×3). The organic layers were combined and washed with saturated brine (40 mL×3), dried over anhydrous sodium sulfate, filtered and the filtrate was concentrated under reduced pressure. The residue was isolated and purified by silica gel column chromatography (1:1 petroleum ether/ethyl acetate, $R_f$=0.4) to give compound 1-6 (3.1 g, colorless oil); yield 71%.

$^1$H NMR: (400 MHz, Methonal-d$_4$) δ 7.87 (d, J=8.0 Hz, 1H), 7.70 (d, J=8.0 Hz, 1H), 7.74 (t, J=8.0 Hz, 1H), 5.26 (d, J=7.2 Hz, 1H), 3.82-3.70 (m, 3H), 3.51-3.49 (m, 1H), 3.30-3.27 (m, 1H), 3.01-2.81 (m, 3H), 2.45-2.41 (m, 1H), 0.93 (s, 9H), 0.00 (s, 6H). MS-ESI [M+H]$^+$: calculated value: 357; measured value: 357.

Step 5

Compound 1-6 (3.00 g, 8.41 mmol) was dissolved in anhydrous ethanol (8 mL), and hydroxylamine hydrochloride (1.75 g, 25.2 mmol) and triethylamine (3.40 g, 33.6 mmol) were added. The mixture was stirred at 60° C. for 12 hour under nitrogen atmosphere. Water (50 mL) was added after the mixture was cooled to room temperature, and the mixture was extracted with ethyl acetate (50 mL×3) three times. The organic layers were combined and washed with saturated brine (40 mL×2), dried over anhydrous sodium sulfate, filtered and the filtrate was concentrated under reduced pressure. The residue was isolated and purified by silica gel column chromatography (0:1 petroleum ether/ethyl acetate, $R_f$=0.4) to give compound 1-7 (3.0 g, white solid); yield 92%.

$^1$H NMR: (400 MHz, CDCl$_3$) δ 7.49 (d, J=8.0 Hz, 1H), 7.40 (d, J=8.0 Hz, 1H), 7.21 (t, J=8.0 Hz, 1H), 5.07 (d, J=7.2 Hz, 1H), 4.73 (s, 2H), 3.78-3.75 (m, 1H), 3.67-3.62 (m, 2H), 3.44-3.42 (m, 1H), 2.97-2.90 (m, 3H), 2.71-2.65 (m, 1H), 2.37-2.33 (m, 1H), 0.84 (s, 9H), 0.00 (s, 6H). MS-ESI [M+H]$^+$: calculated value: 390; measured value: 390.

Step 6

Compound 1-8 (695 mg, 3.39 mmol) was dissolved in N,N-dimethylformamide (10 mL), and 1-hydroxybenzotriazole (763 mg, 5.65 mmol) and 1-(3-dimethylaminopropyl)-3-ethylcarbodiimide hydrochloride (1.08 g, 5.65 mmol) were added. The reaction was stirred at 25° C. for 30 minutes under nitrogen atmosphere. Then, compound 1-7 (1.10 g, 2.82 mmol) was added to the reaction mixture, and the mixture was stirred at 25° C. for 1 hour, then heated to 80° C. and stirred for 12 hours. Water (30 mL) was added after the mixture was cooled to room temperature, and the mixture was extracted with ethyl acetate (30 mL×3). The organic layers were combined and washed with brine (25 mL×2), dried over anhydrous sodium sulfate, filtered and the filtrate was concentrated under reduced pressure. The residue was isolated and purified by high performance liquid chromatography to give compound 1-9 (420 mg); yield 33%.

$^1$H NMR: (400 MHz, Methonal-$d_4$) δ 8.46-8.42 (m, 2H), 8.19 (d, J=7.2 Hz, 1H), 7.78 (d, J=7.2 Hz, 1H), 7.51-7.44 (m, 2H), 5.26 (d, J=7.2 Hz, 1H), 4.99-4.94 (m, 1H), 3.83-3.71 (m, 4H), 3.26-3.23 (m, 2H), 3.15-3.13 (m, 1H), 2.92-2.86 (m, 1H), 2.48-2.43 (m, 1H), 1.47 (d, J=6.0 Hz, 6H). MS-ESI [M+H]$^+$: calculated value: 445; measured value: 445.

Step 7

Compound 1-9 (200 mg, 0.450 mmol) was isolated and purified by chiral liquid chromatography to give compound 1-10 (isomer 1) and compound 1-11 (isomer 2).

SFS isolation method:

Chromatographic column: AD 250 mm×30 mm, 10 um;

Mobile phase: A: $CO_2$; B: 45%.-45%. Ethanol (0.1% aqueous ammonia)

Flow rate: 80 mL/min

Column temperature: 40° C.

Compound 1-10 (56.0 mg), yield: 28%. The retention time in the high performance chiral liquid column is 5.276.

$^1$H NMR: (400 MHz, Methonal-$d_4$) δ 8.42-8.40 (m, 2H), 8.17 (d, J=7.6 Hz, 1H), 7.77 (d, J=7.6 Hz, 1H), 7.50-7.42 (m, 2H), 5.26 (d, J=7.2 Hz, 1H), 4.99-4.95 (m, 1H), 3.81-3.71 (m, 4H), 3.26-3.23 (m, 2H), 3.13-3.08 (m, 1H), 2.92-2.86 (m, 1H), 2.48-2.44 (m, 1H), 1.47 (d, J=6.0 Hz, 6H). MS-ESI [M+H]$^+$: calculated value: 445; measured value: 445.

Compound 1-11 (25.4 mg), yield: 13%. The retention time in the chiral high performance liquid column is 6.427.

$^1$H NMR: (400 MHz, Methonal-$d_4$) δ 8.45-8.42 (m, 2H), 8.19 (d, J=7.6 Hz, 1H), 7.77 (d, J=7.6 Hz, 1H), 7.51-7.44 (m, 2H), 5.27 (d, J=7.2 Hz, 1H), 4.99-4.94 (m, 1H), 3.83-3.71 (m, 4H), 3.26-3.23 (m, 2H), 3.15-3.13 (m, 1H), 2.92-2.88 (m, 1H), 2.48-2.44 (m, 1H), 1.47 (d, J=6.0 Hz, 6H). MS-ESI [M+H]$^+$: calculated value: 445; measured value: 445.

Example 2

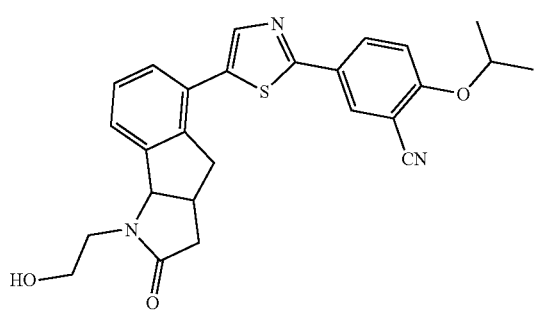

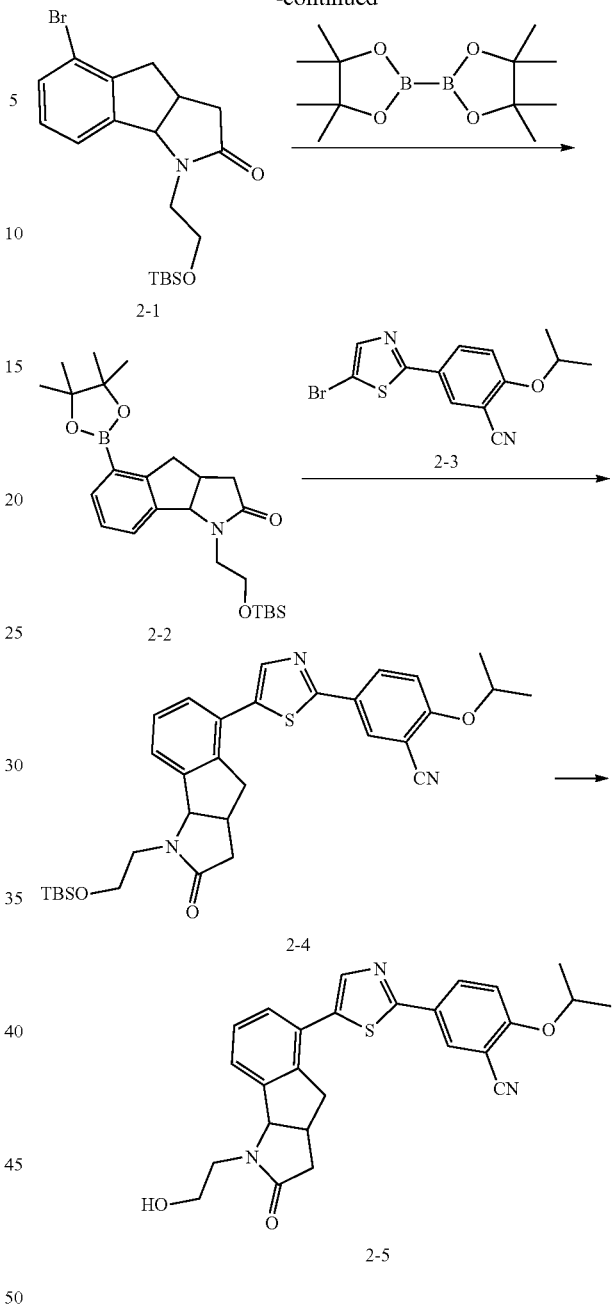

Step 1

Compound 2-1 (3.10 g, 7.55 mmol) was dissolved in dioxane (30 mL), and bis(pinacolato)diboron (2.88 g, 11.3 mmol), potassium acetate (1.48 g, 15.1 mmol) and 1,1'-bis(diphenylphosphino)ferrocene palladium chloride (553 mg, 0.755 mmol) were added. The reaction was stirred at 80° C. for 12 hours under nitrogen atmosphere. Water (30 mL) was added after the mixture was cooled to room temperature, and the mixture was extracted with ethyl acetate (30 mL×3). The organic layers were combined and washed with saturated brine (30 mL×3), dried over anhydrous sodium sulfate, filtered and the filtrate was concentrated under reduced pressure. The residue was isolated and purified by silica gel column chromatography (1:1 petroleum ether/ethyl acetate, $R_f$=0.6) to give compound 2-2 (3.00 g, colorless oil); yield 87%.

¹H NMR: (400 MHz, CDCl₃) δ 7.68 (d, J=8.0 Hz, 1H), 7.51 (d, J=8.0 Hz, 1H), 7.16 (t, J=8.0 Hz, 1H), 5.04 (d, J=7.2 Hz, 1H), 3.76-3.70 (m, 1H), 3.65-3.60 (m, 2H), 3.49-3.47 (m, 1H), 3.06-3.03 (m, 2H), 2.72-2.67 (m, 1H), 2.65-2.63 (m, 1H), 2.37-2.32 (m, 1H), 1.21 (s, 12H), 0.83 (s, 9H), 0.00 (s, 6H). MS-ESI [M+H]⁺: calculated value: 458; measured value: 458.

Step 2

Compound 2-3 (100 mg, 0.309 mmol) was dissolved in dioxane (5 mL) and water (1 mL), and Compound 2-2 (142 mg, 0.309 mmol), potassium phosphate (131 mg, 0.619 mmol) and 1,1'-bis(diphenylphosphino)ferrocene palladium chloride (22.6 mg, 0.0309 mmol) were added. The reaction was stirred at 100° C. for 12 hours under nitrogen atmosphere. Water (30 mL) was added after the mixture was cooled to room temperature, and the mixture was extracted with ethyl acetate (30 mL×3). The organic layers were combined and washed with saturated brine (30 mL×3), dried over anhydrous sodium sulfate, filtered and the filtrate was concentrated under reduced pressure. The residue was isolated and purified by silica gel column chromatography (1:1 petroleum ether/ethyl acetate, R_f=0.4) to give compound 2-4 (70 mg, pale yellow oil); yield 39%.

¹H NMR: (400 MHz, CDCl₃) δ 8.06-8.00 (m, 2H), 7.79 (s, 1H), 7.47-7.42 (m, 2H), 7.25 (d, J=7.6 Hz, 1H), 6.95 (d, J=7.6 Hz, 1H), 5.12 (d, J=7.2 Hz, 1H), 4.67-4.63 (m, 1H), 3.79-3.77 (m, 1H), 3.69-3.65 (m, 2H), 3.38-3.36 (m, 1H), 3.18-3.05 (m, 2H), 2.75-2.70 (m, 1H), 2.69-2.67 (m, 1H), 2.38-2.33 (m, 1H), 1.35 (d, J=6.0 Hz, 6H), 0.84 (s, 9H), 0.00 (s, 6H). MS-ESI [M+H]⁺: calculated value: 574; measured value: 574.

Step 3

Compound 2-4 (70.0 mg, 0.122 mmol) was dissolved in dioxane (3 mL), and dioxane hydrochloride (4M, 1 mL) was added. The reaction was stirred at 25° C. for 10 minutes under nitrogen atmosphere. The reaction mixture was cooled and concentrated under reduced pressure. The residue was isolated and purified by high performance liquid chromatography to give compound 2-5 (40.0 mg); yield: 71%.

¹H NMR: (400 MHz, DMSO-d₆) δ 8.27 (d, J=2.0 Hz, 1H), 7.21 (d, J=8.0 Hz, 1H), 8.17 (s, 1H), 7.64-7.59 (m, 2H), 7.45-7.40 (m, 2H), 5.12 (d, J=7.2 Hz, 1H), 4.94-4.88 (m, 1H), 3.58-3.53 (m, 4H), 3.24-3.22 (m, 1H), 3.01-2.97 (m, 2H), 2.69-2.68 (m, 1H), 2.32-2.31 (m, 1H), 1.36 (d, J=6.0 Hz, 6H). MS-ESI [M+H]⁺: calculated value: 460; measured value: 460.

Example 3

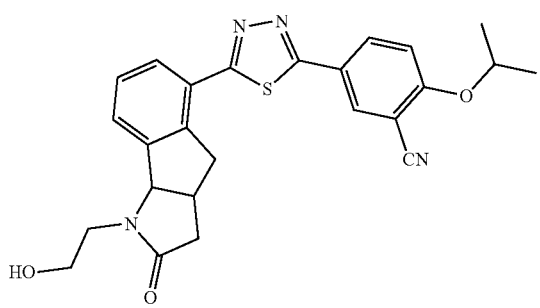

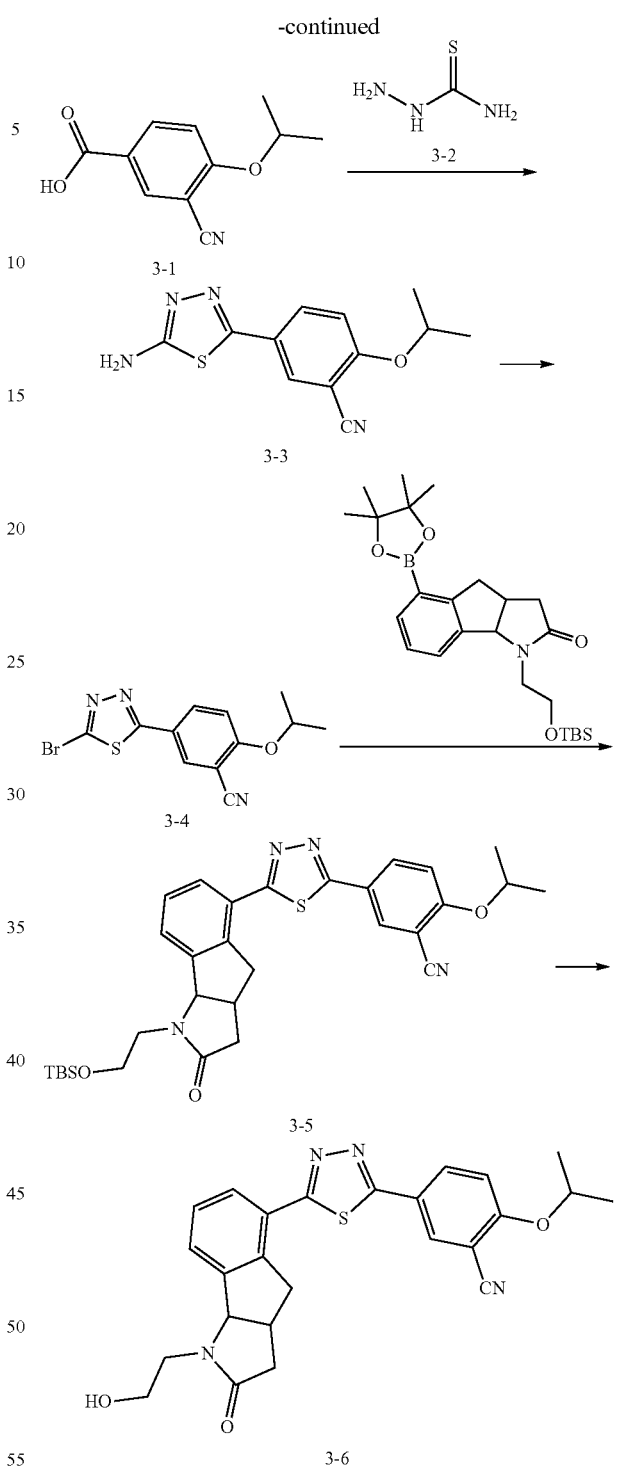

Step 1

Compound 3-1 (1.00 g, 4.87 mmol) was dissolved in phosphorus oxychloride (10 mL), and compound 3-2 (488 mg, 14.6 mmol) was added. The reaction was stirred at 85° C. for 8 hours under nitrogen atmosphere. Aqueous sodium hydroxide solution (6M, 40 mL) was added dropwise after the mixture was cooled to room temperature, and the mixture was extracted with ethyl acetate (50 mL×3). The organic layers were combined and washed with saturated brine (30 mL×3), dried over anhydrous sodium sulfate, filtered and the filtrate was concentrated under reduced pressure. The residue was isolated and purified by silica gel column chromatography (0:1 petroleum ether/ethyl acetate, R$_f$=0.4) to give compound 3-3 (450 mg, pale yellow solid); yield: 36%.

$^1$H NMR: (400 MHz, DMSO-d$_6$) δ 8.05-8.01 (m, 2H), 7.45 (s, 2H), 7.37 (d, J=8.8 Hz, 1H), 4.90-4.84 (m, 1H), 1.34 (d, J=6.0 Hz, 6H). MS-ESI [M+H]$^+$: calculated value: 261; measured value: 261.

Step 2

Compound 3-3 (450 mg, 1.73 mmol) was dissolved in acetonitrile (5 mL), and cuprous bromide (298 mg, 2.08 mmol) and isoamyl nitrite (243 mg, 2.08 mmol) were added. The reaction was stirred at 25° C. for 6 hours under nitrogen atmosphere. Dilute hydrochloric acid (1 M, 20 mL) was added to the reaction mixture, and the mixture was extracted with ethyl acetate (20 mL×3). The organic layers were combined and washed with saturated brine (10 mL×2), dried over anhydrous sodium sulfate, filtered and the filtrate was concentrated under reduced pressure. The residue was isolated and purified by silica gel column chromatography (3:1 petroleum ether/ethyl acetate, R$_f$=0.5) to give compound 3-4 (170 mg, pale yellow solid); yield 30%.

$^1$H NMR: (400 MHz, DMSO-d$_6$) δ 8.33 (s, 1H), 8.23 (d, J=8.8 Hz, 1H), 7.47 (d, J=8.8 Hz, 1H), 4.97-4.91 (m, 1H), 1.36 (d, J=6.0 Hz, 6H). MS-ESI [M+H]$^+$: calculated value: 324 and 326; measured value: 324 and 326.

Step 3

The reaction referred to Step 2 of Example 2, and the residue was isolated and purified by TLC (1:1 petroleum ether/ethyl acetate, R$_f$=0.4) to give compound 3-5 (50 mg, pale yellow oil); yield: 71%. MS-ESI [M+H]$^+$: calculated value: 575; measured value: 575.

Step 4

The reaction referred to Step 3 of Example 2, and the residue was isolated and purified by high performance liquid chromatography to give compound 3-6 (15 mg); yield: 37%.

$^1$H NMR: (400 MHz, DMSO-d$_6$) δ 8.37 (s, 1H), 8.28 (d, J=7.2 Hz, 1H), 7.95 (d, J=7.2 Hz, 1H), 7.77 (d, J=7.2 Hz, 1H), 7.50-7.48 (m, 2H), 5.17 (d, J=7.2 Hz, 1H), 4.96-4.90 (m, 1H), 3.69-3.62 (m, 3H), 3.52-3.51 (m, 1H), 3.23-3.21 (m, 1H), 3.06-2.98 (m, 2H), 2.72-2.68 (m, 1H), 2.33-2.28 (m, 1H), 1.37 (d, J=6.0 Hz, 6H). MS-ESI [M+H]$^+$: calculated value: 461; measured value: 461.

Example 4

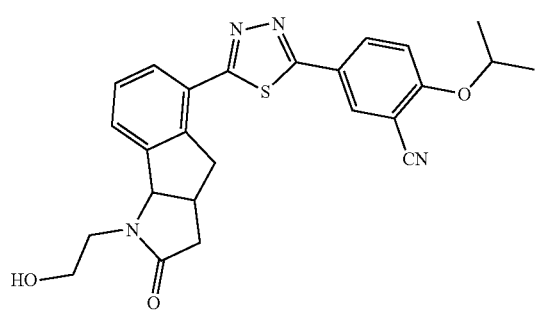

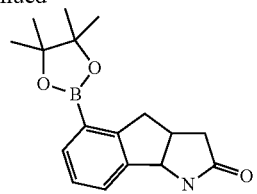

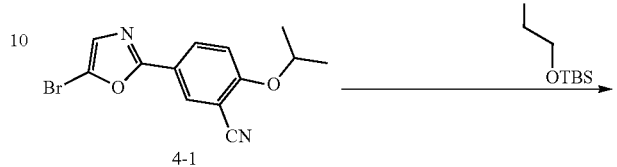

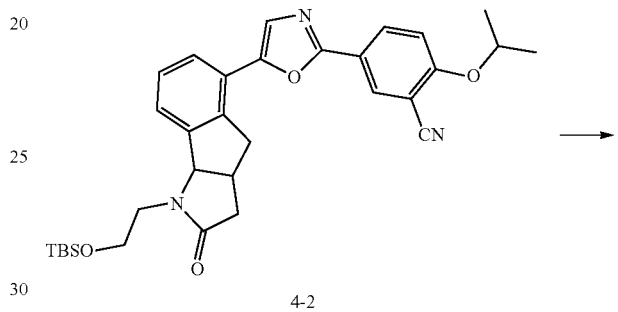

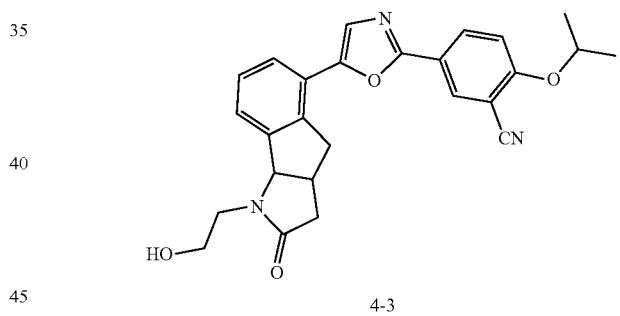

Step 1

The reaction referred to Step 2 of Example 2, and the residue was isolated and purified by TLC (3:1 petroleum ether/ethyl acetate, R$_f$=0.4) to give compound 4-2 (70.0 mg, pale yellow oil); yield: 77%. MS-ESI [M+H]$^+$: calculated value: 558; measured value: 558.

Step 2

The reaction referred to Step 3 of Example 2, and the residue was isolated and purified by high performance liquid chromatography to give compound 4-3 (20.0 mg); yield: 42%.

$^1$H NMR: (400 MHz, DMSO-d$_6$) δ 8.41 (s, 1H), 8.31 (d, J=8.8 Hz, 1H), 7.91 (d, J=8.8 Hz, 1H), 7.65 (s, 1H), 7.60 (d, J=8.8 Hz, 1H), 7.48-7.42 (m, 2H), 5.13 (d, J=7.2 Hz, 1H), 4.95-4.89 (m, 1H), 3.57-3.53 (m, 3H), 3.24-3.23 (m, 2H), 3.01-2.97 (m, 2H), 2.72-2.68 (m, 1H), 2.35-2.31 (m, 1H), 1.37 (d, J=6.0 Hz, 6H). MS-ESI [M+H]$^+$: calculated value: 444; measured value: 444.

Example 5

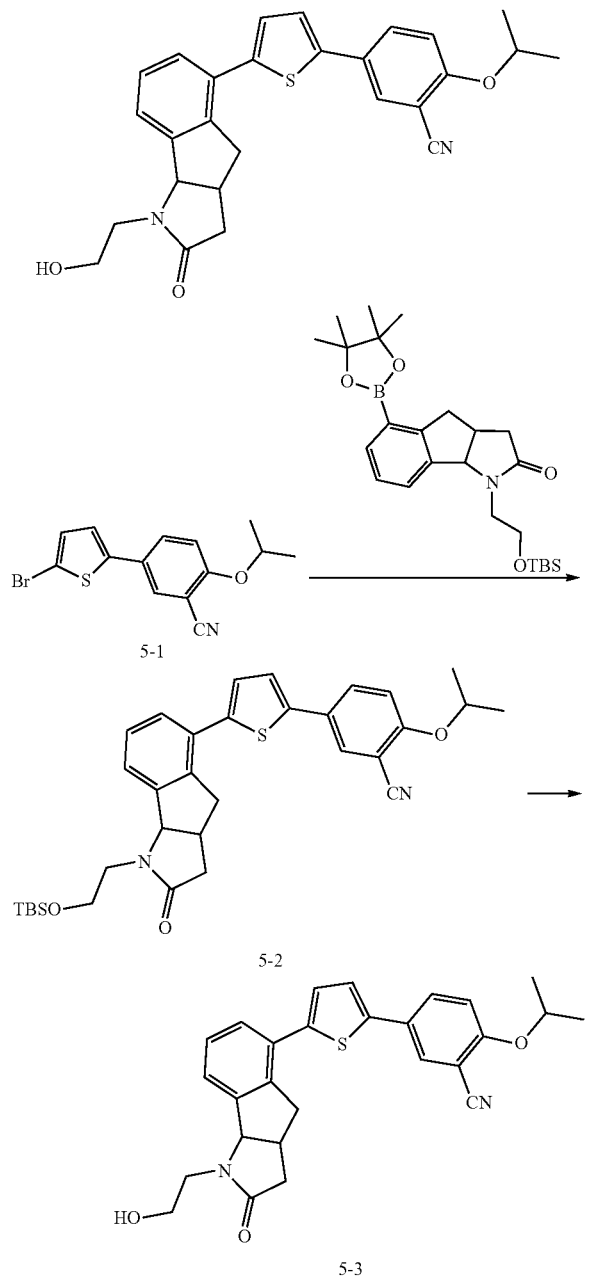

Step 1
The reaction referred to Step 2 of Example 2, and the residue was isolated and purified by TLC (1:1 petroleum ether/ethyl acetate, $R_f$=0.4) to give compound 5-2 (60.0 mg, pale yellow oil); yield: 68%. MS-ESI [M+H]$^+$: calculated value: 573; measured value: 573.

Step 2
The reaction referred to Step 3 of Example 2, and the residue was isolated and purified by high performance liquid chromatography to give compound 5-3 (20.0 mg); yield: 42%.

$^1$H NMR: (400 MHz, DMSO-d$_6$) δ 8.09 (s, 1H), 7.91 (d, J=7.2 Hz, 1H), 7.60-7.59 (m, 2H), 7.54 (d, J=7.2 Hz, 1H), 7.41-7.33 (m, 3H), 5.10 (d, J=7.2 Hz, 1H), 4.88-4.82 (m, 1H), 3.57-3.50 (m, 2H), 3.24-3.22 (m, 3H), 3.01-2.97 (m, 2H), 2.69-2.66 (m, 1H), 2.32-2.28 (m, 1H), 1.35 (d, J=6.0 Hz, 6H). MS-ESI [M+H]$^+$: calculated value: 459; measured value: 459.

Example 6

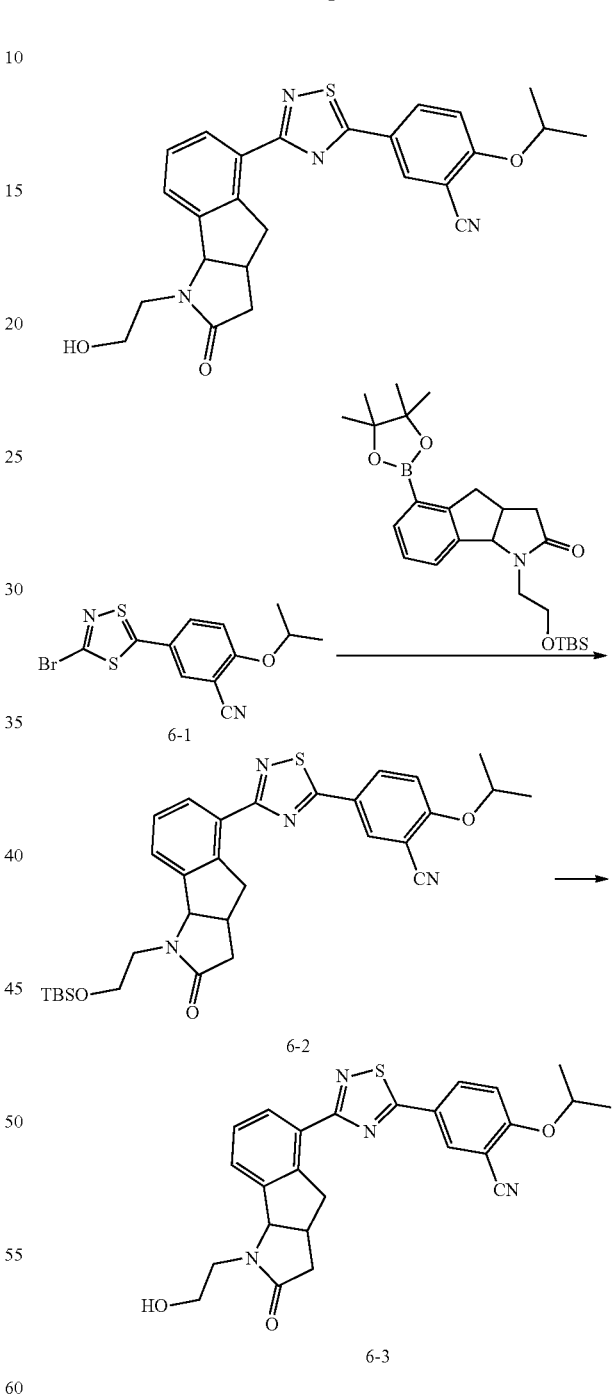

Step 1
The reaction referred to Step 2 of Example 2, and the residue was isolated and purified by TLC (1:1 petroleum ether/ethyl acetate, $R_f$=0.4) to give compound 6-2 (70.0 mg, pale yellow oil); yield: 79%. MS-ESI [M+H]$^+$: calculated value: 575; measured value: 575.

Step 2

The reaction referred to Step 3 of Example 2, and the residue was isolated and purified by high performance liquid chromatography to give compound 6-3 (25.0 mg); yield: 45%.

$^1$H NMR: (400 MHz, DMSO-$d_6$) δ 8.53 (s, 1H), 8.38 (d, J=7.6 Hz, 1H), 8.31 (d, J=7.6 Hz, 1H), 7.73 (d, J=7.6 Hz, 1H), 7.52-7.46 (m, 2H), 5.14 (d, J=7.2 Hz, 1H), 4.98-4.93 (m, 1H), 3.86-3.82 (m, 1H), 3.59-3.50 (m, 3H), 3.20-3.16 (m, 2H), 3.01-2.97 (m, 1H), 2.69-2.67 (m, 1H), 2.34-2.30 (m, 1H), 1.38 (d, J=6.0 Hz, 6H). MS-ESI [M+H]$^+$: calculated value: 461; measured value: 461.

Example 7

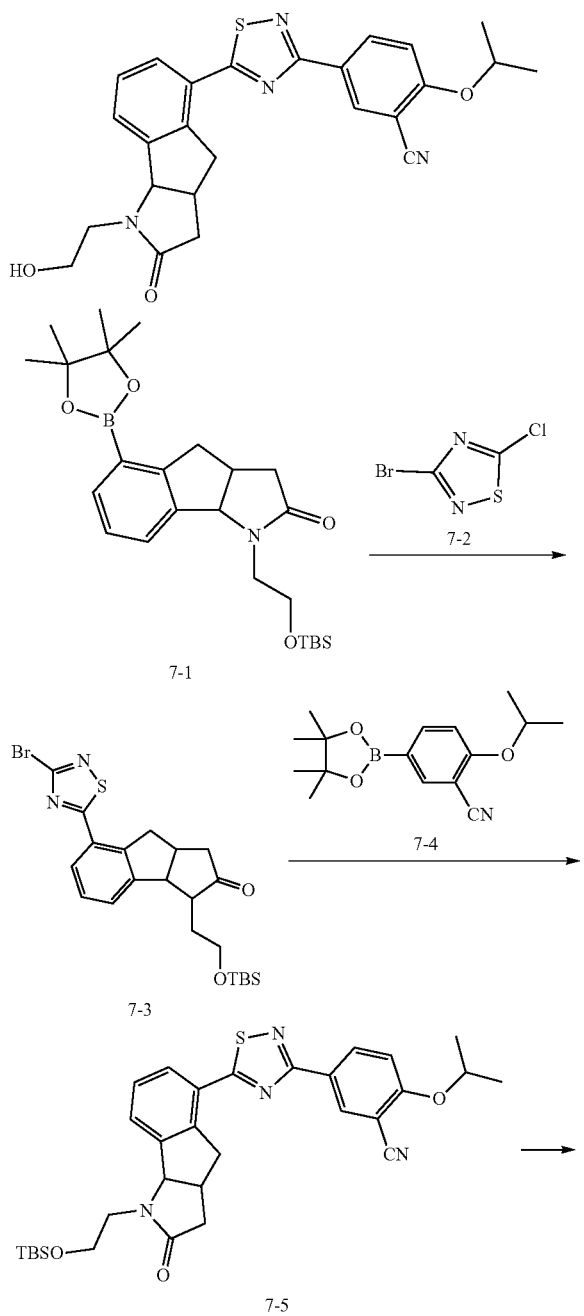

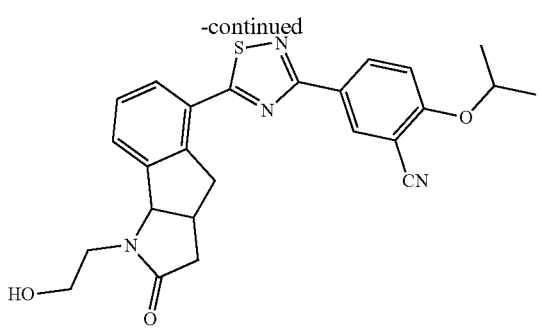

Step 1

Compound 7-1 (229 mg, 0.501 mmol) was dissolved in dioxane (5 mL) and water (1 mL), and Compound 7-2 (100 mg, 0.501 mmol), potassium phosphate (213 mg, 1.00 mmol) and 1,1'-bis(diphenylphosphino)ferrocene]dichloropalladium(II) (36.7 mg, 0.0501 mmol) were added. The reaction was stirred at 100° C. for 12 hours under nitrogen atmosphere. Water (30 mL) was added after the mixture was cooled to room temperature, and the mixture was extracted with ethyl acetate (30 mL×3). The organic layers were combined and washed with saturated brine (30 mL×3), dried over anhydrous sodium sulfate, filtered and the filtrate was concentrated under reduced pressure. The residue was isolated and purified by TLC (3:1 petroleum ether/ethyl acetate, $R_f$=0.6) to give compound 7-3 (150 mg, pale yellow oil); yield: 61%.

$^1$H NMR: (400 MHz, CDCl$_3$) δ 7.96 (d, J=8.0 Hz, 1H), 7.67 (d, J=8.0 Hz, 1H), 7.47 (t, J=8.0 Hz, 1H), 5.17 (d, J=7.2 Hz, 1H), 3.78-3.77 (m, 1H), 3.70-3.65 (m, 2H), 3.53-3.49 (m, 1H), 3.23-3.20 (m, 1H), 3.03-2.96 (m, 2H), 2.78-2.72 (m, 1H), 2.42-2.37 (m, 1H), 0.83 (s, 9H), 0.00 (s, 6H). MS-ESI [M+H]$^+$: calculated value: 494 and 496; measured value: 494 and 496.

Step 2

Compound 7-3 (150 mg, 0.303 mmol) was dissolved in dioxane (5 mL) and water (1 mL), and Compound 7-4 (104 mg, 0.364 mmol), potassium phosphate (129 mg, 0.607 mmol) and 1,1'-bis(diphenylphosphino)ferrocene]dichloropalladium(II) (22.2 mg, 0.0303 mmol) were added. The reaction was stirred at 100° C. for 12 hours under nitrogen atmosphere. Water (30 mL) was added after the mixture was cooled to room temperature, and the mixture was extracted with ethyl acetate (30 mL×3). The organic layers were combined and washed with saturated brine (30 mL×3), dried over anhydrous sodium sulfate, filtered and the filtrate was concentrated with reduced pressure. The residue was isolated and purified by TLC (1:1 petroleum ether/ethyl acetate, $R_f$=0.4) to give compound 2-4 (150 mg, pale yellow oil); yield: 86%. MS-ESI [M+H]$^+$: calculated value: 575; measured value: 575.

Step 3

Compound 7-5 (150 mg, 0.261 mmol) was dissolved in dioxane (3 mL), and dioxane hydrochloride (4M, 1 mL) was added. The reaction was stirred at 25° C. for 10 minutes under nitrogen atmosphere. The reaction mixture was cooled and concentrated under reduced pressure. The residue was isolated and purified by high performance liquid chromatography to give compound 7-6 (80.0 mg); yield: 66%.

$^1$H NMR: (400 MHz, DMSO-$d_6$) δ 8.54-8.52 (m, 2H), 8.22 (d, J=7.6 Hz, 1H), 7.84 (d, J=7.6 Hz, 1H), 7.55-7.47 (m, 2H), 5.20 (d, J=7.2 Hz, 1H), 4.95-4.89 (m, 1H), 3.65-3.54 (m, 4H), 3.10-3.04 (m, 3H), 2.72-2.70 (m, 1H), 2.40-2.35

(m, 1H), 1.38 (d, J=6.0 Hz, 6H). MS-ESI [M+H]+: calculated value: 461; measured value: 461.

Example 8

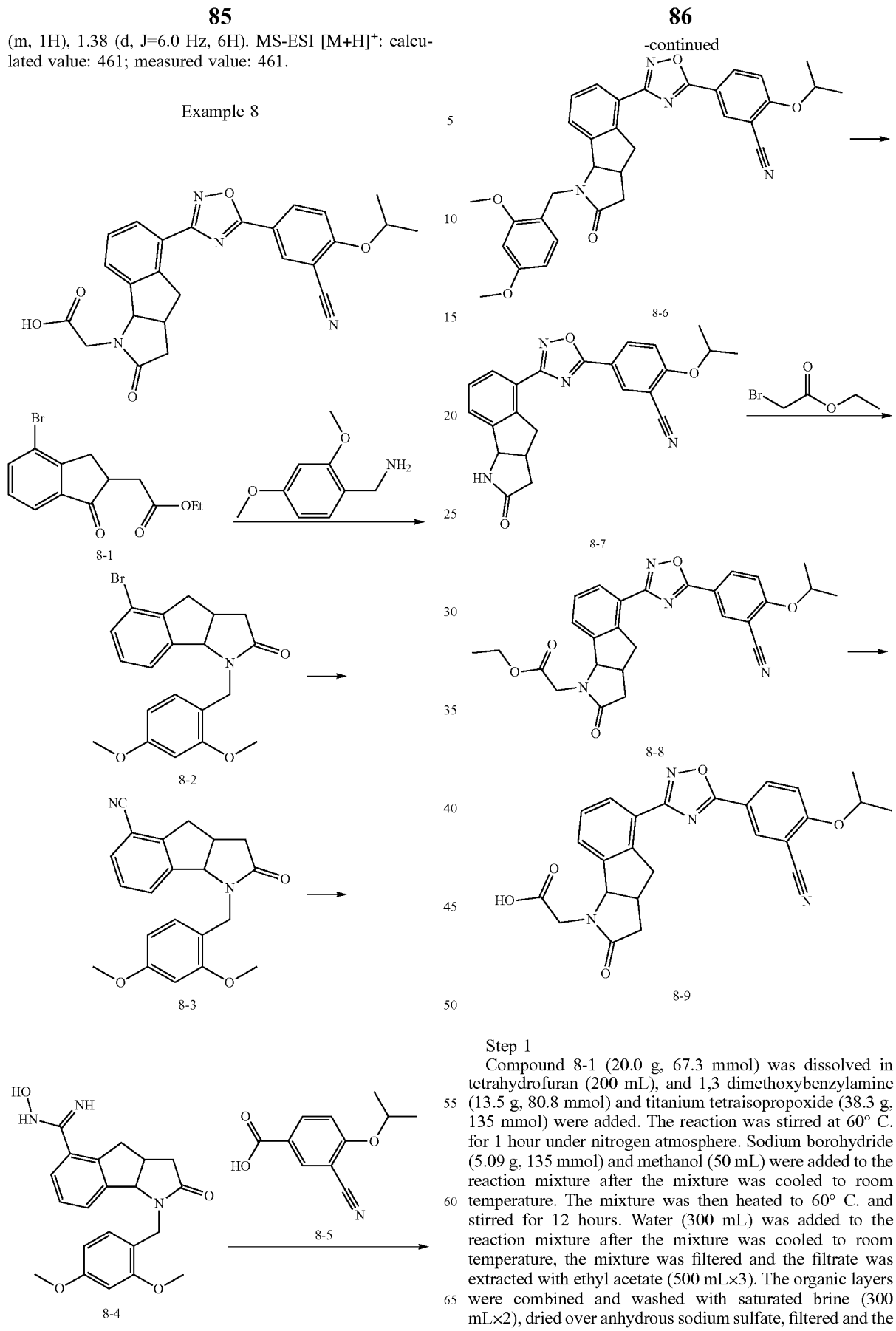

Step 1

Compound 8-1 (20.0 g, 67.3 mmol) was dissolved in tetrahydrofuran (200 mL), and 1,3 dimethoxybenzylamine (13.5 g, 80.8 mmol) and titanium tetraisopropoxide (38.3 g, 135 mmol) were added. The reaction was stirred at 60° C. for 1 hour under nitrogen atmosphere. Sodium borohydride (5.09 g, 135 mmol) and methanol (50 mL) were added to the reaction mixture after the mixture was cooled to room temperature. The mixture was then heated to 60° C. and stirred for 12 hours. Water (300 mL) was added to the reaction mixture after the mixture was cooled to room temperature, the mixture was filtered and the filtrate was extracted with ethyl acetate (500 mL×3). The organic layers were combined and washed with saturated brine (300 mL×2), dried over anhydrous sodium sulfate, filtered and the filtrate was concentrated with reduced pressure. The residue was isolated and purified by silica gel column chromatography (1:1 petroleum ether/ethyl acetate, $R_f$=0.5) to give compound 8-2 (10.0 g, pale yellow oil); yield: 37%.

$^1$H NMR: (400 MHz, CDCl$_3$) δ 7.39-7.35 (m, 2H), 7.14 (d, J=7.6 Hz, 1H), 7.04 (d, J=7.6 Hz, 1H), 6.42-6.39 (m, 2H), 4.94 (d, J=7.2 Hz, 1H), 4.76-4.47 (m, 1H), 4.13-4.09 (m, 1H), 3.80 (s, 3H), 3.74 (s, 3H), 3.28-3.23 (m, 1H), 3.21-3.19 (m, 1H), 2.79-2.65 (m, 2H), 2.36-2.31 (m, 1H). MS-ESI: calculated value [M+H]$^+$: 402 and 404; measured value: 402 and 404.

Step 2

Compound 8-2 (8.00 g, 19.9 mmol) was dissolved in acetonitrile (100 mL), and zinc cyanide (4.67 g, 39.8 mmol), 2-dicyclohexylphosphine-2',4',7'-triisopropylbiphenyl (1.96 g, 3.98 mmol) and tris(dibenzylideneacetone) palladium (1.82 g, 1.99 mmol) were added. The reaction was stirred at 90° C. for 16 hours under nitrogen atmosphere. Water (100 mL) was added to the reaction mixture after the mixture was cooled to room temperature, and the mixture was extracted with ethyl acetate (200 mL×3). The organic layer was combined and washed with saturated brine (200 mL×2), dried over anhydrous sodium sulfate, filtered and the filtrate was concentrated with reduced pressure. The residue was isolated and purified by silica gel column chromatography (1:1 petroleum ether/ethyl acetate, $R_f$=0.3) to give compound 8-3 (5.00 g, pale yellow solid); yield: 72%.

$^1$H NMR: (400 MHz, CDCl$_3$) δ 7.72 (d, J=8.0 Hz, 1H), 7.58 (d, J=8.0 Hz, 1H), 7.34 (d, J=8.0 Hz, 1H), 7.22 (d, J=8.0 Hz, 1H), 6.49-6.41 (m, 2H), 4.88 (d, J=7.2 Hz, 1H), 4.86-4.81 (m, 1H), 4.19-4.16 (m, 1H), 3.81 (s, 3H), 3.80 (s, 3H), 3.48-3.44 (m, 1H), 3.20-3.19 (m, 1H), 3.05-3.00 (m, 1H), 2.82-2.75 (m, 1H), 2.43-2.38 (m, 1H). MS-ESI: calculated value [M+H]$^+$: 349; measured value: 349.

Step 3

Compound 8-3 (5.00 g, 14.4 mmol) was dissolved in anhydrous ethanol (50 mL), and add hydroxylamine hydrochloride (2.99 g, 43.1 mmol) and triethylamine (5.81 g, 57.4 mmol) were added. The reaction was stirred at 60° C. for 12 hours under nitrogen atmosphere. Water (100 mL) was added to the reaction mixture after the mixture was cooled to room temperature, and the mixture was extracted with dichloromethane (100 mL×3). The organic layer were combined and washed with saturated brine (100 mL×2), dried over anhydrous sodium sulfate, filtered and the filtrate was concentrated with reduced pressure. The residue was compound 8-4 (3.70 g, white solid); yield: 68%.

$^1$H NMR: (400 MHz, DMSO-d$_6$) δ 9.55 (s, 1H), 7.42 (d, J=7.6 Hz, 1H), 7.35 (d, J=7.6 Hz, 1H), 7.26 (d, J=7.6 Hz, 1H), 7.02 (d, J=8.8 Hz, 1H), 6.60 (s, 1H), 6.48 (d, J=8.8 Hz, 1H), 5.73 (s, 2H), 4.73 (d, J=7.2 Hz, 1H), 4.56-4.52 (m, 1H), 4.08-4.04 (m, 1H), 3.84 (s, 3H), 3.74 (s, 3H), 3.39-3.35 (m, 1H), 3.04-3.00 (m, 1H), 2.92-2.87 (m, 1H), 2.69-2.63 (m, 1H), 2.25-2.20 (m, 1H). MS-ESI [M+H]$^+$: calculated value: 382; measured value: 382.

Step 4

Compound 8-5 (1.01 g, 4.91 mmol) was dissolved in N,N-dimethylformamide (10 mL), and 1-hydroxybenzotriazole (1.21 g, 8.92 mmol) and 1-(3-dimethylaminopropyl)-3-ethylcarbodiimide hydrochloride (1.71 g, 8.92 mmol) were added. The reaction was stirred at 25° C. for 0.5 hour under nitrogen atmosphere. Then, Compound 8-4 (1.70 g, 4.46 mmol) was added to the reaction mixture and the mixture was stirred at 25° C. for 1 hour, then heated to 80° C. and stirred for 12 hours. Water (30 mL) was added to the reaction mixture after the mixture was cooled to room temperature and the mixture was extracted with ethyl acetate (30 mL×3). The organic layers were combined and washed with saturated brine (25 mL×2), dried over anhydrous sodium sulfate, filtered and the filtrate was concentrated under reduced pressure. The residue was isolated and purified by silica gel column chromatography (1:1 petroleum ether/ethyl acetate, $R_f$=0.7) to give compound 8-6 (1.2 g, white solid); yield: 49%.

$^1$H NMR: (400 MHz, DMSO-d$_6$) δ 8.50 (d, J=2.0 Hz, 1H), 8.40 (d, J=8.8 Hz, 1H), 8.08 (d, J=7.2 Hz, 1H), 7.62-7.48 (m, 3H), 7.04 (d, J=7.2 Hz, 1H), 6.61 (d, J=2.0 Hz, 1H), 6.48 (d, J=8.8 Hz, 1H), 5.01-4.96 (m, 1H), 4.86 (d, J=7.2 Hz, 1H), 4.61-4.57 (m, 1H), 4.16-4.12 (m, 1H), 3.88 (s, 3H), 3.76 (s, 3H), 3.68-3.65 (m, 1H), 3.24-3.21 (m, 1H), 3.11-3.09 (m, 1H), 2.77-2.70 (m, 1H), 2.38-2.33 (m, 1H), 1.38 (d, J=6.0 Hz, 6H). MS-ESI [M+H]$^+$: calculated value: 551; measured value: 551.

Step 5

Compound 8-6 (1.20 g, 2.18 mmol) was dissolved in trifluoroacetic acid (5 mL). The reaction was stirred at 50° C. for 12 hours under nitrogen atmosphere. Saturated sodium bicarbonate aqueous solution (50 mL) was added to the mixture and the mixture was extracted with dichloromethane (50 mL×3). The organic layers were combined and washed with saturated brine (25 mL×2), dried over anhydrous sodium sulfate, filtered and the filtrate was concentrated with reduced pressure. The residue was isolated and purified by silica gel column chromatography (0:1 petroleum ether/ethyl acetate, $R_f$=0.2) to give compound 8-7 (800 mg, white solid); yield: 92%.

$^1$H NMR: (400 MHz, DMSO-d$_6$) δ 8.51 (d, J=2.0 Hz, 1H), 8.41 (d, J=8.0 Hz, 1H), 8.32 (d, J=2.0 Hz, 1H), 8.06 (d, J=8.0 Hz, 1H), 7.57-7.50 (m, 3H), 5.02 (d, J=7.2 Hz, 1H), 5.00-4.97 (m, 1H), 3.59-3.57 (m, 2H), 3.17-3.12 (m, 1H), 2.77-2.76 (m, 1H), 2.08-2.02 (m, 1H), 1.38 (d, J=6.0 Hz, 6H). MS-ESI [M+H]$^+$: calculated value: 401; measured value: 401.

Step 6

Compound 8-7 (50.0 mg, 0.125 mmol) was dissolved in N,N-dimethylformamide (3 mL), and sodium hydride (10.0 mg, 0.250 mmol, 60% purity) was added in batches at 0° C. The reaction was stirred for 30 minutes at this temperature. Then, ethyl bromoacetate (31.3 mg, 0.187 mmol) was added to the reaction mixture, and the mixture was stirred at 25° C. for 1 hour. Water (10 mL) was added to the reaction mixture and the mixture was extracted with ethyl acetate (20 mL×3). The organic layer were combined and washed with saturated brine (10 mL×2), dried over anhydrous sodium sulfate, filtered and the filtrate was concentrated with reduced pressure. The residue was isolated and purified by TLC (0:1 petroleum ether/ethyl acetate, $R_f$=0.3) to give compound 8-8 (50.0 mg, white solid); yield: 82%. MS-ESI [M+H]$^+$: calculated value: 487; measured value: 487.

Step 7

Compound 8-8 (50.0 mg, 0.103 mmol) was dissolved in tetrahydrofuran (4 mL) and water (1 mL), and lithium hydroxide monohydrate (8.6 mg, 0.206 mmol) was added. The reaction was stirred at 25° C. for 12 hours under nitrogen atmosphere. The mixture was cooled and concentrated under reduced pressure. The residue was isolated and purified by high performance liquid chromatography to give compound 8-9 (25.0 mg); yield: 53%.

$^1$H NMR: (400 MHz, Methonal-d$_4$) δ 8.48-8.43 (m, 2H), 8.20 (d, J=7.2 Hz, 1H), 7.63 (d, J=7.2 Hz, 1H), 7.51-7.45 (m, 2H), 5.20 (d, J=7.2 Hz, 1H), 4.97-4.95 (m, 1H), 4.34-4.30 (m, 1H), 3.90-3.82 (m, 2H), 3.39-3.38 (m, 1H), 3.18-3.14 (m, 1H), 2.95-2.89 (m, 1H), 2.56-2.51 (m, 1H), 1.47 (d, J=6.0 Hz, 6H). MS-ESI [M+H]$^+$: calculated value: 459; measured value: 459.

Example 9

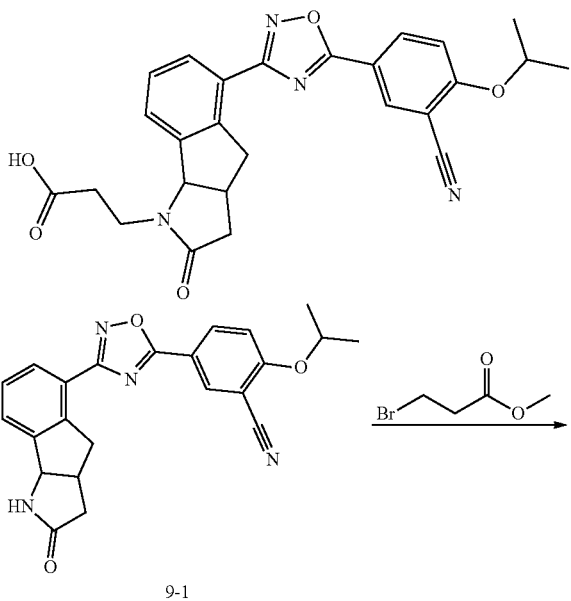

added to the reaction mixture and the mixture was extracted with ethyl acetate (20 mL×3). The organic layers were combined and washed with saturated brine (10 mL×2), dried over anhydrous sodium sulfate, filtered and the filtrate was concentrated with reduced pressure. The residue was isolated and purified by TLC (0:1 petroleum ether/ethyl acetate, $R_f$=0.3) to give compound 9-2 (30.0 mg, white solid); yield: 62%. MS-ESI [M+H]$^+$: calculated value: 487; measured value: 487.

Step 2

Compound 9-2 (30.0 mg, 0.0617 mmol) was dissolved in methanol (3 mL) and water (1 mL), and lithium hydroxide monohydrate (5.2 mg, 0.123 mmol) was added. The reaction was stirred at 25° C. for 12 hours under nitrogen atmosphere. The mixture was cooled and concentrated under reduced pressure. The residue was isolated and purified by high performance liquid chromatography to give compound 9-3 (20.0 mg); yield: 69%.

$^1$H NMR: (400 MHz, Methonal-d$_4$) δ 8.48-8.43 (m, 2H), 8.21 (d, J=7.6 Hz, 1H), 7.84 (d, J=7.6 Hz, 1H), 7.52-7.45 (m, 2H), 5.20 (d, J=7.2 Hz, 1H), 4.98-4.97 (m, 1H), 3.86-3.79 (m, 2H), 3.49-3.47 (m, 1H), 3.30-3.29 (m, 1H), 3.16-3.14 (m, 1H), 2.88-2.82 (m, 1H), 2.74-2.70 (m, 1H), 2.48-2.43 (m, 2H), 1.47 (d, J=6.0 Hz, 6H). MS-ESI [M+H]$^+$: calculated value: 473; measured value: 473.

Example 10

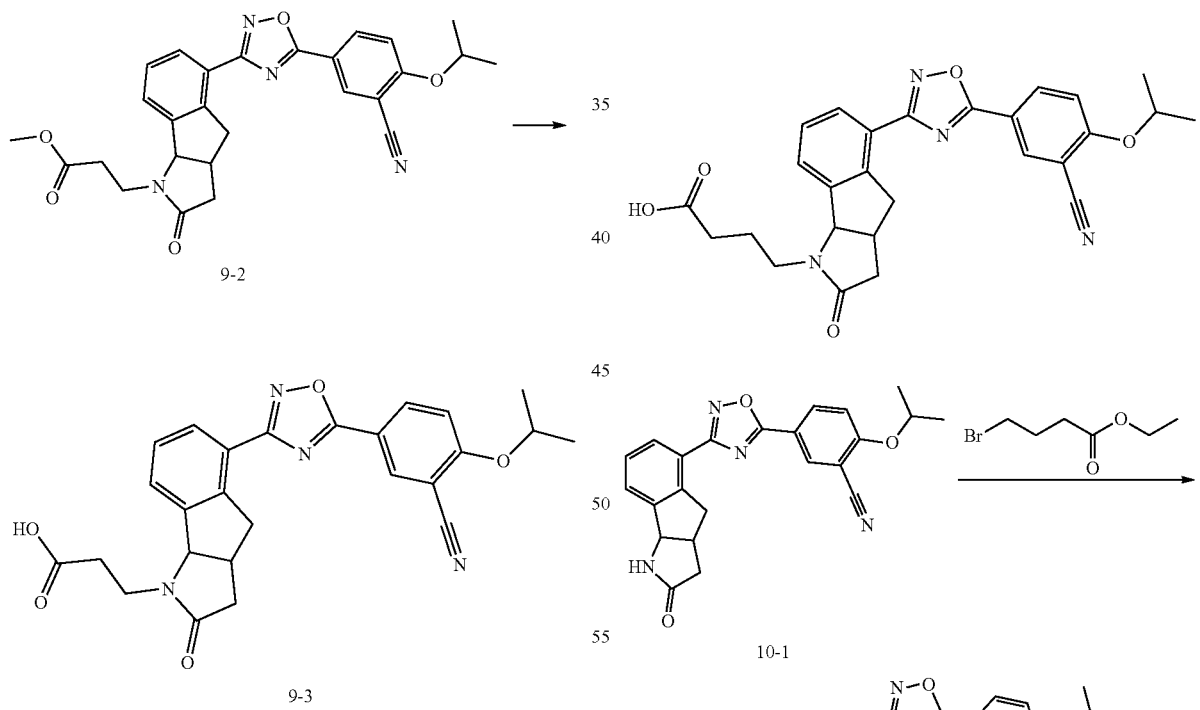

Step 1

Compound 9-1 (40.0 mg, 0.100 mmol) was dissolved in anhydrous N,N-dimethylformamide (3 mL), and sodium hydrogen (8.0 mg, 0.200 mmol, 60% purity) was added in batches at 0° C. The reaction was stirred at this temperature for 30 minutes. Then, methyl bromopropionate (25.0 mg, 0.150 mmol) was added to the reaction mixture, and the mixture was stirred at 25° C. for 1 hour. Water (10 mL) was

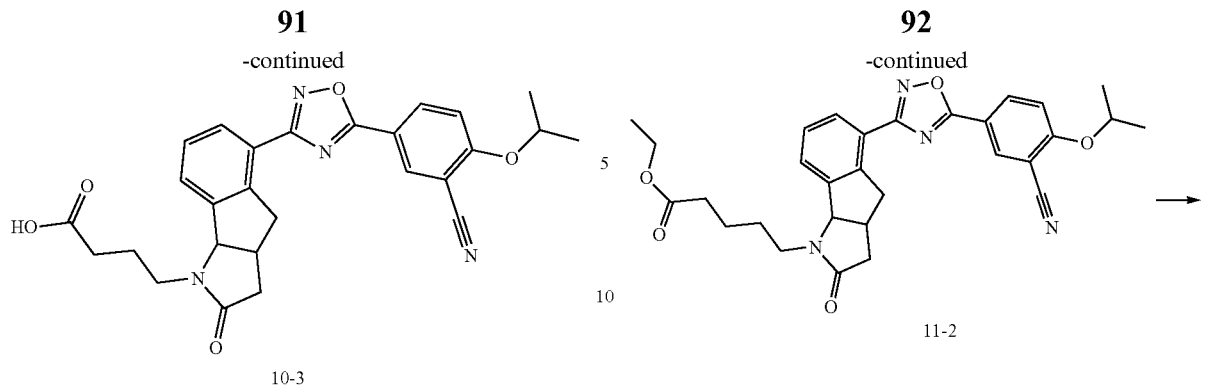

10-3

Step 1

The reaction referred to Step 6 of Example 8, and the residue was isolated and purified by TLC (0:1 petroleum ether/ethyl acetate, $R_f$=0.3) to give compound 10-2 (80 mg, white solid); yield: 62%. MS-ESI [M+H]$^+$: calculated value: 515; measured value: 515.

Step 2

The reaction referred to Step 7 of Example 8, and the residue was isolated and purified by high performance liquid chromatography to give compound 10-3 (30.0 mg); yield: 40%.

$^1$H NMR: (400 MHz, Methonal-d$_4$) δ 8.48-8.43 (m, 2H), 8.21 (d, J=7.2 Hz, 1H), 7.77 (d, J=7.2 Hz, 1H), 7.52-7.45 (m, 2H), 5.17 (d, J=7.2 Hz, 1H), 4.98-4.97 (m, 1H), 3.87-3.85 (m, 1H), 3.82-3.80 (m, 1H), 3.19-3.14 (m, 3H), 2.90-2.83 (m, 1H), 2.48-2.36 (m, 3H), 1.97-1.96 (m, 1H), 1.86-1.84 (m, 1H), 1.47 (d, J=6.0 Hz, 6H). MS-ESI [M+H]$^+$: calculated value: 487; measured value: 487.

Example 11

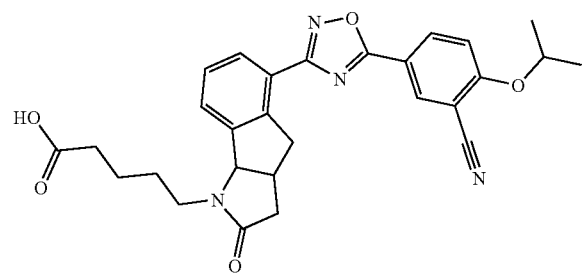

11-1

11-2

11-3

Step 1

The reaction referred to Step 6 of Example 8, and the residue was isolated and purified by TLC (0:1 petroleum ether/ethyl acetate, $R_f$=0.3) to give compound 11-2 (40.0 mg, white solid); yield: 87%. MS-ESI [M+H]$^+$: calculated value: 529; measured value: 529.

Step 2

The reaction referred to Step 7 of Example 8, and the residue was isolated and purified by high performance liquid chromatography to give compound 11-3 (15.0 mg); yield: 40%.

$^1$H NMR: (400 MHz, Methonal-d$_4$) δ 8.47-8.42 (m, 2H), 8.20 (d, J=7.2 Hz, 1H), 7.71 (d, J=7.2 Hz, 1H), 7.52-7.44 (m, 2H), 5.16 (d, J=7.2 Hz, 1H), 4.98-4.97 (m, 1H), 3.86-3.79 (m, 1H), 3.63-3.62 (m, 1H), 3.13-3.09 (m, 2H), 2.88-2.84 (m, 1H), 2.49-2.44 (m, 1H), 2.37-2.35 (m, 2H), 1.64-1.59 (m, 5H), 1.47 (d, J=6.0 Hz, 6H). MS-ESI [M+H]$^+$: calculated value: 501; measured value: 501.

Example 12

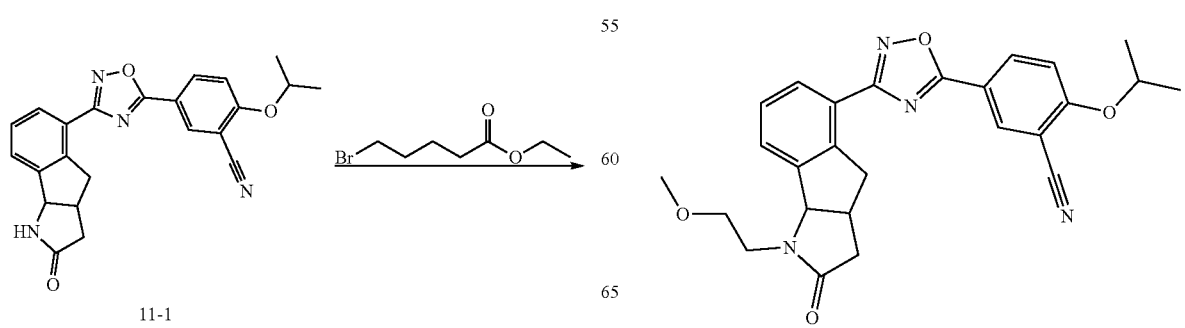

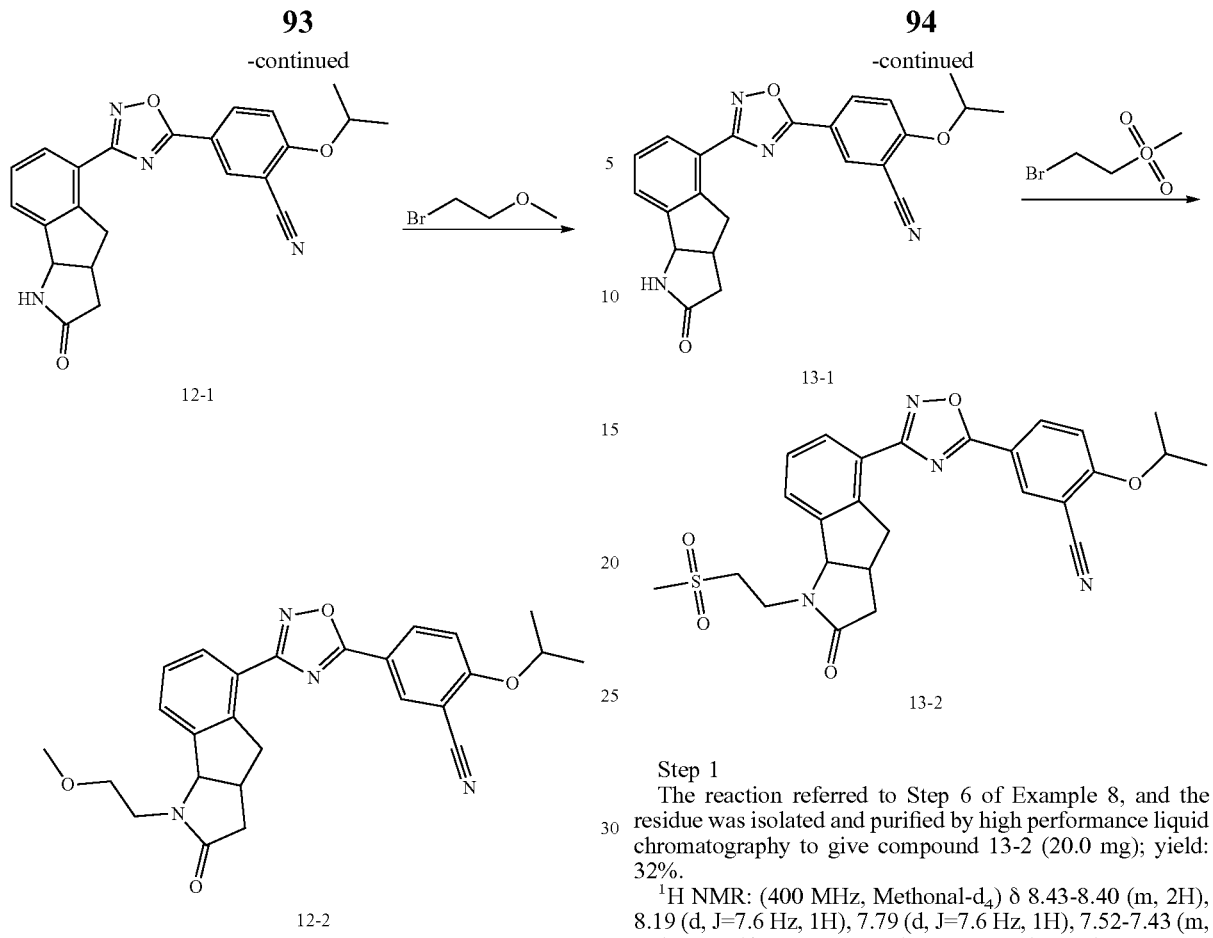

Step 1

The reaction referred to Step 6 of Example 8, and the residue was isolated and purified by high performance liquid chromatography to give compound 12-2 (20.0 mg); yield: 35%.

$^1$H NMR: (400 MHz, Methonal-d$_4$) δ 8.48-8.43 (m, 2H), 8.20 (d, J=7.6 Hz, 1H), 7.79 (d, J=7.6 Hz, 1H), 7.50-7.45 (m, 2H), 5.26 (d, J=7.2 Hz, 1H), 4.97-4.95 (m, 1H), 3.86-3.79 (m, 2H), 3.62-3.58 (m, 2H), 3.41 (s, 3H), 3.24-3.22 (m, 2H), 3.12-3.10 (m, 1H), 2.91-2.84 (m, 1H), 2.49-2.44 (m, 1H), 1.47 (d, J=6.0 Hz, 6H). MS-ESI [M+H]$^+$: calculated value: 459; measured value: 459.

Example 13

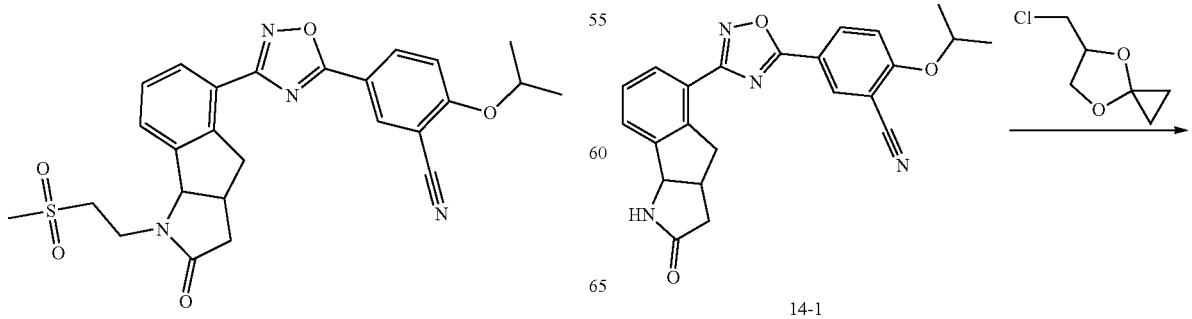

Step 1

The reaction referred to Step 6 of Example 8, and the residue was isolated and purified by high performance liquid chromatography to give compound 13-2 (20.0 mg); yield: 32%.

$^1$H NMR: (400 MHz, Methonal-d$_4$) δ 8.43-8.40 (m, 2H), 8.19 (d, J=7.6 Hz, 1H), 7.79 (d, J=7.6 Hz, 1H), 7.52-7.43 (m, 2H), 5.24 (d, J=7.2 Hz, 1H), 4.96-4.94 (m, 1H), 4.05-4.02 (m, 1H), 3.80-3.78 (m, 1H), 3.54-3.49 (m, 2H), 3.36-3.34 (m, 2H), 3.12-3.06 (m, 4H), 2.88-2.82 (m, 1H), 2.49-2.44 (m, 1H), 1.47 (d, J=6.0 Hz, 6H). MS-ESI [M+H]$^+$: calculated value: 507; measured value: 507.

Example 14

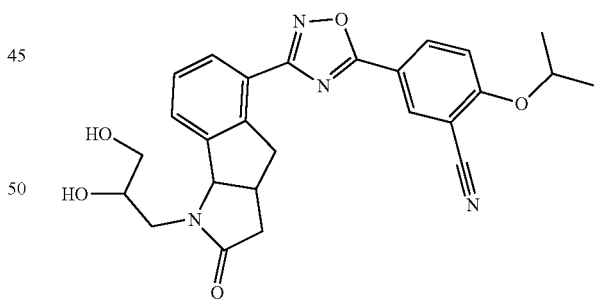

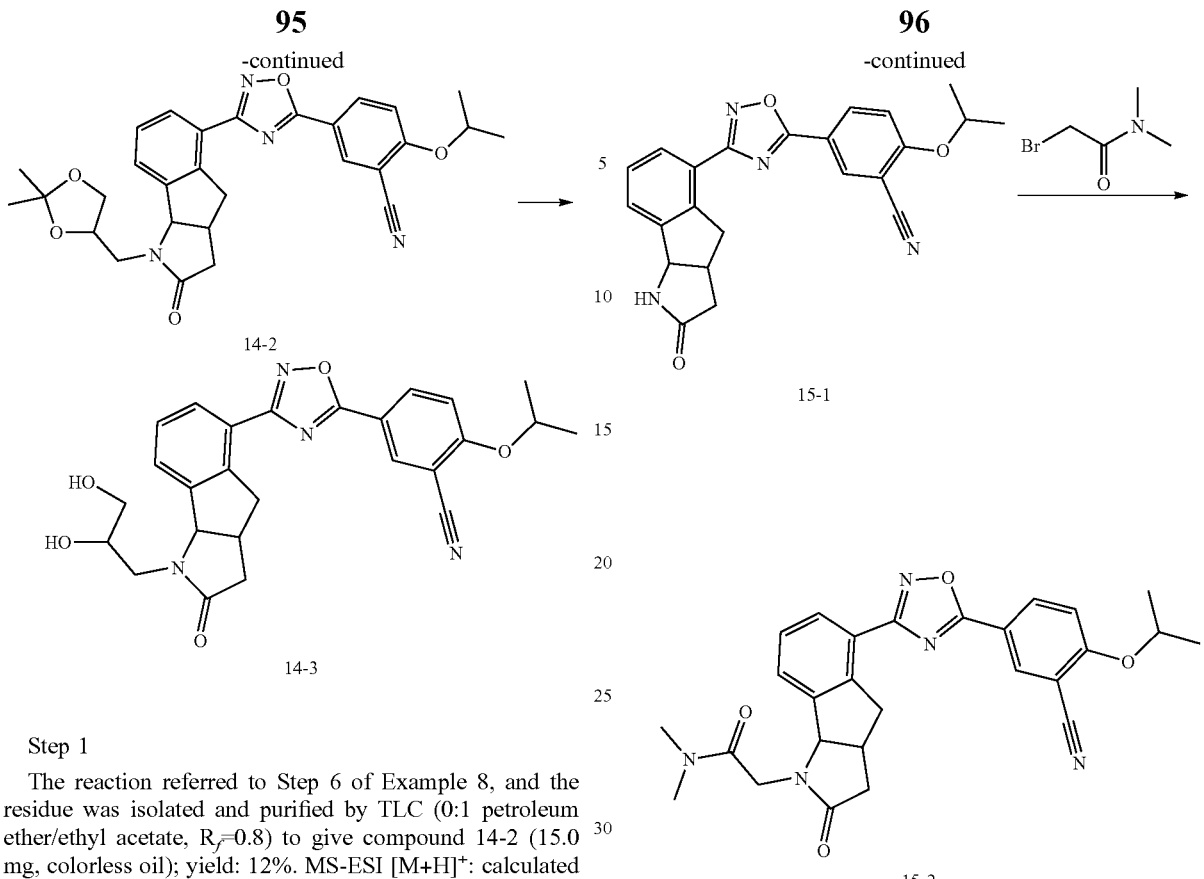

Step 1

The reaction referred to Step 6 of Example 8, and the residue was isolated and purified by TLC (0:1 petroleum ether/ethyl acetate, $R_f$=0.8) to give compound 14-2 (15.0 mg, colorless oil); yield: 12%. MS-ESI [M+H]$^+$: calculated value: 515; measured value: 515.

Step 2

Compound 14-2 (15.0 mg, 0.0292 mmol) was dissolved in tetrahydrofuran (1 mL), and hydrochloric acid (1 M, 0.75 mL) was added to the mixture. The reaction was stirred at 60° C. for 30 minutes under nitrogen atmosphere. The mixture was cooled and concentrated under reduced pressure. The residue was isolated and purified by high performance liquid chromatography to give compound 14-3 (5.0 mg); yield: 36%.

$^1$H NMR: (400 MHz, Methonal-d$_4$) δ 8.48-8.43 (m, 2H), 8.20 (d, J=7.6 Hz, 1H), 7.82 (d, J=7.6 Hz, 1H), 7.52-7.45 (m, 2H), 5.35 (d, J=7.2 Hz, 1H), 4.97-4.96 (m, 1H), 3.93-3.91 (m, 1H), 3.87-3.84 (m, 1H), 3.73-3.69 (m, 1H), 3.56-3.53 (m, 2H), 3.28-3.26 (m, 2H), 3.12-3.10 (m, 1H), 2.93-2.90 (m, 1H), 2.50-2.48 (m, 1H), 1.47 (d, J=6.0 Hz, 6H). MS-ESI [M+H]$^+$: calculated value: 475; measured value: 475.

Step 1

The reaction referred to Step 6 of Example 8, and the residue was isolated and purified by high performance liquid chromatography to give compound 15-2 (25.0 mg); yield: 41%.

$^1$H NMR: (400 MHz, Methonal-d$_4$) δ 8.48-8.43 (m, 2H), 8.20 (d, J=7.6 Hz, 1H), 7.64 (d, J=7.6 Hz, 1H), 7.50-7.45 (m, 2H), 5.19 (d, J=7.2 Hz, 1H), 4.98-4.97 (m, 1H), 4.53-4.49 (m, 1H), 3.93-3.82 (m, 2H), 3.39-3.38 (m, 1H), 3.18-3.10 (m, 4H), 2.98-2.91 (m, 4H), 2.55-2.50 (m, 1H), 1.47 (d, J=6.0 Hz, 6H). MS-ESI [M+H]$^+$: calculated value: 486; measured value: 486.

Example 16

Example 15

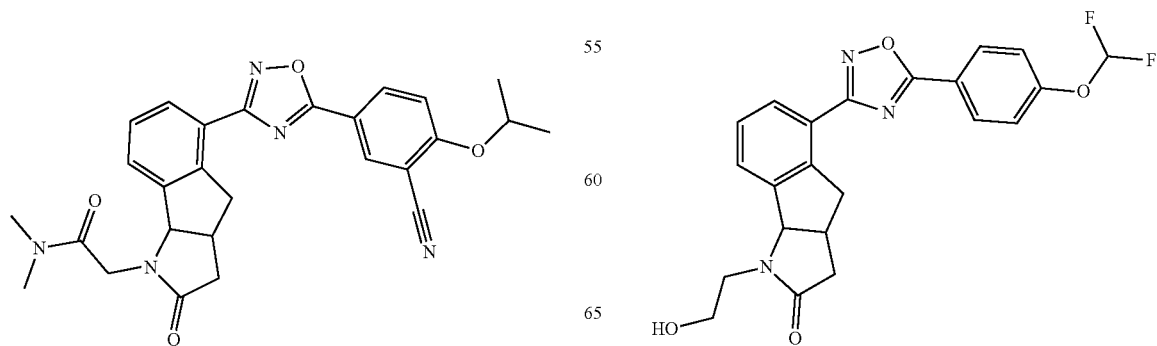

-continued

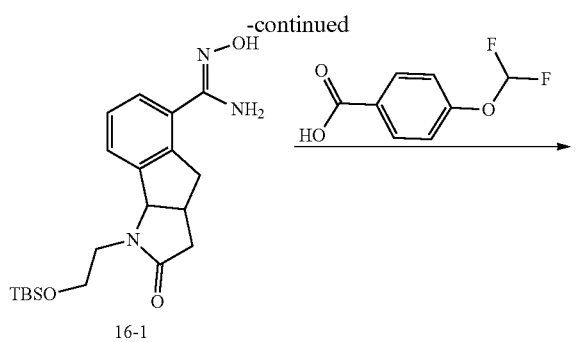

Example 17

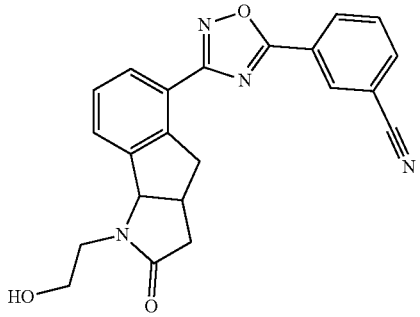

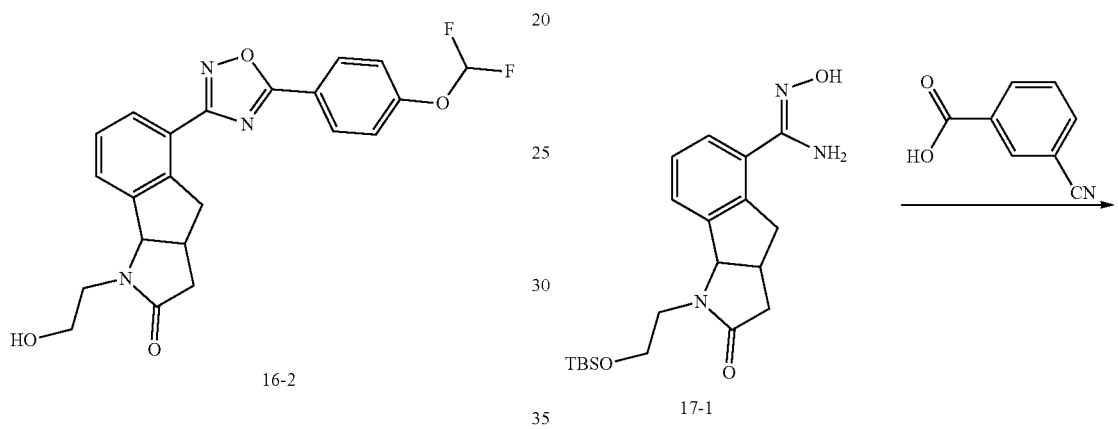

Step 1

4-(Difluoromethoxy)benzoic acid (29.0 mg, 154 umol) was dissolved in anhydrous N,N-dimethylformamide (0.2 mL), and 1-(3-dimethylaminopropyl)-3-ethylcarbodiimide (44.3 mg, 0.231 mmol), 1-hydroxybenzotriazole (41.6 mg, 0.308 mmol) were added at 20° C. under nitrogen atmosphere. The reaction was stirred at 20° C. for 1 hour. Then, Compound 16-1 (60.0 mg, 0.154 mmol) was added in N,N-dimethylformamide (0.3 mL) to the reaction mixture, and the mixture was stirred at 20° C. for 1 hour, then heated to 85° C. and stirred for 10 hours. The mixture was quenched with saturated sodium chloride aqueous solution (20 mL) and extracted with ethyl acetate (50 mL×3). The organic layer was washed with saturated brine (20 mL×3), dried over anhydrous sodium sulfate, filtered and the filtrate was concentrated with reduced pressure, then isolated and purified by high performance liquid chromatography to give compound 16-2 (50.0 mg); yield: 76%.

$^1$H NMR: (400 MHz, Methonal-$d_4$) δ 8.26 (d, J=8.8 Hz, 2H), 8.18 (d, J=7.6 Hz, 1H), 7.76 (d, J=7.6 Hz, 1H), 7.47 (t, J=7.6 Hz, 1H), 7.37 (d, J=8.8 Hz, 2H), 7.04 (t, J=73.2 Hz, 1H), 5.24 (d, J=7.2 Hz, 1H), 3.79-3.69 (m, 4H), 3.31-3.12 (m, 3H), 2.91-2.84 (m, 1H), 2.46-2.42 (m, 1H).

MS-ESI [M+H]$^+$: calculated value: 428; measured value: 428.

Step 1

The reaction referred to Step 1 of Example 16, and the residue was isolated and purified by high performance liquid chromatography to give compound 17-2 (55.0 mg); yield: 70%.

$^1$H NMR: (400 MHz, Methonal-$d_4$) δ 8.58 (s, 1H), 8.52 (d, J=8.0 Hz, 1H), 8.22 (d, J=8.0 Hz, 1H), 8.06 (d, J=8.0 Hz, 1H), 7.85 (d, J=8.0 Hz, 1H), 7.80 (t, J=8.0 Hz, 1H), 7.52 (t, J=8.0 Hz, 1H), 5.27 (d, J=7.2 Hz), 1H), 3.79-3.72 (m, 4H), 3.34-3.12 (m, 3H), 2.91-2.86 (m, 1H), 2.49-2.45 (m, 1H).

MS-ESI [M+H]$^+$: calculated value: 387; measured value: 387.

Example 18

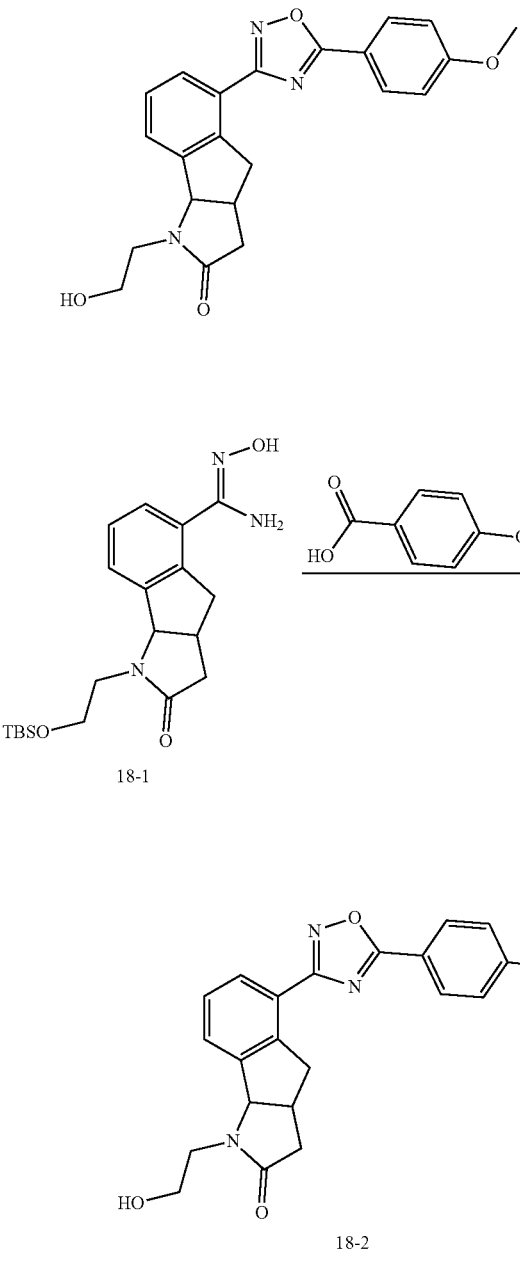

Step 1

4-Methoxybenzoic acid (19.5 mg, 0.128 mmol) was dissolved in anhydrous N,N-dimethylformamide (2.00 mL), and 1-hydroxybenzotriazole (34.6 mg, 0.256 mmol) and 1-ethyl-(3-dimethylaminopropyl)carbonyldiimide hydrochloride (36.9 mg, 0.192 mmol) were added. The reaction was stirred at 25° C. for 1 hour. Then, Compound 18-1 (50.0 mg, 0.128 mmol) was added to the reaction mixture, and the mixture was stirred at 25° C. for 1 hour, then stirred at 90° C. for 12 hours under nitrogen atmosphere. The mixture was quenched with saturated sodium chloride aqueous solution (20 mL) and extracted with ethyl acetate (50 mL×3). The organic layer was washed with saturated brine (20 mL×3), dried over anhydrous sodium sulfate, filtered and the filtrate was concentrated under reduced pressure. The residue was isolated and purified by high performance liquid chromatography to give compound 18-2 (3.0 mg); yield: 6%.

$^1$H NMR: (400 MHz, DMSO-$d_6$) δ 8.22-8.04 (m, 3H), 7.78 (d, J=7.6 Hz, 1H), 7.50 (t, J=7.6 Hz, 1H), 7.20 (d, J=8.4 Hz, 2H), 5.15 (d, J=7.2 Hz, 1H), 3.89 (s, 3H), 3.74-3.46 (m, 3H), 3.22-3.20 (m, 2H), 3.06-2.92 (m, 2H), 2.75-2.63 (m, 1H), 2.31-2.28 (m, 1H). MS-ESI [M+H]$^+$: calculated value: 392; measured value: 392.

Example 19

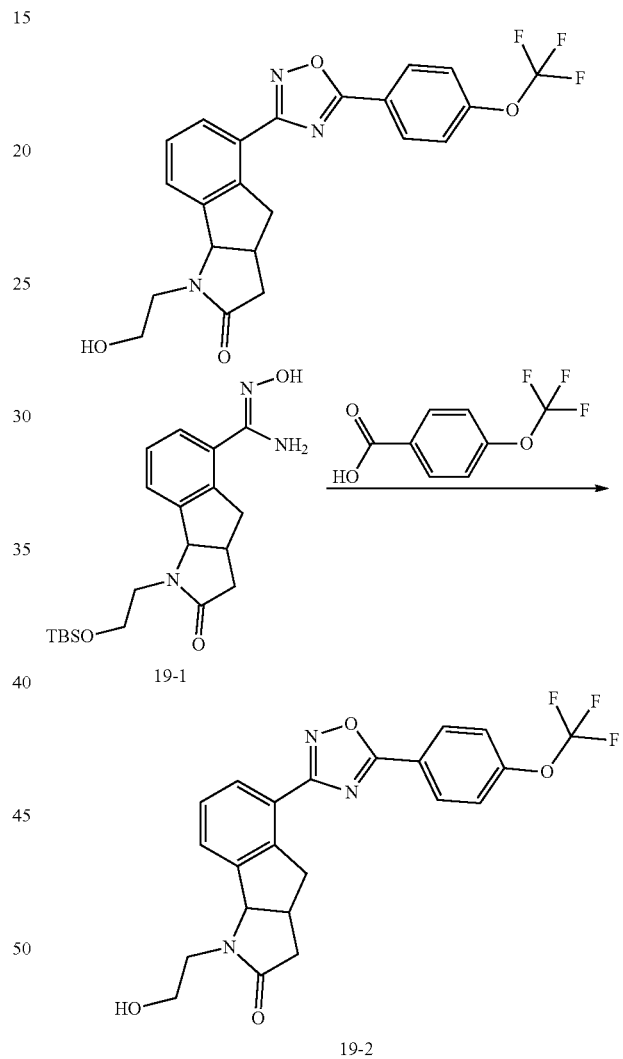

The reaction referred to Step 1 of Example 16, and the residue was isolated and purified by high performance liquid chromatography to give compound 19-2 (14.0 mg); yield: 25%.

$^1$H NMR: (400 MHz, DMSO-$d_6$) δ 8.34 (d, J=8.4 Hz, 2H), 8.11 (d, J=7.2 Hz, 1H), 7.81 (d, J=7.2 Hz, 1H), 7.68 (d, J=8.4 Hz, 2H), 7.52 (t, J=7.2 Hz, 1H), 5.17 (d, J=7.2 Hz, 1H), 4.87 (t, J=5.2 Hz, 1H), 3.76-3.46 (m, 4H), 3.26-3.17 (m, 1H), 3.06-2.95 (m, 2H), 2.74-2.67 (m, 1H), 2.34-2.28 (m, 1H). MS-ESI [M+H]$^+$: calculated value: 446; measured value: 446.

Example 20

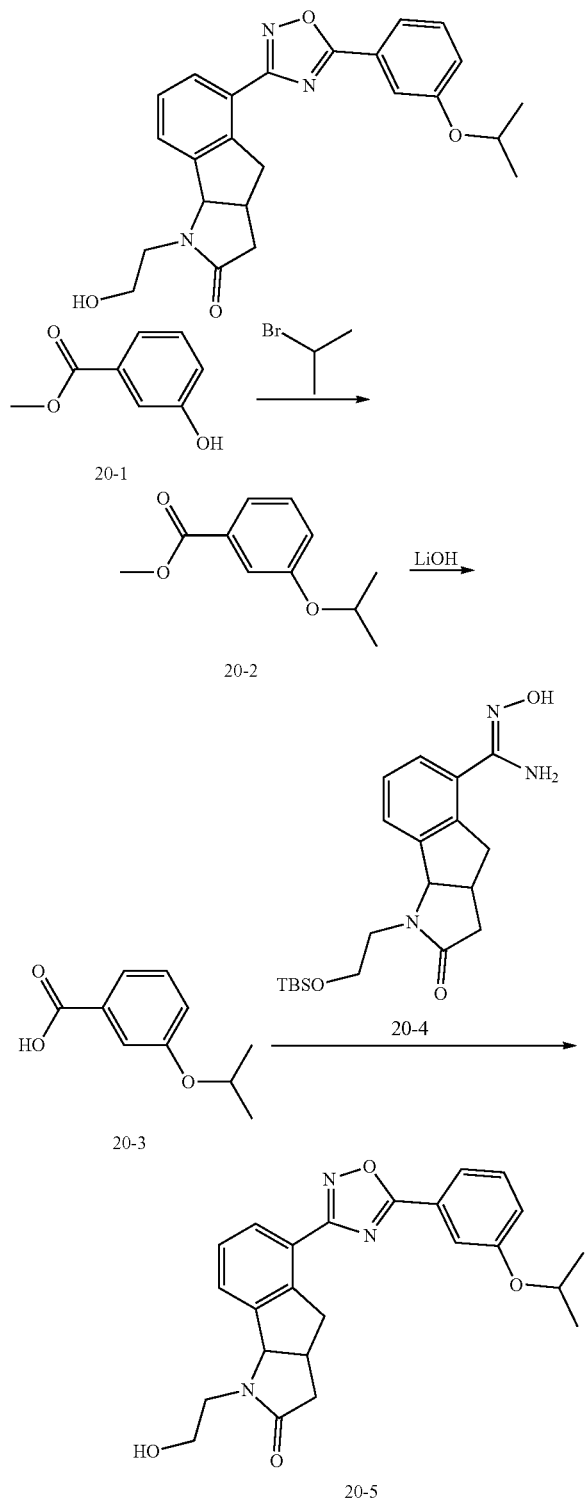

Step 1
Compound 20-1 (1.00 g, 6.57 mmol) was dissolved in N,N-dimethylformamide (10 mL), and isopropyl bromide (1.62 g, 13.1 mmol) and potassium carbonate (2.27 g, 16.4 mmol) were add. The reaction was stirred at 65° C. for 3 hours under nitrogen atmosphere. Water (30 mL) was added to the reaction mixture after the mixture was cooled to 25° C. and the mixture was extracted with ethyl acetate (50 mL×3). The combined organic layer was washed with saturated brine (40 mL×4), dried over anhydrous sodium sulfate and concentrated under reduced pressure. The residue was subject to silica gel column chromatography (10:1 petroleum ether/ethyl acetate, $R_f$=0.5) to give compound 20-2 (1.10 g, colorless oil); yield: 86%.

$^1$H NMR: (400 MHz, CDCl$_3$) δ 7.61 (d, J=7.6 Hz, 1H), 7.50 (s, 1H), 7.33 (t, J=7.6 Hz, 1H), 7.07 (d, J=7.6 Hz, 1H), 4.65-4.60 (m, 1H), 3.92 (s, 3H), 1.36 (d, J=6.0 Hz, 6H).

Step 2
Compound 20-2 (1.10 g, 5.66 mmol) was dissolved in tetrahydrofuran (10 mL), and aqueous lithium hydroxide (712 mg, 16.9 mmol) solution (2 mL) was added. The reaction was stirred at 50° C. for 4 hours. The solution was acidified with 1 M hydrochloric acid to pH=4 after the mixture was cooled to 25° C.; and the mixture was extracted with ethyl acetate (40 mL×2). The combined organic layer was washed with saturated brine (20 mL×2), dried over anhydrous sodium sulfate and concentrated under reduced pressure to give compound 20-3 (880 mg, yellow solid); yield: 86%.

$^1$H NMR: (400 MHz, Methonal-d$_4$) δ 7.61 (d, J=7.6 Hz, 1H), 7.50 (s, 1H), 7.33 (t, J=7.6 Hz, 1H), 7.07 (d, J=7.6 Hz, 1H), 4.65-4.60 (m, 1H), 1.36 (d, J=6.0 Hz, 6H).

Step 3
Compound 20-3 (23.1 mg, 0.128 mmol) was dissolved in N,N-dimethylformamide (2 mL), and 1-hydroxybenzotriazole (34.6 mg, 0.256 mmol) and 1-ethyl-(3-dimethylaminopropyl)carbodiimide hydrochloride (36.9 mg, 0.192 mmol) were added. The reaction was stirred at 25° C. for 1 hour. Then, Compound 20-4 (50.0 mg, 0.128 mmol) was added, and the mixture was stirred at 25° C. for 1 hour, then heated to 80° C. and stirred for 10 hours under nitrogen atmosphere. The mixture was quenched with saturated aqueous sodium chloride solution (20 mL) and extracted with ethyl acetate (50 mL×3). The organic layer was washed with saturated brine (20 mL×3), dried over anhydrous sodium sulfate, filtered and the filtrate was concentrated under reduced pressure. The residue was isolated and purified by high performance liquid chromatography to give compound 20-5 (10.0 mg); yield: 18%.

$^1$H NMR: (400 MHz, Methonal-d$_4$) δ 8.18 (d, J=7.6 Hz, 1H), 7.78-7.68 (m, 3H), 7.54-7.45 (m, 2H), 7.22 (d, J=7.6 Hz, 1H), 5.25 (d, J=7.2 Hz, 1H), 4.79-4.66 (m, 1H), 3.97-3.62 (m, 5H), 3.27-3.18 (m, 1H), 3.13-3.07 (m, 1H), 2.91-2.85 (m, 1H), 2.46-2.43 (m, 1H), 1.39 (d, J=6.0 Hz, 6H). MS-ESI [M+H]$^+$: calculated value: 420; measured value: 420.

Example 21

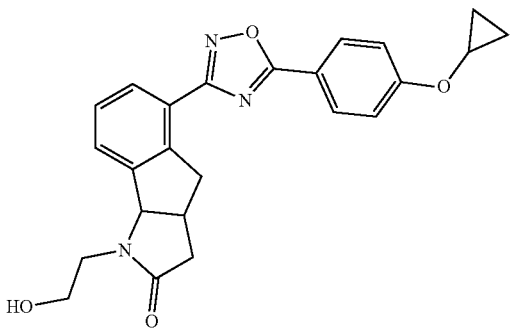

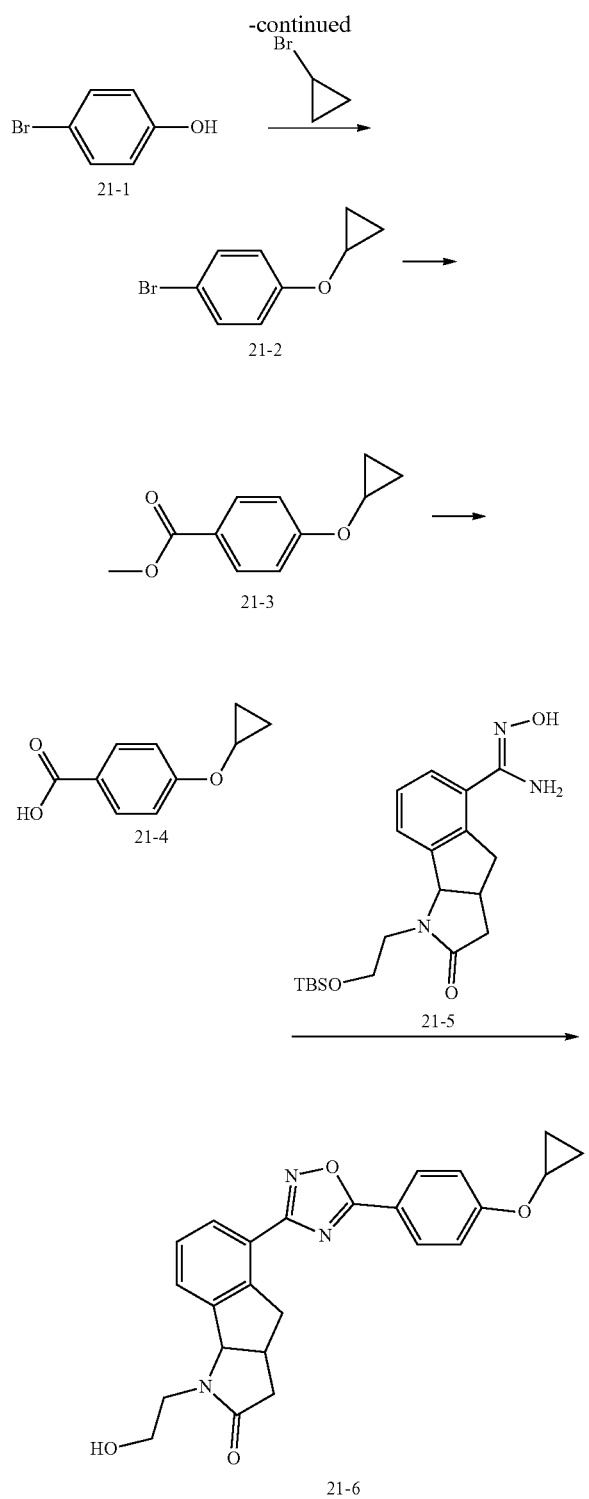

Step 1

Compound 21-1 (2.00 g, 11.5 mmol) was dissolved in N-methylpyrrolidone (40 mL), and cyclopropyl bromide (2.80 g, 23.1 mmol) and cesium carbonate (9.42 g, 28.9 mmol) were added. The reaction was stirred at 130° C. for 16 hours under nitrogen atmosphere. Water (30 mL) was added to the reaction mixture after the mixture was cooled to 25° C.; and the mixture was extracted with ethyl acetate (50 mL×3). The combined organic layer was washed with saturated brine (40 mL×4), dried over anhydrous sodium sulfate and concentrated under reduced pressure. The residue was subject to silica gel column chromatography (petroleum ether, $R_f$=0.5) to give compound 21-2 (1.20 g, colorless oil); yield: 48%.

$^1$H NMR: (400 MHz, CDCl$_3$) δ 7.38 (d, J=9.2 Hz, 2H), 6.93 (d, J=9.2 Hz, 2H), 3.77-3.61 (m, 1H), 0.83-0.70 (m, 4H).

Step 2

Compound 21-2 (1.20 g, 5.63 mmol) was dissolved in methanol (30 mL), and triethylamine (2.85 g, 28.1 mmol) and 1,1′-[bis(diphenylphosphino)ferrocene]dichloropalladium(II) (205 mg, 281 umol) were added. The reaction was stirred at 70° C. for 12 hours under carbon monoxide atmosphere (50 psi). The reaction mixture was filtered with diatomite after cooled to 25° C. and then concentrated under reduced pressure. The residue was subject to silica gel column chromatography (10:1 petroleum ether/ethyl acetate, $R_f$=0.5) to give compound 21-3 (20 mg, colorless oil); yield: 2%.

$^1$H NMR: (400 MHz, CDCl$_3$) δ 7.99 (d, J=9.2 Hz, 2H), 7.07 (d, J=9.2 Hz, 2H), 3.89 (s, 3H), 3.81-3.77 (m, 1H), 0.86-0.75 (m, 4H).

Step 3

Compound 21-3 (20.0 mg, 0.104 mmol) was dissolved in tetrahydrofuran (1 mL), and aqueous lithium hydroxide (13.1 mg, 0.312 mmol) solution (1 mL) was added. The reaction was stirred at 50° C. for 4 hours. The solution was acidified with 1 M hydrochloric acid to pH=4 after cooled to 25° C. and then the mixture was extracted with ethyl acetate (40 mL×2). The combined organic layer was washed with saturated brine (20 mL×2), dried over anhydrous sodium sulfate and concentrated under reduced pressure to give compound 21-4 (14.0 mg, white solid); yield: 75%.

$^1$H NMR: (400 MHz, Methanol-d$_4$) δ 7.86 (d, J=9.2 Hz, 2H), 7.00 (d, J=9.2 Hz, 2H), 3.77-3.72 (m, 1H), 0.78-0.68 (m, 2H), 0.64-0.53 (m, 2H).

Step 4

Compound 21-4 (13.7 mg, 0.0770 mmol) was dissolved in N,N-dimethylformamide (2 mL), and 1-hydroxybenzotriazole (20.8 mg, 0.154 mmol) and 1-ethyl-(3-dimethylaminopropyl)carbonyldiimide hydrochloride (22.1 mg, 0.115 mmol) were added. The reaction was stirred at 25° C. for 1 hour. Then, Compound 21-5 (30.0 mg, 0.770 mmol) was added, and the mixture was stirred at 25° C. for 1 hour, then 80° C. for 10 hours under nitrogen atmosphere. The mixture was quenched with saturated aqueous sodium chloride solution (20 mL) and extracted with ethyl acetate (50 mL×3). The organic layer was washed with saturated brine (20 mL×3), dried over anhydrous sodium sulfate, filtered and the filtrate was concentrated under reduced pressure. The residue was purified by high performance liquid chromatography to give compound 21-6 (1.0 mg); yield: 3%.

$^1$H NMR: (400 MHz, Methonal-d$_4$) δ 8.25-8.13 (m, 3H), 7.77 (d, J=7.6 Hz, 1H), 7.49 (t, J=7.6 Hz, 1H), 7.29 (d, J=9.2 Hz, 2H), 5.26 (d, J=7.2 Hz, 1H), 3.95-3.93 (m, 1H), 3.85-3.70 (m, 4H), 3.30-3.19 (m, 2H), 3.13-3.11 (m, 1H), 2.90-2.88 (m, 1H), 2.48-2.43 (m, 1H), 0.93-0.85 (m, 2H), 0.81-0.74 (m, 2H). MS-ESI [M+H]$^+$: calculated value: 418; measured value: 418.

Example 22

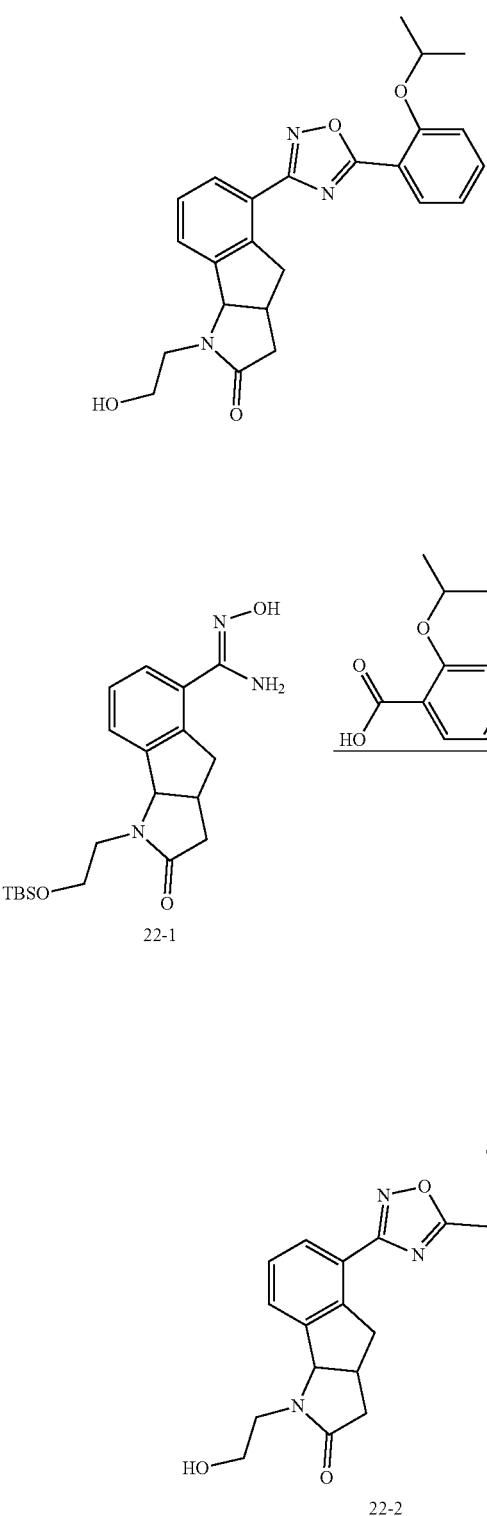

The reaction referred to Step 1 of Example 16, and the residue was isolated and purified by high performance liquid chromatography to give compound 22-4 (6.0 mg); yield: 11%.

$^1$H NMR: (400 MHz, Methonal-d$_4$) δ 8.20 (d, J=8.0 Hz, 1H), 8.20 (d, J=8.0 Hz, 1H), 7.77 (d, J=8.0 Hz, 1H), 7.61 (t, J=8.0 Hz, 1H), 7.50 (t, J=8.0 Hz, 1H), 7.28 (d, J=8.0 Hz, 1H), 7.14 (t, J=8.0 Hz, 1H), 5.27 (d, J=7.2 Hz, 1H), 4.85-4.79 (m, 2H), 3.90-3.70 (m, 4H), 3.27-3.11 (m, 2H), 2.92-2.86 (m, 1H), 2.48-2.43 (m, 1H), 1.44 (d, J=6.0 Hz, 6H). MS-ESI [M+H]$^+$: calculated value: 420; measured value: 420.

Example 23

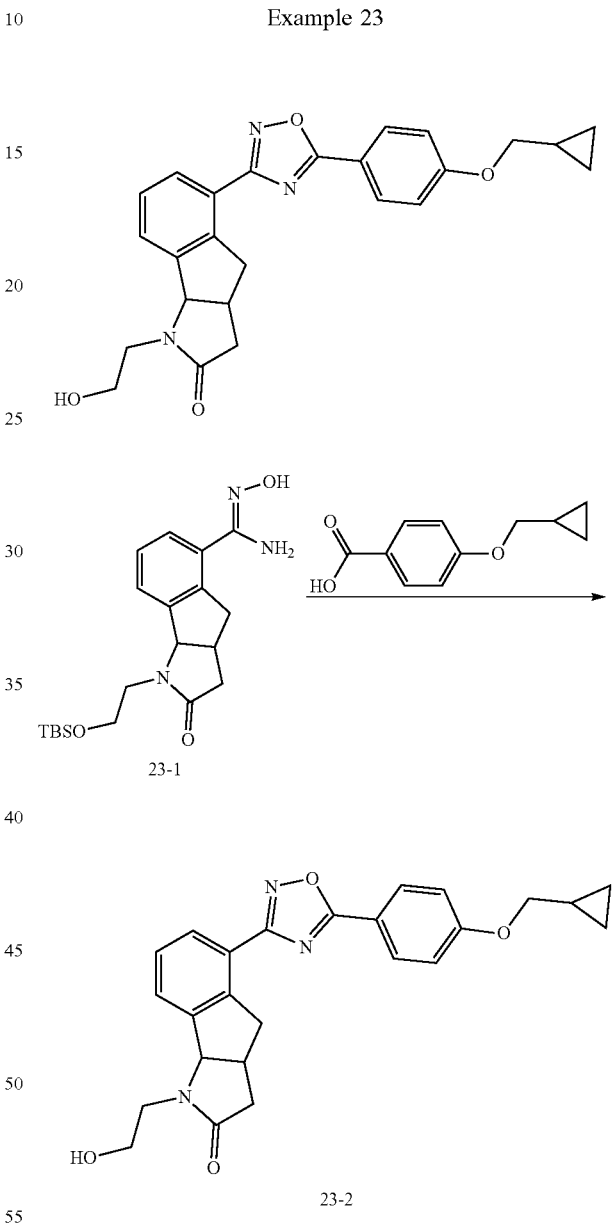

The reaction referred to Step 1 of Example 16, and the residue was isolated and purified by high performance liquid chromatography to give compound 23-2 (30.0 mg); yield: 45%.

$^1$H NMR: (400 MHz, Methonal-d$_4$) δ 8.18-8.13 (m, 3H), 7.75 (d, J=7.6 Hz, 1H), 7.48 (t, J=7.6 Hz, 1H), 7.12 (d, J=9.2 Hz, 2H), 5.25 (d, J=7.2 Hz, 1H), 3.96-3.94 (m, 2H), 3.77-3.69 (m, 4H), 3.34-3.12 (m, 3H), 2.90-2.84 (m, 1H), 2.47-2.42 (m, 1H), 1.31-1.30 (m, 1H), 0.68-0.63 (m, 2H), 0.41-0.38 (m, 2H). MS-ESI [M+H]$^+$: calculated value: 432; measured value: 432.

Example 24

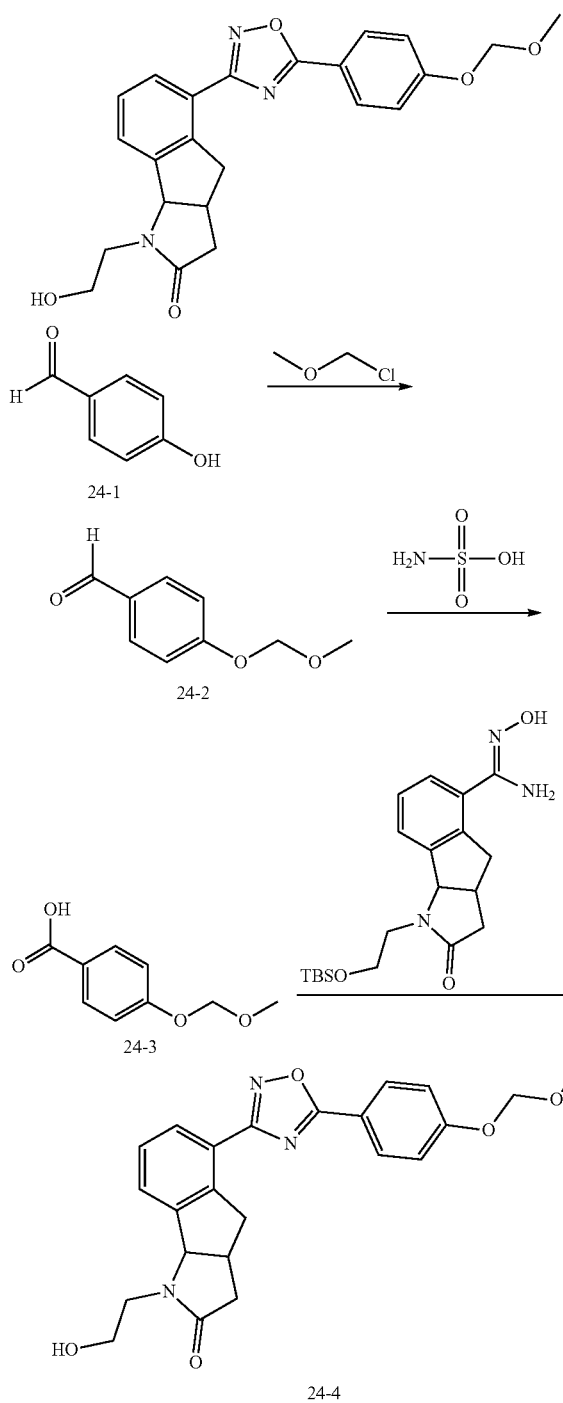

Step 1

Compound 24-1 (2.00 g, 16.4 mmol) was dissolved in acetone (40 mL), and potassium carbonate (5.66 g, 41.0 mmol) and chloromethyl methyl ether (1.58 g, 19.7 mmol) were added at 0° C. under nitrogen atmosphere. The reaction was stirred at 20° C. for 12 hours. The mixture was added with saturated aqueous sodium bicarbonate solution (20 mL) and extracted with ethyl acetate (70 mL×3). The organic layer was washed with saturated brine (20 mL), dried over anhydrous sodium sulfate, filtered and the filtrate was concentrated under reduced pressure and purified by silica gel column chromatography (5:1 petroleum ether/ethyl acetate, $R_f$=0.6) to give compound 24-2 (1.50 g, white solid), yield: 55%.

$^1$H NMR: (400 MHz, CDCl$_3$) δ 9.91 (s, 1H), 7.85 (d, J=8.8 Hz, 2H), 7.16 (d, J=8.8 Hz, 2H), 5.27 (s, 2H), 3.50 (s, 3H).

Step 2

Compound 24-2 (1.00 g, 6.02 mmol) and sulfamic acid (701 mg, 7.22 mmol) were dissolved in tetrahydrofuran (10 mL) and water (5 mL), and sodium chlorite (599 mg, 6.62 mmol) was added in portions at 0° C. under nitrogen atmosphere. The reaction was stirred at 20° C. for 12 hours. Water (30 mL) was added and the mixture was concentrated to 40 mL under reduced pressure, followed by filtrating off solid. The residue was washed with water (20 mL×3) and dried in vacuum to give compound 24-3 (800 mg, yellow solid); yield: 73%.

$^1$H NMR: (400 MHz, DMSO-d$_6$) δ 12.7 (brs, 1H), 7.89 (d, J=8.8 Hz, 2H), 7.12 (d, J=8.8 Hz, 2H), 5.24 (s, 2H), 3.46 (s, 3H).

Step 3

The reaction referred to Step 1 of Example 16, and the residue was isolated and purified by high performance liquid chromatography to give compound 22-4 (40.0 mg); yield: 60%.

$^1$H NMR: (400 MHz, Methonal-d$_4$) δ 8.19-8.16 (m, 3H), 7.76 (d, J=7.6 Hz, 1H), 7.48 (t, J=7.6 Hz, 1H), 7.26-7.24 (d, J=8.0 Hz, 2H), 5.31 (s, 2H), 5.25 (d, J=7.2 Hz, 1H), 3.77-3.69 (m, 4H), 3.49 (s, 3H), 3.30-3.12 (m, 3H), 2.91-2.84 (m, 1H), 2.47-2.46 (m, 1H). MS-ESI [M+H]$^+$: calculated value: 422; measured value: 422.

Example 25

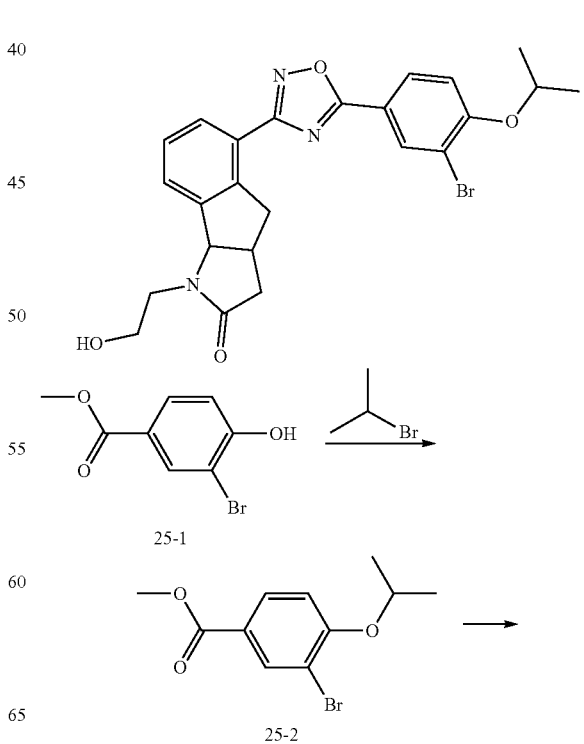

-continued

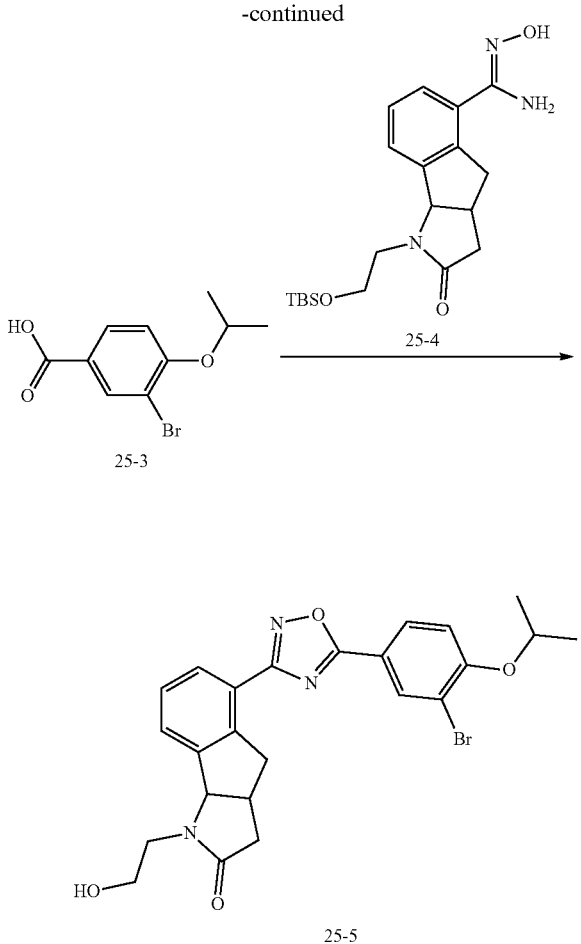

Step 1

Compound 25-1 (800 mg, 3.46 mmol) was dissolved in N,N-dimethylformamide (10 mL), and potassium carbonate (957 mg, 6.93 mmol) and bromoisopropane (639 mg, 5.19 mmol) were added. The reaction was stirred at 80° C. for 12 hours under nitrogen atmosphere. Water (30 mL) was added to the reaction mixture after the mixture was cooled to room temperature and the mixture was extracted with ethyl acetate (30 mL×3). The organic layer was combined and washed with saturated brine (30 mL×2), dried over anhydrous sodium sulfate, filtered and the filtrate was concentrated under reduced pressure. The residue was purified by silica gel column chromatography (10:1 petroleum ether/ethyl acetate, $R_f$=0.8) to give compound 25-2 (600 mg, colorless oil); yield: 63%.

$^1$H NMR: (400 MHz, Methonal-d$_4$) δ 8.15 (s, 1H), 7.96 (d, J=8.8 Hz, 1H), 7.11 (d, J=8.8 Hz, 1H), 4.81-4.75 (m, 1H), 3.89 (s, 3H), 1.39 (d, J=6.0 Hz, 6H). MS-ESI [M+H]$^+$: calculated value: 273 and 275; measured value: 273 and 275.

Step 2

Compound 25-2 (600 mg, 2.20 mmol) was dissolved in tetrahydrofuran (5 mL) and water (1 mL), and lithium hydroxide monohydrate (185 mg, 4.40 mmol) was added. The reaction was stirred at 25° C. for 12 hours under nitrogen atmosphere. The filtrate was concentrated under reduced pressure. Then, diluted hydrochloric acid (1 M, 10 mL) was added into the resultant, the mixture was filtered and the filtrate was concentrated with reduced pressure to give compound 25-3 (500 mg, white solid); yield: 88%.

$^1$H NMR: (400 MHz, Methonal-d$_4$) δ 8.16 (s, 1H), 7.98 (d, J=8.8 Hz, 1H), 7.11 (d, J=8.8 Hz, 1H), 4.81-4.75 (m, 1H), 1.39 (d, J=6.0 Hz, 6H). MS-ESI [M+H]$^+$: calculated value: 259 and 261; measured value: 259 and 261.

Step 3

Compound 25-3 (79.8 mg, 0.308 mmol) was dissolved in N,N-dimethylformamide (3 mL), and 1-hydroxybenzotriazole (69.4 mg, 0.513 mmol) and 1-(3-dimethylaminopropyl)-3-ethylcarbodiimide hydrochloride (98.4 mg, 0.513 mmol) were added. The reaction was stirred at 25° C. for 0.5 hour under nitrogen atmosphere. Then, Compound 25-4 (100 mg, 0.257 mmol) was added to the reaction mixture, and the mixture was stirred at 25° C. for 1 hour, then heated to 80° C. and stirred for 12 hours. Water (30 mL) was added to the reaction mixture after the mixture was cooled to room temperature and the mixture was extracted with ethyl acetate (30 mL×3). The organic layers were combined and washed with saturated brine (25 mL×2), dried over anhydrous sodium sulfate, filtered and the filtrate was concentrated under reduced pressure. The residue was isolated and purified by high performance liquid chromatography to give compound 25-5 (50.0 mg); yield: 39%.

$^1$H NMR: (400 MHz, Methonal-d$_4$) δ 8.40 (s, 1H), 8.21-8.17 (m, 2H), 7.78 (d, J=7.2 Hz, 1H), 7.50 (d, J=7.2 Hz, 1H), 7.29 (d, J=8.8 Hz, 1H), 5.27 (d, J=7.2 Hz, 1H), 4.97-4.95 (m, 1H), 3.84-3.82 (m, 1H), 3.79-3.61 (m, 3H), 3.36-3.35 (m, 1H), 3.24-3.22 (m, 1H), 3.16-3.15 (m, 1H), 2.90-2.86 (m, 1H), 2.49-2.45 (m, 1H), 1.44 (d, J=6.0 Hz, 6H). MS-ESI [M+H]$^+$: calculated value: 498 and 500; measured value: 498 and 500.

Example 26

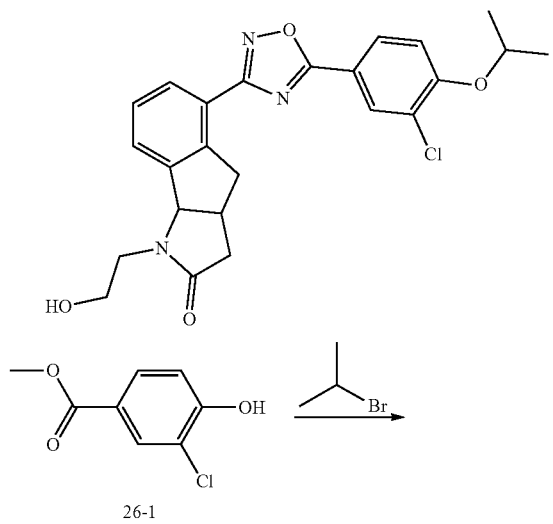

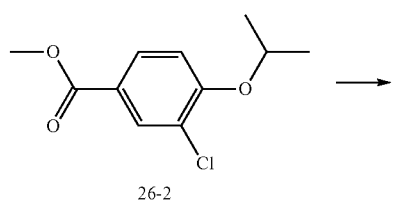

-continued

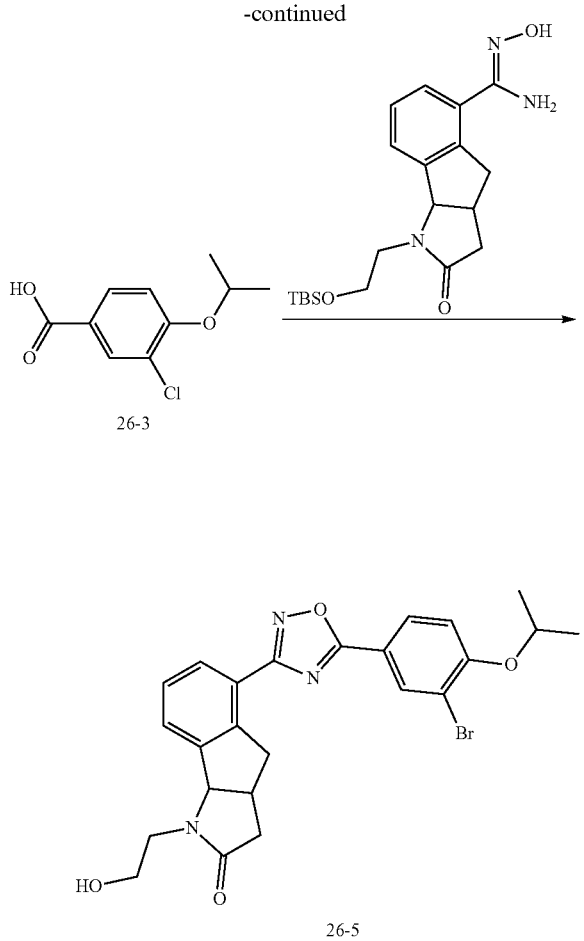

¹H NMR: (400 MHz, Methonal-d₄) δ 8.22-8.20 (m, 2H), 8.16 (d, J=8.8 Hz, 1H), 7.77 (d, J=7.6 Hz, 1H), 7.50 (d, J=7.6 Hz, 1H), 7.32 (d, J=8.8 Hz, 1H), 5.27 (d, J=7.2 Hz, 1H), 4.86-4.84 (m, 1H), 3.81-3.71 (m, 4H), 3.36-3.35 (m, 1H), 3.24-3.22 (m, 1H), 3.16-3.15 (m, 1H), 2.92-2.86 (m, 1H), 2.49-2.45 (m, 1H), 1.44 (d, J=6.0 Hz, 6H). MS-ESI [M+H]⁺: calculated value: 454; measured value: 454.

Example 27

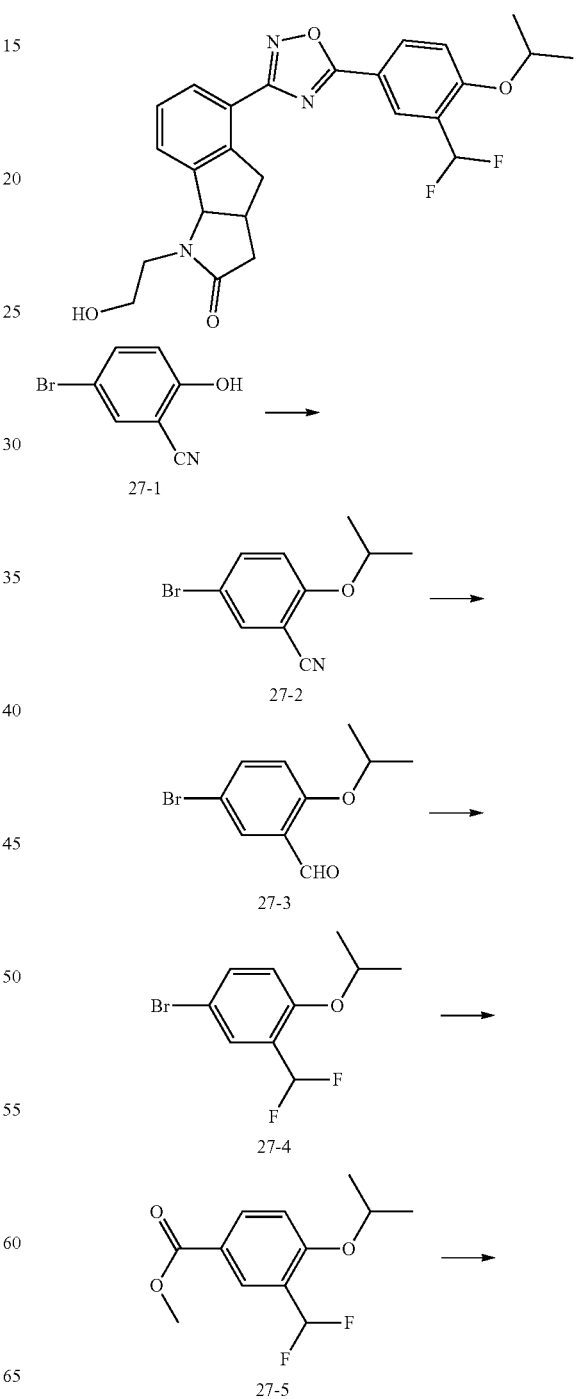

Step 1

The reaction referred to Step 1 of Example 25, and the residue was isolated and purified by silica gel column chromatography (10:1 petroleum ether/ethyl acetate, $R_f$=0.8) to give compound 26-2 (1.20 g, colorless oil); yield: 98%. MS-ESI [M+H]⁺: calculated value: 229; measured value: 229.

¹H NMR: (400 MHz, Methanol-d₄) δ 7.98 (s, 1H), 7.90 (d, J=8.8 Hz, 1H), 7.14 (d, J=8.8 Hz, 1H), 4.81-4.74 (m, 1H), 3.88 (s, 3H), 1.39 (d, J=6.0 Hz, 6H).

Step 2

The reaction referred to Step 2 of Example 25, the residue was compound 26-3 (1.00 g, white solid); yield: 89%. MS-ESI [M+H]⁺: calculated value: 215; measured value: 215.

¹H NMR: (400 MHz, Methanol-d₄) δ 7.99 (s, 1H), 7.93 (d, J=8.8 Hz, 1H), 7.15 (d, J=8.8 Hz, 1H), 4.83-4.76 (m, 1H), 1.39 (d, J=6.0 Hz, 6H).

Step 3

The reaction referred to Step 3 of Example 25, and the residue was isolated and purified by high performance liquid chromatography to give compound 26-4 (30.0 mg); yield: 25%.

-continued

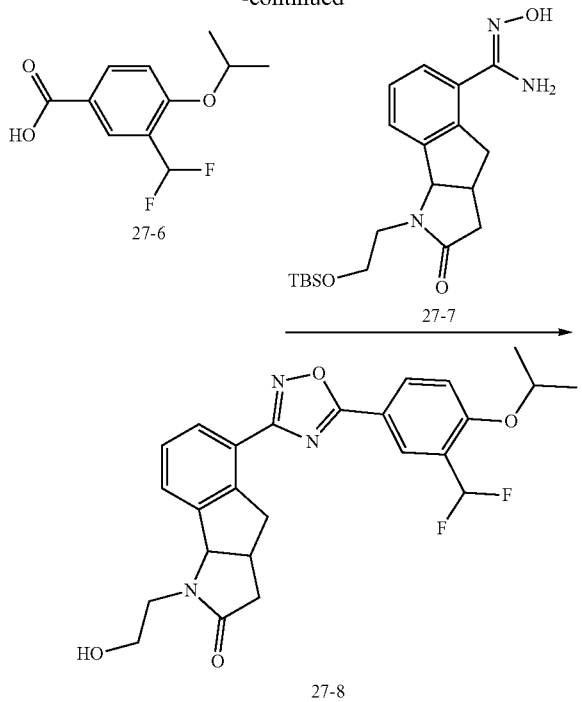

Step 1
Compound 27-1 (3.00 g, 15.1 mmol), 2-bromopropane (3.70 g, 30.3 mmol), potassium carbonate (6.30 g, 45.4 mmol) were dissolved in N,N-dimethylformamide (10 mL). The mixture was heated to 80° C. and stirred for 15 hours. The mixture was filtered after cooled to the room temperature, the filtrate was concentrated under reduced pressure. The residue was dissolved in dichloromethane (30 mL) and washed with water (20 mL). The aqueous layer was extracted with dichloromethane (30 mL×3), the organic layer was dried over anhydrous sodium sulfate, filtered and concentrated. The residue was purified by silica gel column chromatography (4:1 petroleum ether/ethyl acetate, $R_f$=0.6) to give compound 27-2 (3.40 g, white solid); yield: 93%.

$^1$H NMR (400 MHz, CDCl$_3$) δ 7.57 (d, J=2.4 Hz, 1H), 7.52 (d, J=2.4, 9.2 Hz, 1H), 6.78 (d, J=9.2 Hz, 1H), 4.58-4.52 (m, 1H), 1.33 (d, J=6.4 Hz, 6H).

Step 2
Compound 27-2 (2.00 g, 8.30 mmol) was dissolved in anhydrous toluene (20 mL), and diisobutylaluminum hydride (1 M in toluene, 9.16 mL) was added at −78° C. The reaction was stirred at this temperature for 2 hours. The mixture was quenched with saturated aqueous ammonia chloride solution (10 mL). Sodium potassium tartrate solution (10 mL) was added and the mixture was stirred for 12 hours. The aqueous layer was extracted with ethyl acetate (30 mL×3). The organic layer was dried over anhydrous sodium sulfate, filtered and concentrated. The residue was purified by silica gel column chromatography (20:1-10:1 petroleum ether/ethyl acetate, $R_f$=0.3) to give compound 27-3 (1.60 g, colorless oil); yield: 79%.

$^1$H NMR (400 MHz, CDCl$_3$) δ 10.39 (s, 1H), 7.92 (d, J=2.8 Hz, 1H), 7.62-7.57 (d, J=2.8, 8.8 Hz, 1H), 6.89 (d, J=8.8 Hz, 1H), 4.68-4.62 (m, 1H), 1.40 (d, J=6.0 Hz, 6H).

Step 3
Compound 27-3 (1.30 g, 5.30 mmol) was dissolved in anhydrous dichloromethane (30 mL), and diethylamine sulfur trifluoride (5.10 g, 32.1 mmol) was added dropwise. The reaction was stirred at 20° C. for 15 hours. The mixture was quenched with water (20 mL) and stirred for 5 minutes. The aqueous layer was extracted with dichloromethane (20 mL×3). The organic layer was combined and dried over anhydrous sodium sulfate, filtered and concentrated. The residue was purified by silica gel column chromatography (1:0 petroleum ether/ethyl acetate, $R_f$=0.6) to give compound 27-4 (1.00 g, colorless oil); yield: 70%.

$^1$H NMR (400 MHz, CDCl$_3$) δ 7.59 (d, J=2.8 Hz, 1H), 7.41 (d, J=2.8, 9.2 Hz, 1H), 6.81 (t, J=55.2 Hz, 1H), 6.74 (d, J=9.2 Hz, 1H), 4.54-4.44 (m, 1H), 1.27 (d, J=6.0 Hz, 6H).

Step 4
Compound 27-4 (1.00 g, 3.70 mmol), [1,1'-Bis(diphenylphosphino)ferrocene]dichloropalladium(II) (275 mg, 0.370 mmol) were dissolved in N,N-dimethylformamide (6 mL), methanol (6 mL), triethylamine (6 mL). The solution was charged with argon three times and heated to 80° C., stirred at this temperature for 15 hours under carbon monoxide atmosphere (50 psi). The solution was cooled to the room temperature and concentrated under reduced pressure. The residue was dissolved in dichloromethane (20 mL) and washed with water (10 mL). The aqueous layer was extracted with dichloromethane (20 mL×3). The organic layer was dried over anhydrous sodium sulfate, filtered and concentrated. The residue was purified by silica gel column chromatography (1:0-0:1 petroleum ether/ethyl acetate, $R_f$=0.1) to give compound 27-5 (120 mg, colorless oil); yield: 13%.

$^1$H NMR (400 MHz, CDCl$_3$) δ 8.27 (s, 1H), 8.12 (d, J=8.8 Hz, 1H), 6.98 (d, J=8.8 Hz, 1H), 6.94 (t, J=55.2 Hz, 1H), 4.77-4.67 (m, 1H), 1.41 (d, J=6.0 Hz, 6H).

Step 5
Compound 27-5 (100 mg, 0.410 mmol) was dissolved in methanol (2 mL) and water (2 mL), and potassium hydroxide (46.0 mg, 0.820 mmol) was added. The reaction was stirred at 20° C. for 15 hours. The solution was concentrated with reduced pressure to remove methanol. The aqueous layer was acidified with diluted hydrochloric acid to pH=7, extracted with dichloromethane (10 mL×3). The organic layer were combined and dried over anhydrous sodium sulfate, filtered, concentrated. The residue was purified by silica gel column chromatography (3:1 petroleum ether/ethyl acetate, $R_f$=0.1) to give compound 27-6 (90 mg, white solid); yield: 95%.

$^1$H NMR (400 MHz, CDCl$_3$) δ 8.26 (s, 1H), 8.10 (d, J=8.8 Hz, 1H), 6.91 (d, J=8.8 Hz, 1H), 6.86 (t, J=55.2 Hz, 1H), 4.69-4.62 (m, 1H), 1.33 (d, J=6.0 Hz, 6H).

Step 6
Compound 27-6 (90.0 mg, 0.391 mmol), 1-hydroxybenzotriazole (106 mg, 0.782 mmol), 1-ethyl-3-(3-dimethylaminopropyl)carbodiimide hydrochloride (150 mg, 0.782 mmol) were dissolved in anhydrous N,N-dimethylformamide (4 mL). The solution was charged with nitrogen three times. After the mixture was stirred for 1 hour at 20° C., a solution of Compound 27-7 (152 mg, 0.391 mmol) in anhydrous N,N-dimethylformamide (2 mL) was added. After stirred for another 1 hour, the mixture was heated to 90° C. stirred for another 13 hours. The solution was concentrated under reduced pressure. The residue was dissolved in dichloromethane (20 mL) and washed with water (10 mL). The aqueous layer was extracted with dichloromethane (20 mL×3). The organic layer was dried over anhydrous sodium sulfate, filtered and concentrated. The residue was purified by high performance liquid chromatography to give compound 27-8 (27.0 mg); yield: 15%.

$^1$H NMR (400 MHz, Methonal-d$_4$) δ 8.38-8.30 (m, 2H), 8.20 (d, J=8.0 Hz, 1H), 7.77 (d, J=7.6 Hz, 1H), 7.50 (t, J=7.6

Hz, 1H), 7.36 (d, J=8.0 Hz, 1H), 7.04 (t, J=55.2 Hz, 1H), 5.27 (d, J=7.2 Hz, 1H), 4.89-4.93 (m, 2H), 3.83 (d, J=9.2, 18.0 Hz, 1H), 3.67-3.77 (m, 3H), 3.14-3.16 (m, 1H), 3.12 (dd, J=6.8, 18.0 Hz, 1H), 2.89 (dd, J=9.2, 17.6 Hz, 1H), 2.46 (dd, J=2.0, 17.0 Hz, 1H), 1.44 (d, J=6.0 Hz, 6H). MS-ESI [M+H]$^+$: calculated value: 470; measured value: 470.

Example 28

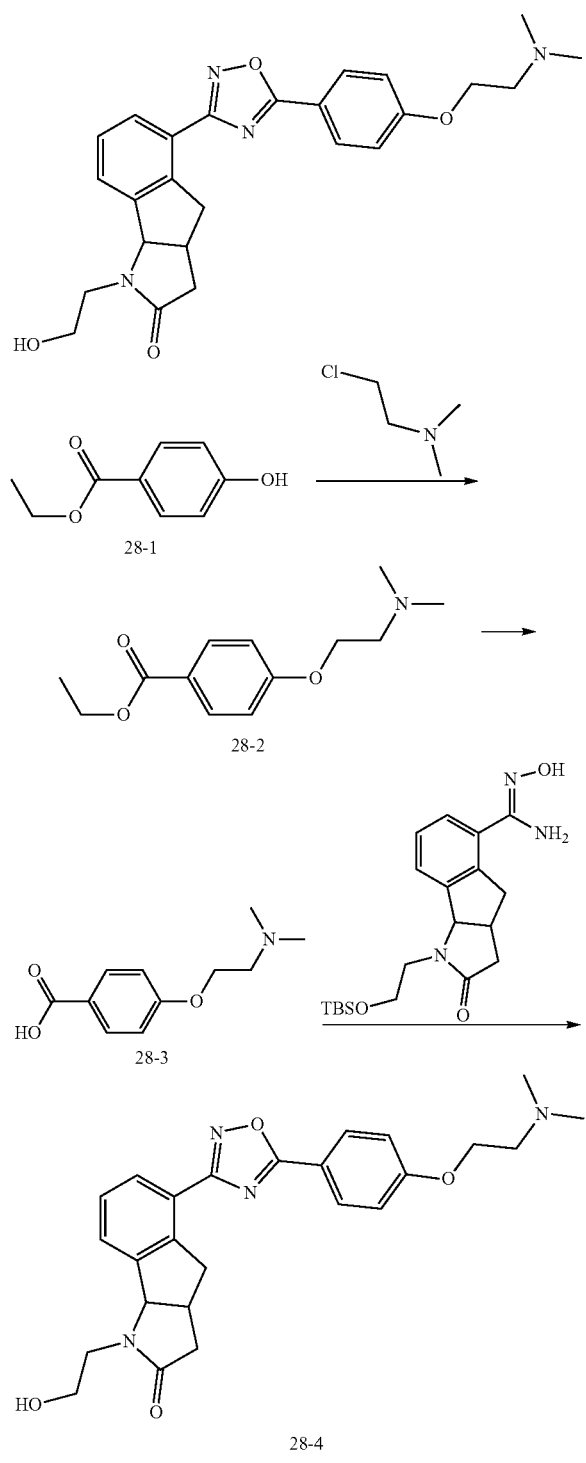

Step 1

Compound 28-1 (500 mg, 3.01 mmol) was dissolved in tetrahydrofuran (13 mL), and cesium carbonate (2.94 g, 9.03 mmol) and potassium iodide (50.0 mg, 0.301 mmol) and 2-chloro-N,N-dimethylethylamine hydrochloride (650 mg, 4.51 mmol) were added at 20° C. under nitrogen atmosphere. The reaction was stirred at 80° C. for 12 hours. The mixture was added with saturated aqueous sodium chloride solution (50 mL) and extracted with ethyl acetate (70 mL×3). The organic layer was washed with saturated brine (20 mL), dried over anhydrous sodium sulfate, filtered and the filtrate was concentrated under reduced pressure. The residue was purified by silica gel column chromatography (1:1 petroleum ether/ethyl acetate, $R_f$=0.3) to give compound 28-2 (538 mg, white solid) yield: 73%.

$^1$H NMR: (400 MHz, CDCl$_3$) δ 8.00 (d, J=8.8 Hz, 2H), 6.94 (d, J=8.8 Hz, 2H), 4.35 (q, J=6.8 Hz, 2H), 4.13 (t, J=5.6 Hz, 2H), 2.76 (t, J=5.6 Hz, 2H), 1.66 (s, 6H), 1.35 (t, J=6.8 Hz, 3H).

Step 2

Compound 28-2 (538 mg, 2.27 mmol) and lithium hydroxide monohydrate (143 mg, 3.40 mmol were dissolved in methanol (11 mL) and water (3.5 mL), and the mixture was stirred at 40° C. for 12 hours under nitrogen atmosphere. The mixture was added with 1M hydrochloric acid (3.7 mL), concentrated to gain solid. Then, a mixture of 30 mL/30 mL chloroform and methanol was added. The mixture was stirred for 0.5 hour and filtered. The filtrate was concentrated by a rotary evaporator and dried in vacuum to obtain compound 28-3 (500 mg, pale yellow solid), yield: 84%.

$^1$H NMR: (400 MHz, DMSO-d$_6$) δ 10.78 (brs, 1H), 7.91 (d, J=8.8 Hz, 2H), 7.08 (d, J=8.8 Hz, 2H), 4.44 (t, J=4.8 Hz, 2H), 3.51 (t, J=4.8 Hz, 2H), 2.82 (s, 6H). MS-ESI [M+H]$^+$: calculated value: 210; measured value: 210.

Step 3

The reaction referred to Step 3 of Example 25, and the residue was isolated and purified by high performance liquid chromatography to give compound 26-4 (5.0 mg); yield: 7%.

$^1$H NMR: (400 MHz, CDCl$_3$) δ 8.22-8.18 (m, 3H), 7.57 (d, J=7.6 Hz, 1H), 7.43 (t, J=7.6 Hz, 1H), 7.10 (d, J=7.6 Hz, 2H), 5.10 (d, J=7.2 Hz, 1H), 4.68-4.64 (m, 2H), 3.86-3.69 (m, 4H), 3.55-3.51 (m, 2H), 3.44-3.30 (m, 2H), 3.24-3.18 (m, 2H), 2.98 (s, 6H), 2.91-2.84 (m, 1H), 2.55-2.51 (m, 1H). MS-ESI [M+H]$^+$: calculated value: 449; measured value: 449.

Example 29

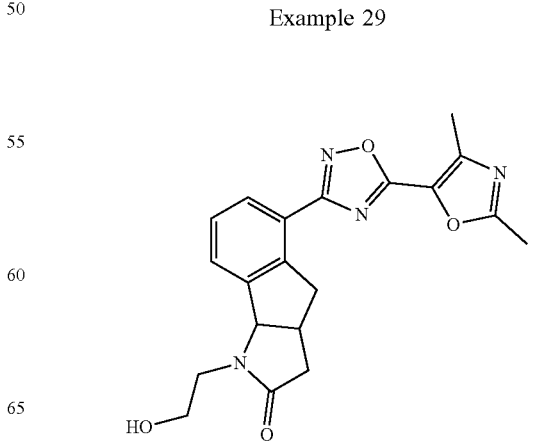

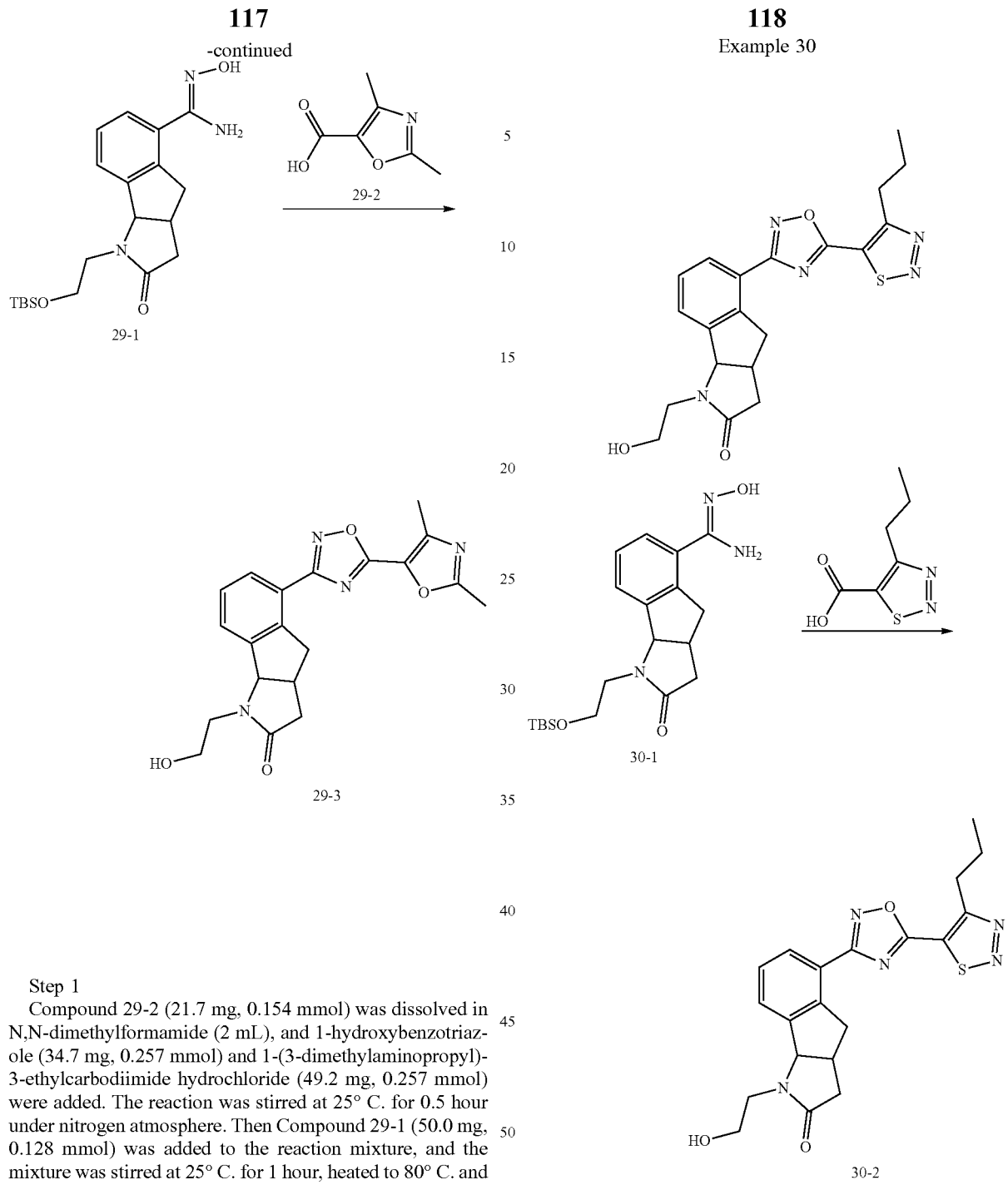

Example 30

Step 1

Compound 29-2 (21.7 mg, 0.154 mmol) was dissolved in N,N-dimethylformamide (2 mL), and 1-hydroxybenzotriazole (34.7 mg, 0.257 mmol) and 1-(3-dimethylaminopropyl)-3-ethylcarbodiimide hydrochloride (49.2 mg, 0.257 mmol) were added. The reaction was stirred at 25° C. for 0.5 hour under nitrogen atmosphere. Then Compound 29-1 (50.0 mg, 0.128 mmol) was added to the reaction mixture, and the mixture was stirred at 25° C. for 1 hour, heated to 80° C. and stirred for 12 hours. Water (10 mL) was added to the reaction mixture after the mixture was cooled to room temperature and the mixture was extracted with ethyl acetate (10 mL×3). The organic layers were combined and washed with saturated brine (10 mL×2), dried over anhydrous sodium sulfate, filtered and the filtrate was concentrated under reduced pressure. The residue was purified by high performance liquid chromatography to give compound 29-3 (30.0 mg); yield: 61%.

$^1$H NMR: (400 MHz, Methonal-d$_4$) δ 8.18 (d, J=7.6 Hz, 1H), 7.79 (d, J=7.6 Hz, 1H), 7.50 (t, J=7.6 Hz, 1H), 5.28 (d, J=7.2 Hz, 1H), 3.82-3.71 (m, 4H), 3.24-3.20 (m, 2H), 3.14-3.10 (m, 1H), 2.93-2.87 (m, 1H), 2.61 (s, 6H), 2.48-2.44 (m, 1H). MS-ESI [M+H]$^+$: calculated value: 381; measured value: 381.

Step 1

The reaction referred to Step 1 of Example 29, and the residue was isolated and purified by high performance liquid chromatography to give compound 30-2 (30.0 mg); yield: 57%.

$^1$H NMR: (400 MHz, Methonal-d$_4$) δ 8.19 (d, J=7.6 Hz, 1H), 7.82 (d, J=7.6 Hz, 1H), 7.52 (t, J=7.6 Hz, 1H), 5.28 (d, J=7.2 Hz, 1H), 3.82-3.72 (m, 4H), 3.60-3.56 (m, 2H), 3.32-3.28 (m, 2H), 3.17-3.15 (m, 1H), 2.93-2.87 (m, 1H), 2.48-2.43 (m, 1H), 2.04-1.99 (m, 2H), 1.14-1.10 (m, 3H). MS-ESI [M+H]$^+$: calculated value: 412; measured value: 412.

Example 31

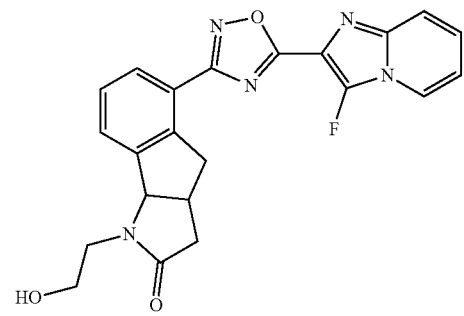

Example 32

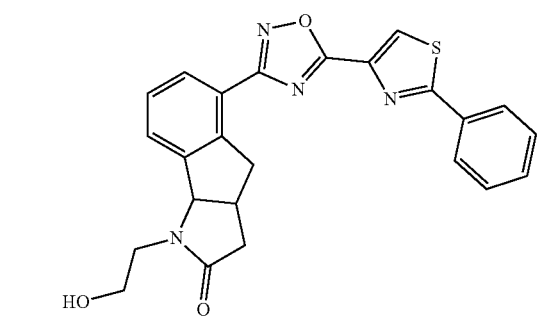

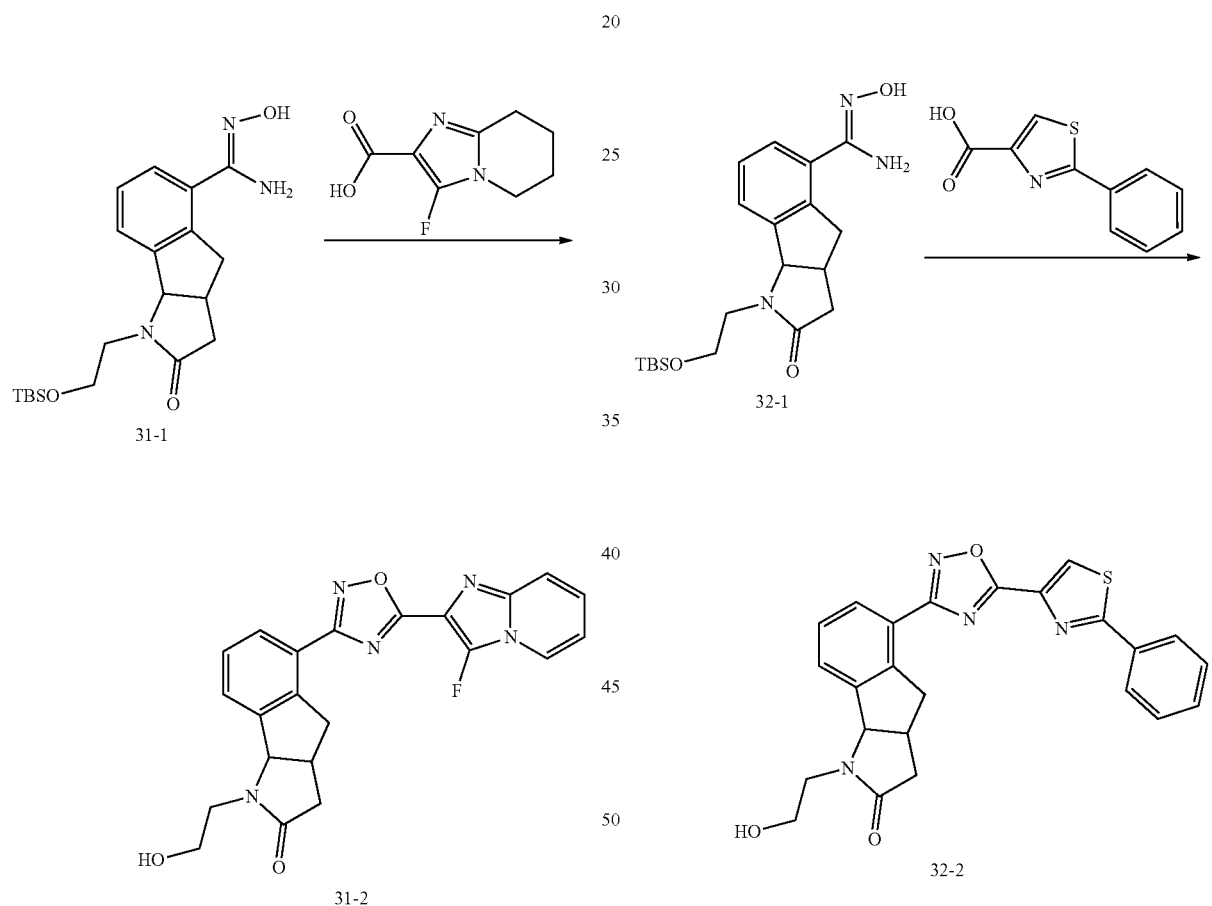

Step 1

The reaction referred to Step 1 of Example 29, and the residue was isolated and purified by high performance liquid chromatography to give compound 31-2 (30.0 mg); yield: 56%.

$^1$H NMR: (400 MHz, Methonal-d$_4$) δ 8.66 (d, J=7.2 Hz, 1H), 8.20 (d, J=7.2 Hz, 1H), 7.91-7.79 (m, 3H), 7.52-7.48 (m, 2H), 5.28 (d, J=7.2 Hz, 1H), 3.85-3.73 (m, 4H), 3.35-3.34 (m, 1H), 3.25-3.22 (m, 1H), 3.16-3.13 (m, 1H), 2.95-2.88 (m, 1H), 2.46-2.44 (m, 1H). MS-ESI [M+H]$^+$: calculated value: 420; measured value: 420.

Step 1

The reaction referred to Step 1 of Example 29, and the residue was isolated and purified by high performance liquid chromatography to give compound 32-2 (20.0 mg); yield: 35%.

$^1$H NMR: (400 MHz, DMSO-d$_6$) δ 8.94 (s, 1H), 8.14-8.08 (m, 3H), 7.82 (d, J=7.6 Hz, 1H), 7.60-7.57 (m, 3H), 7.54 (d, J=7.6 Hz, 1H), 5.18 (d, J=7.2 Hz, 1H), 4.88-4.87 (m, 1H), 3.72-3.67 (m, 1H), 3.58-3.55 (m, 3H), 3.27-3.25 (m, 1H), 3.06-3.00 (m, 2H), 2.72-2.70 (m, 1H), 2.34-2.30 (m, 1H). MS-ESI [M+H]$^+$: calculated value: 445; measured value: 445.

Example 33

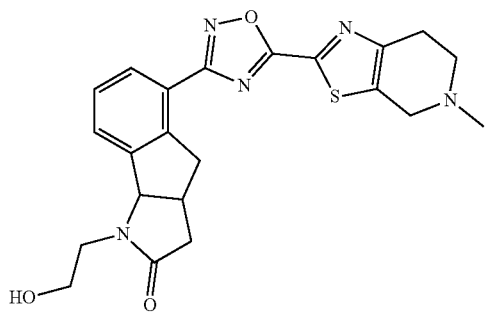

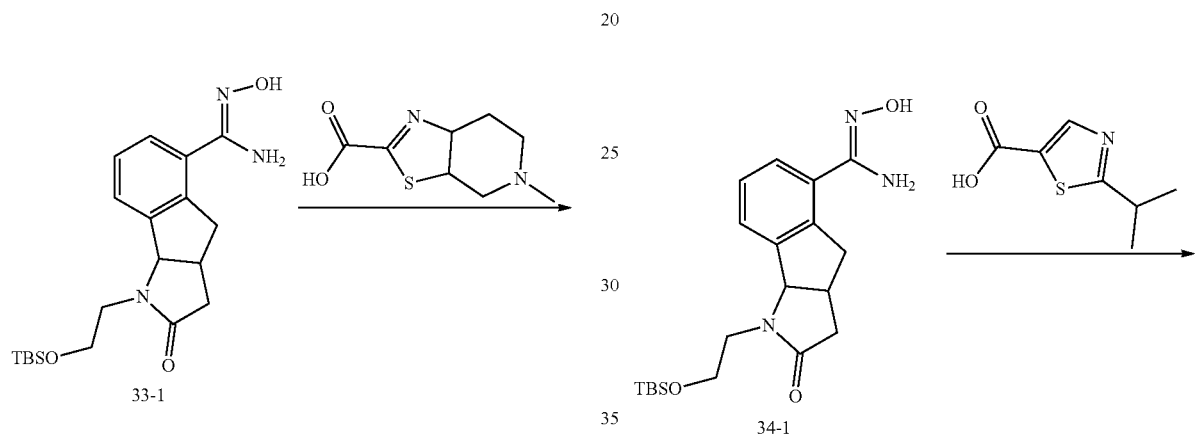

Step 1

The reaction referred to Step 1 of Example 29, and the residue was isolated and purified by high performance liquid chromatography to give compound 33-2 (30.0 mg); yield: 53%.

$^1$H NMR: (400 MHz, Methonal-d$_4$) δ 8.18 (d, =7.6 Hz, 1H), 7.81 (d, J=7.6 Hz, 1H), 7.50 (t, J=7.6 Hz, 1H), 5.28 (d, J=7.2 Hz, 1H), 4.67-4.65 (m, 1H), 3.83-3.80 (m, 1H), 3.78-3.72 (m, 5H), 3.40-3.38 (m, 4H), 3.25-3.15 (m, 5H), 2.93-2.89 (m, 1H), 2.48-2.44 (m, 1H). MS-ESI [M+H]$^+$: calculated value: 438; measured value: 438.

Example 34

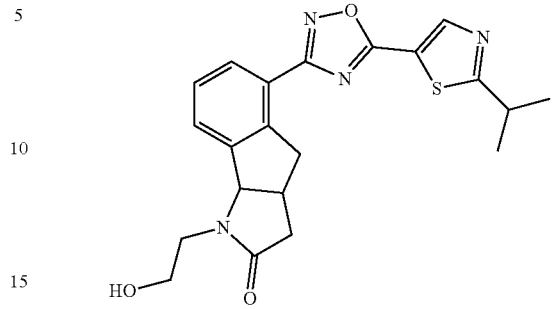

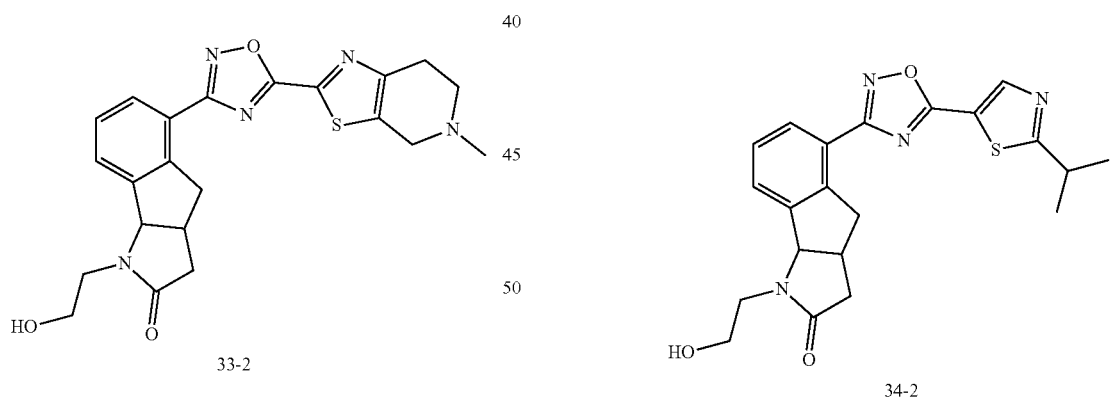

Step 1

The reaction referred to Step 1 of Example 29, and the residue was isolated and purified by high performance liquid chromatography to give compound 34-2 (25.0 mg); yield: 47%.

$^1$H NMR: (400 MHz, Methonal-d$_4$) δ 8.54 (s, 1H), 8.16 (d, J=7.6 Hz, 1H), 7.79 (d, J=7.6 Hz, 1H), 7.50 (t, J=7.6 Hz, 1H), 5.26 (d, J=7.2 Hz, 1H), 3.82-3.71 (m, 4H), 3.46-3.45 (m, 1H), 3.24-3.22 (m, 2H), 3.14-3.11 (m, 1H), 2.92-2.85 (m, 1H), 2.48-2.43 (m, 1H), 1.49 (d, J=6.0 Hz, 6H). MS-ESI [M+H]$^+$: calculated value: 411; measured value: 411.

Example 35

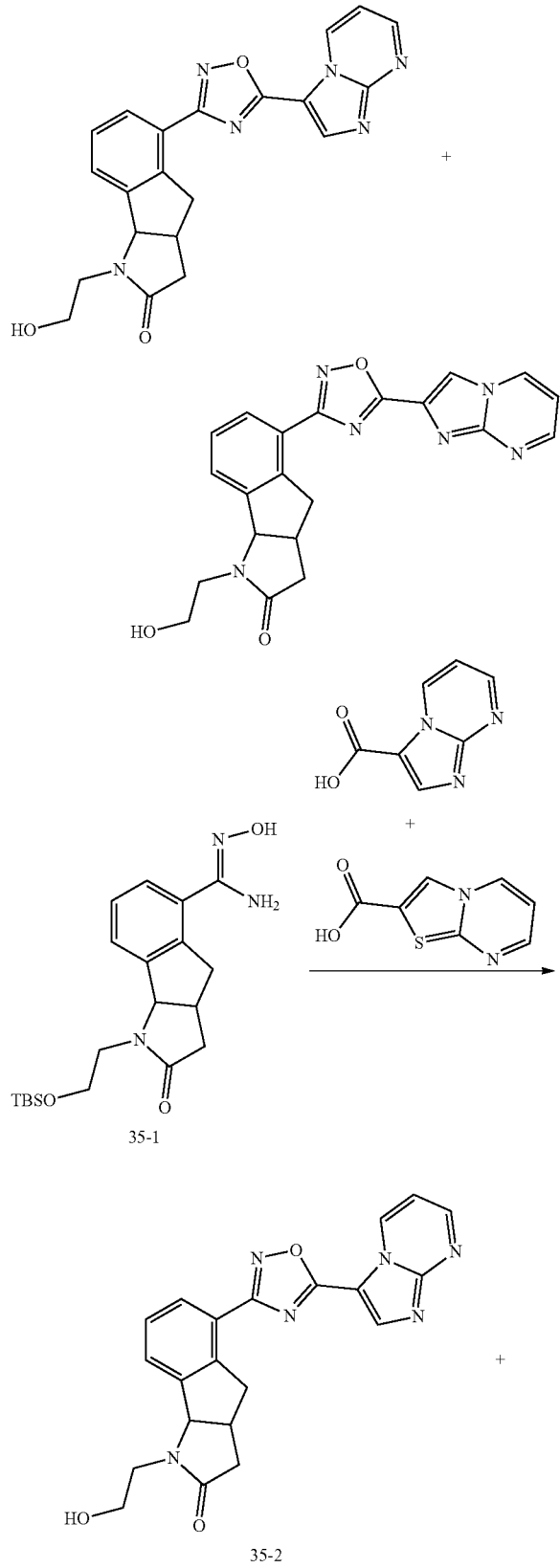
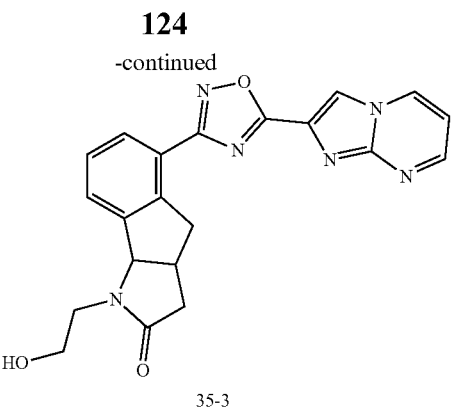
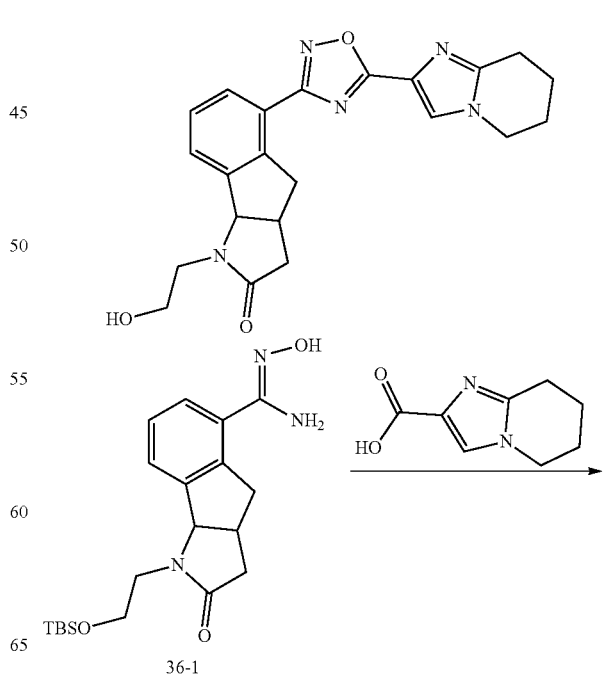

Step 1

The reaction referred to Step 1 of Example 29, and the residue was isolated and purified by high performance liquid chromatography to obtain compound 35-2 and compound 35-3.

Compound 35-2 (25.0 mg); yield: 48%.

$^1$H NMR: (400 MHz, Methonal-$d_4$) δ 9.33 (d, J=7.2 Hz, 1H), 9.17 (d, J=7.2 Hz, 1H), 9.12 (s, 1H), 8.26 (d, J=7.6 Hz, 1H), 7.84 (d, J=7.6 Hz, 1H), 7.72 (t, J=7.2 Hz, 1H), 7.55 (t, J=8.0 Hz, 1H), 5.30 (d, J=7.2 Hz), 1H), 3.86-3.73 (m, 4H), 3.37-3.36 (m, 1H), 3.24-3.14 (m, 2H), 2.95-2.89 (m, 1H), 2.49-2.45 (m, 1H). MS-ESI [M+H]$^+$: calculated value: 403; measured value: 403.

Compound 35-3 (20.0 mg); yield: 38%.

$^1$H NMR: (400 MHz, Methonal-$d_4$) δ 10.20 (d, J=7.2 Hz, 1H), 9.36 (s, 1H), 9.30 (d, J=7.2 Hz, 1H), 8.37 (d, J=7.6 Hz, 1H), 7.99 (d, J=7.6 Hz, 1H), 7.86 (t, J=8.0 Hz, 1H), 7.56 (t, J=8.0 Hz, 1H), 5.31 (d, J=7.2 Hz, 1H), 3.88-3.84 (m, 1H), 3.77-3.73 (m, 3H), 3.38-3.37 (m, 1H), 3.27-3.21 (m, 2H), 2.95-2.89 (m, 1H), 2.51-2.47 (m, 1H). MS-ESI [M+H]$^+$: calculated value: 403; measured value: 403.

Example 36

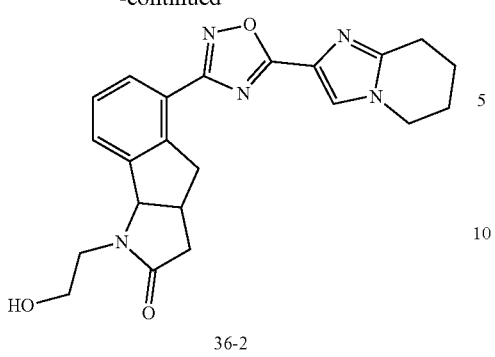

36-2

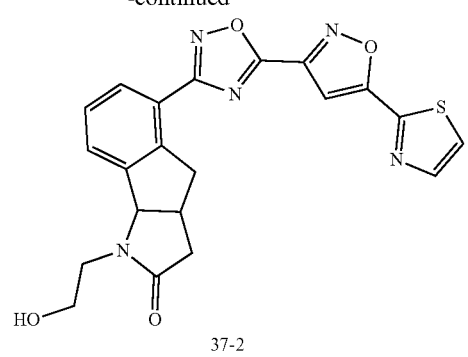

37-2

Step 1

The reaction referred to Step 1 of Example 29, and the residue was isolated and purified by high performance liquid chromatography to give compound 36-2 (20.0 mg); yield: 38%.

$^1$H NMR: (400 MHz, DMSO-d$_6$) δ 8.11 (s, 1H), 8.05 (d, J=7.6 Hz, 1H), 7.77 (d, J=7.6 Hz, 1H), 7.50 (t, J=7.6 Hz, 1H), 5.15 (d, J=7.2 Hz, 1H), 4.85 (s, 1H), 4.08-4.07 (m, 2H), 3.65-3.50 (m, 4H), 3.22-3.21 (m, 1H), 3.01-2.96 (m, 2H), 3.84-3.82 (m, 2H), 2.69-2.67 (m, 1H), 2.31-2.27 (m, 1H), 1.93-1.90 (m, 4H). MS-ESI [M+H]$^+$: calculated value: 406; measured value: 406.

Step 1

The reaction referred to Step 1 of Example 29, and the residue was isolated and purified by high performance liquid chromatography to give compound 37-2 (30.0 mg); yield: 54%.

$^1$H NMR: (400 MHz, DMSO-d$_6$) δ 8.20-8.19 (m, 2H), 8.10 (d, J=7.6 Hz, 1H), 7.95 (s, 1H), 7.83 (d, J=7.6 Hz, 1H), 7.55 (t, J=7.6 Hz, 1H), 5.17 (d, J=7.2 Hz, 1H), 3.72-3.58 (m, 4H), 3.26-3.24 (m, 1H), 3.06-3.00 (m, 2H), 2.70-2.68 (m, 1H), 2.34-2.30 (m, 1H). MS-ESI [M+H]$^+$: calculated value: 436; measured value: 436.

Example 37

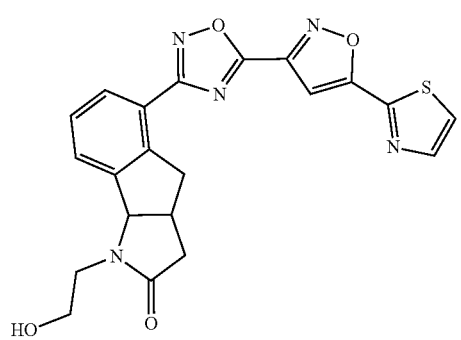

Example 38

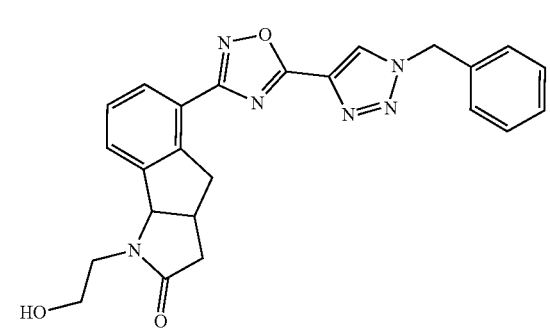

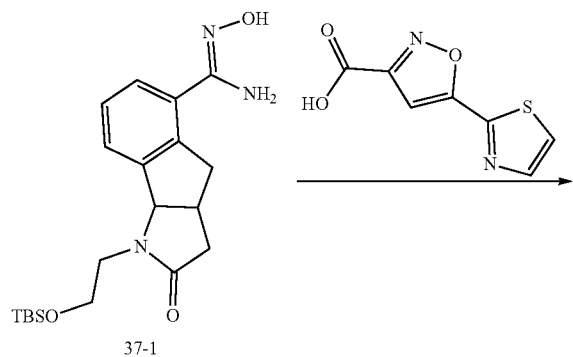

37-1

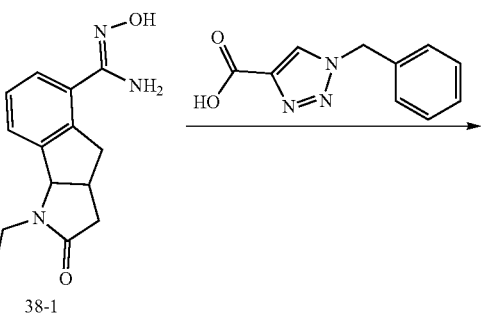

38-1

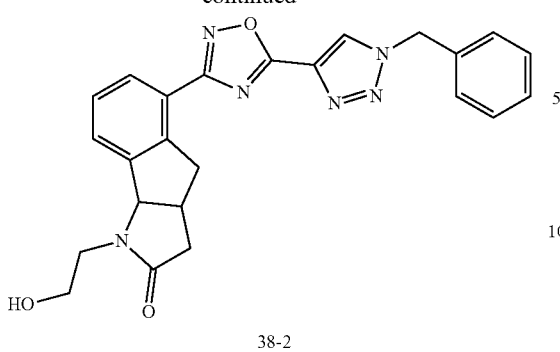

38-2

Step 1

The reaction referred to Step 1 of Example 29, and the residue was isolated and purified by high performance liquid chromatography to give compound 38-2 (20.0 mg); yield: 35%.

¹H NMR: (400 MHz, DMSO-d₆) δ 9.32 (s, 1H), 8.08 (d, J=7.6 Hz, 1H), 7.80 (d, J=7.6 Hz, 1H), 7.52 (t, J=7.6 Hz, 1H), 7.42-7.38 (m, 5H), 5.78 (s, 2H), 5.16 (d, J=7.2 Hz, 1H), 3.67-3.51 (m, 3H), 3.20-3.18 (m, 2H), 3.02-2.97 (m, 2H), 2.69-2.67 (m, 1H), 2.32-2.31 (m, 1H). MS-ESI [M+H]⁺: calculated value: 443; measured value: 443.

Example 39

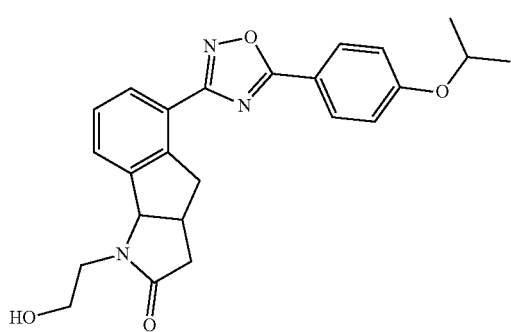

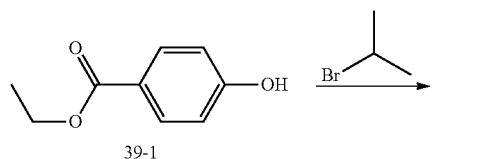

39-1

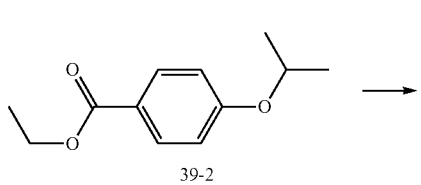

39-2

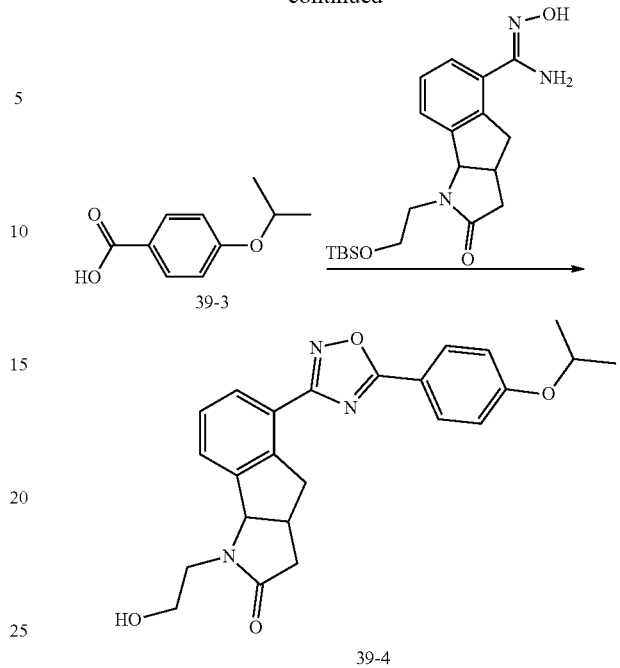

Step 1

Compound 39-1 (300 mg, 1.81 mmol) was dissolved in tetrahydrofuran (5 mL), and cesium carbonate (1.77 g, 5.43 mmol) and potassium iodide (30.1 mg, 0.181 mmol) and 2-bromopropane (668 mg, 5.43 mmol) were added at 20° C. under nitrogen atmosphere. The reaction was stirred at 80° C. for 12 hours. Then, the mixture was added with saturated aqueous sodium chloride solution (50 mL), and extracted with ethyl acetate (70 mL×3). The organic layer was washed with saturated brine (20 mL), dried over anhydrous sodium sulfate, filtered and the filtrate was concentrated with reduced pressure. The residue was purified by silica gel column chromatography (1:1 petroleum ether/ethyl acetate, R_f=0.5) to give compound 39-2 (166 mg, white solid); yield: 44%.

¹H NMR: (400 MHz, CDCl₃) δ 7.98 (d, J=8.8 Hz, 2H), 6.89 (d, J=8.8 Hz, 2H), 4.67-4.61 (m, 1H), 4.38-4.32 (q, J=7.2 Hz, 2H), 1.40-1.36 (m, 9H).

Step 2

Compound 39-2 (166 mg, 0.797 mmol), lithium hydroxide monohydrate (50.2 mg, 1.20 mmol) were dissolved in methanol (3 mL) and water (1 mL). The mixture was stirred at 40° C. for 12 hours under nitrogen atmosphere. The mixture was added with 1M hydrochloric acid (1.2 mL). The mixture was concentrated under reduced pressure to gain solid. Then, a mixture of 20 mL/20 mL chloroform and methanol was added. The mixture was stirred for 0.5 hour and filtered. The filtrate was concentrated by a rotary evaporator and dried in vacuum to obtain compound 39-3 (144 mg, pale yellow solid) yield: 70%.

¹H NMR: (400 MHz, Methonal-d₄) δ 7.95 (d, J=8.8 Hz, 2H), 6.95 (d, J=8.8 Hz, 2H), 4.74-4.66 (m, 1H), 1.35-1.29 (d, J=6.0 Hz, 6H).

Step 3

The reaction referred to Step 1 of Example 29, and the residue was isolated and purified by high performance liquid chromatography to give compound 39-3 (10.0 mg); yield: 15%.

¹H NMR: (400 MHz, Methonal-d₄) δ 8.19-8.14 (m, 3H), 7.77 (d, J=7.6 Hz, 1H), 7.48 (t, J=7.6 Hz, 1H), 7.11 (d, J=8.0 Hz, 2H), 5.25 (d, J=7.2 Hz, 1H), 4.81-4.76 (m, 2H), 3.82-3.69 (m, 4H), 3.22-3.09 (m, 2H), 2.91-2.84 (m, 1H), 2.47-2.42 (m, 1H), 1.38-1.37 (m, 6H). MS-ESI [M+H]⁺: calculated value: 420; measured value: 420.

Example 40

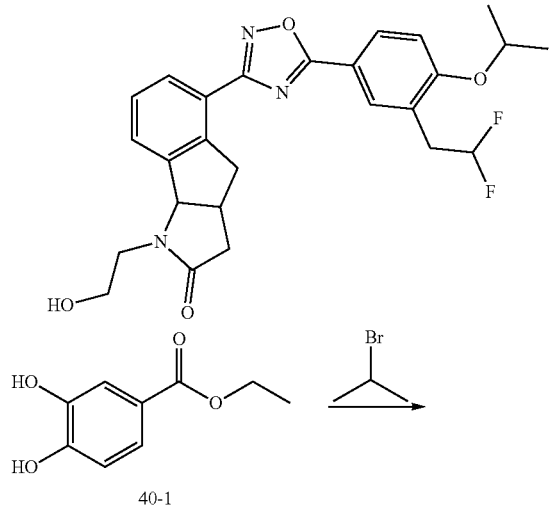

40-1

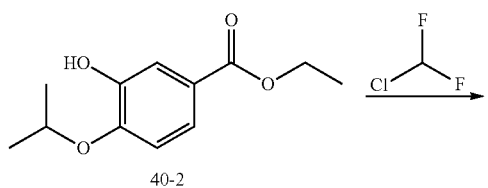

40-2

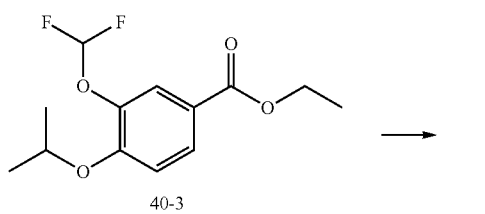

40-3

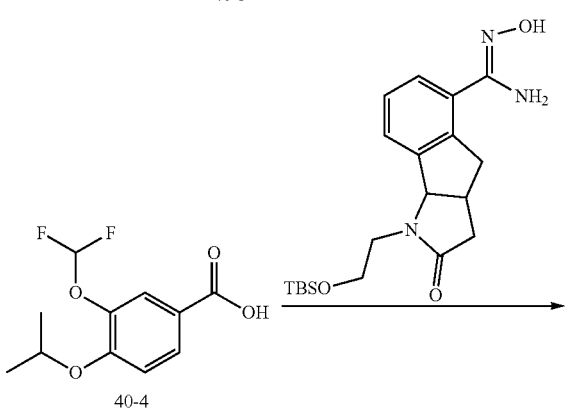

40-4

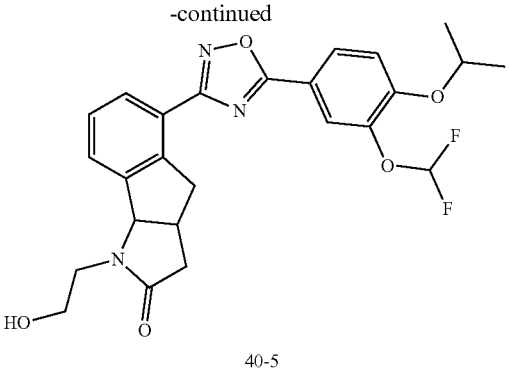

40-5

Step 1

Compound 40-1 (10.0 g, 54.9 mmol), 2-bromopropane (6.75 g, 54.9 mmol), potassium carbonate (7.59 g, 54.9 mmol) were dissolved in N,N-dimethylformamide (200 mL) at 0° C. and the mixture was stirred for 2 hours, then heated to 20° C. and further stirred for 13 hours. The solution was filtered and the filtrated was concentrated under reduced pressure. The residue was dissolved in dichloromethane (50 mL) and washed with water (30 mL). The aqueous layer was extracted with dichloromethane (50 mL×3). The organic layer was dried over anhydrous sodium sulfate, filtered and concentrated. The residue was purified by silica gel column chromatography (10:1-3:1 petroleum ether/ethyl acetate, $R_f$=0.7) to give compound 40-2 (5.20 g, colorless oil); yield: 42%.

¹H NMR (400 MHz, CDCl₃) δ 7.59-7.63 (m, 2H), 6.88 (d, J=8.0 Hz, 1H), 5.74 (s, 1H), 4.75-4.66 (m, 1H), 4.36 (q, J=7.2 Hz, 2H), 1.42 (d, J=6.0 Hz, 6H), 1.39 (t, J=7.2 Hz, 3H).

Step 2

Compound 40-2 (300 mg, 1.34 mmol) was dissolved in anhydrous N,N-dimethylformamide (3 mL). Sodium hydride (107 mg, 2.68 mmol, purity: 60%) was added slowly at 20° C. and the mixture was stirred for 30 minutes. Difluoromonochloromethane (gas) was introduced into the reaction solution slowly and the mixture was stirred for 30 minutes. The mixture was quenched with water (5 mL) and diluted with dichloromethane (10 mL). The aqueous layer was extracted with dichloromethane (10 mL×3). The organic layer was dried over anhydrous sodium sulfate, filtered and concentrated. The residue was purified by column chromatography (10:1-5:1 petroleum ether/ethyl acetate, $R_f$=0.5) to give compound 40-3 (180 mg, colorless oil); yield: 49%.

¹H NMR (400 MHz, CDCl₃) δ 7.91 (dd, J=2.0, 8.8 Hz, 1H), 7.85 (d, J=2.0 Hz, 1H), 7.00 (d, J=8.8 Hz, 1H), 6.58 (t, J=74.8 Hz, 1H), 4.73-4.64 (m, 1H), 4.37 (q, J=7.2 Hz, 2H), 1.42 (d, J=6.0 Hz, 6H), 1.40 (t, J=7.2) Hz, 3H).

Step 3

Compound 40-3 (180 mg, 0.656 mmol) was dissolved in tetrahydrofuran (2 mL) and water (2 mL), and lithium hydroxide (31.4 mg, 1.31 mmol) was added to the mixture. The reaction was stirred at 20° C. for 15 hours. The solution was concentrated under reduced pressure to remove tetrahydrofuran. The aqueous layer was acidified with diluted hydrochloric acid to pH=7, then extracted with dichloromethane (10 mL×3). The organic layers were combined and dried over anhydrous sodium sulfate, filtered and concentrated. The residue was purified by TLC (10:1 dichloromethane/methanol, $R_f$=0.05) to give compound 40-4 (160 mg, white solid); yield: 99%.

$^1$H NMR (400 MHz, CDCl$_3$) δ 7.89 (dd, J=2.0, 8.4 Hz, 1H), 7.83 (d, J=2.0 Hz, 1H), 6.94 (d, J=8.4 Hz, 1H), 6.50 (t, J=74.8 Hz, 1H), 4.69-4.56 (m, 1H), 1.34 (d, J=6.0 Hz, 6H).

Step 4

The reaction referred to Step 1 of Example 29, and the residue was isolated and purified by high performance liquid chromatography to give compound 40-5 (18.0 mg); yield: 18%.

$^1$H NMR (400 MHz, Methonal-d$_4$) δ 8.21 (d, J=7.6 Hz, 1H), 8.11 (dd, J=2.0, 8.8 Hz, 1H), 7.98 (d, J=2.0 Hz, 1H), 7.78 (d, J=7.6 Hz, 1H), 7.50 (t, J=7.6 Hz, 1H), 7.37 (d, J=8.8 Hz, 1H), 6.86 (t, J=74.8 Hz, 1H), 5.27 (d, J=7.6 Hz, 1H), 4.62 (s, 2H), 3.86-3.79 (m, 1H), 3.78-3.71 (m, 3H), 3.29-3.21 (m, 1H), 3.16-3.09 (m, 1H), 2.93-2.85 (m, 1H), 2.46 (d, J=15.6 Hz, 1H), 1.44 (d, J=6.0 Hz, 6H). MS-ESI [M+H]$^+$: calculated value: 486; measured value: 486.

Example 41

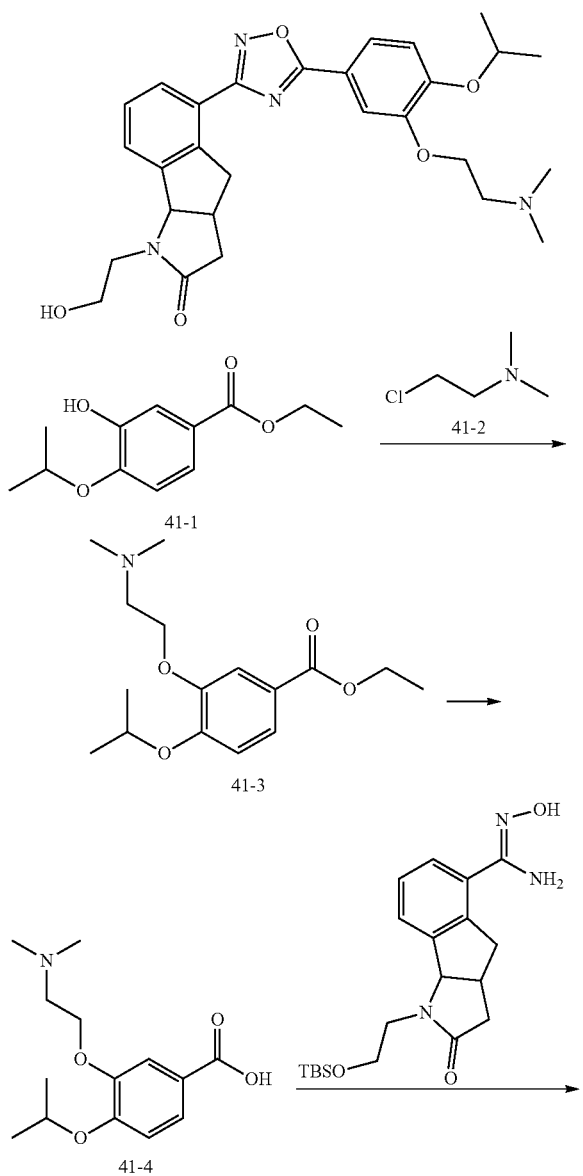

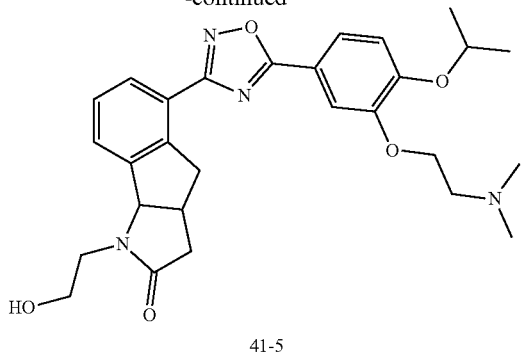

41-5

Step 1

Compound 41-1 (200 mg, 0.892 mmol), Compound 41-2 (192 mg, 1.78 mmol), cesium carbonate (581 mg, 1.78 mmol) and potassium iodide (13.4 mg, 0.0892 mmol) were dissolved in tetrahydrofuran (4 mL). The mixture was heated to 70° C. and stirred for 15 hours. The mixture was filtered and the filtrate was concentrated with reduced pressure. The residue was dissolved in dichloromethane (10 mL) and washed with water (10 mL). The aqueous layer was extracted with dichloromethane (10 mL×3). The organic layer was dried over anhydrous sodium sulfate, filtered and concentrated. The residue was purified by silica gel column chromatography (10:1-0:1 petroleum ether/ethyl acetate, R$_f$=0.05) to give compound 41-3 (170 mg, white solid); yield: 65%.

$^1$H NMR (400 MHz, CDCl$_3$) δ 7.67 (dd, J=2.0, 8.8 Hz, 1H), 7.59 (d, J=2.0 Hz, 1H), 6.91 (d, J=8.8 Hz, 1H), 4.58-4.69 (m, 1H), 4.36 (q, J=7.2 Hz, 2H), 4.16 (t, J=6.0 Hz, 2H), 2.81 (t, J=6.0 Hz, 2H), 2.38 (s, 6H), 1.36-1.43 (m, 9H). MS-ESI [M+H]$^+$: calculated value: 296; measured value: 296.

Step 2

Compound 41-3 (170 mg, 0.576 mmol) was dissolved in tetrahydrofuran (2 mL) and water (2 mL), and lithium hydroxide (48.3 mg, 1.15 mmol) was added. The reaction was stirred at 20° C. for 15 hours. The solution was concentrated under reduced pressure to remove tetrahydrofuran. The aqueous layer was acidified with diluted hydrochloric acid to pH=7, extracted with dichloromethane (10 mL×3). The organic layers were combined and dried with anhydrous sodium sulfate, filtered and concentrated. The residue was purified by TLC (10:1 dichloromethane/methanol, R$_f$=0.03) to give compound 41-4 (120 mg, white solid); yield: 62%.

$^1$H NMR (400 MHz, Methonal-d$_4$) δ 7.69 (dd, J=2.0, 8.8 Hz, 1H), 7.64 (d, J=2.0 Hz, 1H), 7.04 (d, J=8.8 Hz, 1H), 4.68-4.78 (m, 1H), 4.36 (d, J=4.8 Hz, 2H), 3.53 (d, J=4.8 Hz, 2H), 3.00 (s, 6H), 1.38 (d, J=6.0 Hz, 6H). MS-ESI [M+H]$^+$: calculated value: 268; measured value: 268.

Step 3

The reaction referred to Step 1 of Example 29, and the residue was isolated and purified by high performance liquid chromatography to give compound 41-5 (1.5 mg); yield: 1%.

$^1$H NMR (400 MHz, Methonal-d$_4$) δ 8.19 (d, J=7.6 Hz, 1H), 7.97 (dd, J=2.0, 8.4 Hz, 1H), 7.90 (d, J=2.0 Hz, 1H), 7.79 (d, J=7.6 Hz, 1H), 7.51 (t, J=7.6 Hz, 1H), 7.30 (d, J=8.4 Hz, 1H), 5.28 (d, J=7.2 Hz, 1H), 4.47-4.52 (m, 2H), 3.79-3.85 (m, 1H), 3.66-3.77 (m, 5H), 3.21-3.27 (m, 1H), 3.11-3.15 (m, 1H), 3.11 (s, 6H), 2.85-2.93 (m, 1H), 2.48-2.42 (m, 1H), 1.96 (s, 2H), 1.44 (d, J=6.0 Hz, 6H). MS-ESI [M+H]⁺: calculated value: 507; measured value: 507.

Example 42

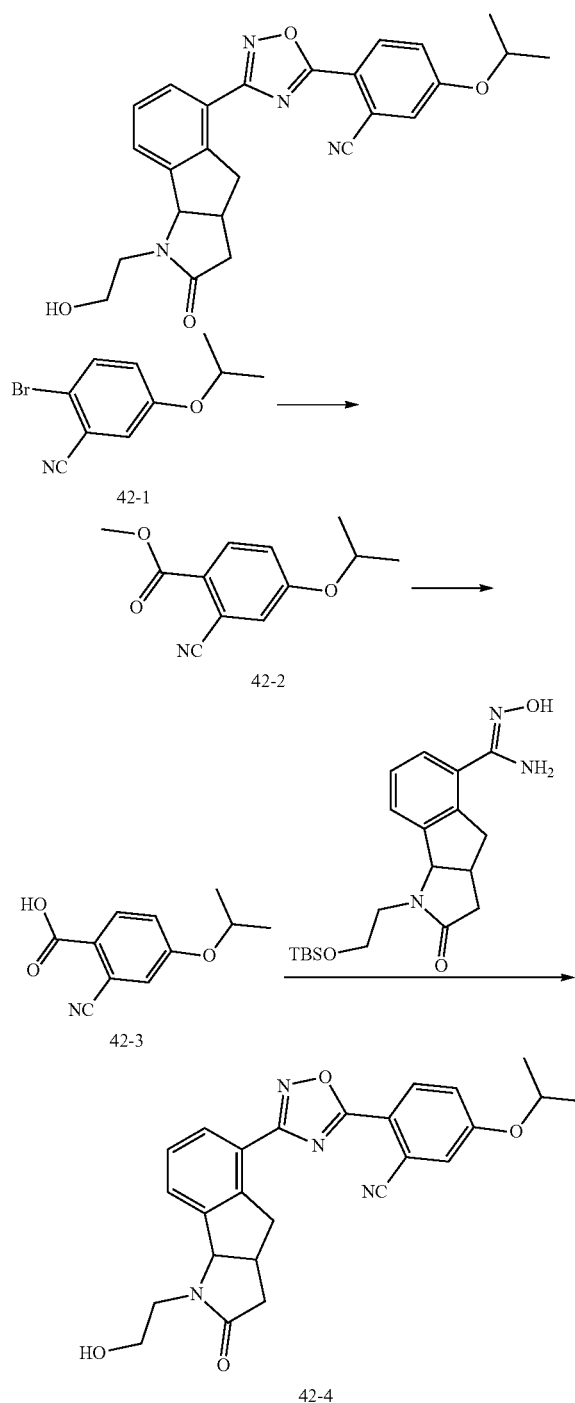

Step 1

Compound 42-1 (500 mg, 2.08 mmol) was dissolved in a mixture of methanol (9 mL), N,N-dimethylformamide (3 mL) and triethylamine (3 mL) and [1,1'-bis(diphenylphosphino)ferrocene]dichloropalladium(II) (152 mg, 0.208 mmol) was added. The reaction solution was stirred at 80° C. for 12 hours under carbon monoxide atmosphere (50 psi). Water (30 mL) was added to the reaction mixture after the mixture was cooled to the room temperature, and the mixture was extracted with ethyl acetate (30 mL×3). The organic layers were combined and washed with saturated brine (30 mL×2), dried over anhydrous sodium sulfate, filtered and the filtrate was concentrated under reduced pressure. The residue was purified by silica gel column chromatography (10:1 petroleum ether/ethyl acetate, $R_f$=0.5) to give compound 42-2 (400 mg, white solid); yield: 88%. MS-ESI [M+H]⁺: calculated value: 220; measured value: 220.

¹H NMR: (400 MHz, Methanol-d₄) δ 8.10 (dJ=7.2 Hz, 1H), 7.38 (s, 1H), 7.27 (d, J=7.2 Hz, 1H), 4.82-4.76 (m, 1H), 3.95 (s, 3H), 1.38 (d, J=6.0 Hz, 6H).

Step 2

The reaction referred to Step 2 of Example 25, the residue was compound 42-3 (350 mg, white solid); yield: 94%.

¹H NMR: (400 MHz, Methanol-d₄) δ 8.10 (d, J=7.2 Hz, 1H), 7.37 (s, 1H), 7.27 (d, J=7.2 Hz, 1H), 4.82-4.76 (m, 1H), 1.38 (d, J=6.0 Hz, 6H). MS-ESI [M+H]⁺: calculated value: 206; measured value: 206.

Step 3

The reaction referred to Step 3 of Example 25, and the residue was isolated and purified by high performance liquid chromatography to give compound 42-4 (30.0 mg); yield: 26%.

¹H NMR: (400 MHz, DMSO-d₆) δ 8.29 (d, J=7.2 Hz, 1H), 8.09 (d, J=7.6 Hz, 1H), 7.81 (d, J=7.6 Hz, 1H), 7.71 (d, J=7.2 Hz, 1H), 7.55-7.49 (m, 2H), 5.17 (d, J=7.2 Hz, 1H), 4.92-4.86 (m, 2H), 3.71-3.70 (m, 1H), 3.59-3.52 (m, 3H), 3.24-3.22 (m, 1H), 3.06-3.01 (m, 2H), 2.71-2.68 (m, 1H), 2.31-2.29 (m, 1H), 1.34 (d, J=6.0 Hz, 6H). MS-ESI [M+H]⁺: calculated value: 445; measured value: 445.

Example 43

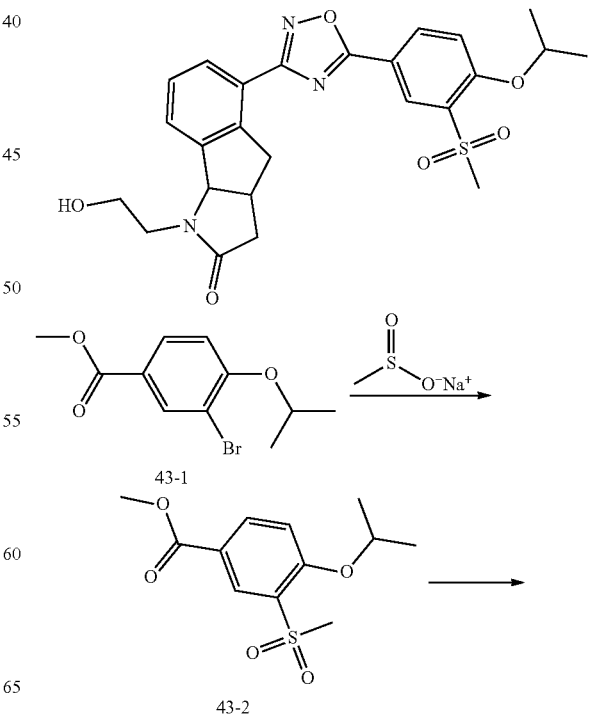

135

-continued

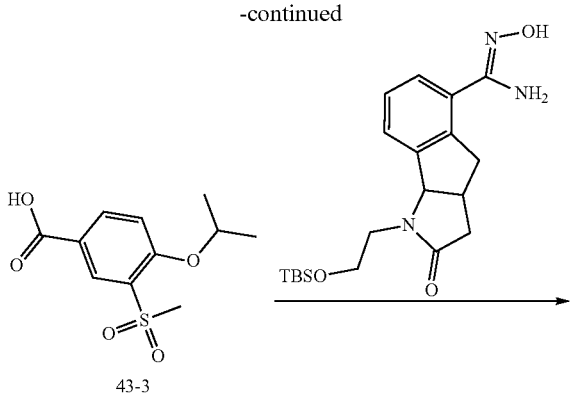

43-3

Step 1

Compound 43-1 (800 mg, 2.93 mmol) was dissolved in dimethyl sulfoxide (10 mL), and sodium methylsulfinate (897 mg, 8.79 mmol), cuprous iodide (112 mg, 0.586 mmol), L-valine (135 mg, 1.17 mmol) and sodium hydroxide (46.9 mg, 1.17 mmol) were added. The reaction solution was stirred at 100° C. for 18 hours under nitrogen atmosphere. Water (30 mL) was added to the reaction mixture after the mixture was cooled to the room temperature, and the mixture was extracted with ethyl acetate (30 mL×3). The organic layers were combined and washed with saturated brine (30 mL×2), dried over anhydrous sodium sulfate, filtered and the filtrate was concentrated with reduced pressure. The residue was purified by silica gel column chromatography (3:1 petroleum ether/ethyl acetate, $R_f$=0.2) to give compound 43-2 (80.0 mg, white solid); yield: 10%.

$^1$H NMR: (400 MHz, Methonal-d$_4$) δ 8.54 (s, 1H), 8.30 (d, J=8.8 Hz, 1H), 7.37 (d, J=8.8 Hz, 1H), 5.03-4.99 (m, 1H), 3.93 (s, 3H), 3.28 (s, 3H), 1.47 (d, J=6.0 Hz, 6H). MS-ESI [M+H]$^+$: calculated value: 273; measured value: 273.

Step 2

The reaction referred to Step 2 of Example 39, the residue was compound 43-3 (70.0 mg, white solid); yield: 92%.

$^1$H NMR: (400 MHz, Methonal-d$_4$) δ 8.55 (s, 1H), 8.30 (d, J=8.8 Hz, 1H), 7.36 (d, J=8.8 Hz, 1H), 5.01-4.98 (m, 1H), 3.28 (s, 3H), 1.47 (d, J=6.0 Hz, 6H). MS-ESI [M+H]$^+$: calculated value: 259; measured value: 259.

136

Step 3

The reaction referred to Step 1 of Example 29, and the residue was isolated and purified by high performance liquid chromatography to give compound 43-4 (25.0 mg); yield: 33%.

$^1$H NMR: (400 MHz, Methonal-d$_4$) δ 8.71 (s, 1H), 8.48 (d, J=7.6 Hz, 1H), 8.21 (d, J=7.6 Hz, 1H), 7.78 (d, J=7.6 Hz, 1H), 7.54-7.48 (m, 2H), 5.27 (d, J=7.2 Hz, 1H), 5.09-5.03 (m, 1H), 3.82-3.79 (m, 1H), 3.76-3.72 (m, 3H), 3.34 (s, 3H), 3.24-3.22 (m, 2H), 3.15-3.11 (m, 1H), 2.93-2.87 (m, 1H), 2.49-2.45 (m, 1H), 1.51 (d, J=6.0 Hz, 6H). MS-ESI [M+H]$^+$: calculated value: 498; measured value: 498.

Example 44

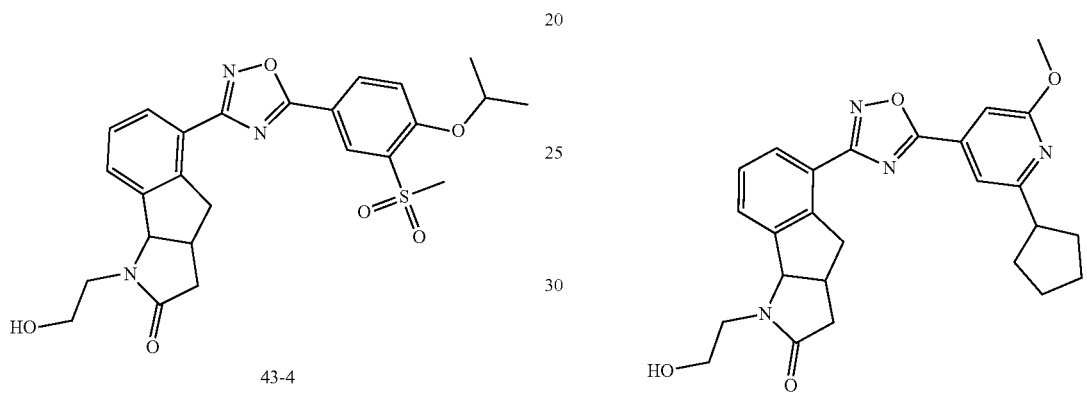

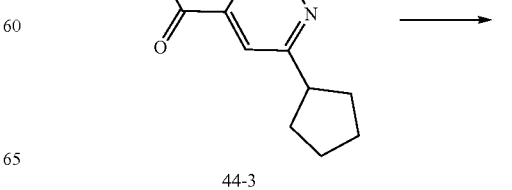

44-3

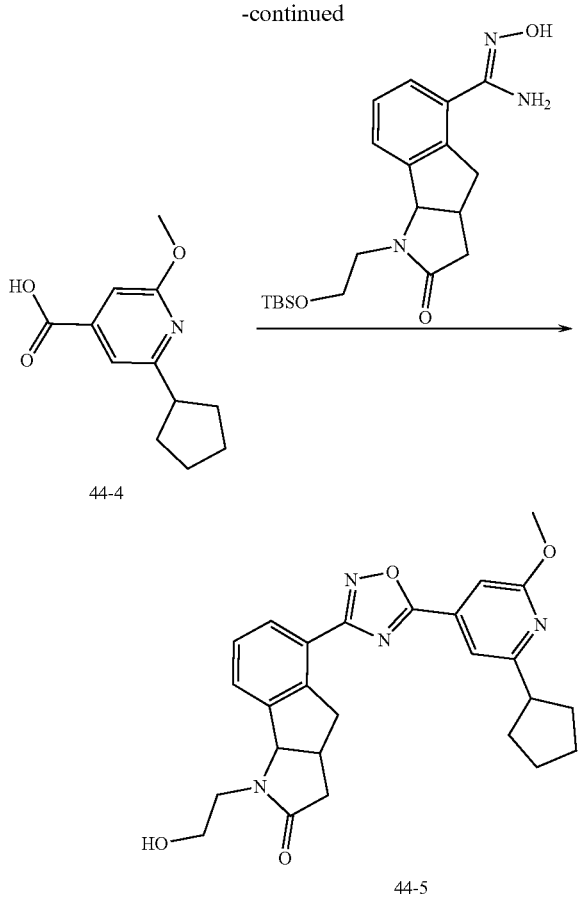

¹H NMR: (400 MHz, CDCl₃) δ 7.28 (s, 1H), 7.09 (s, 1H), 3.95 (s, 3H), 3.92 (s, 3H), 3.21-3.10 (m, 1H), 2.10-1.97 (m, 2H), 1.89-1.67 (m, 6H).

Step 3

Compound 44-3 (50.0 mg, 0.212 mmol) was dissolved in methanol (3 mL), and lithium hydroxide (35.6 mg, 0.85 mmol) and water (0.5 mL) were added. The reaction solution was stirred at 40° C. for 2 hours. The mixture was concentrated under reduced pressure. The residue was dissolved in ethyl acetate (30 mL). The solution was acidified with 1 M hydrochloric acid to pH=3. The organic layer was washed with saturated brine (20 mL×2), dried over anhydrous sodium sulfate, concentrated to give Compound 44-4 (46 mg, white solid).

¹H NMR: (400 MHz, Methonal-d₄) δ 7.28 (s, 1H), 7.04 (s, 1H), 3.92 (s, 3H), 3.21-3.09 (m, 1H), 2.08-1.97 (m, 2H), 1.89-1.64 (m, 6H).

Step 4

The reaction referred to Step 1 of Example 16, and the residue was isolated and purified by high performance liquid chromatography to give compound 44-5 (36.0 mg); yield: 38%.

¹H NMR: (400 MHz, Methonal-d₄) δ 8.13 (d, J=7.2 Hz, 1H), 7.74 (d, J=7.2 Hz, 1H), 7.49-7.43 (m, 2H), 7.19 (s, 1H), 5.23 (d, J=7.2 Hz, 1H), 3.97 (s, 3H), 3.78-3.70 (m, 4H), 3.31-3.16 (m, 3H), 3.09-3.03 (m, 1H), 2.91-2.84 (m, 1H), 2.47-2.42 (m, 1H), 2.12-2.04 (m, 2H), 1.91-1.73 (m, 6H).

MS-ESI [M+H]⁺: calculated value: 461; measured value: 461.

Example 45

Step 1

Sodium (122 mg, 5.33 mmol) was dissolved in methanol (8 mL), and Compound 44-1 (1.00 g, 4.85 mmol) was added. The reaction solution was stirred at 65° C. with 1 hour under nitrogen atmosphere. Saturated aqueous ammonium chloride solution (10 mL) was added to the reaction mixture after the mixture was cooled to 25° C., and the mixture was extracted with ethyl acetate (30 mL×2). The organic layers were combined and washed with saturated brine (20 mL×2), dried over anhydrous sodium sulfate and concentrated under reduced pressure. The residue was subject to silica gel column chromatography (petroleum ether, R$_f$=0.6) to give compound 44-2 (620 mg, white solid); yield: 63%.

¹H NMR: (400 MHz, CDCl₃) δ 7.45 (s, 1H), 7.23 (s, 1H), 3.98 (s, 3H), 3.95 (s, 3H).

Step 2

Compound 44-2 (420 mg, 2.08 mmol) was dissolved in toluene (15 mL), and cyclopentylboronic acid (308 mg, 2.70 mmol), tricyclohexylphosphine (233 mg, 0.832 mmol), potassium phosphate (1.32 g, 6.24 mmol), palladium acetate (93.4 mg, 0.416 mmol) and water (2 mL) were added. The reaction solution was stirred at 100° C. for 12 hours under nitrogen atmosphere. Ethyl acetate (50 mL) was added to the reaction mixture after the mixture was cooled to 25° C. and the mixture was washed with water (20 mL×2) and saturated brine (20 mL×2), dried over anhydrous sodium sulfate and concentrated under reduced pressure. The residue was subject to silica gel chromatography (100:1 petroleum ether/acetone, R$_f$=0.3) to give compound 50-3 (50 mg, colorless oil); yield: 10%.

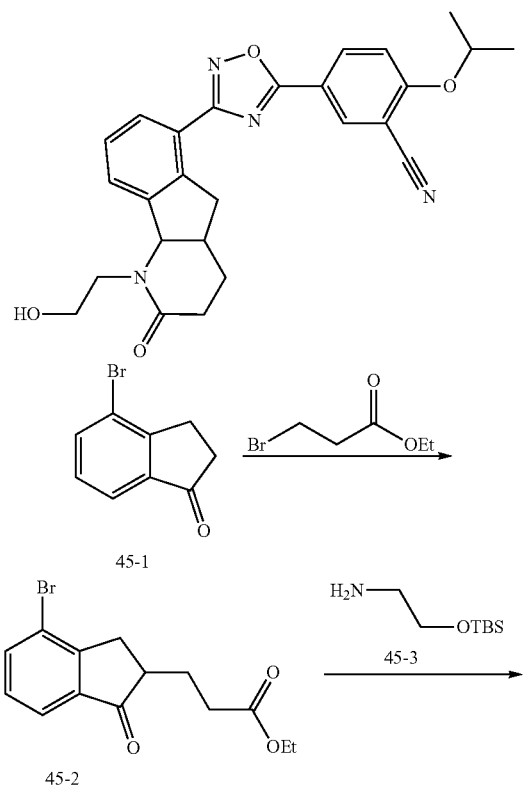

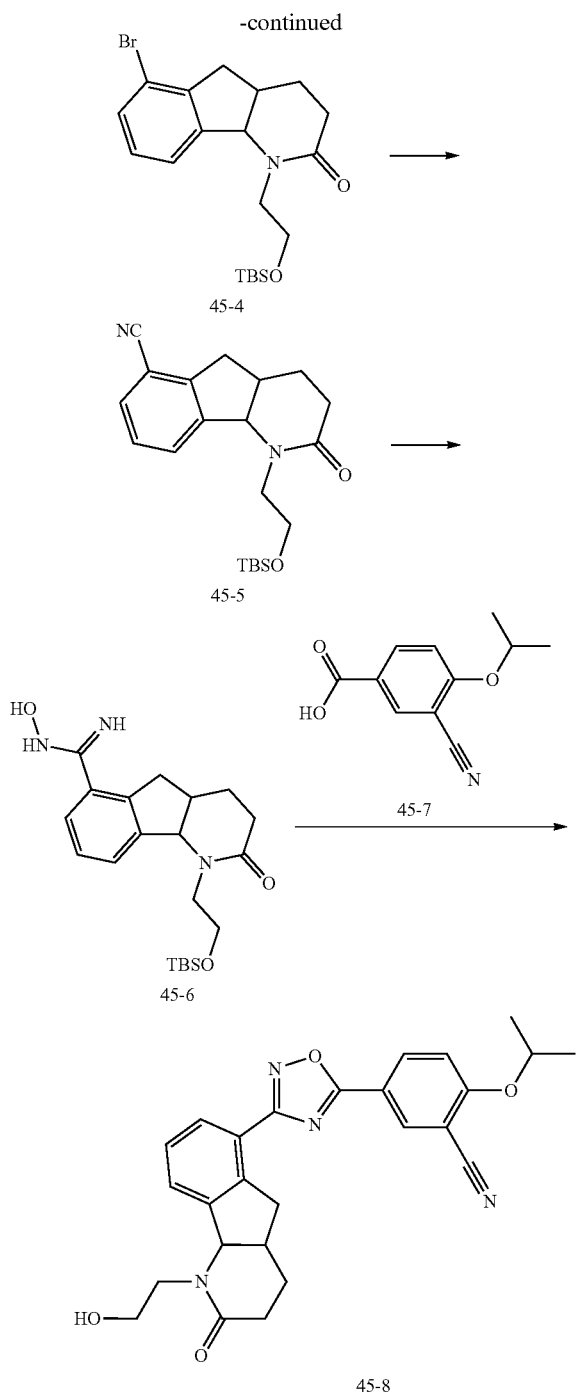

fied by silica gel column chromatography (10:1 petroleum ether/ethyl acetate, $R_f$=0.7) to give compound 45-2 (300 mg, pale yellow oil); yield: 10%.

$^1$H NMR: (400 MHz, Methonal-$d_4$) δ 7.87 (d, J=8.0 Hz, 1H), 7.71 (d, J=8.0 Hz, 1H), 7.38 (t, J=8.0 Hz, 1H), 4.15 (q, J=7.2 Hz, 2H), 3.38-3.36 (m, 1H), 2.83-2.75 (m, 2H), 2.57-2.53 (m, 2H), 2.21-2.18 (m, 1H), 1.84-1.82 (m, 1H), 1.28 (t, J=7.2 Hz, 3H). MS-ESI [M+H]$^+$: calculated value: 311 and 313; measured value: 311 and 313.

Step 2

Compound 45-2 (300 mg, 0.964 mmol) was dissolved in tetrahydrofuran (3 mL), and Compound 45-3 (186 mg, 1.06 mmol) and titanium tetraisopropoxide (548 mg, 1.93 mmol) were added. The reaction was stirred at 60° C. for 1 hour under nitrogen atmosphere. Then, sodium borohydride (72.9 mg, 1.93 mmol) and methanol (10 mL were added to the reaction mixture which was cooled to room temperature. The mixture was then heated to 60° C. and stirred for 12 hours. Water (30 mL) was added to the reaction mixture after the mixture was cooled to room temperature, followed by filtering. The filtrate was extracted with ethyl acetate (20 mL×3). The organic layers were combined and washed with saturated brine (20 mL×2), dried over anhydrous sodium sulfate, filtered and the filtrate was concentrated under reduced pressure. The residue was purified by silica gel column chromatography (3:1 petroleum ether/ethyl acetate, $R_f$=0.5) to give compound 45-4 (150 mg, pale yellow oil); yield: 37%.

$^1$H NMR: (400 MHz, CDCl$_3$) δ 7.34 (d, J=8.0 Hz, 1H), 7.25 (d, J=8.0 Hz, 1H), 7.04 (t, J=8.0 Hz, 1H), 5.13 (d, J=7.2 Hz, 1H), 4.23-4.19 (m, 1H), 3.90-3.88 (m, 1H), 3.70-3.67 (m, 1H), 3.29-3.27 (m, 1H), 3.02-2.98 (m, 1H), 2.74-2.69 (m, 1H), 2.40-2.19 (m, 3H), 1.76-1.75 (m, 1H), 1.63-1.61 (m, 1H), 0.79 (s, 9H), 0.00 (s, 6H). MS-ESI [M+H]$^+$: calculated value: 424 and 426; measured value: 424 and 426.

Step 3

Compound 45-4 (150 mg, 0.353 mmol) was dissolved in acetonitrile (5 mL), and zinc cyanide (83.0 mg, 0.707 mmol), 2-dicyclohexylphosphine-2',4',7'-triisopropylbiphenyl (34.9 mg, 0.0707 mmol) and tris(dibenzylideneacetone)dipalladium(0) (32.4 mg, 0.0353 mmol) were added. The reaction was stirred at 90° C. for 16 hours under nitrogen atmosphere. Water (10 mL) was added to the reaction mixture after the mixture was cooled to room temperature. The mixture was extracted with ethyl acetate (20 mL×3). The organic layers were combined and washed with saturated brine (20 mL×2), dried over anhydrous sodium sulfate, filtered and the filtrate was concentrated under reduced pressure. The residue was purified by TLC (1:1 petroleum ether/ethyl acetate, $R_f$=0.3) to give compound 45-5 (100 mg, pale yellow oil); yield: 76%.

$^1$H NMR: (400 MHz, Methonal-$d_4$) δ 7.65 (d, J=8.0 Hz, 1H), 7.53 (d, J=8.0 Hz, 1H), 7.33 (t, J=8.0 Hz, 1H), 5.14 (d, J=7.2 Hz, 1H), 4.12-4.08 (m, 1H), 3.87-3.85 (m, 1H), 3.70-3.69 (m, 1H), 3.39-3.37 (m, 1H), 3.16-3.14 (m, 1H), 2.90-2.89 (m, 1H), 2.46-2.44 (m, 1H), 2.25-2.24 (m, 1H), 2.15-2.14 (m, 1H), 1.80-1.78 (m, 1H), 1.60-1.58 (m, 1H), 0.82 (s, 9H), 0.00 (s, 6H). MS-ESI [M+H]$^+$: calculated value: 371; measured value: 371.

Step 4

Compound 45-5 (100 mg, 0.270 mmol) was dissolved in anhydrous ethanol (3 mL), and hydroxylamine hydrochloride (56.3 mg, 0.810 mmol) and triethylamine (109 mg, 1.08 mmol) were added. The reaction was stirred at 60° C. for 12 hours under nitrogen atmosphere. Water (10 mL) was added to the reaction mixture after the mixture was cooled to room Step 1

Compound 45-1 (2.00 g, 94.8 mmol) was dissolved in anhydrous tetrahydrofuran (10 mL), and bis(trimethylsilyl)amide lithium (1M in tetrahydrofuran, 11.4 mL) was added dropwise at −78° C. The reaction was stirred at this temperature for 30 minutes. Then, ethyl bromopropionate (1.89 g, 10.4 mmol) was added to the reaction mixture, and the mixture was stirred at 25° C. for 2 hours. Water (20 mL) was added to the reaction mixture, and the mixture was extracted with ethyl acetate (20 mL×3). The organic layers were combined and washed with saturated brine (30 mL×2), dried over anhydrous sodium sulfate, filtered and the filtrate was concentrated with reduced pressure. The residue was puritemperature. The mixture was extracted with ethyl acetate (10 mL×3). The organic layers were combined and washed with saturated brine (10 mL×2), dried over anhydrous sodium sulfate, filtered and the filtrate was concentrated under reduced pressure. The residue was purified by gel column chromatography (0:1 petroleum ether/ethyl acetate, $R_f$=0.4) to give compound 45-6 (60.0 mg, pale yellow oil); yield: 55%.

$^1$H NMR: (400 MHz, CDCl$_3$) δ 7.37-7.35 (m, 2H), 7.22-7.20 (t, J=8.0 Hz, 1H), 5.07 (d, J=7.2 Hz, 1H), 4.74 (s, 2H), 4.24-4.20 (m, 1H), 3.92-3.91 (m, 1H), 3.70-3.68 (m, 1H), 3.30-3.28 (m, 1H), 3.13-3.11 (m, 1H), 2.95-2.91 (m, 1H), 2.76-2.74 (m, 1H), 2.27-2.19 (m, 2H), 1.72-1.70 (m, 1H), 1.59-1.56 (m, 1H), 0.83 (s, 9H), 0.00 (s, 6H). MS-ESI [M+H]$^+$: calculated value: 404; measured value: 404.

Step 5

Compound 45-7 (33.6 mg, 0.164 mmol) was dissolved in N,N-dimethylformamide (5 mL), and 1-hydroxybenzotriazole (40.2 mg, 0.297 mmol) and 1-(3-dimethylaminopropyl)-3-ethylcarbodiimide hydrochloride (57.0 mg, 0.297 mmol) were added. The reaction was stirred at 25° C. for 0.5 hour under nitrogen atmosphere. Then, Compound 45-6 (60.0 mg, 0.149 mmol) was added into the reaction mixture and the mixture was stirred at 25° C. for 1 hour, then heated to 80° C. and further stirred for 12 hours. Water (30 mL) was added to the reaction mixture after the mixture was cooled to room temperature. The mixture was extracted with ethyl acetate (30 mL×3). The organic layers were combined and washed with brine (25 mL×2), dried over anhydrous sodium sulfate, filtered and the filtrate was concentrated under reduced pressure. The residue was purified by high performance liquid chromatography to give compound 45-8 (25.0 mg); yield: 36%.

$^1$H NMR: (400 MHz, DMSO-d$_6$) δ 8.52 (s, 1H), 8.41 (d, J=7.6 Hz, 1H), 8.04 (d, J=7.6 Hz, 1H), 7.67 (d, J=7.6 Hz, 1H), 7.56 (d, J=7.6 Hz, 1H), 7.48 (t, J=7.6 Hz, 1H), 5.12 (d, J=7.2 Hz, 1H), 4.99-4.96 (m, 1H), 4.83-4.82 (m, 1H), 4.04-4.00 (m, 1H), 3.63-3.60 (m, 1H), 3.51-3.49 (m, 2H), 3.20-3.19 (m, 1H), 2.94-2.93 (m, 1H), 2.23-2.21 (m, 1H), 2.15-2.12 (m, 1H), 1.82-1.81 (m, 1H), 1.60-1.58 (m, 1H), 1.38 (d, J=6.0 Hz, 6H). MS-ESI [M+H]$^+$: calculated value: 459; measured value: 459.

Example 46

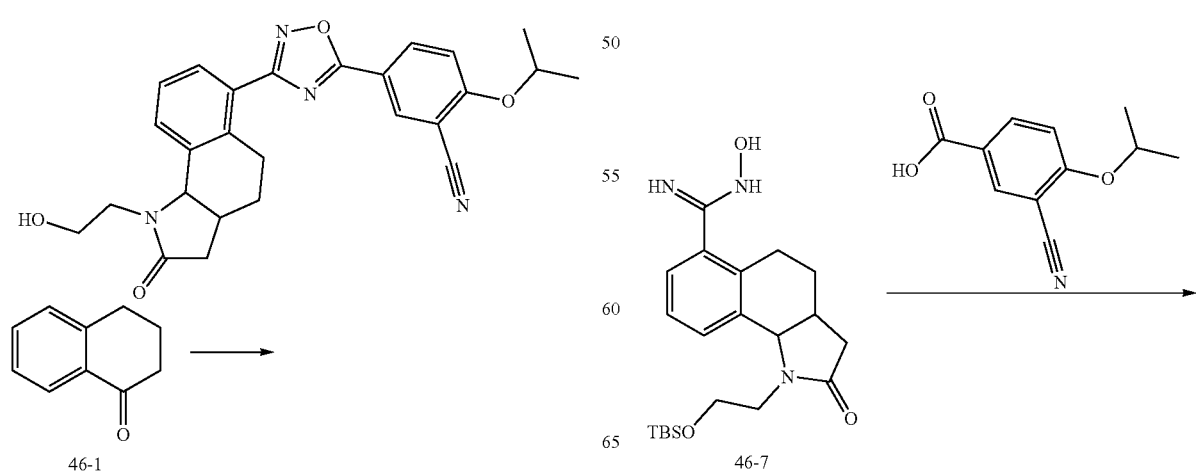

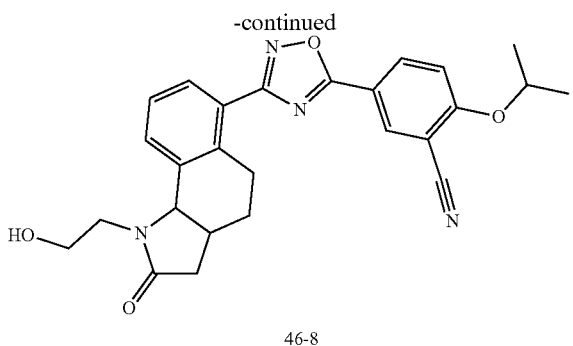

46-8

Step 1

Aluminum trichloride (57.0 g, 427 mmol) was heated to 80° C. and Compound 46-1 (25.0 g, 171 mmol) was slowly added dropwise, the mixture was stirred for 5 minutes. Bromine (32.0 g, 205 mmol) was added dropwise to the reaction mixture, and the mixture was continued stirred for 5 minutes. After the mixture was cooled to room temperature, a mixture of ice (200 g) and concentrated hydrochloric acid (12M, 50 mL) was poured into the mixture, the resultant was stirred for 20 minutes. The reaction solution was diluted with ethyl acetate (200 mL) and the aqueous layer was extracted with ethyl acetate (200 mL×3). The organic layers were combined and dried over anhydrous sodium sulfate, filtered and concentrated. The residue was purified by column chromatography (1:0 petroleum ether/ethyl acetate, $R_f$=0.5) to give compound 46-2 (12.0 g, pale yellow oil); yield: 31%.

$^1$H NMR (400 MHz, CDCl$_3$) δ 8.04 (dd, J=1.2, 8.0 Hz, 1H), 7.76 (dd, J=1.2, 8.0 Hz, 1H), 7.21. (t, J=8.0 Hz, 1H), 3.04 (t, J=6.0 Hz, 2H), 2.68 (t, J=6.0 Hz, 2H), 2.18-2.23 (m, 2H).

Step 2

Compound 46-2 (10.0 g, 44.4 mmol) was dissolved in anhydrous tetrahydrofuran (150 mL), and bis(trimethylsilyl)amide lithium (1M in tetrahydrofuran, 44.4 mL) was added dropwise at −78° C., the mixture was stirred for 30 minutes. Ethyl bromoacetate (7.42 g, 44.4 mmol) was added to the reaction mixture and continued stirred at −78° C. for 2 hours. The mixture was quenched with saturated aqueous ammonia chloride solution (50 mL). The aqueous layer was extracted with ethyl acetate (100 mL×3). The organic layers were combined and dried over anhydrous sodium sulfate, filtered and concentrated. The residue was purified by column chromatography (20:1-10:1 petroleum ether/ethyl acetate, $R_f$=0.3) to give compound 46-3 (6.00 g, pale yellow oil); yield: 31%.

$^1$H NMR (400 MHz, CDCl$_3$) δ 7.93 (dd, J=1.2, 8.0 Hz, 1H), 7.67 (dd, J=1.2, 8.0 Hz, 1H), 7.13 (t, J=8.0 Hz, 1H), 4.12 (t, J=7.2 Hz, 2H), 3.10-3.18 (m, 1H), 2.94-3.03 (m, 1H), 2.89-2.93 (m, 1H), 2.77-2.86 (m, 1H), 2.33-2.41 (m, 1H), 2.20-2.26 (m, 1H), 1.86-1.91 (m, 1H), 1.22 (t, J=7.2 Hz, 3H). MS-ESI [M+H]$^+$: calculated value: 311 and 313; measured value: 311 and 313.

Step 3

Compound 46-3 (6.00 g, 19.3 mmol), compound 46-4 (6.76 g, 38.6 mmol), and tetraisopropoxytitanium (10.9 g, 38.6 mmol) were dissolved in anhydrous tetrahydrofuran (50 mL). The solution was charged with nitrogen three times, heated to 70° C. and stirred for 15 hours. Then, sodium borohydride (1.46 g, 38.6 mmol) was added to the reaction mixture in portions after the mixture was cooled to 25° C. and the resultant was stirred for 2 hours, then heated to 70° C. again and continued stirred for 13 hours. The reaction mixture was cooled to room temperature and poured into water (30 mL), stirred for 5 minutes to precipitate white solid. The mixture was filtered and the filter cake was washed with ethyl acetate (20 mL×3). The filtrate was combined and partitioned, the aqueous layer was extracted with ethyl acetate (50 mL×3). The organic layers were combined and dried over anhydrous sodium sulfate, filtered and concentrated. The residue was purified by column chromatography (10:1-3:1 petroleum ether/ethyl acetate, $R_f$=0.3) to give compound 46-5 (700 mg, pale yellow oil); yield: 4%.

$^1$H NMR (400 MHz, CDCl$_3$) δ 7.50 (d, J=8.0 Hz, 1H), 7.46 (d, J=8.0 Hz, 1H), 7.06 (t, J=8.0 Hz, 1H), 4.82 (d, J=6.4 Hz, 1H), 3.82-3.72 (m, 1H), 3.52-3.44 (m, 2H), 3.03-2.96 (m, 1H), 2.78-2.72 (m, 2H), 2.71-2.60 (m, 2H), 2.22 (d, J=14.4 Hz, 1H), 1.76-1.66 (m, 2H), 0.85 (s, 9H), 0.01 (d, J=4.8 Hz, 6H). MS-ESI [M+H]$^+$: calculated value: 424 and 426; measured value: 424 and 426.

Step 4

Compound 46-5 (700 mg, 0.792 mmol), zinc cyanide (279 mg, 2.37 mmol), tris(dibenzylideneacetone) dipalladium (36.2 mg, 39.5 umol), 2-dicyclohexylphosphon-2',4',6'-triisopropylbiphenyl (37.7 mg, 79.1 umol) were dissolved in acetonitrile (10 mL). The solution was charged with nitrogen three times and heated to 90° C., stirred for 15 hours. After the reaction mixture was cooled to room temperature, the mixture was concentrated under reduced pressure and the residue was dissolved in dichloromethane (20 mL), washed with water (10 mL) and the aqueous layer was extracted with dichloromethane (20 mL×3). The organic layer was dried over anhydrous sodium sulfate, filtered and concentrated. The residue was purified by column chromatography (10:1-3:1 petroleum ether/ethyl acetate, $R_f$=0.2) to give compound 46-6 (210 mg, pale yellow oil); yield: 63%.

$^1$H NMR (400 MHz, CDCl$_3$) δ 7.75 (d, J=8.0 Hz, 1H), 7.56 (d, J=8.0 Hz, 1H), 7.28 (t, J=8.0 Hz, 1H), 4.87 (d, J=6.8 Hz, 1H), 3.84-3.73 (m, 1H), 3.54-3.47 (m, 2H), 2.94-2.83 (m, 3H), 2.78-2.67 (m, 2H), 2.29-2.18 (m, 1H), 1.75 (q, J=6.0 Hz, 2H), 0.84 (s, 9H), 0.01 (d, J=4.0 Hz, 6H). MS-ESI [M+H]$^+$: calculated value: 371; measured value: 371.

Step 5

Compound 46-6 (210 mg, 0.493 mmol) was dissolved in ethanol (10 mL), and hydroxylamine hydrochloride (103 mg, 1.48 mmol), triethylamine (199 mg, 1.97 mmol) were added in turn. The mixture was heated to 75° C. and stirred for 20 hours. After the reaction mixture was cooled to room temperature, the mixture was concentrated under reduced pressure and the residue was dissolved in dichloromethane (20 mL), washed with water (10 mL) and the aqueous layer was extracted with dichloromethane (20 mL×3). The organic layer was dried over anhydrous sodium sulfate, filtered and concentrated. The residue was purified by TLC (1:1 petroleum ether/ethyl acetate, $R_f$=0.1) to give compound 46-7 (130 mg, white solid); yield: 57%.

$^1$H NMR (400 MHz, CDCl$_3$) δ 7.52 (d, J=8.0 Hz, 1H), 7.40 (d, J=8.0 Hz, 1H), 7.26 (t, J=8.0 Hz, 1H), 4.97-4.90 (m, 1H), 4.82 (brs, 2H), 3.85-3.77 (m, 1H), 3.56-3.40 (m, 2H), 2.96-2.88 (m, 2H), 2.80-2.74 (m, 3H), 2.35-2.26 (m, 1H), 1.74-1.69 (m, 2H), 0.91 (s, 9H), 0.06 (d, J=4.0 Hz, 6H). MS-ESI [M+H]$^+$: calculated value: 404; measured value: 404.

Step 6

3-Cyano-4-isopropoxybenzoic acid (66.1 mg, 0.322 mmol), 1-hydroxybenzotriazole (87.1 mg, 0.644 mmol), 1-ethyl-3-(3-dimethyl aminopropyl) carbodiimide hydrochloride (123 mg, 0.644 mmol) were dissolved in anhydrous N,N-dimethylformamide (2 mL). The solution was charged with nitrogen three times. After the mixture was stirred at 20° C. for 30 minutes, a solution of Compound 46-7 (130 mg, 0.322 mmol) in anhydrous N,N-dimethylformamide (2 mL) was added. After further stirred for 30 minutes, the mixture was heated to 90° C. and continued stirred for 14 hours. The mixture was concentrated under reduced pressure and the residue was dissolved in dichloromethane (20 mL), washed with water (10 mL) and the aqueous layer was extracted with dichloromethane (20 mL×3). The organic layer was dried over anhydrous sodium sulfate, filtered and concentrated. The residue was purified by high performance liquid chromatography to give compound 46-8 (19.0 mg); yield: 13%.

$^1$H NMR (400 MHz, Methonal-$d_4$) δ 8.46-8.36 (m, 2H), 7.99 (d, J=7.6 Hz, 1H), 7.68 (d, J=7.6 Hz, 1H), 7.51-7.41 (m, 2H), 5.07 (d, J=7.2 Hz, 1H), 4.99-4.93 (m, 1H), 3.62-3.51 (m, 1H), 3.54-3.40 (m, 1H), 3.42-3.38 (m, 1H), 3.27-3.22 (m, 1H), 3.04-2.83 (m, 4H), 2.23-2.29 (m, 1H), 1.85-1.70 (m, 2H), 1.47 (d, J=6.0 Hz, 6H). MS-ESI [M+H]$^+$: calculated value: 459; measured value: 459.

Example 47

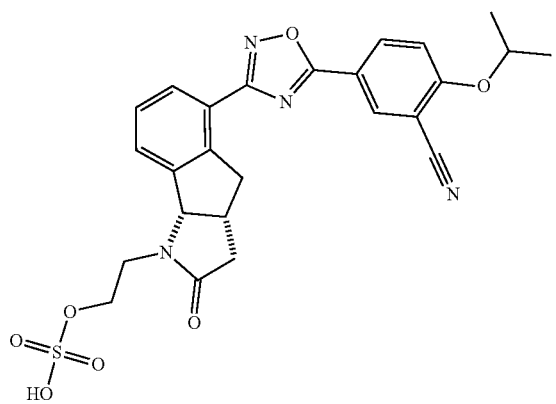

47-1

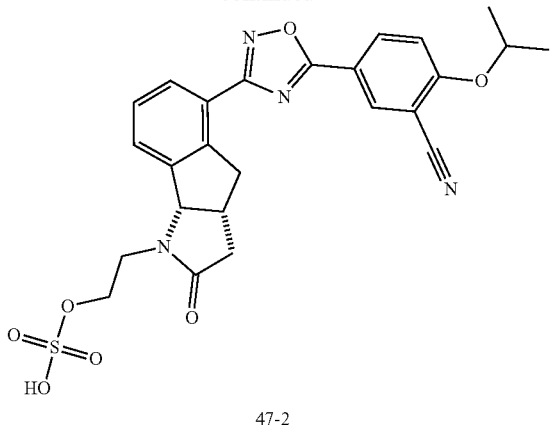

47-2

Step 1

Compound 47-1 (i.e., Compound 1-11) (80.0 mg, 0.180 mmol) and pyridine sulfur trioxide hydrochloride were dissolved in anhydrous N,N-dimethylformamide (5.0 mL). The reaction was stirred at 50° C. for 16 hours. The reaction mixture was concentrated under reduced pressure directly. The residue was purified by TLC (silica, methylene chloride:methanol=8:1) to give Compound 47-2.

$^1$H NMR (400 MHz, DMSO-$d_6$) δ 8.52 (s, 1H), 8.40 (d, J=8.0 Hz, 1H), 8.09 (d, J=7.6 Hz, 1H), 7.89 (d, J=7.6 Hz, 1H), 7.58 (d, J=8.0 Hz, 1H), 7.49 (t, J=7.6 Hz, 1H), 5.21 (d, J=7.2 Hz, 1H), 5.00-4.95 (m, 1H), 3.93-3.83 (m, 2H), 3.71-3.64 (m, 2H), 3.27-3.11 (m, 3H), 3.04-2.98 (m, 1H), 2.75-2.64 (m, 1H), 2.33-2.28 (m, 1H), 1.38 (d, J=6.0 Hz, 6H).

MS-ESI [M+H]$^+$: calculated value: 525; measured value: 525.

Example 48

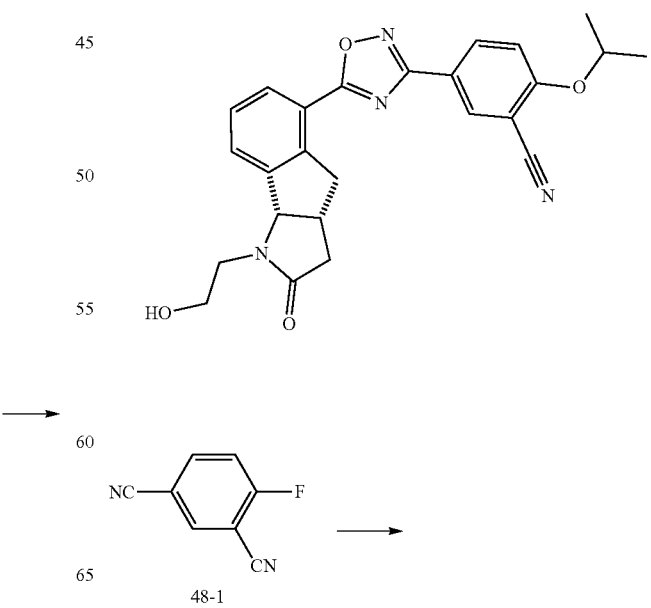

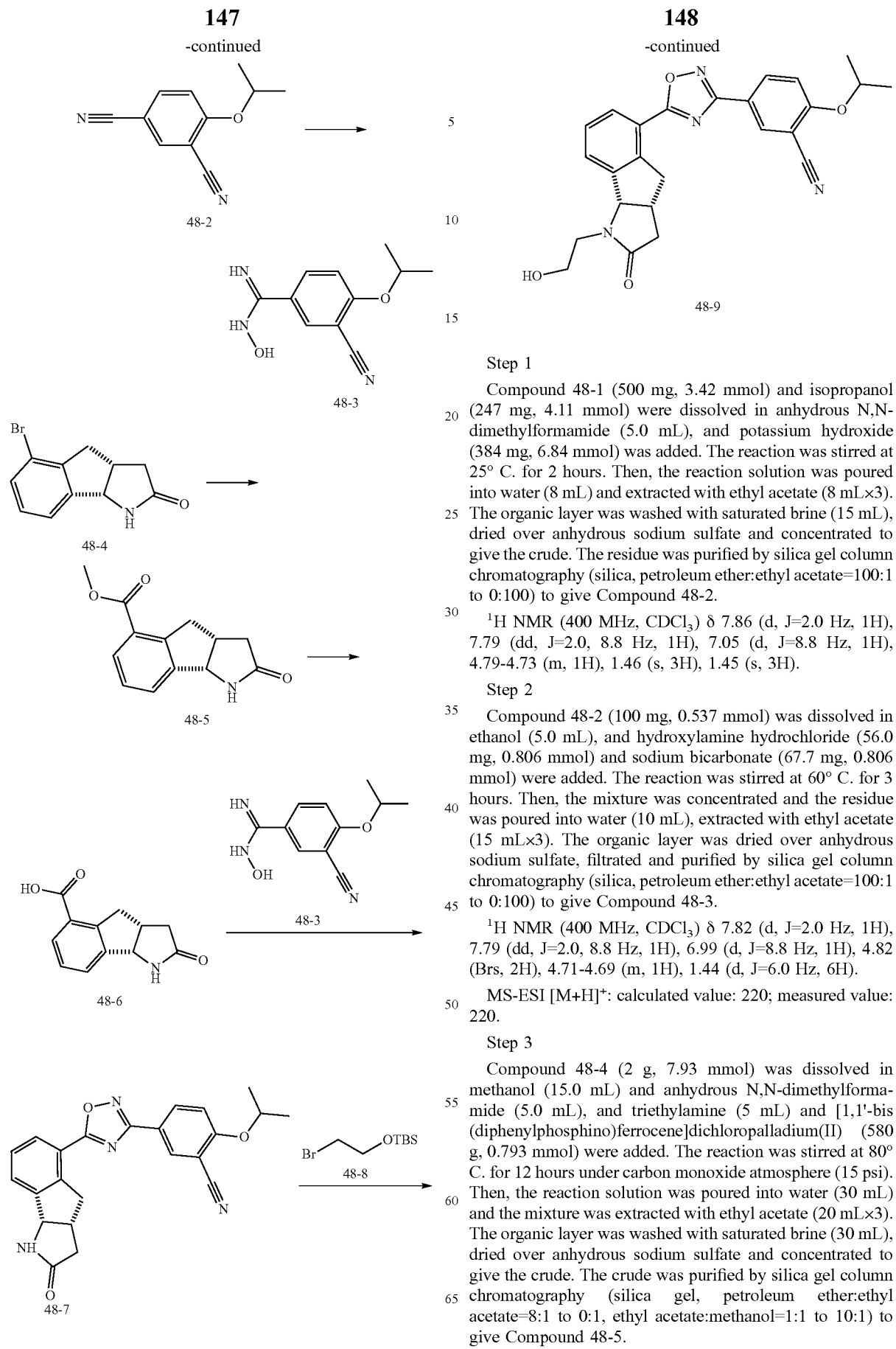

Step 1

Compound 48-1 (500 mg, 3.42 mmol) and isopropanol (247 mg, 4.11 mmol) were dissolved in anhydrous N,N-dimethylformamide (5.0 mL), and potassium hydroxide (384 mg, 6.84 mmol) was added. The reaction was stirred at 25° C. for 2 hours. Then, the reaction solution was poured into water (8 mL) and extracted with ethyl acetate (8 mL×3). The organic layer was washed with saturated brine (15 mL), dried over anhydrous sodium sulfate and concentrated to give the crude. The residue was purified by silica gel column chromatography (silica, petroleum ether:ethyl acetate=100:1 to 0:100) to give Compound 48-2.

$^1$H NMR (400 MHz, CDCl$_3$) δ 7.86 (d, J=2.0 Hz, 1H), 7.79 (dd, J=2.0, 8.8 Hz, 1H), 7.05 (d, J=8.8 Hz, 1H), 4.79-4.73 (m, 1H), 1.46 (s, 3H), 1.45 (s, 3H).

Step 2

Compound 48-2 (100 mg, 0.537 mmol) was dissolved in ethanol (5.0 mL), and hydroxylamine hydrochloride (56.0 mg, 0.806 mmol) and sodium bicarbonate (67.7 mg, 0.806 mmol) were added. The reaction was stirred at 60° C. for 3 hours. Then, the mixture was concentrated and the residue was poured into water (10 mL), extracted with ethyl acetate (15 mL×3). The organic layer was dried over anhydrous sodium sulfate, filtrated and purified by silica gel column chromatography (silica, petroleum ether:ethyl acetate=100:1 to 0:100) to give Compound 48-3.

$^1$H NMR (400 MHz, CDCl$_3$) δ 7.82 (d, J=2.0 Hz, 1H), 7.79 (dd, J=2.0, 8.8 Hz, 1H), 6.99 (d, J=8.8 Hz, 1H), 4.82 (Brs, 2H), 4.71-4.69 (m, 1H), 1.44 (d, J=6.0 Hz, 6H).

MS-ESI [M+H]$^+$: calculated value: 220; measured value: 220.

Step 3

Compound 48-4 (2 g, 7.93 mmol) was dissolved in methanol (15.0 mL) and anhydrous N,N-dimethylformamide (5.0 mL), and triethylamine (5 mL) and [1,1'-bis(diphenylphosphino)ferrocene]dichloropalladium(II) (580 g, 0.793 mmol) were added. The reaction was stirred at 80° C. for 12 hours under carbon monoxide atmosphere (15 psi). Then, the reaction solution was poured into water (30 mL) and the mixture was extracted with ethyl acetate (20 mL×3). The organic layer was washed with saturated brine (30 mL), dried over anhydrous sodium sulfate and concentrated to give the crude. The crude was purified by silica gel column chromatography (silica gel, petroleum ether:ethyl acetate=8:1 to 0:1, ethyl acetate:methanol=1:1 to 10:1) to give Compound 48-5.

$^1$H NMR (400 MHz, CDCl$_3$) δ 7.90 (d, J=8.0 Hz, 1H), 7.40 (d, J=8.0 Hz, 1H), 7.25 (t, J=8.0 Hz, 1H), 6.72 (s, 1H), 4.98 (d, J=7.6 Hz, 1H), 3.83 (s, 3H), 3.68-3.63 (m, 1H), 3.31-3.22 (m, 1H), 3.19-1.35 (m, 1H), 2.69-2.64 (m, 1H), 2.19-2.15 (m, 1H).

MS-ESI [M+H]$^+$: calculated value: 232; measured value: 232.

Step 4

Compound 48-5 (300 mg, 1.30 mmol) was dissolved in tetrahydrofuran (8.0 mL) and water (2.0 mL), and lithium hydroxide (218 mg, 5.19 mmol) was added. The reaction was stirred at 25° C. for 16 hours. Then, the mixture was concentrated and acidified with 2 M hydrochloric acid to pH=2 to precipitate pale yellow solid, filtered to give Compound 48-6.

$^1$H NMR (400 MHz, DMSO-d$_6$) δ 12.87 (s, 1H), 8.25 (s, 1H), 7.84 (d, J=6.8 Hz, 1H), 7.54 (d, J=7.6 Hz, 1H), 7.38-7.34 (m, 1H), 4.93 (d, J=8.0 Hz, 1H), 3.54-3.47 (m, 1H), 3.24-3.18 (m, 1H), 3.07 (dd, J=4, 18.4 Hz, 1H), 2.56-2.52 (m, 1H), 1.99 (dd, J=5.6, 22.8 Hz, 1H).

MS-ESI [M+H]$^+$: calculated value: 218; measured value: 218.

Step 5

Compound 48-3 (50 mg, 0.228 mmol) was dissolved in N,N-dimethylformamide (3.00 mL), and 1-hydroxybenzotriazole (9.2 mg, 0.0684 mmol), 1-(3-dimethylaminopropyl)-3-ethylcarbodiimide hydrochloride (52.5 mg, 0.274 mmol) and 48-6 (49.5 mg, 0.228 mmol) were added. The reaction was stirred at 20° C. for 2 hours, then heated to 80° C. and continued stirred for 12 hours. Then, water (30 mL) was added and the mixture was extracted with ethyl acetate (8 mL×3). The organic layer was washed with saturated brine (10 mL), dried over anhydrous sodium sulfate and concentrated to give crude. The crude was purified by silica gel column chromatography (silica gel, dichloromethane:methanol=10:1) to give Compound 48-7.

$^1$H NMR (400 MHz, CDCl$_3$) δ 8.39 (d, J=2.0 Hz, 1H), 8.31 (dd, J=2.0, 8.8 Hz, 1H), 8.19 (d, J=7.6 Hz, 1H), 7.55 (d, J=7.6 Hz, 1H), 7.46 (t, J=7.6 Hz, 1H), 7.10 (d, J=8.8 Hz, 1H), 6.25 (s, 1H), 5.14 (d, J=7.6 Hz, 1H), 4.81-4.75 (m, 1H), 3.88-3.82 (m, 1H), 3.49-3.39 (m, 2H), 2.90-2.79 (m, 1H), 2.37-3.31 (m, 1H), 1.48 (d, J=6.0 Hz, 6H).

MS-ESI [M+H]$^+$: calculated value: 401; measured value: 401

Step 6

Compound 48-7 (56 mg, 0.140 mmol) was dissolved in anhydrous N,N-dimethylformamide (5.0 mL), and sodium hydride (11.2 mg, 0.280 mmol, 60% purity) was added in portions at 0° C. The reaction was stirred at this temperature for 0.5 hour. Then, Compound 48-8 (66.9 mg, 0.280 mmol) was added to the reaction solution and stirred at 20° C. for 12 hours. Methanol hydrochloride (2.0 mL, 4 M) was added to reaction solution and the mixture was stirred for 0.5 hour, then concentrated under reduced pressure. The residue was purified by high performance liquid chromatography to obtain Compound 2-9.

$^1$H NMR (400 MHz, DMSO-d$_6$) δ 8.33 (s, 2H), 8.29 (d, J=9.2 Hz, 1H), 8.14 (d, J=7.6 Hz, 1H), 7.89 (d, J=7.6 Hz), 1H), 7.54 (t, J=7.6 Hz, 1H), 7.50 (d, J=9.2 Hz, 1H), 5.17 (d, J=7.6 Hz, 1H), 4.95-4.90 (m, 2H), 3.82-3.75 (m, 1H), 3.63-3.56 (m, 3H), 3.27-3.23 (m, 1H), 3.16-3.10 (m, 1H), 3.03-2.96 (m, 1H), 2.74-2.67 (m, 1H), 2.36-2.32 (m, 1H), 1.36 (d, J=6.0 Hz, 6H).

MS-ESI [M+H]$^+$: calculated value: 445; measured value: 445.

Example 49

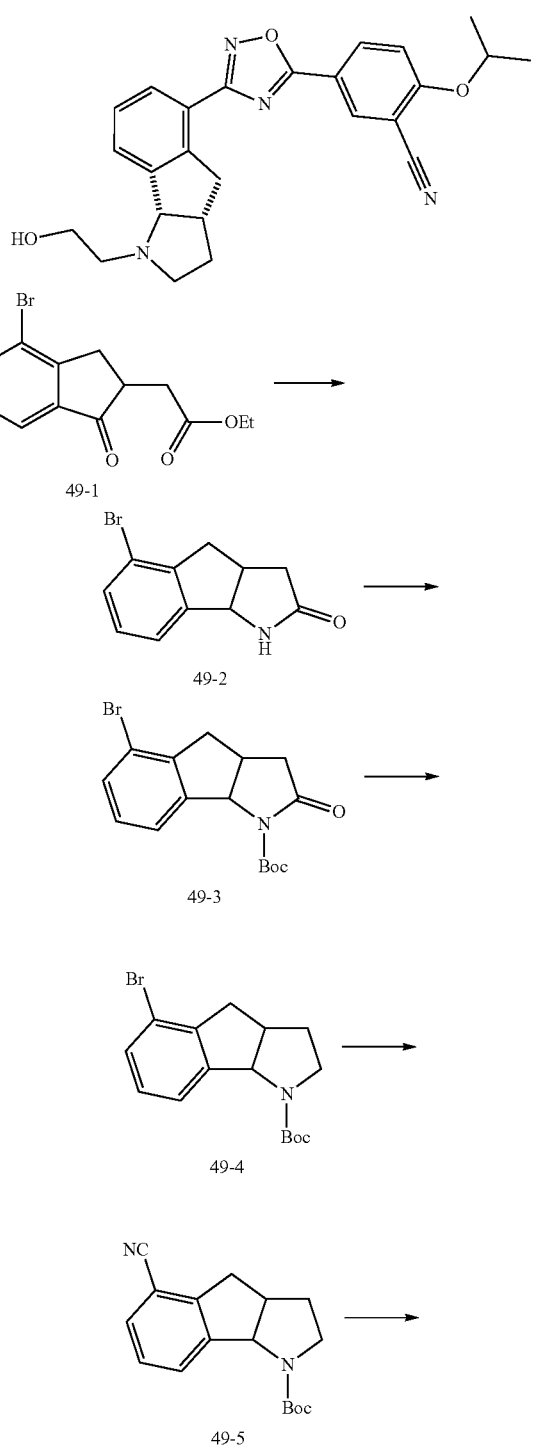

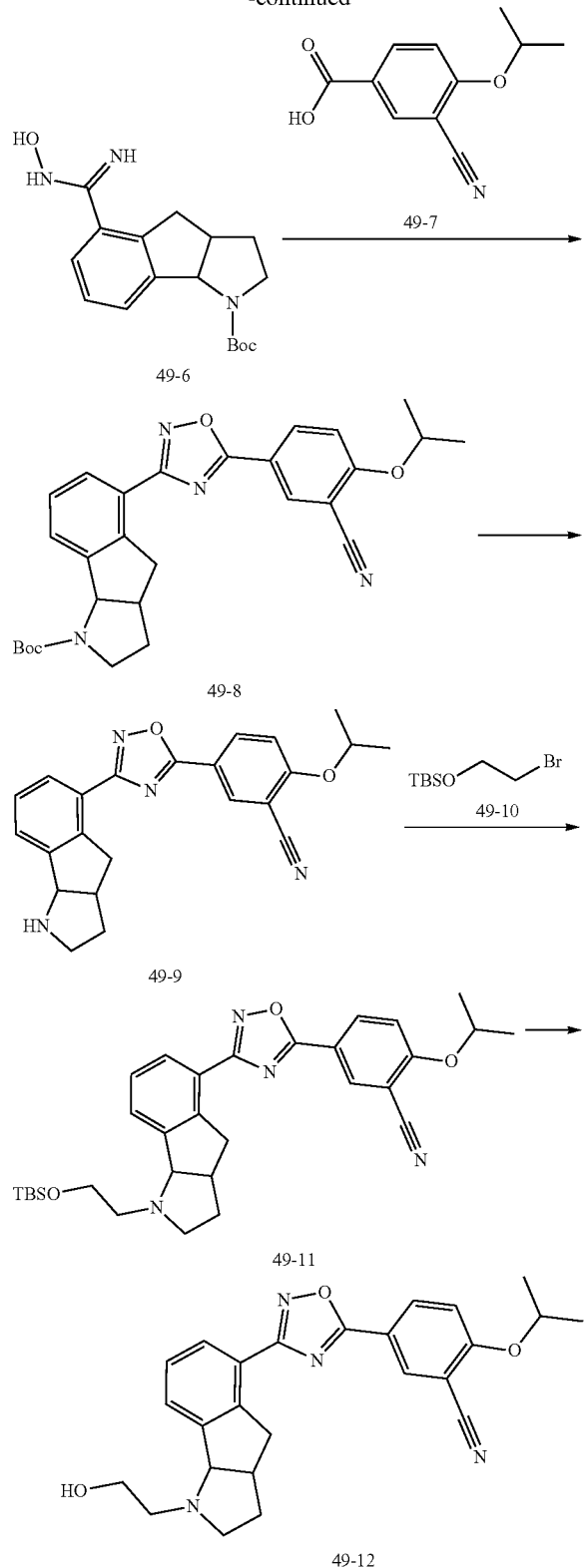

dride (3.17 g, 50.5 mmol) was added to the mixture, the resultant was stirred at 80° C. for 12 hours. Water (300 mL) was added to the reaction mixture and the mixture was extracted with ethyl acetate (400 mL×3). The organic layers were combined and washed with saturated brine (200 mL×2), dried over anhydrous sodium sulfate, filtered and the filtrate was concentrated under reduced pressure. The residue was purified by silica gel column chromatography (10:1 ethyl acetate/methanol, $R_f$=0.4) to give Compound 49-2.

MS-ESI [M+H]$^+$: calculated value: 252 and 254; measured value: 252 and 254.

Step 2

Compound 49-2 (3.50 g, 5.55 mmol) was dissolved in anhydrous dichloromethane (40 mL), and di-tert-butyl dicarbonate (3.64 g, 16.7 mmol) and triethylamine (1.69 g, 16.7 mmol) were added. The reaction was stirred at 25° C. for 12 hours. Then, water (20 mL) was added to the reaction mixture and the resultant was extracted with dichloromethane (30 mL×3). The organic layers were combined and washed with saturated brine (20 mL×2), dried over anhydrous sodium sulfate, filtered and the filtrate was concentrated under reduced pressure. The residue was purified by silica gel column chromatography (5:1 petroleum ether/ethyl acetate, $R_f$=0.6) to obtain Compound 49-3. $^1$H NMR: (400 MHz, CDCl$_3$) δ 7.69-7.67 (m, 0.5H), 7.53-7.51 (m, 0.5H), 7.40-7.37 (m, 1H), 7.11-7.06 (m, 1H), 5.39-5.37 (m, 0.5H), 5.31-5.29 (m, 0.5H), 3.53-3.40 (m, 1H), 3.36-3.33 (m, 1H), 3.11-3.05 (m, 1H), 2.81-2.77 (m, 1H), 2.14-2.09 (m, 1H), 1.57 (s, 9H).

MS-ESI [M+H]$^+$: calculated value: 352 and 354; measured value: 352 and 354.

Step 3

Compound 49-3 (600 mg, 1.70 mmol) was dissolved in anhydrous tetrahydrofuran (5 mL), and a solution of borane in dimethyl sulfide (0.850 mL, 8.50 mmol, 10 M) was slowly added dropwise at 0° C. The reaction was stirred at 70° C. for 12 hours. Then, methanol (50 mL) was slowly added to the reaction mixture and the mixture was concentrated under reduced pressure. The residue was purified by silica gel column chromatography (10:1 petroleum ether/ethyl acetate, $R_f$=0.6) to give Compound 49-4. MS-ESI [M+H]$^+$: calculated value: 338 and 340; measured value: 338 and 340.

Step 4

Compound 49-4 (100 mg, 0.296 mmol) was dissolved in acetonitrile (5 mL), and zinc cyanide (69.4 mg, 0.591 mmol), 2-dicyclohexylphosphine-2',4',7'-triisopropylbiphenyl (14.1 mg, 0.0296 mmol) and tris(dibenzylideneacetone)dipalladium(0) (13.5 mg, 0.0148 mmol) were added. The reaction was stirred at 90° C. for 16 hours under nitrogen atmosphere. Then, water (20 mL) was added to the reaction mixture after the mixture was cooled to room temperature, and the mixture was extracted with ethyl acetate (20 mL×3). The organic layers were combined and washed with saturated brine (20 mL×2), dried over anhydrous sodium sulfate, filtered and the filtrate was concentrated under reduced pressure. The residue was purified by TLC (10:1 petroleum ether/ethyl acetate, $R_f$=0.5) to obtain Compound 49-5.

$^1$H NMR: (400 MHz, CDCl$_3$) δ 8.00-7.98 (m, 0.5H), 7.81-7.79 (m, 0.5H), 7.54-7.51 (m, 1H), 7.33-7.29 (m, 1H), 5.35-5.33 (m, 0.5H), 5.30-5.26 (m, 0.5H), 3.54-3.42 (m, 1H), 3.38-3.24 (m, 4H), 3.00-2.95 (m, 1H), 2.18-2.13 (m, 1H), 1.58 (s, 9H).

MS-ESI [M+H]$^+$: calculated value: 285; measured value: 285.

Step 5

Compound 49-5 (70.0 mg, 0.246 mmol) was dissolved in anhydrous ethanol (3 mL), and hydroxylamine hydrochlo- Step 1

Compound 49-1 (5.00 g, 16.8 mmol) was dissolved in anhydrous ethanol (300 mL), and ammonium acetate (13.0 g, 168 mmol) was added at 25° C. The reaction was stirred at this temperature for 1 hour. Then, sodium cyanoborohyride (51.3 mg, 0.739 mmol) and triethylamine (99.6 mg, 0.985 mmol) were added. The reaction was stirred at 70° C. for 12 hours under nitrogen atmosphere. Then, water (20 mL) was added to the reaction mixture after the mixture was cooled to room temperature, and the mixture was extracted with ethyl acetate (10 mL×3). The organic layers were combined and washed with saturated brine (10 mL×2), dried over anhydrous sodium sulfate, filtered and the filtrate was concentrated under reduced pressure. The residue was purified by TLC (3:1 petroleum ether/ethyl acetate, $R_f$=0.2) to obtain Compound 49-6.

$^1$H NMR: (400 MHz, CDCl$_3$) δ 7.50-7.48 (m, 1H), 7.41-7.39 (m, 1H), 7.23-7.19 (m, 1H), 5.08-5.06 (m, 1H), 4.73 (s), 2H), 3.78-3.76 (m, 1H), 3.67-3.62 (m, 2H), 3.44-3.42 (m, 1H), 2.97-2.90 (m, 3H), 2.71-2.65 (m, 1H), 2.37-2.33 (m, 1H), 0.84 (s, 9H), 0.02-0.00 (m, 6H).

MS-ESI [M+H]$^+$: calculated value: 318; measured value: 318.

Step 6

Compound 49-7 (49.8 mg, 0.243 mmol) was dissolved in N,N-dimethylformamide (3 mL), and 1-hydroxybenzotriazole (59.6 mg, 0.441 mmol) and 1-(3-dimethylaminopropyl)-3-ethylcarbodiimide hydrochloride (84.6 mg, 0.441 mmol) were added. The reaction was stirred at 25° C. for 1 hour under nitrogen atmosphere. Then, Compound 49-6 (70.0 mg, 0.221 mmol) was added to the reaction mixture and the mixture was stirred at 25° C. for 1 hour, then heated to 80° C. and continued stirred for 12 hours. Water (20 mL) was added to the reaction mixture after the mixture was cooled to room temperature, and the mixture was extracted with ethyl acetate (20 mL×3). The organic layers were combined and washed with saturated brine (20 mL×2), dried over anhydrous sodium sulfate, filtered and the filtrate was concentrated under reduced pressure. The residue was purified by TLC (3:1 petroleum ether/ethyl acetate, $R_f$=0.7) to give Compound 49-8.

$^1$H NMR: (400 MHz, CDCl$_3$) δ 8.42 (s, 1H), 8.33 (d, J=9.2 Hz, 1H), 8.12-8.08 (m, 1H), 7.93-7.92 (m, 0.5H), 7.77-7.76 (m, 0.5H), 7.40-7.38 (m, 1H), 7.12 (d, J=9.2 Hz, 1H), 5.40-5.38 (m, 0.5H), 5.32-5.30 (m, 0.5H), 4.82-4.76 (m, 1H), 3.57-3.42 (m, 3H), 3.36-3.17 (m, 2H), 2.16-2.12 (m, 1H), 1.67-1.59 (m, 10H), 1.47 (d, J=6.0 Hz, 6H).

MS-ESI [M+H]$^+$: calculated value: 487; measured value: 487.

Step 7

Compound 49-8 (55.0 mg, 0.113 mmol) was dissolved in dioxane (3 mL), and hydrochloric acid dioxane (4M, 1 mL) was added. The reaction was stirred at 25° C. for 1 hour under nitrogen atmosphere. Then, saturated aqueous sodium bicarbonate solution (30 mL) was added to the reaction mixture and the mixture was extracted with ethyl acetate (20 mL×3). The organic layers were combined and washed with saturated brine (20 mL×2), dried over anhydrous sodium sulfate, filtered and concentrate the filtrate was concentrated under reduced pressure to obtain Compound 49-9.

MS-ESI [M+H]$^+$: calculated value: 387; measured value: 387.

Step 8

Compound 49-9 (20.0 mg, 0.0518 mmol) was dissolved in acetonitrile (3 mL), and Compound 49-10 (12.4 mg, 0.0518 mmol), potassium carbonate (21.5 mg, 0.155 mmol) and sodium iodide (23.3 mg, 0.155 mmol) were added. The reaction was stirred at 90° C. for 48 hours under nitrogen atmosphere. Then, water (10 mL) was added to the reaction mixture after the mixture was cooled to room temperature, and the mixture was extracted with ethyl acetate (10 mL×3). The organic layers were combined and washed with saturated brine (10 mL×2), dried over anhydrous sodium sulfate, filtered and the filtrate was concentrated under reduced pressure. The residue was purified by TLC (3:1 petroleum ether/ethyl acetate, $R_f$=0.4) to obtain Compound 49-11.

MS-ESI [M+H]$^+$: calculated value: 545; measured value: 545.

Step 9

Compound 49-11 (20.0 mg, 0.0367 mmol) was dissolved in dioxane (3 mL), and dioxane hydrochloride (4M, 1 mL) was added. The reaction was stirred at 25° C. for 10 minutes under nitrogen atmosphere. The mixture was concentrated under reduced pressure. The residue was purified by high performance liquid chromatography to obtain Compound 49-12.

$^1$H NMR: (400 MHz, CD$_3$OD) δ 8.47-8.43 (m, 2H), 8.32 (d, J=7.6 Hz, 1H), 7.91 (d, J=7.6 Hz, 1H), 7.64-7.60 (m, 1H), 7.46 (d, J=8.8 Hz, 1H), 5.34-5.32 (m, 1H), 4.99-4.96 (m, 1H), 4.04-4.03 (m, 2H), 3.80-3.77 (m, 2H), 3.68-3.62 (m, 1H), 3.56-3.36 (m, 4H), 2.63-2.60 (m, 1H), 1.96-1.91 (m, 1H), 1.47 (d, J=6.0 Hz, 6H).

MS-ESI [M+H]$^+$: calculated value: 431; measured value: 431.

Example 50

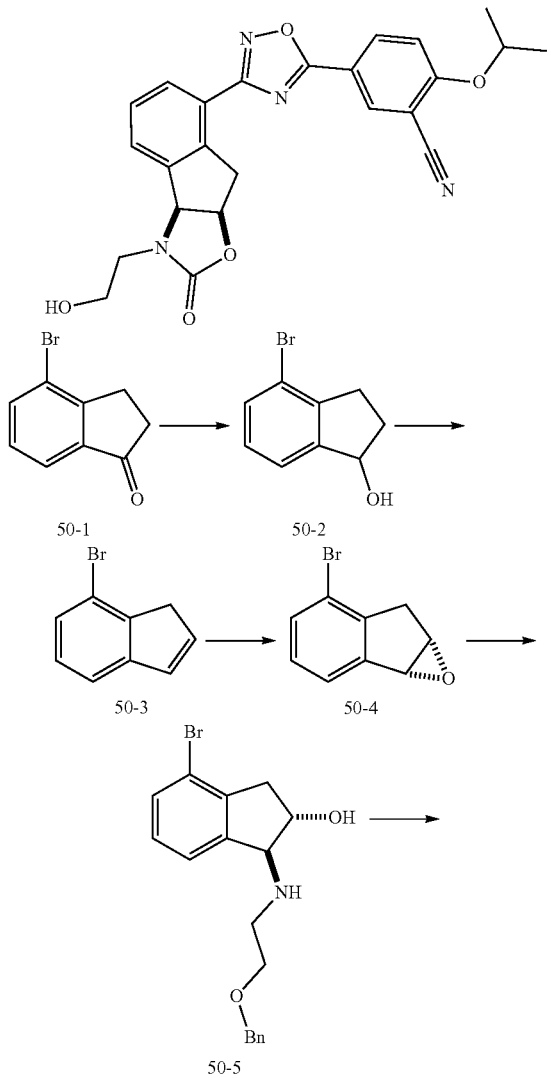

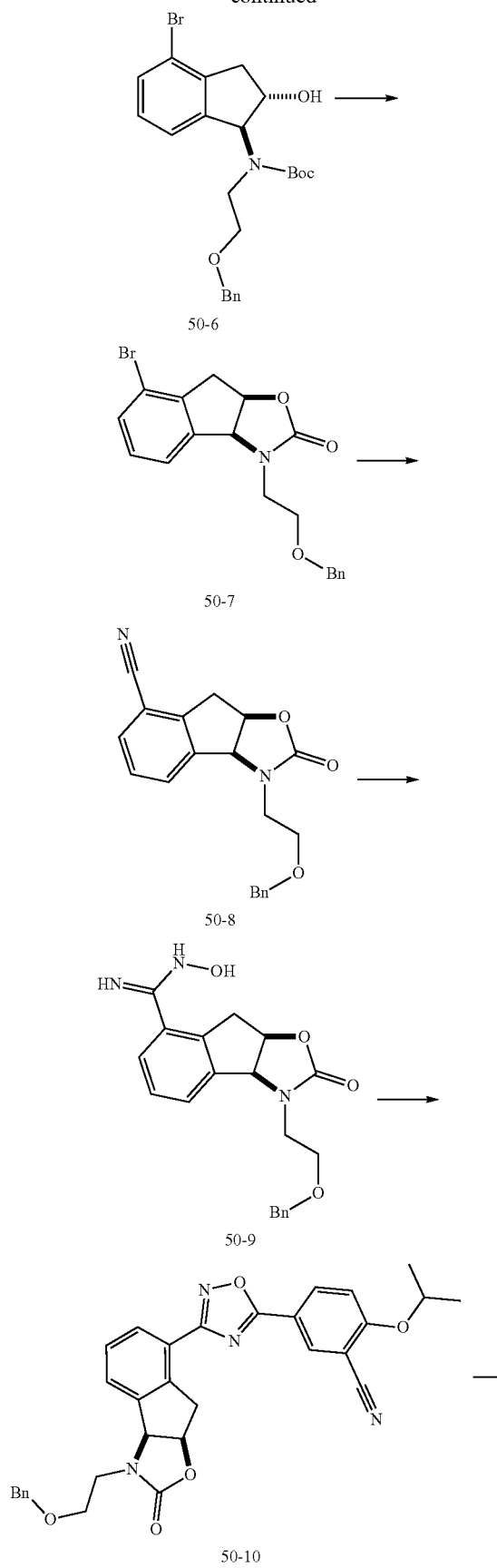

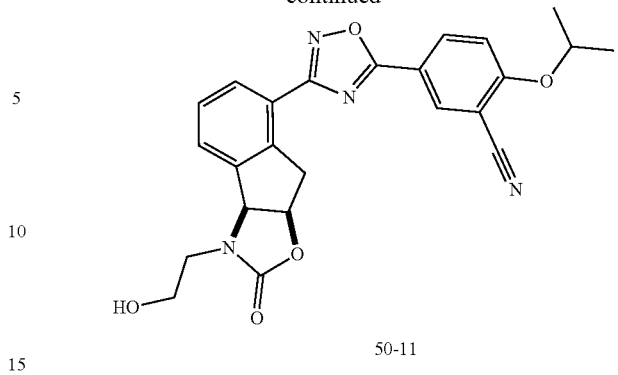

Step 1

Compound 50-1 (2.00 g, 9.48 mmol) was dissolved in ethanol (20.0 mL), and sodium borohydride (466 mg, 12.3 mmol) was added. The reaction was stirred at 20° C. for 12 hours, then concentrated under reduced pressure. The residue was dissolved in dichloromethane (40 mL). Then, 1M hydrochloric acid (20 mL) was added to the reaction mixture, and the aqueous layer was extracted with ethyl acetate (20 mL×2). The organic layers were combined and washed with saturated brine (30 mL×2), dried over anhydrous sodium sulfate and concentrated under reduced pressure to give Compound 50-2.

1H NMR: (400 MHz, CDCl$_3$) δ 7.43 (d, J=7.6 Hz, 1H), 7.36 (d, J=7.6 Hz, 1H), 7.13 (t, J=7.6 Hz, 1H), 5.35-5.27 (m, 1H), 3.11-3.04 (m, 1H), 2.91-2.76 (m, 1H), 2.60-2.44 (m, 1H), 2.02-1.91 (m, 1H), 1.87 (s, 1H).

Step 2

Compound 50-2 (11.7 g, 54.9 mmol) was dissolved in toluene (80 mL), and p-toluenesulfonic acid (1.04 g, 5.49 mmol) was added. The reaction was stirred at 80° C. for 2 hours under nitrogen atmosphere. The reaction mixture was washed with saturated sodium bicarbonate (40 mL×2) and brine (40 mL×2), dried over anhydrous sodium sulfate and concentrated under reduced pressure. The residue was subject to silica gel chromatography (petroleum ether, R$_f$=0.7) to obtain Compound 50-3.

$^1$H NMR: (400 MHz, CDCl$_3$) δ 7.36-7.34 (m, 2H), 7.17 (t, J=7.6 Hz, 1H), 6.96-6.89 (m, 1H), 6.66-6.60 (m, 1H), 3.41 (s, 2H).

Step 3

Compound 50-3 (3.90 g, 19.9 mmol) was dissolved in dichloromethane (150 mL), and sodium bicarbonate (5.04 g, 59.9 mmol) and m-chloroperoxybenzoic acid (5.68 g, 27.9 mmol) were added at 0° C. The mixture was slowly heated to 10° C. and stirred at this temperature for 12 hours under nitrogen atmosphere. Then, saturated sodium thiosulfate solution (40 mL) was added and the mixture was washed with saturated brine (50 mL×2), dried over anhydrous sodium sulfate and concentrated to give Compound 50-4.

$^1$H NMR: (400 MHz, CDCl$_3$) δ 7.46-7.42 (m, 2H), 7.11 (t, J=7.6 Hz, 1H), 4.33 (d, J=1.2 Hz, 1H), 4.16 (t, J=3.2 Hz, 1H), 3.25 (d, J=18.6 Hz, 1H), 2.94 (dd, J=3.2, 18.6 Hz, 1H).

Step 4

Compound 50-4 (3.80 g, 18.0 mmol) was dissolved in ethanol (150 mL), and 2-benzylethanolamine (4.08 g, 27.0 mmol) and water (5 mL) were added. The reaction was stirred at 60° C. for 2 hours. Then, ethyl acetate (150 mL) was added and the mixture was washed with water (40 mL×2) and saturated brine (40 mL×2), dried over anhydrous sodium sulfate and concentrated under reduced pressure.

The residue was subject to silica gel chromatography (10:1 dichloromethane/methanol, $R_f$=0.7) to obtain Compound 50-5.

$^1$H NMR: (400 MHz, CDCl$_3$) δ 7.33-7.22 (m, 6H), 7.16 (d, J=7.6 Hz, 1H), 7.01 (t, J=7.6 Hz, 1H), 4.48 (s, 2H), 4.29-4.26 (m, 1H), 4.06 (d, J=5.6 Hz, 1H), 3.57 (t, J=5.2 Hz, 2H), 3.28-3.22 (m, 1H), 3.05-2.89 (m, 2H), 2.72-2.70 (m, 1H).

Step 5

Compound 50-5 (1.00 g, 2.76 mmol) was dissolved in dichloromethane (20 mL), and triethylamine (418 mg, 4.14 mmol) and di-tert-butyl dicarbonate (783 mg, 3.59 mmol) were added. The reaction was stirred at 25° C. for 3 hours. Then, the mixture was washed with water (15 mL×2) and saturated brine (15 mL×2), dried over anhydrous sodium sulfate and concentrated under reduced pressure. The residue was subject to silica gel chromatography (3:1 petroleum ether/ethyl acetate, $R_f$=0.2) to obtain Compound 50-6.

$^1$H NMR: (400 MHz, CDCl$_3$) δ 7.41-7.27 (m, 6H), 7.08-7.06 (m, 1H), 6.98-6.95 (m, 1H), 4.94-4.66 (m, 1H), 4.65-4.47 (m, 2H), 3.87-3.22 (m, 6H), 2.78-2.74 (m, 1H), 1.46 (s, 3H), 1.35-1.08 (m, 6H).

MS-ESI [M+H]$^+$: calculated value: 484 and 486; measured value: 484 and 486.

Step 6

Compound 50-6 (680 mg, 1.47 mmol) was dissolved in tetrahydrofuran (8 mL), and 4-nitrobenzoic acid (294 mg, 1.76 mmol) and triphenylphosphine (963 mg, 3.68 mmol) were added. Then, a solution of diisopropyl azodicarboxylate (743 mg, 3.68 mmol) in tetrahydrofuran (2 mL) was added at 0° C. The reaction was stirred at 20° C. for 24 hours under nitrogen atmosphere. Then, saturated brine (20 mL) was added to the reaction mixture and the mixture was extracted with ethyl acetate (40 mL×2). The organic layers were combined and washed with saturated brine (20 mL×2), dried over anhydrous sodium sulfate and concentrated under reduced pressure. The residue was subject to silica gel chromatography (3:1 petroleum ether/ethyl acetate, $R_f$=0.3) to obtain Compound 50-7.

$^1$H NMR: (400 MHz, CDCl3) δ7.52-7.48 (m, 2H), 7.41-7.29 (m, 5H), 7.15 (t, J=7.6 Hz, 1H), 5.47-5.45 (m, 1H), 5.36-5.24 (m, 1H), 4.68-4.53 (m, 2H), 3.85-3.73 (m, 3H), 3.51-3.22 (m, 3H).

MS-ESI [M+H]$^+$: calculated value: 388 and 390; measured value: 388 and 390.

Step 7

Compound 50-7 (650 mg, 1.67 mmol) was dissolved in acetonitrile (10 mL), and zinc cyanide (588 mg, 5.01 mmol), tris(dibenzylideneacetone)dipalladium (305 mg, 0.334 mmol) and 2-dicyclohexylphosphorin-2',4',6'-triisopropylbiphenyl (318 mg, 0.668 mmol) were added. The reaction was stirred at 90° C. for 12 hours under nitrogen atmosphere. Then, ethyl acetate (30 mL) was added to the reaction mixture and the mixture was washed with water (20 mL×2) and saturated brine (20 mL×2), dried over anhydrous sodium sulfate and concentrated under reduced pressure. The residue was subject to silica gel chromatography (1:1 petroleum ether/ethyl acetate, $R_f$=0.3) to obtain Compound 50-8.

$^1$H NMR: (400 MHz, CDCl$_3$) δ 7.81 (d, J=7.6 Hz, 1H), 7.65 (d, J=7.6 Hz, 1H), 7.42-7.30 (m, 6H), 5.46 (d, J=7.6 Hz, 1H), 5.39-5.29 (m, 1H), 4.68-4.52 (m, 2H), 3.88-3.75 (m, 3H), 3.68-3.58 (m, 1H), 3.55-3.47 (m, 1H), 3.44-3.34 (m, 1H).

MS-ESI [M+H]$^+$: calculated value: 335; measured value: 335.

Step 8

Compound 50-8 (270 mg, 807 umol) was dissolved in ethanol (6 mL), and hydroxylamine hydrochloride (168 mg, 2.42 mmol) and triethylamine (245 mg, 2.42 mmol) were added. The reaction was stirred at 60° C. for 12 hours under nitrogen atmosphere. The mixture was concentrated under reduced pressure and the residue was dissolved in ethyl acetate (30 mL). The mixture was washed with water (15 mL×2) and saturated brine (15 mL×2), dried over anhydrous sodium sulfate and concentrated under reduced pressure to obtain Compound 50-9.

MS-ESI [M+H]$^+$: calculated value: 368; measured value: 368.

Step 9

3-Cyano-4-isopropylbenzoic acid (150 mg, 0.734 mmol) was dissolved in N,N-dimethylformamide (3 mL), and 1-hydroxybenzotriazole (198 mg, 1.47 mmol) and 1-ethyl-(3-dimethylaminopropyl)carbodiimide hydrochloride (211 mg, 1.10 mmol) were added. The reaction was stirred at 20° C. for 1 hour. Compound 50-9 (270 mg, 0.734 mmol) in N,N-dimethylformamide (1 mL) was added and the mixture was stirred at 20° C. for 1 hour. Then, the reaction was stirred at 90° C. for 10 hours under nitrogen atmosphere. The reaction mixture was cooled and concentrated under reduced pressure. The residue was subject to silica gel chromatography (1:1 petroleum ether/ethyl acetate, $R_f$=0.4) to obtain Compound 50-10.

$^1$H NMR: (400 MHz, CDCl$_3$) δ 8.43 (d, J=2.0 Hz, 1H), 8.34 (dd, J=2.0, 9.2 Hz, 1H), 8.22 (d, J=7.6 Hz, 1H), 7.71 (d, J=7.6 Hz, 1H), 7.46-7.44 (m, 1H), 7.39-7.29 (m, 5H), 7.13 (d, J=9.2 Hz, 1H), 5.49-5.43 (m, 1H), 5.41-5.32 (m, 1H), 4.82-4.78 (m, 1H), 4.68-4.54 (m, 2H), 3.88-3.70 (m, 5H), 3.48-3.40 (m, 1H), 1.48 (d, J)=6.0 Hz, 6H).

MS-ESI [M+H]$^+$: calculated value: 537; measured value: 537.

Step 10

Compound 50-10 (180 mg, 0.335 mmol) was dissolved in trifluoroacetic acid (5 mL), and the mixture was stirred at 70° C. for 4 hours. The mixture was concentrated under reduced pressure and the residue was dissolved in methanol (4 mL). Potassium carbonate (40 mg) was added and the mixture was stirred at 25° C. for 1 hour. Then, dichloromethane (50 mL) was added to the reaction mixture and the mixture was washed with water (20 mL×2) and saturated brine (20 mL×2), dried over anhydrous sodium sulfate, filtered and concentrated under reduced pressure. The residue was purified by high performance liquid chromatography to obtain Compound 50-11.

$^1$H NMR: (400 MHz, DMSO) δ 8.51 (s, 1H), 8.41 (d, J=9.2 Hz, 1H), 8.14 (d, J=7.6 Hz, 1H), 7.82 (d, J=7.6 Hz, 1H), 7.55 (d, J=8.0 Hz, 2H), 5.43 (s, 2H), 4.99 (s, 2H), 3.81-3.50 (m, 5H), 1.38 (d, J=5.4 Hz, 6H).

MS-ESI [M+H]$^+$: calculated value: 447; measured value: 447.

Example 51

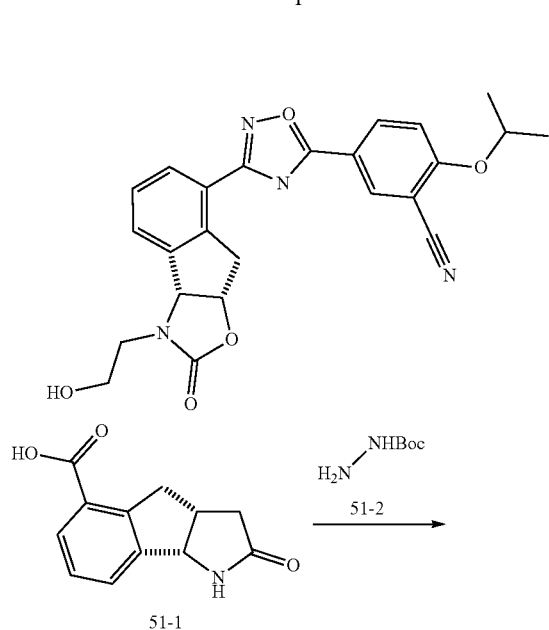

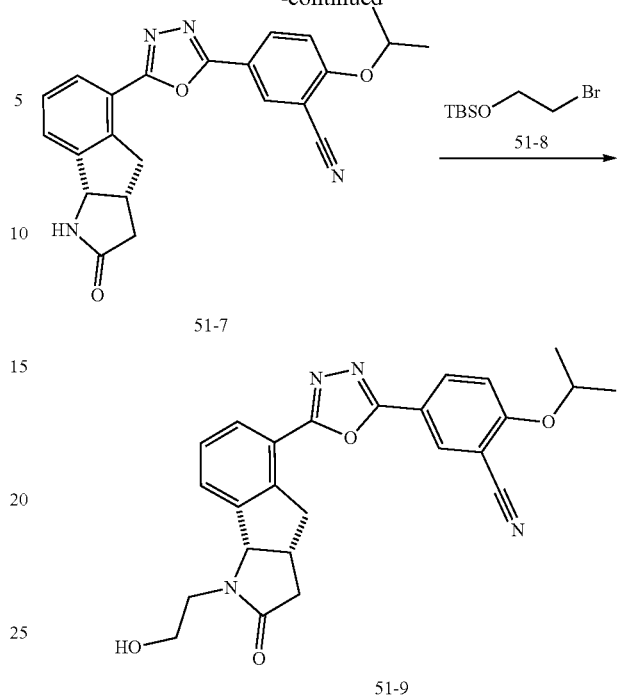

Step 1

Compound 51-1 (1.2 g, 5.52 mmol) was dissolved in N,N-dimethylformamide (20.0 mL), and 1-hydroxybenzotriazole (1.49 g, 11.05 mmol), 1-(3-dimethylaminopropyl)-3-ethyl carbodiimide hydrochloride (2.12 g, 11.05 mmol), triethylamine (1.12 g, 11.05 mmol) and 51-2 (730.1 mg, 5.52 mmol) were added. The reaction was stirred at 25° C. for 16 hours. Then, water (25 mL) was added to the reaction mixture, and the mixture was extracted with ethyl acetate (30 mL×3). The combined organic layer was dried over anhydrous sodium sulfate and concentrated to give crude. The crude was purified by silica gel column chromatography (silica, methylene chloride:methanol=100 to 10:1) to obtain Compound 51-3.

$^1$H NMR (400 MHz, CDCl$_3$) δ 8.87 (brs, 1H), 7.61 (d, J=7.6 Hz, 1H), 7.32 (d, J=7.6 Hz, 1H), 7.22 (t, J=7.6 Hz, 1H), 7.12 (brs, 1H), 6.73 (brs, 1H), 4.98 (d, J=7.6 Hz, 1H), 3.59-3.55 (m, 1H), 3.31-3.27 (m, 1H), 3.14-3.10 (m, 1H), 2.77-2.73 (m, 1H), 2.14-2.10 (m, 1H), 1.53 (s, 9H).

MS-ESI [M+H]$^+$: calculated value: 354; measured value: 354.

Step 2

Compound 51-3 (1.45 g, 4.38 mmol) was dissolved in methanol (2 mL), and methanol hydrochloride (4M, 10 mL) was added. The reaction was stirred at 25° C. for 4 hours. The reaction mixture was concentrated directly to obtain Compound 51-4.

MS-ESI [M+H]$^+$: calculated value: 254; measured value: 254.

Step 3

Compound 51-4 (0.6 g, 2.59 mmol) was dissolved in dichloromethane (5 mL), and diisopropylethylamine (503 mg, 3.89 mmol) and 51-5 (609 mg, 2.72 mmol) were added. The reaction was stirred at 25° C. for 16 hours. Then, water (10 mL) was added to the reaction mixture, and the mixture was extracted with dichloromethane (15 mL×3), dried over anhydrous sodium sulfate and concentrated to give the crude. The crude was washed with ethyl acetate (10 mL), followed by filtering to obtain Compound 51-6. MS-ESI [M+H]+: calculated value: 419; measured value: 419.

Step 4

Compound 51-6 (100 mg, 0.240 mmol) was dissolved in acetonitrile (2 mL), and diisopropylethylamine (77.2 mg, 0.597 mmol) and p-toluenesulfonyl chloride (54.7 mg, 0.287 mmol) were added. The reaction was stirred at 60° C. for 16 hours. The reaction mixture was concentrated directly to give crude and the crude was washed with ethyl acetate (8 mL), followed by filtering to obtain Compound 51-7.

$^1$H NMR (400 MHz, DMSO-d$_6$) δ 8.48 (s, 1H), 8.37-8.32 (m, 2H), 8.12 (d, J=7.2 Hz, 1H), 7.59 (d, J=7.2 Hz, 1H), 7.55-7.50 (m, 2H), 5.03 (d, J=7.6 Hz, 1H), 4.99-4.93 (m, 1H), 3.67-3.64 (m, 1H), 3.26-3.22 (m, 1H), 2.62-2.55 (m, 2H), 2.11-2.05 (m, 1H), 1.39 (d, J=6.0 Hz, 6H).

MS-ESI [M+H]+: calculated value: 401; measured value: 401.

Step 5

Compound 51-7 (70.0 mg, 0.175 mmol) was dissolved in N,N-dimethylformamide (5.0 mL), and sodium hydride (14.0 mg, 0.350 mmol, 60% purity) was added in portions at 0° C. The reaction was stirred at this temperature for 0.5 hour. Then, Compound 51-8 (83.6 mg, 0.350 mmol) was added to the reaction mixture and the mixture was stirred at 20° C. for 12 hours. Then, methanol hydrochloride (2.0 mL, 4 M) was added to the reaction mixture and the mixture was stirred for 0.5 hour. The mixture was concentrated under reduced pressure. The residue was purified by preparative high performance liquid chromatography (hydrochloride system) to obtain Compound 51-9.

$^1$H NMR (400 MHz, DMSO-d$_6$) δ 8.48 (d, J=2.2 Hz, 1H), 8.35 (dd, J=2.0, 8.8 Hz, 1H), 8.15 (d, J=7.6 Hz, 1H), 7.82 (d, J=7.6 Hz, 1H), 7.54-7.50 (m, 2H), 5.17 (d, J=7.6 Hz, 1H), 4.98-4.92 (m, 1H), 4.88-4.84 (m, 1H), 3.77-3.73 (m, 1H), 3.63-3.49 (m, 3H), 3.28-3.21 (m, 1H), 3.15-3.08 (m, 1H), 3.03-2.97 (m, 1H), 2.74-2.70 (m, 1H), 2.36-2.31 (m, 1H), 1.38 (d, J=6.0 Hz, 6H).

MS-ESI [M+H]+: calculated value: 445; measured value: 445.

Example 52

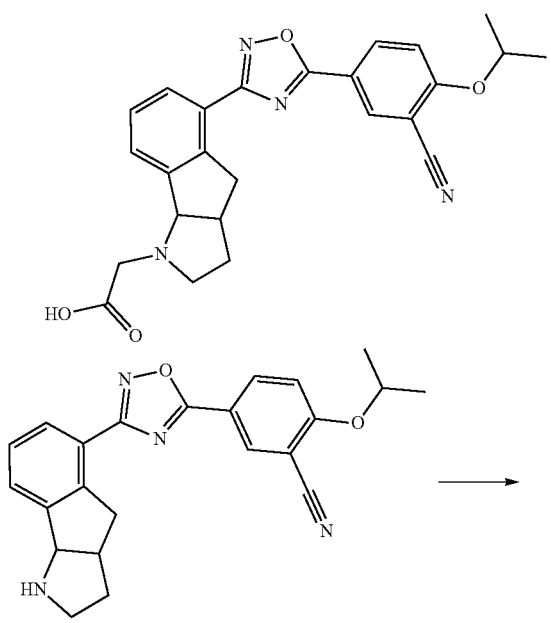

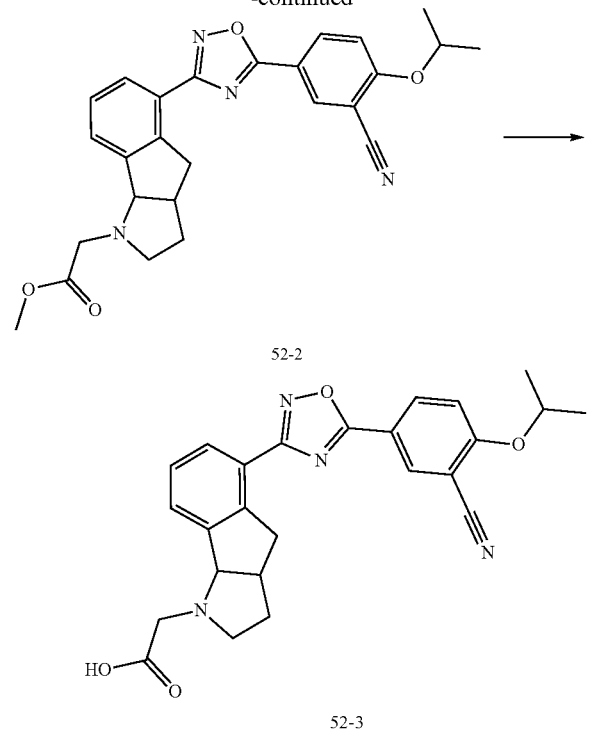

Step 1

Compound 52-1 (100 mg, 0.259 mmol) was dissolved in acetonitrile (6 mL), and methyl bromoacetate (39.6 mg, 0.259 mmol), potassium carbonate (107 mg, 0.776 mmol) and sodium iodide (116 mg, 0.776 mmol) were added. The mixture was stirred at 90° C. for 16 hours. Then, water (10 mL) was added to the reaction mixture, and the mixture was extracted with ethyl acetate (20 mL×3). The organic layer was dried over anhydrous sodium sulfate and concentrated to give the crude. The crude was purified by TLC (silica, petroleum ether:ethyl acetate=1:1) to obtain Compound 52-2.

$^1$H NMR (400 MHz, CDCl$_3$) δ 8.43 (d, J=2.0 Hz, 1H), 8.34 (dd, J=2.0, 8.8 Hz, 1H), 8.11 (d, J=7.6 Hz, 1H), 7.54 (d, J=7.6 Hz, 1H), 7.39 (t, J=7.6 Hz 1H), 7.13 (d, J=8.8 Hz, 1H), 4.83-4.77 (m, 1H), 4.44 (d, J=7.6 Hz), 1H), 3.78 (s, 3H), 3.74-3.71 (m, 1H), 3.67-3.62 (m, 1H), 3.58-3.51 (m, 1H), 3.28-3.23 (m, 2H), 3.10-3.05 (m, 1H), 2.89-2.83 (m, 1H), 2.28-2.20 (m, 1H), 1.78-1.70 (m, 1H), 1.49 (d, J=6.0 Hz, 6H).

MS-ESI [M+H]+: calculated value: 459; measured value: 459.

Step 2

Compound 52-2 (100 mg, 0.218 mmol) was dissolved in tetrahydrofuran (8 mL) and water (2 mL), and lithium hydroxide (36.6 mg, 0.872 mmol) was added. The mixture was stirred at 25° C. for 16 hours. The reaction mixture was concentrated under reduced pressure. The residue was purified by preparative high performance liquid chromatography (hydrochloride system) to obtain Compound 52-3.

$^1$H NMR (400 MHz, METHANOL-d$_4$) δ 8.46 (s, 2H), 8.43 (d, J=8.8 Hz, 1H), 8.32 (d, J=7.6 Hz, 1H), 8.05 (d, J=7.6) Hz, 1H), 7.61 (t, J=7.6 Hz, 1H), 7.46 (d, J=8.8 Hz,

1H), 5.38 (d, J=7.6 Hz, 1H), 5.00-4.97 (m, 1H), 4.41-4.37 (m, 1H), 4.14-4.10 (m, 1H), 3.82-3.75 (m, 1H), 3.63-3.57 (m, 1H), 3.51-3.50 (m, 2H), 3.40-3.39 (m, 1H), 2.62-2.53 (m, 1H), 2.13-2.09 (m, 1H), 1.48 (d, J=6.0 Hz, 6H).

MS-ESI [M+H]$^+$: calculated value: 445; measured value: 445.

Example 53

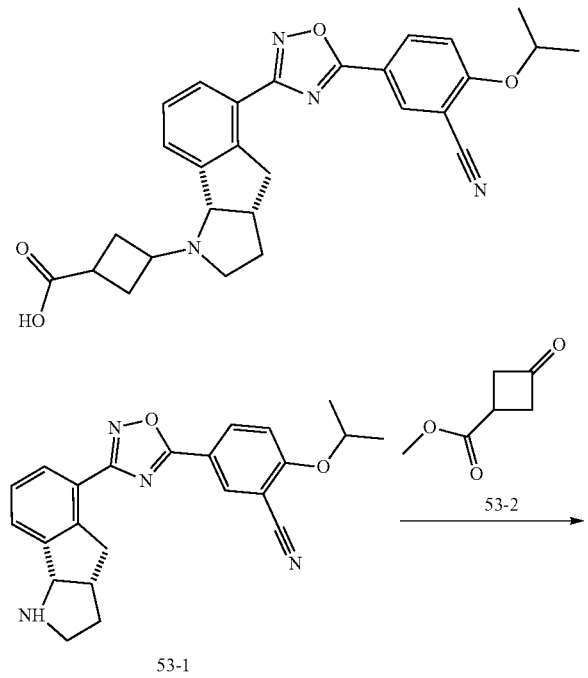

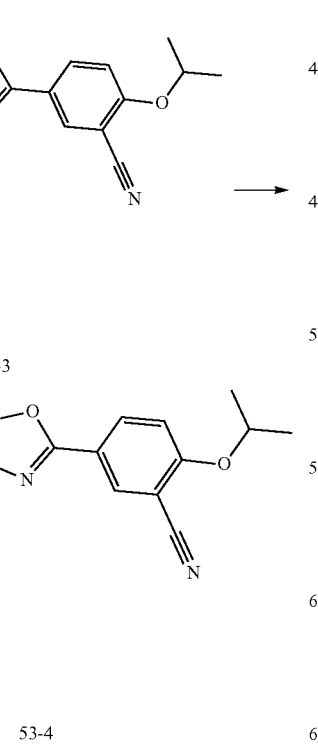

Step 1

Compound 53-1 (30.0 g, 0.078 mmol) was dissolved in ethylene glycol dimethyl ether (5 mL), and Compound 53-2 (10.0 mg, 0.078 mmol) and tetraisopropyl titanate (44.1 mg, 0.155 mmol) were added at 50° C. The reaction was stirred for 1 hour. Then, sodium triacetoxyborohydride (32.9 mg, 0.155 mmol) was added and the mixture was stirred at 80° C. for 12 hours. Then, water (5 mL) was added and the mixture was extracted with ethyl acetate (8 mL×3). The organic layer was dried over anhydrous sodium sulfate and concentrated to obtain crude Compound 53-3.

MS-ESI [M+H]$^+$: calculated value: 491; measured value: 499.

Step 2

Compound 53-3 (38.0 mg, 0.076 mmol) was dissolved in tetrahydrofuran (4 mL) and water (1 mL), and lithium hydroxide (12.8 mg, 0.305 mmol) was added. The mixture was stirred at 60° C. for 16 hours. The reaction mixture was concentrated under reduced pressure. The residue was purified by preparative high performance liquid chromatography (hydrochloride system) to obtain Compound 53-4.

$^1$H NMR (400 MHz, METHANOL-d$_4$) δ 8.48-8.43 (m, 2H), 8.29 (d, J=8.8 Hz, 1H), 7.78 (d, J=7.6 Hz, 1H), 7.61 (t, J=7.6 Hz, 1H), 7.46 (d, J=8.8 Hz, 1H), 5.12 (d, J=7.6 Hz, 1H), 5.01-4.98 (m, 1H), 3.94-3.87 (m, 1H), 3.74-3.67 (m, 1H), 3.54-3.51 (m, 1H), 3.42-3.35 (m, 2H), 3.29-3.27 (m, 1H), 2.93-2.82 (m, 2H), 2.69-2.67 (m, 1H), 2.56-2.47 (m, 2H), 2.42-2.35 (m, 1H), 1.99-1.91 (m, 1H), 1.48 (d, J=6.0 Hz, 6H).

MS-ESI [M+H]$^+$: calculated value: 485; measured value: 485.

Example 54

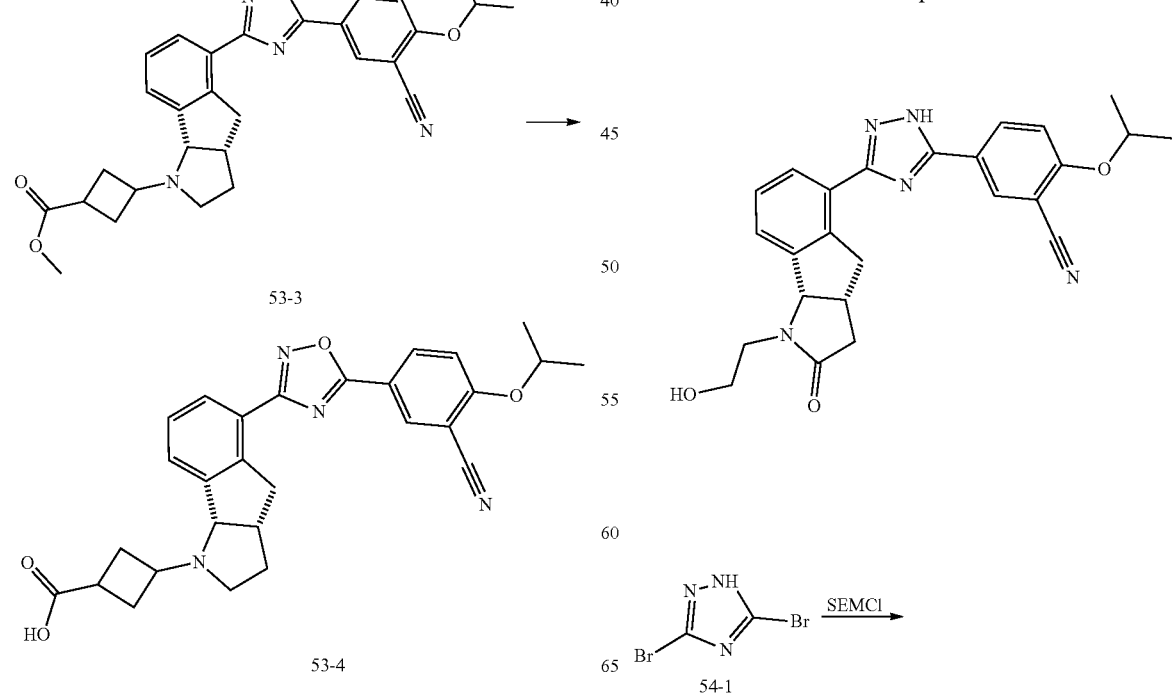

-continued

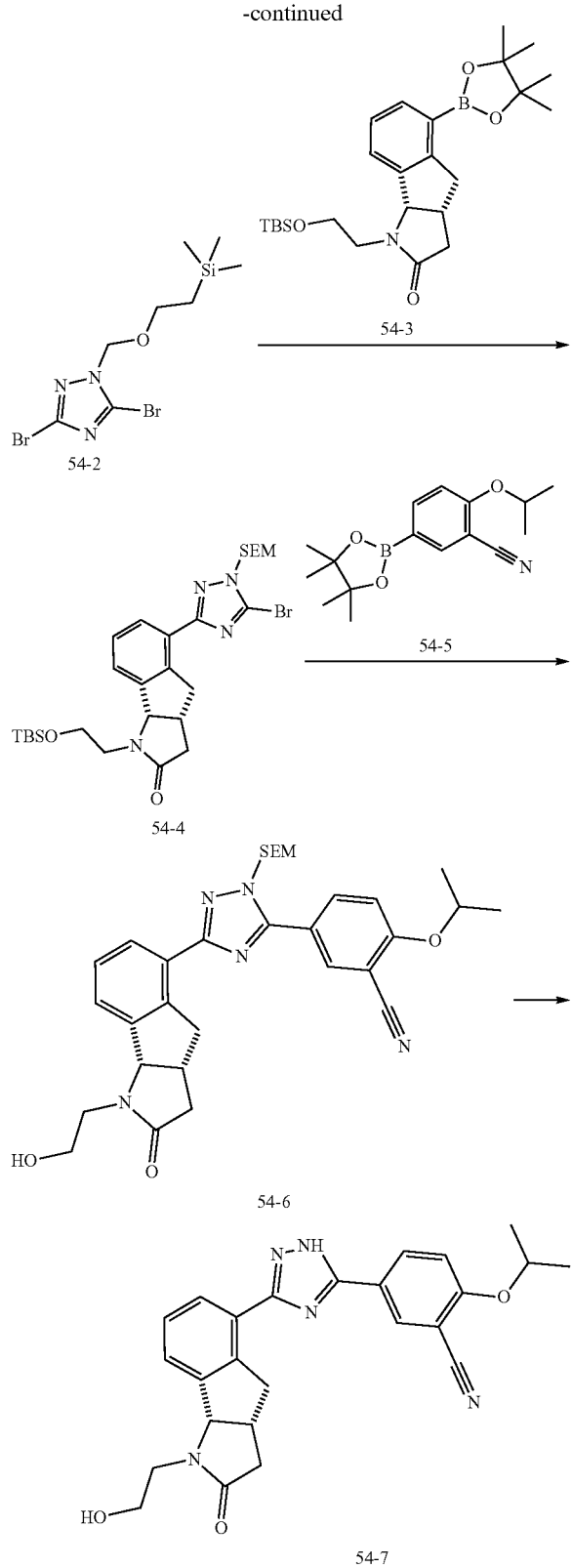

Step 1

Compound 54-1 (300 mg, 1.32 mmol) was dissolved in tetrahydrofuran (5 mL), and N,N-dicyclohexylmethylamine (387 mg, 1.98 mmol) and 2-(trimethylsilyl)ethoxymethyl chloride (264.57 mg, 1.59 mmol) were added. The reaction was stirred at 25° C. for 16 hours. Then, water (10 mL) was added and the mixture was extracted with ethyl acetate (10 mL×3). The organic layer was dried over anhydrous sodium sulfate and concentrated to give the crude. The crude was purified by silica gel column chromatography (silica, petroleum ether:ethyl acetate=5:1) to obtain Compound 54-2.

$^1$H NMR (400 MHz, CDCl$_3$) δ 5.46 (s, 2H), 3.68 (d, J=8.0 Hz, 2H), 0.93 (d, J=8.0 Hz, 2H), 0.01 (s, 9H).

Step 2

Compound 54-3 (50 mg, 0.109 mmol) was dissolved in N,N-dimethylformamide (5.0 mL), and Compound 54-2 (46.8 mg, 0.131 mmol), [1,1'-Bis(diphenylphosphino)ferrocene]dichloropalladium(II) (8.0 mg, 0.011 mmol) and cesium carbonate (107 mg, 0.328 mmol) were added. The solution was charged with nitrogen three times. The mixture was stirred at 100° C. for 16 hours. Then, the reaction mixture was poured into water (8 mL) and extracted with ethyl acetate (5 mL×3). The organic layer was washed with saturated brine (20 mL×2), dried over anhydrous sodium sulfate and concentrated to give the crude. The residue was purified by TLC (silica, petroleum ether:ethyl acetate=1:1) to obtain Compound 54-4.

$^1$H NMR (400 MHz, CDCl$_3$) δ 7.71 (d, J=7.6 Hz, 2H), 7.40 (t, J=7.6 Hz, 1H), 5.37 (s, 2H), 5.23 (d, J=7.2 Hz, 1H), 3.91-3.76 (m, 4H), 3.58-3.50 (m, 2H), 3.19-3.14 (m, 2H), 2.98-2.92 (m, 1H), 2.80-2.73 (m, 1H), 2.42-2.37 (m, 1H), 1.00-0.95 (m, 2H), 0.94 (s, 9H), 0.11 (s, 3H), 0.10 (s, 3H), 0.03-0.01 (s, 9H).

MS-ESI [M+H]$^+$: calculated value: 607 and 609; measured value: 607 and 609

Step 3

Compound 54-4 (30.0 mg, 0.049 mmol) was dissolved in N,N-dimethylformamide (1.0 mL), and Compound 54-5 (17.0 mg, 0.059 mmol), [1,1'-Bis(diphenylphosphino)ferrocene]dichloropalladium(II) (3.6 mg, 0.005 mmol) and cesium carbonate (48.3 mg, 0.148 mmol) were added. The solution was charged with nitrogen three times. The mixture was stirred at 100° C. for 16 hours. Then, the reaction mixture was added into water (8 mL) and extracted with ethyl acetate (5 mL×3). The organic layer was washed with saturated brine (20 mL×2), dried over anhydrous sodium sulfate and concentrated to obtain 54-6.

MS-ESI [M+H]$^+$: calculated value: 574; measured value: 574.

Step 4

Compound 54-6 (0.028 g, 0.049 mmol) was dissolved in dioxane (2 mL), and hydrochloric acid/dioxane (2 mL, 4 M) was added. The mixture was stirred at 60° C. for 10 minutes. The reaction mixture was concentrated under reduced pressure. The residue was purified by preparative high performance liquid chromatography (hydrochloride system) to obtain Compound 54-7.

$^1$H NMR (400 MHz, METHANOL-d$_4$) δ 8.33-8.24 (m, 2H), 7.93 (d, J=8.0 Hz, 1H), 7.75 (d, J=7.6 Hz, 1H), 7.48 (t, J=7.6 Hz, 1H), 7.39 (d, J=8.0 Hz, 1H), 5.24 (d, J=7.2 Hz, 1H), 4.94-4.90 (m, 1H), 3.84-3.65 (m, 4H), 3.25-3.11 (m, 3H), 2.89-2.83 (m, 1H), 2.46-2.42 (m, 1H), 1.44 (d, J=6.0 Hz, 6H).

MS-ESI [M+H]$^+$: calculated value: 444; measured value: 444.

Example 55

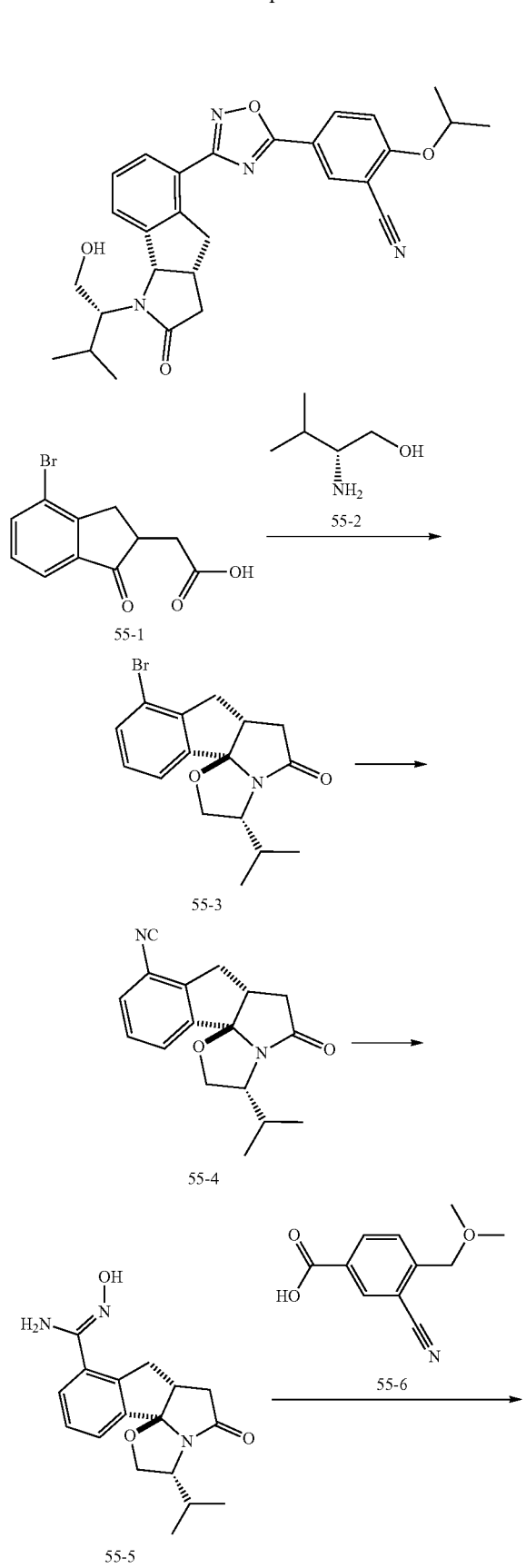

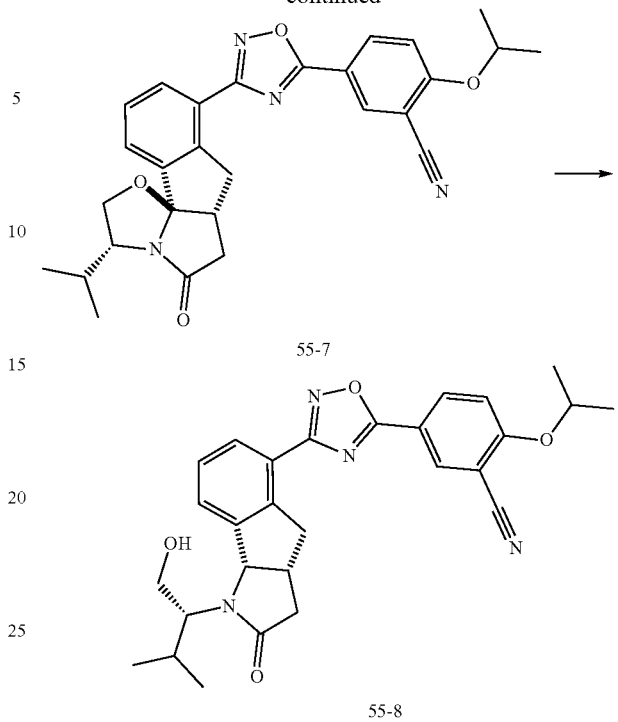

Step 1

Compound 55-1 (200 mg, 0.743 mmol) was dissolved in anhydrous toluene (3 mL), and Compound 55-2 (153 mg, 1.49 mmol) and p-toluenesulfonic acid monohydrate (28.3 mg, 0.149 mmol) were added. The mixture was stirred at 130° C. for 12 hours while water was separated by a water separator. Water (10 mL) was added after the mixture was cooled to room temperature and the mixture was extracted with ethyl acetate (10 mL×3). The organic layers were combined and washed with saturated brine (10 mL×2), dried over anhydrous sodium sulfate, filtered and the filtrate was concentrated under reduced pressure. The residue was purified by TLC (3:1 petroleum ether/ethyl acetate, $R_f$=0.5) to obtain Compound 55-3. MS-ESI [M+H]$^+$: calculated value: 336 and 338; measured value: 336 and 338.

Step 2

The reaction was referred to Step 4 of Example 1. The residue was purified by TLC (3:1 petroleum ether/ethyl acetate, $R_f$=0.5) to obtain Compound 55-4.

$^1$H NMR: (400 MHz, CDCl$_3$) δ 7.68 (d, J=7.6 Hz, 1H), 7.59 (d, J=7.6 Hz, 1H), 7.43 (t, J=7.6 Hz, 1H), 4.21-4.17 (m, 1H), 4.12-4.08 (m, 1H), 3.84-3.82 (m, 1H), 3.48-3.42 (m, 1H), 3.03-2.94 (m, 2H), 2.90-2.87 (m, 1H), 2.41-2.35 (m, 1H), 1.95-1.93 (m, 1H), 1.09 (d, J=6.4 Hz, 3H), 1.04 (d, J=6.4 Hz, 3H).

MS-ESI [M+H]$^+$: calculated value: 283; measured value: 283.

Step 3

The reaction referred to Step 5 of Example 1. The residue was purified by TLC (0:1 petroleum ether/ethyl acetate, $R_f$=0.2) to obtain Compound 55-5. MS-ESI [M+H]$^+$: calculated value: 316; measured value: 316.

Step 4

The reaction referred to Step 6 of Example 1. The residue was purified by TLC (1:1 petroleum ether/ethyl acetate, $R_f$=0.5) to obtain Compound 55-7.

¹H NMR: (400 MHz, CDCl₃) δ 8.37 (s, 1H), 8.26 (d, J=8.8 Hz, 1H), 8.20 (d, J=7.6 Hz, 1H), 7.49-7.42 (m, 2H), 7.06 (d, J=7.6 Hz, 1H), 4.76-4.72 (m, 1H), 4.18-4.15 (m, 1H), 4.08-4.04 (m, 1H), 3.78-3.77 (m, 1H), 3.53-3.51 (m, 1H), 3.28-3.24 (m, 1H), 3.01-2.97 (m, 1H), 2.86-2.80 (m, 1H), 2.39-2.32 (m, 1H), 1.96-1.93 (m, 1H), 1.48 (d, J=6.0 Hz, 6H), 1.05 (d, J=6.4 Hz, 3H), 0.98 (d, J=6.4 Hz, 3H).

MS-ESI [M+H]⁺: calculated value: 485; measured value: 485.

Step 5

Compound 55-7 (40.0 mg, 0.0823 mmol) was dissolved in anhydrous dichloromethane (2 mL), and triethylsilylhydrogen (24.0 mg, 0.206 mmol) was added. Then, titanium tetrachloride (39.2 mg, 0.206 mmol) was slowly added dropwise at −78° C. The mixture was stirred at 25° C. for 12 hours under nitrogen atmosphere. Then, saturated aqueous ammonium chloride solution (10 mL) was added into the reaction mixture and the mixture was extracted with dichloromethane (10 mL×3). The organic layers were combined and washed with saturated brine (10 mL×2), dried over anhydrous sodium sulfate, filtered and the filtrate was concentrated under reduced pressure. The residue was purified by high performance liquid chromatography to obtain Compound 55-8.

¹H NMR: (400 MHz, Methonal-d₄) δ 8.49-8.44 (m, 2H), 8.19 (d, J=7.6 Hz, 1H), 7.80 (d, J=7.6 Hz, 1H), 7.48-7.45 (m, 2H), 5.23 (d, J=7.2 Hz, 1H), 4.95-4.93 (m, 1H), 4.58-4.56 (m, 1H), 4.05-4.03 (m, 1H), 3.81-3.76 (m, 2H), 3.61-3.59 (m, 1H), 3.21-3.15 (m, 1H), 2.90-2.83 (m, 1H), 2.53-2.49 (m, 1H), 2.00-1.96 (m, 1H), 1.48 (d, J=6.0 Hz, 6H), 0.99 (d, J=6.4 Hz, 3H), 0.69 (d, J=6.4 Hz, 3H).

MS-ESI [M+H]⁺: calculated value: 487; measured value: 487.

Example 56

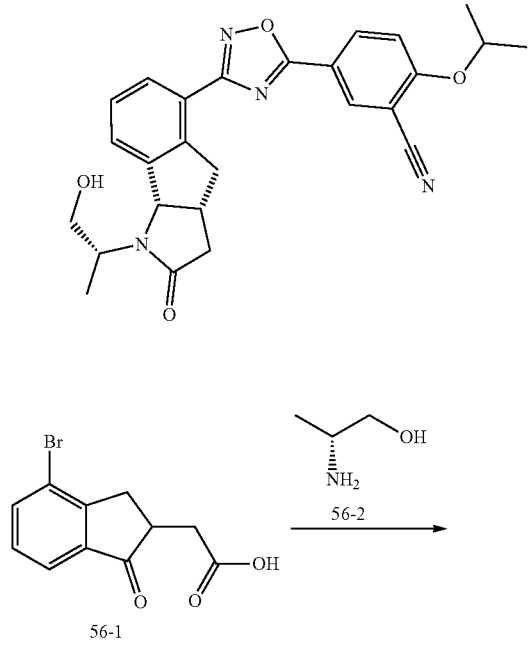

56-1

56-2

-continued

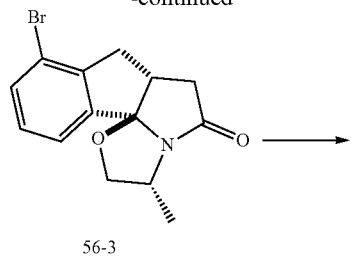

56-3

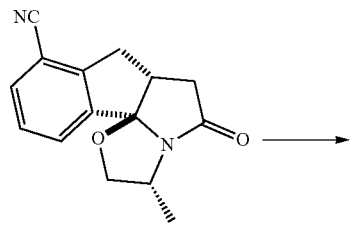

56-4

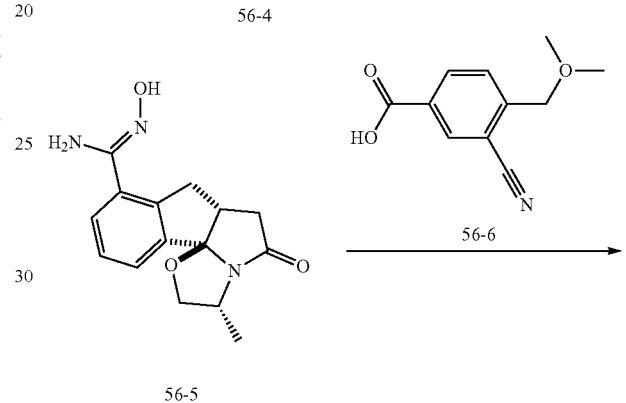

56-5

56-6

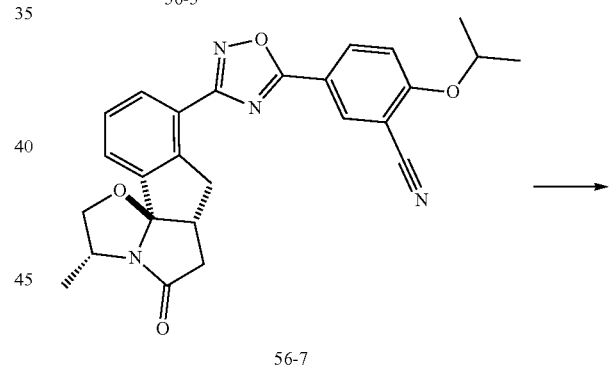

56-7

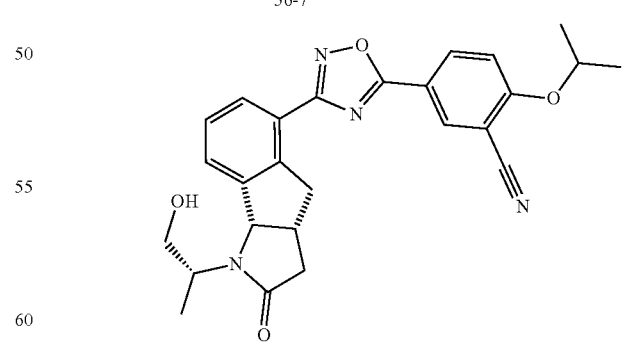

56-8

Step 1

The reaction referred to Step 1 of Example 55. The residue was purified by TLC (3:1 petroleum ether/ethyl acetate, R$_f$=0.5) to obtain Compound 56-3. MS-ESI [M+H]$^+$: calculated value: 308 and 309; measured value: 308 and 309.

Step 2

The reaction referred to Step 4 of Example 1. The residue was purified by TLC (3:1 petroleum ether/ethyl acetate, R$_f$=0.5) to obtain Compound 56-4.

$^1$H NMR: (400 MHz, CDCl$_3$) δ 7.68-7.59 (m, 2H), 7.39 (t, J=15.6 Hz, 1H), 4.32-4.29 (m, 1H), 4.20-4.16 (m, 1H), 4.00-3.97 (m, 1H), 3.42-3.35 (m, 1H), 2.96-2.80 (m, 3H), 2.33-2.26 (m, 1H), 1.44 (d, J=6.4 Hz, 3H).

[M+H]$^+$: calculated value: 255; measured value: 255.

Step 3

The reaction referred to Step 5 of Example 1. The residue was purified by TLC (0:1 petroleum ether/ethyl acetate, R$_f$=0.2) to obtain Compound 56-5. [M+H]$^+$: calculated value: 288; measured value: 288.

Step 4

The reaction referred to Step 6 of Example 1. The residue was purified by TLC (1:1 petroleum ether/ethyl acetate, R$_f$=0.5) to obtain Compound 56-7.

$^1$H NMR: (400 MHz, CDCl$_3$) δ 8.35 (s, 1H), 8.28-8.19 (d, J=8.8 Hz, 1H), 7.58-7.54 (d, J=8.8 Hz, 1H), 7.44 (t, J=8.8 Hz, 1H), 7.06 (d, J=8.8 Hz, 1H), 6.91 (d, J=8.8 Hz, 1H), 4.74-4.73 (m, 1H), 4.64-4.61 (m, 1H), 4.30-4.28 (m, 1H), 4.23-4.19 (m, 1H), 4.06-4.04 (m, 1H), 3.53-3.51 (m, 1H), 3.26-3.22 (m, 1H), 2.83-2.79 (m, 1H), 2.38-2.31 (m, 1H), 1.48 (d, J=6.4 Hz, 3H), 1.47 (d, J=6.0 Hz, 6H).

[M+H]$^+$: calculated value: 457; measured value: 457.

Step 5

The reaction referred to Step 5 of Example 55. The residue was purified by high performance liquid chromatography to obtain Compound 56-8.

$^1$H NMR: (400 MHz, Methonal-d$_4$) δ 8.48-8.43 (m, 2H), 8.19 (d, J=7.6 Hz, 1H), 7.76 (d, J=7.6 Hz, 1H), 7.50-7.45 (m, 2H), 5.20 (d, J=7.2 Hz, 1H), 5.00-4.95 (m, 1H), 3.97-3.95 (m, 1H), 3.77-3.71 (m, 3H), 3.27-3.25 (m, 1H), 3.23-3.21 (m, 1H), 2.84-2.77 (m, 1H), 2.45-2.40 (m, 1H), 1.47 (d, J=6.0 Hz, 6H), 1.27 (d, J=6.4 Hz), 3H).

[M+H]$^+$: calculated value: 459; measured value: 459.

Experimental Example 1

Test Method:

1. Cell Processing i) Thaw the PathHunter cell strain according to the standard procedures.

ii) Seed the cell in the 20 μL 384-microwell plate and incubate at 37° C. for an appropriate period.

2. Agonist i) For agonist testing, cells were incubated with the sample to be test to initiate a reaction;

ii) The stock solution to be tested has been diluted 5 folds to be a buffer solution;

iii) Inject the 5-fold diluted solution (5 μL) into the cells and incubate at 37° C. for 90-180 minutes. The solvent concentration was 1%.

3. Signal Detection i) Add 12.5 μL or 15 μL PathHunter detection reagent (50 vol. %) in one portion. Then, incubate at room temperature for 1 hour and generate the detection signal;

ii) Use PerkinElmer Evision™ instrument to read the microwell plate to proceed with chemiluminescent signal detection.

4. Data Analysis i) Use CBIS data analysis system for the compound activity analysis.

ii) Calculation formula:

$$\%\text{-activity} = 100\% \times (\text{Average } RLU \text{ of samples to be tested} - \text{Average } RLU \text{ of solvents})/(\text{Average maximum control ligand} - \text{Average } RLU \text{ of solvents})$$

The experimental results were shown as Table 1.

TABLE 1

Testing results of S1P1 receptor agonistic activity

| Sample to be tested (Compound prepared in each example) | S1P1 receptor agonistic activity |
|---|---|
| Example 1 Mixture/Isomer 1/Isomer 2 | +++/+++/+++ |
| Example 2 | +++ |
| Example 3 | +++ |
| Example 4 | +++ |
| Example 5 | +++ |
| Example 6 | +++ |
| Example 7 | +++ |
| Example 8 | +++ |
| Example 9 | +++ |
| Example 10 | +++ |
| Example 11 | +++ |
| Example 12 | +++ |
| Example 13 | +++ |
| Example 14 | +++ |
| Example 15 | ++ |
| Example 16 | + |
| Example 17 | + |
| Example 18 | + |
| Example 19 | + |
| Example 20 | + |
| Example 21 | + |
| Example 22 | + |
| Example 23 | + |
| Example 24 | + |
| Example 25 | +++ |
| Example 26 | +++ |
| Example 27 | +++ |
| Example 28 | + |
| Example 29 | + |
| Example 30 | + |
| Example 31 | + |
| Example 32 | + |
| Example 33 | + |
| Example 34 | + |
| Example 35 Compound 35-2/Compound 35-3 | +/+ |
| Example 36 | + |
| Example 37 | + |
| Example 38 | + |
| Example 39 | ++ |
| Example 40 | +++ |
| Example 41 | + |
| Example 42 | + |
| Example 43 | ++ |
| Example 44 | ++ |
| Example 45 | +++ |
| Example 46 | +++ |
| Example 47 | +++ |
| Example 48 | +++ |
| Example 49 | ++ |
| Example 50 | +++ |
| Example 51 | +++ |
| Example 52 | +++ |
| Example 53 | +++ |
| Example 54 | ++ |
| Example 55 | ++ |
| Example 56 | +++ |

Note:
100 nM < "+"; 10 nM ≤ "++" < 100 nM; "+++" < 10 nM

Conclusion: The compounds of the present invention have significant and unexpected S1P1 receptor agonistic activity.

Experimental Example 2: Evaluation of Compound Pharmacokinetic

Aim of the experiments: To test pharmacokinetics of the compounds in SD rats.

Experimental Materials:

Sprague Dawley rats (male, 200-300 g, 7-9 weeks old, Shanghai Slack)

Experimental Procedure:

The rodent pharmacokinetic characteristics of the compounds after intravenous injection and oral administration were tested by the standard protocol. In the experiments, the transparent solution was prepared with the compounds to be test. The rats were administered single intravenous injection and oral administration. The solvent for intravenous injection and oral administration was aqueous hydroxypropyl β-cyclodextrin solution or normal saline solution with a certain concentration. Collect the blood samples within 24 hours and centrifuge at 3000 G for 15 minutes. Separate the supernatant to obtain the plasma samples. A volume of acetonitrile solution containing internal standard was added 4 times as the sample to precipitate the protein. The supernatant was obtained after centrifuge. An equal volume of water was added and then centrifuge again to collect the supernatant. The LC-MS/MS method was used to quantitatively analyze the blood drug concentration and the pharmacokinetic parameters such as peak concentration, peak time, clearance rate, half-life period, area under the curve of the drug concentration, and fraction of bioavailability, etc. were calculated.

Experimental Results:

TABLE 2

Testing results of pharmacokinetics

| Sample to be tested (Compound prepared in each example) | Clearance rate (mL/min/kg) | Half-life period: $T_{1/2}$ (h) | Drug concentration integral: AUC (nM · hr) | Fraction of bioavailability: F (%) |
|---|---|---|---|---|
| Ozanimod (3 mpk) | 46.3 | 5.24 | 1123 | 41.6 |
| Example 1 Isomer 1 (3 mpk) | 44.3 | 1.48 | 1114 | 42.8 |
| Example 1 Isomer 2 (3 mpk) | 11.5 | 3.46 | 6825 | 85.8 |
| Example 14 (2 mpk) | 7.22 | 3.27 | 5763 | 59 |
| Example 26 (2 mpk) | 7.5 | 26.7 | 4353 | 88.2 |
| Example 27 (2 mpk) | 8.86 | 21.2 | 4779 | 92.6 |
| Example 40 (2 mpk) | 14.1 | 10.7 | 444 | 82.3 |
| Example 50 (2 mpk) | 6.59 | 4.82 | 8518 | 72.4 |
| Example 56 (2 mpk) | 14.6 | 1.63 | 3322 | 66.7 |

Conclusion: The compounds of the present invention can significantly increase the single or partial parameters of rat pharmacokinetics compared with Ozanimod.

What is claimed is:

1. A compound represented by formula (II), or a pharmaceutically acceptable salt of the same,

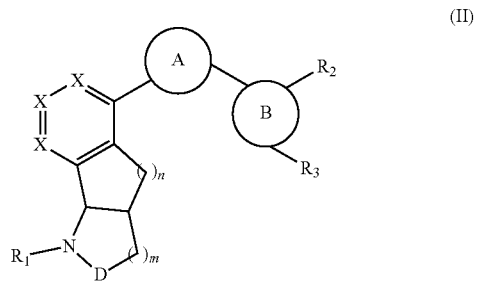

(II)

wherein,

X is independently N or CH;

m is 0, 1 or 2;

n is 1 or 2;

D is —C(═O)—, —C(═O)O—, —CH$_2$—;

R$_1$ is C$_{1-6}$ alkyl, C$_{1-6}$ heteroalkyl or C$_{3-6}$ cycloalkyl, each of which is optionally substituted by one, two or three R;

each of R$_2$ and R$_3$ is H, halogen, OH, NH$_2$, CN or R$_4$-L-, or selected from the group consisting of C$_{1-6}$ alkyl, C$_{1-6}$ heteroalkyl, phenyl and 5-6 membered heteroaryl, each of which is optionally substituted by one, two or three R;

R$_4$ is C$_{3-6}$ cycloalkyl, 3-6 membered heterocyclic alkyl, phenyl or 5-6 membered heteroaryl, each of which is optionally substituted by one, two or three R;

L is —(CRR)$_{1-3}$—, or —O—(CRR)$_{0-3}$—;

ring A is 5 membered heteroaryl;

ring B is phenyl or 5-9 membered heteroaryl;

R is H, F, Cl, Br, I, CN, OH, NH$_2$, COOH,

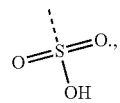

or optionally selected from the group consisting of C$_{1-6}$ alkyl and C$_{1-6}$ heteroalkyl, each of which is optionally substituted by one, two or three R';

R' is H, F, Cl, Br, I, OH, CN, NH$_2$, COOH, Me, Et, CF$_3$, CHF$_2$, CH$_2$F, NHCH$_3$, N(CH$_3$)$_2$;

"hetero" represents a heteroatom or a heteroatom group, which is selected from the group consisting of —C(═O)N(R)—, —N(R)—, —C(═NR)—, —S(═O)$_2$N(R)—, —S(═O)N(R)—, —O—, —S—, ═O, ═S, —O—N═, —C(═O)O—, —C(═O)—, —C(═S)—, —S(═O)—, —S(═O)$_2$—, and —N(R)C(═O)N(R)—;

in any one of the above cases, the number of heteroatom or heteroatom group is independently selected from one, two and three.

2. The compound of claim 1, wherein the compound is represented by formula (I),

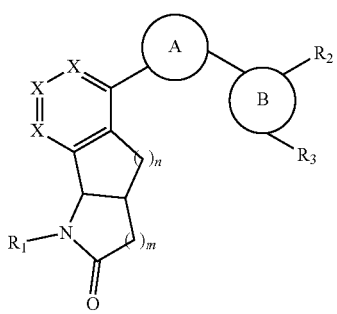

(I)

wherein
X is N or CH;
m and n is independently selected from one or two;
$R_1$ is $C_{1-6}$ alkyl or $C_{1-6}$ heteroalkyl, each of which is optionally substituted by one, two or three R;
each of $R_2$ and $R_3$ is H, halogen, OH, $NH_2$, CN or $R_4$-L-, or is optionally selected from the group consisting of $C_{1-6}$ alkyl, $C_{1-6}$ heteroalkyl, phenyl and 5-6 membered heteroaryl, each of which is optionally substituted by one, two or three R;
$R_4$ is $C_{3-6}$ cycloalkyl, 3-6 membered heterocyclic alkyl, phenyl or 5-6 membered heteroaryl, each of which is optionally substituted by one, two or three R;
L is —$(CRR)_{1-3}$— or —O—$(CRR)_{0-3}$—;
ring A is a 5 membered heteroaryl;
ring B is phenyl or a 5-9 membered heteroaryl;
R is H, F, Cl, Br, I, CN, OH, $NH_2$ or COOH, or selected from the group consisting of $C_{1-6}$ alkyl and $C_{1-6}$ heteroalkyl, each of which is optionally substituted by one, two or three R';
R' is selected from the group consisting of H, F, Cl, Br, I, OH, CN, $NH_2$, COOH, Me, Et, $CF_3$, $CHF_2$, $CH_2F$, $NHCH_3$, and $N(CH_3)_2$;
"hetero" represents a heteroatom or a heteroatom group, which is selected from the group consisting of —C(=O)N(R)—, —N(R)—, —C(=NR)—, —S(=O)$_2$N(R)—, —S(=O)N(R)—, —O—, —S—, =O, =S, —O—N=, —C(=O)O—, —C(=O)—, —C(=S)—, —S(=O)—, —S(=O)$_2$— and —N(R)C(=O)N(R)—;
in any one of the above cases, the number of heteroatom or heteroatom group is independently selected from one, two or three.

3. The compound or the pharmaceutically acceptable salt of the same according to claim 2, wherein R is H, F, Cl, Br, I, CN, OH, $NH_2$ or COOH or selected from the group consisting of $C_{1-3}$ alkyl, $C_{1-3}$ alkoxyl, $C_{1-3}$ alkylthiol, $C_{1-3}$ alkylamino, N, N'-di($C_{1-2}$ alkyl)amino, $C_{1-3}$ alkyl-S(=O)— and $C_{1-3}$ alkyl-S(=O)$_2$—, each of which is optionally substituted by one, two or three R'.

4. The compound or the pharmaceutically acceptable salt of the same according to claim 3, wherein R is selected from the group consisting of H, F, Cl, Br, I, CN, OH, $NH_2$, COOH, Me, Et, $CF_3$,

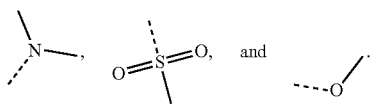

5. The compound or the pharmaceutically acceptable salt of the same according to claim 2, wherein $R_1$ is selected from the group consisting of $C_{1-6}$ alkyl, $C_{1-3}$ alkyl-S(=O)$_2$—$C_{1-3}$ alkyl-, $C_{1-3}$ alkyl-S(=O)—$C_{1-3}$ alkyl-, and $C_{1-3}$ alkyl-NH—C(=O)$_2$—$C_{1-3}$ alkyl-, each of which is optionally substituted by one, two or three R.

6. The compound or the pharmaceutically acceptable salt of the same according to claim 5, wherein $R_1$ is selected from the group consisting of Me,

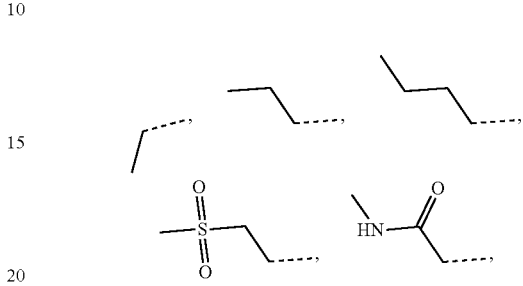

each of which is substituted by one, two or three R.

7. The compound or the pharmaceutically acceptable salt of the same according to claim 6, wherein $R_1$ is selected from the group consisting of

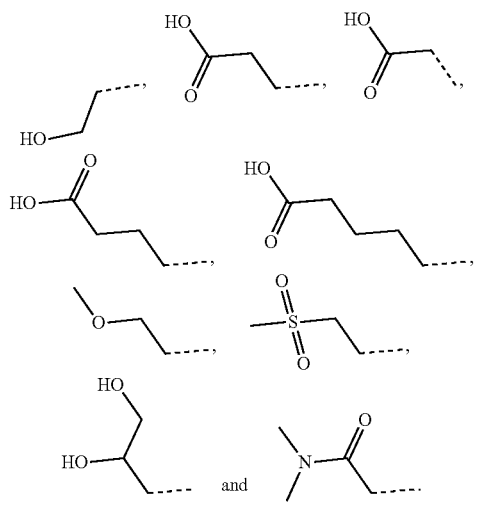

8. The compound or the pharmaceutically acceptable salt of the same according claim 2, wherein L is —$(CH_2)_{1-3}$— or —O—$(CH_2)_{0-3}$—.

9. The compound or the pharmaceutically acceptable salt of the same according to claim 8, wherein L is selected from the group consisting of —$CH_2$—, —$CH_2CH_2$—, —$CH_2CH_2CH_2$—, —O—, —O—$CH_2$—, —O—$CH_2CH_2$— and —O—$CH_2CH_2CH_2$—.

10. The compound or the pharmaceutically acceptable salt of the same according to claim 2, wherein $R_4$ is selected from the group consisting of

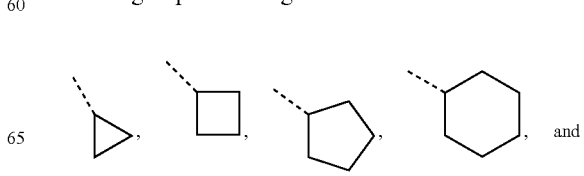

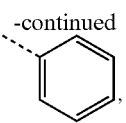

each of which is substituted by one, two or three R.

11. The compound or the pharmaceutically acceptable salt of the same according to claim 10, wherein $R_4$ is

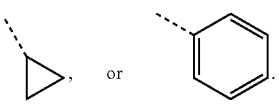

12. The compound or the pharmaceutically acceptable salt of the same according to claim 1, wherein $R_4$-L- is

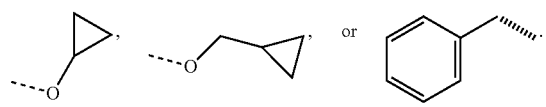

13. The compound or the pharmaceutically acceptable salt of the same according to claim 2, wherein each of $R_2$ and $R_3$ is H, F, Cl, Br, I, OH, $NH_2$, CN or $R_4$-L-, or selected from the group consisting of $C_{1-3}$ alkyl, $C_{1-3}$ alkoxyl, $C_{1-3}$ alkyl-thiol, $C_{1-3}$ alkyl-S(=O)—, $C_{1-3}$ alkyl-S(=O)$_2$—, phenyl, thiazolyl, isothiazolyl, oxazolyl and isoxazolyl, each of which is optionally substituted by one, two or three R.

14. The compound or the pharmaceutically acceptable salt of the same according to claim 13, wherein each of $R_2$ and $R_3$ is H, F, Cl, Br, I, OH, $NH_2$, CN or $R_4$-L-, or selected from the group consisting of Me, Et,

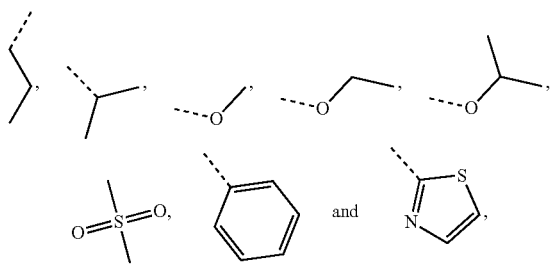

each of which is optionally substituted by one, two or three R.

15. The compound or the pharmaceutically acceptable salt of the same according to claim 14, wherein each of $R_2$ and $R_3$ is H, F, Cl, Br, I, OH, $NH_2$, CN, Me,

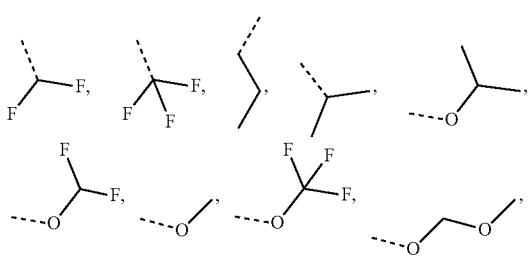

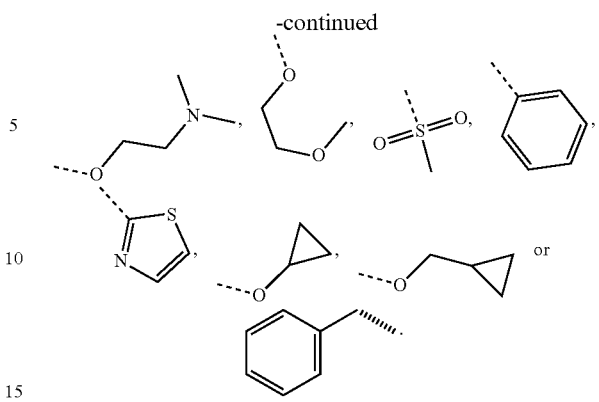

16. The compound or the pharmaceutically acceptable salt of the same according to claim 2, wherein ring A is selected from the group consisting of 1,3,4-oxadiazolyl, 1,3,4-thiadiazolyl, 1,2,4-oxadiazolyl, 1,2,4-thiadiazolyl, thiazolyl, isothiazolyl, oxazolyl, isoxazolyl and thienyl.

17. The compound or the pharmaceutically acceptable salt of the same according to claim 16, wherein ring A is

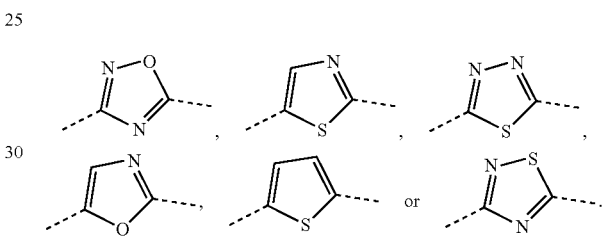

18. The compound or the pharmaceutically acceptable salt of the same according to claim 2, wherein ring B is selected from the group consisting of phenyl, oxazolyl, isoxazolyl, thiazolyl, isothiazolyl, 1,2,3-thiadiazolyl, imidazo[1,2-a]pyridyl, imidazo[1,2-a]pyrimidinyl, 4,5,6,7-tetrahydro[5,4-c]pyridyl, 5,6,7,8-tetrahydroimidazo[1,2-a]pyridyl, 4,5,6,7-tetrahydrothiazolo[5,4-c]pyridyl and 1,2,3-triazolyl.

19. The compound or the pharmaceutically acceptable salt of the same according to claim 18, wherein ring B is

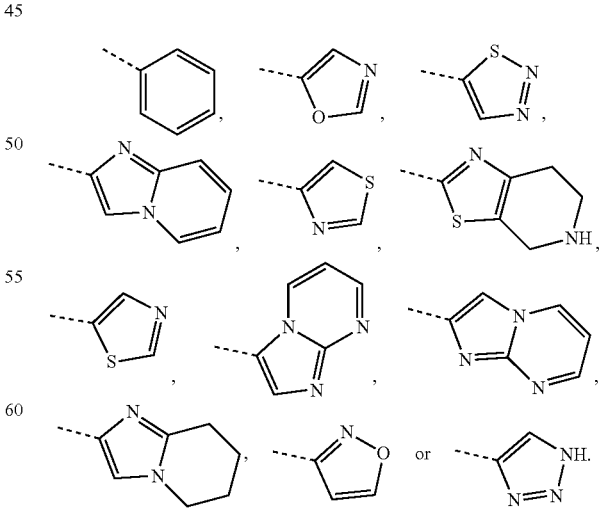

20. The compound or the pharmaceutically acceptable salt of the same according to claim 19, wherein the structure unit

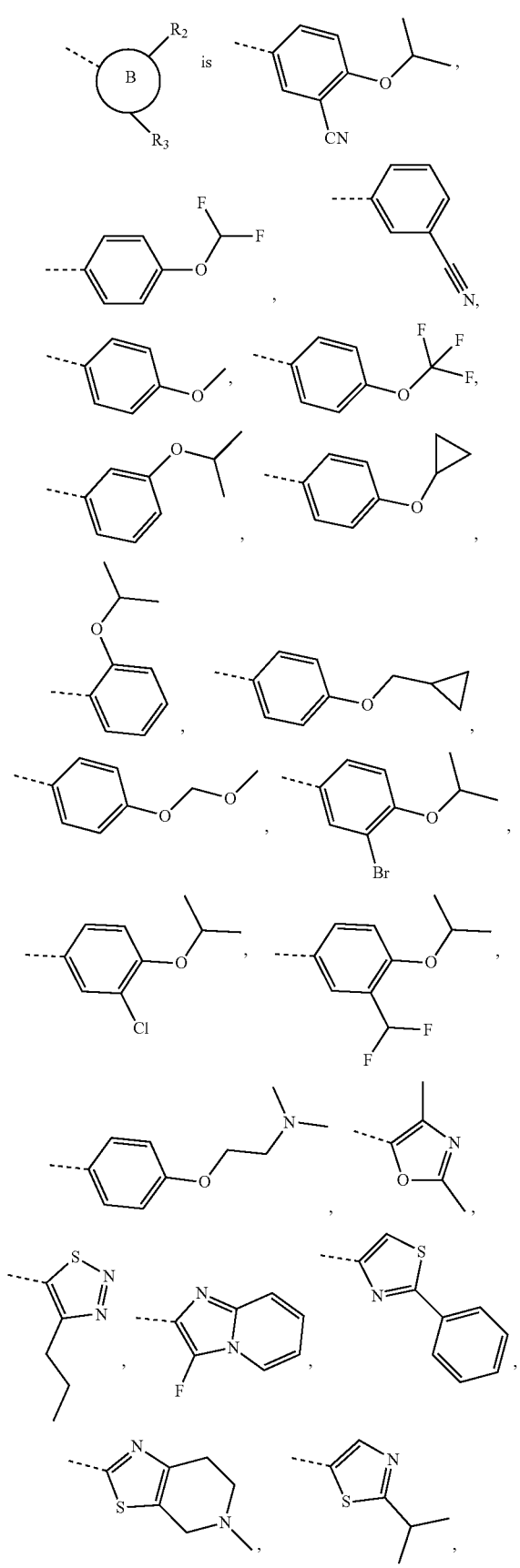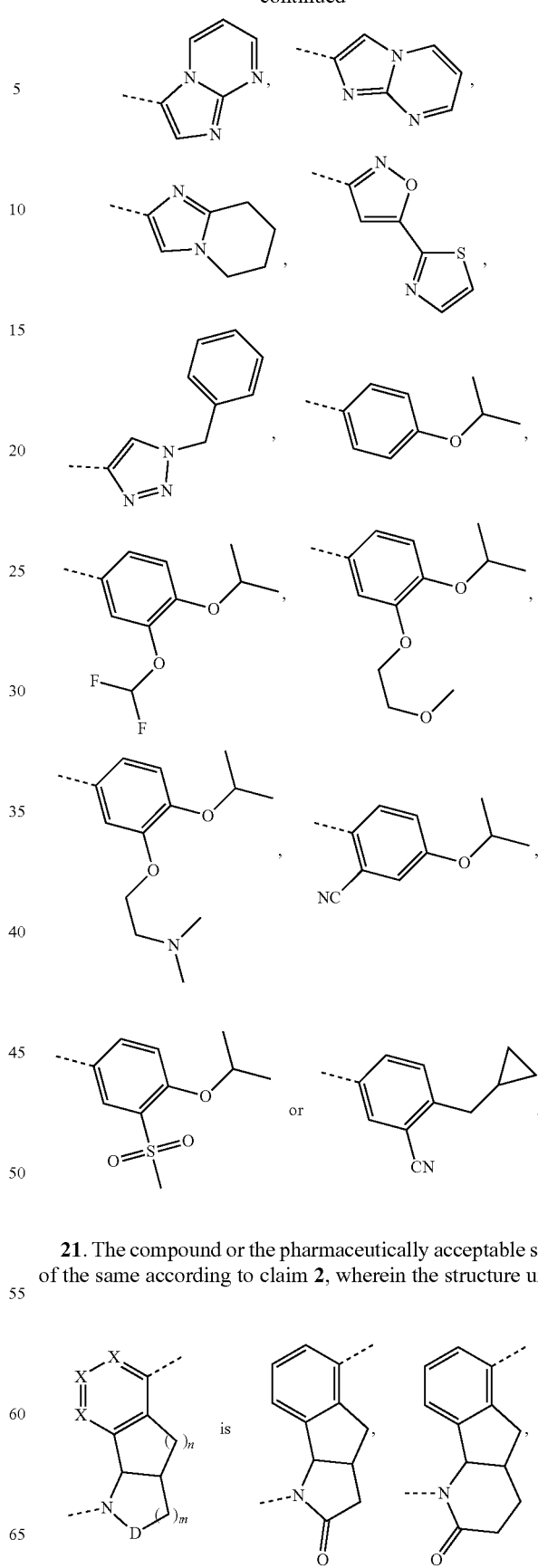
-continued
21. The compound or the pharmaceutically acceptable salt of the same according to claim 2, wherein the structure unit
is -continued

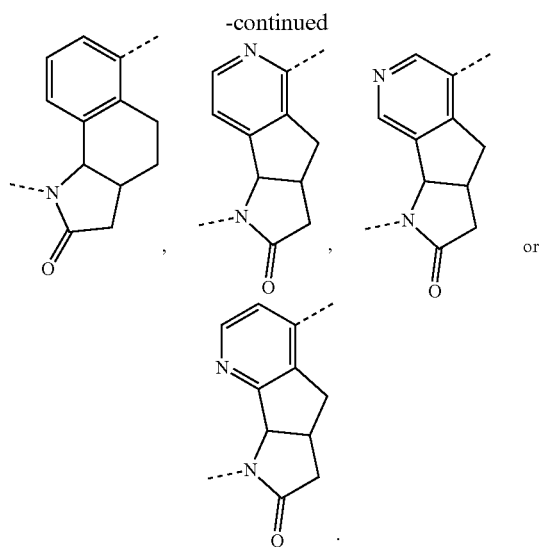

22. The compound or the pharmaceutically acceptable salt of the same according to claim 1, wherein R is H, F, Cl, Br, I, CN, OH, NH₂ COOH or

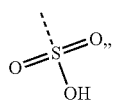

or selected from the group consisting of C₁₋₃ alkyl, C₁₋₃ alkoxyl, C₁₋₃ alkylthiol, C₁₋₃ alkylamino, N, N'-di(C₁₋₂ alkyl)amino, C₁₋₃ alkyl-S(=O)— and C₁₋₃ alkyl-S(=O)₂—, each of which is optionally substituted by one, two or three R'.

23. The compound or the pharmaceutically acceptable salt of the same according to claim 22, wherein R is H, F, Cl, Br, I, CN, OH, NH₂, COOH, Me, Et, CF₃,

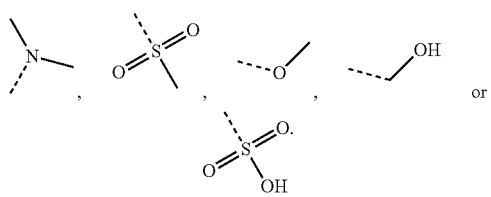

24. The compound or the pharmaceutically acceptable salt of the same according to claim 1, wherein R₁ is selected from the group consisting of C₁₋₆ alkyl, C₁₋₃ alkyl-S(=O)₂—C₁₋₃ alkyl-, C₁₋₃ alkyl-S(=O)—C₁₋₃ alkyl-, C₁₋₃ alkyl-NH—C(=O)—C₁₋₃ alkyl-, and C₃₋₆ cycloalkyl, each of which is substituted by one, two or three R.

25. The compound or the pharmaceutically acceptable salt of the same according to claim 24, wherein R₁ is Me,

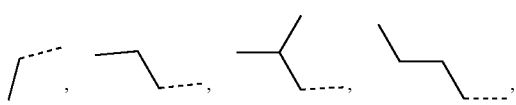

-continued

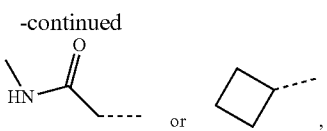

each of which is optionally substituted by one, two or three R.

26. The compound or the pharmaceutically acceptable salt of the same according to claim 25, wherein R₁ is

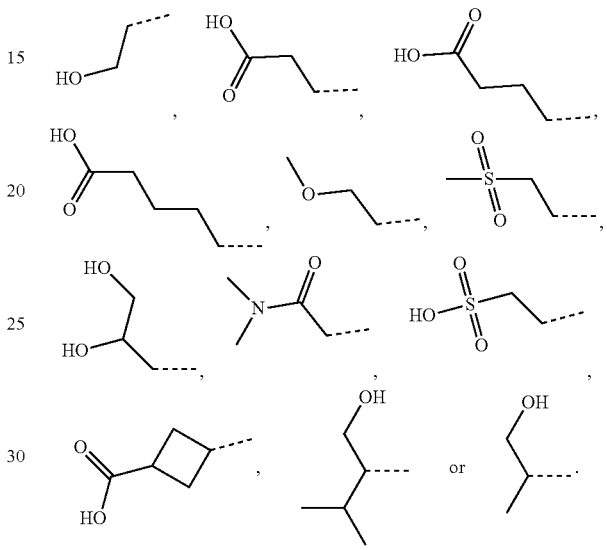

27. The compound or the pharmaceutically acceptable salt of the same according to claim 1, wherein L is —(CH₂)₁₋₃— or —O—(CH₂)₀₋₃—.

28. The compound or the pharmaceutically acceptable salt of the same according to claim 27, wherein L is —CH₂—, —CH₂CH₂—, —CH₂CH₂CH₂—, —O—, —O—CH₂—, —O—CH₂CH₂— or —O—CH₂CH₂CH₂—.

29. The compound or the pharmaceutically acceptable salt of the same according to claim 1, wherein R₄ is

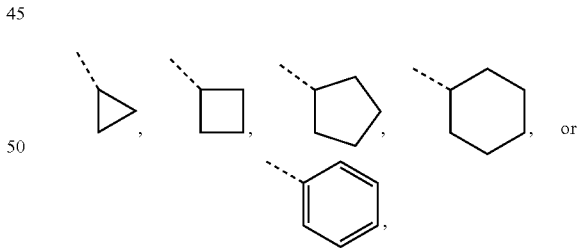

each of which is optionally substituted by one, two or three R.

30. The compound or the pharmaceutically acceptable salt of the same according to claim 29, wherein R₄ is

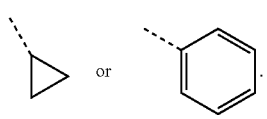

31. The compound or the pharmaceutically acceptable salt of the same according to claim 28, wherein $R_4$-L- is

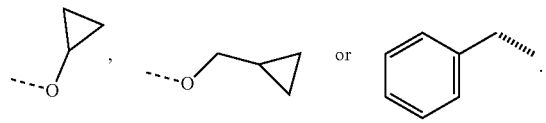

32. The compound or the pharmaceutically acceptable salt of the same according to claim 1, wherein each of $R_2$ and $R_3$ is H, F, Cl, Br, I, OH, $NH_2$, CN or $R_4$-L-, or selected from the group consisting of $C_{1-3}$ alkyl, $C_{1-3}$ alkoxyl, $C_{1-3}$ alkyl-thiol, $C_{1-3}$ alkyl-S(=O)—, $C_{1-3}$ alkyl-S(=O)$_2$—, phenyl, thiazolyl, isothiazolyl, oxazolyl and isoxazolyl, each of which is optionally substituted by one, two or three R.

33. The compound or the pharmaceutically acceptable salt of the same according to claim 32, wherein each of $R_2$ and $R_3$ is H, F, Cl, Br, I, OH, $NH_2$, CN or $R_4$-L-, or selected from the group consisting of Me, Et,

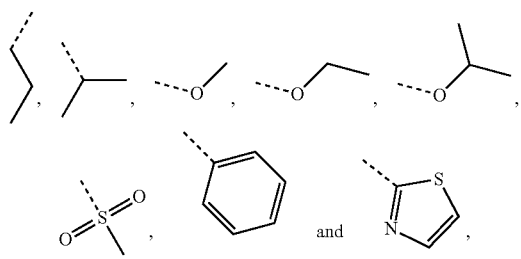

each of which is optionally substituted by one, two or three R.

34. The compound or the pharmaceutically acceptable salt of the same according to claim 33, wherein each of $R_2$ and $R_3$ is H, F, Cl, Br, I, OH, $NH_2$, CN, Me,

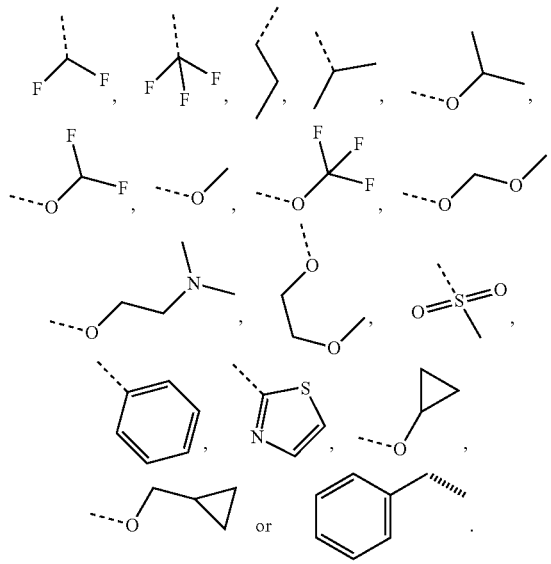

35. The compound or the pharmaceutically acceptable salt of the same according to claim 1, wherein ring A is selected from the group consisting of 1,3,4-oxadiazolyl, 1,3,4-thiadiazolyl, 1,2,4-oxadiazolyl, 1,3,4-oxadiazolyl, 1,2,4-triazolyl, 1,2,4-thiadiazolyl, thiazolyl, isothiazolyl, oxazolyl, isoxazolyl and thienyl.

36. The compound or the pharmaceutically acceptable salt of the same according to claim 35, wherein ring A is

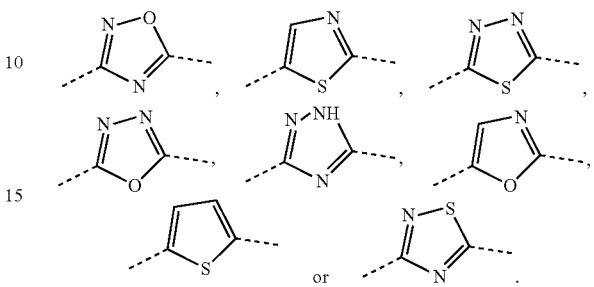

37. The compound or the pharmaceutically acceptable salt of the same according to claim 1, wherein ring B is selected from the group consisting of phenyl, oxazolyl, isoxazolyl, thiazolyl, isothiazolyl, 1,2,3-thiadiazolyl, imidazo[1,2-a]pyridyl, imidazo[1,2-a]pyrimidinyl, 4,5,6,7-tetrahydro[5,4-c]pyridyl, 5,6,7,8-tetrahydroimidazo[1,2-a]pyridyl, 4,5,6,7-tetrahydrothiazolo[5,4-c]pyridyl and 1,2,3-tri azolyl.

38. The compound or the pharmaceutically acceptable salt of the same according to claim 37, wherein ring B is

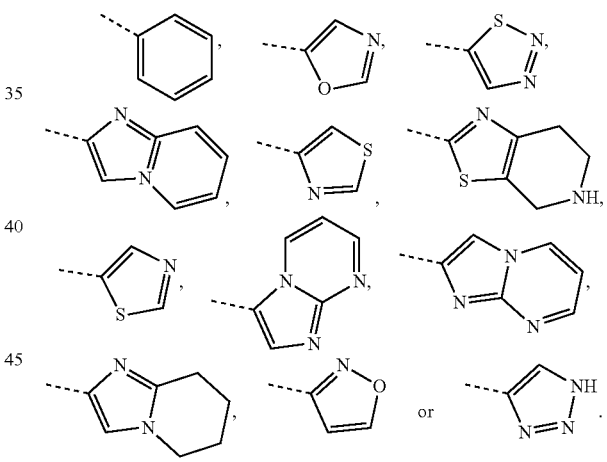

39. The compound or the pharmaceutically acceptable salt of the same according to claim 38, wherein the structure unit

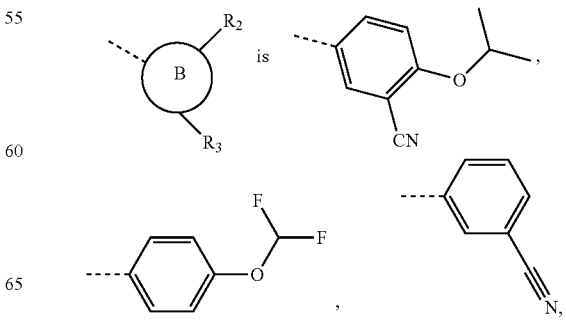

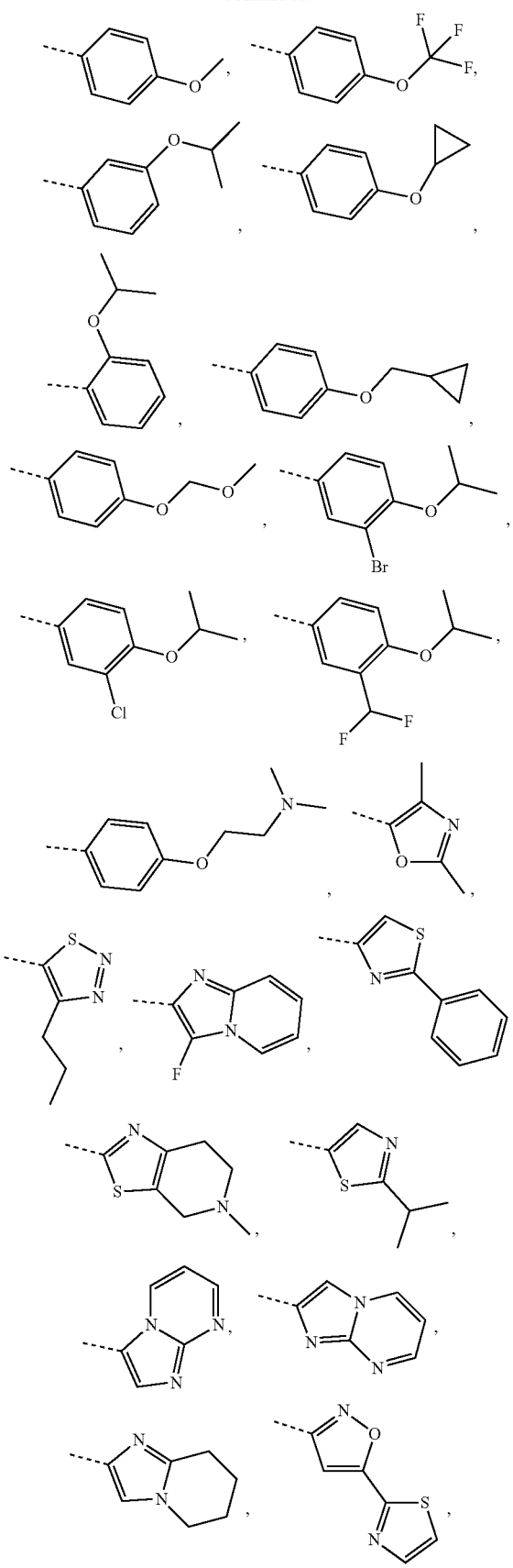
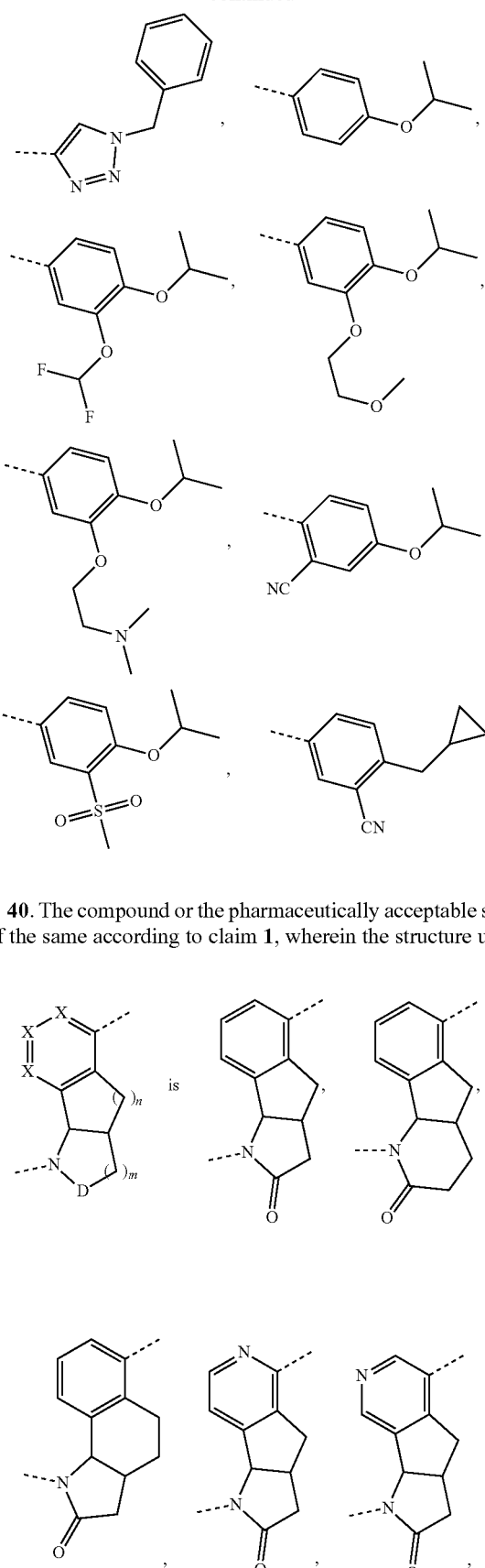
40. The compound or the pharmaceutically acceptable salt of the same according to claim 1, wherein the structure unit
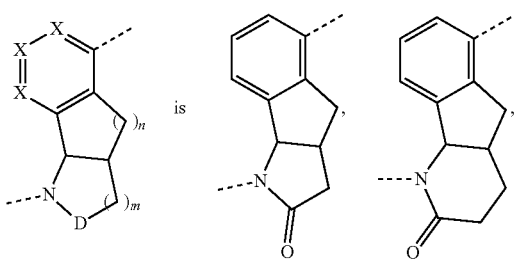
is
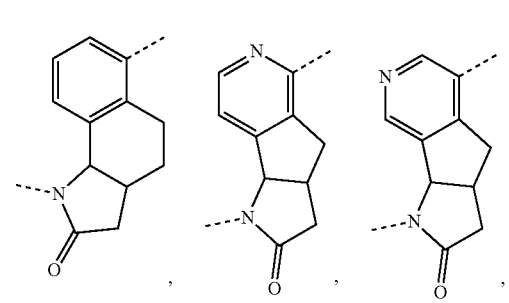

-continued
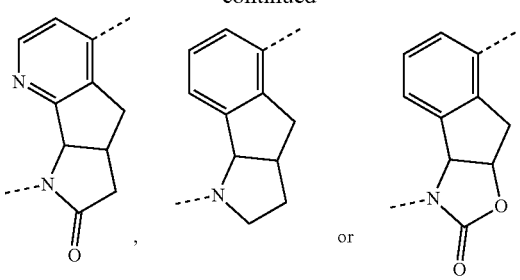
41. The compound or the pharmaceutically acceptable salt of the same according to claim 1, which is selected from the group consisting of
(II-1)
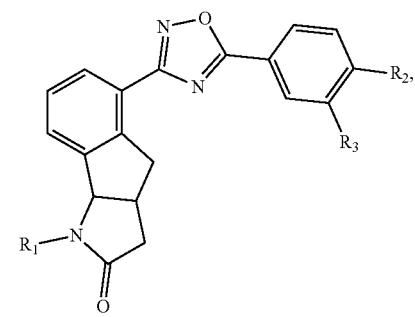
(II-2)
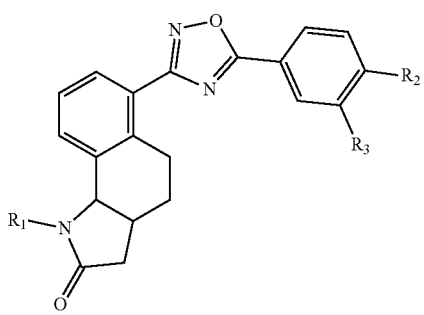
and
(II-3)
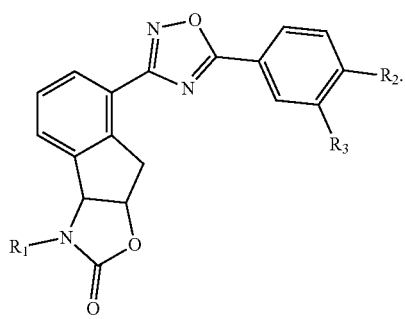
42. The compound or the pharmaceutically acceptable salt of the same according to claim 41, which is selected from the group consisting of
(II-1A)
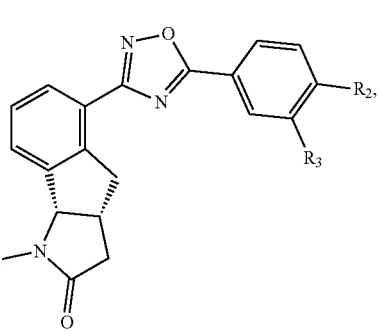
(II-1B)
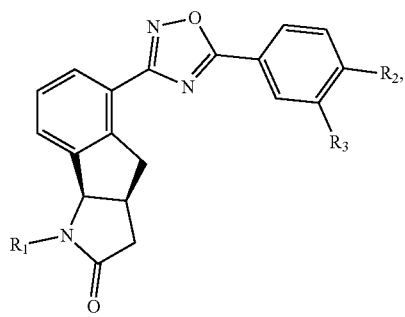
(II-2A)
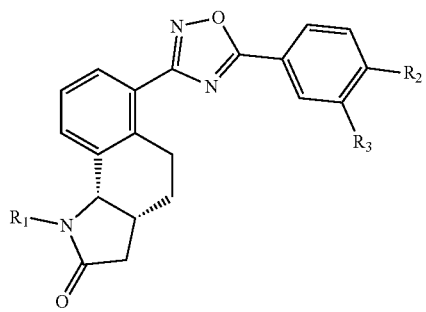
(II-2B)
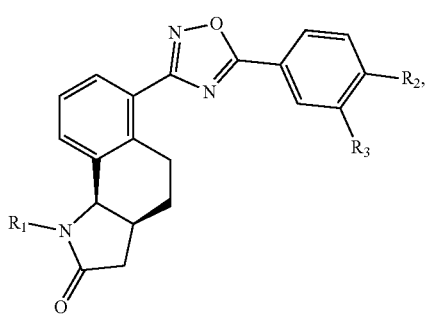
(II-3A)
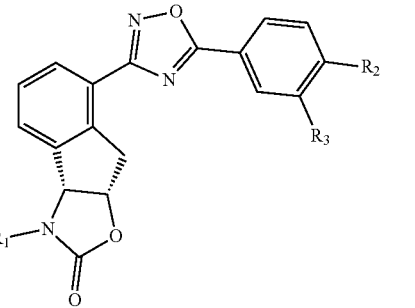
and

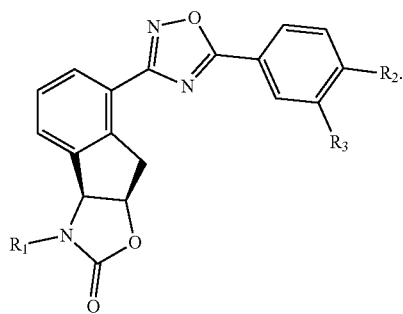
(II-3B)
43. The compound or the pharmaceutically acceptable salt of the same according to claim 1, which is selected from the group consisting of
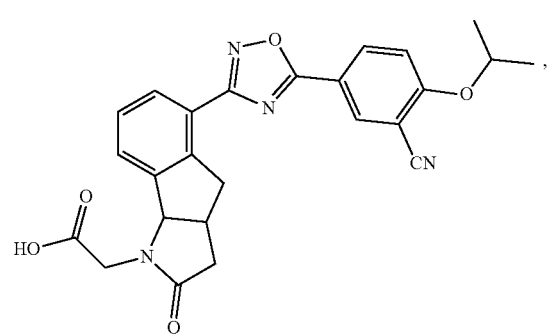
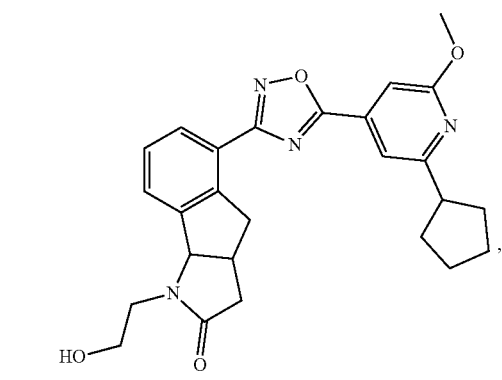
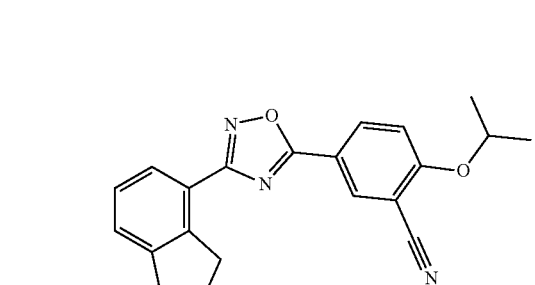
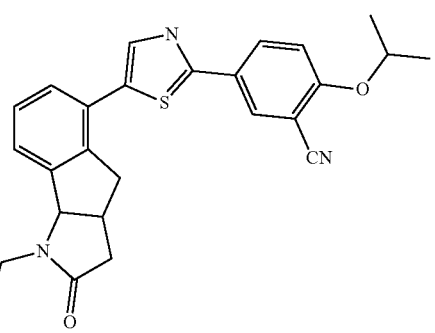
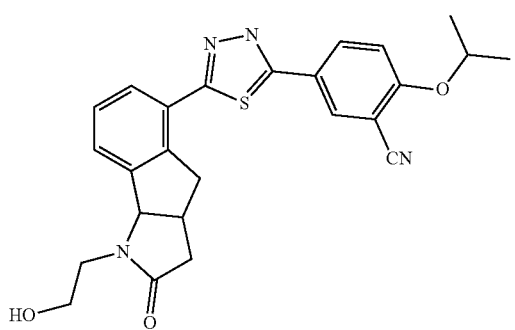
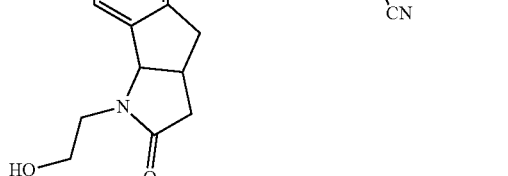
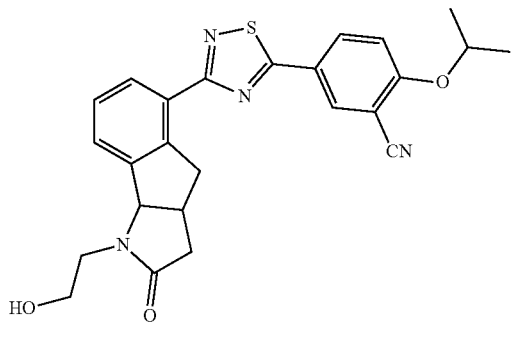
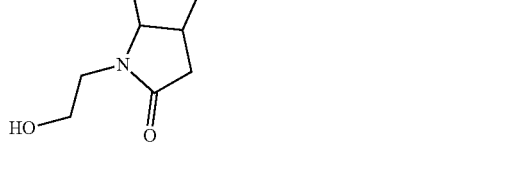

191
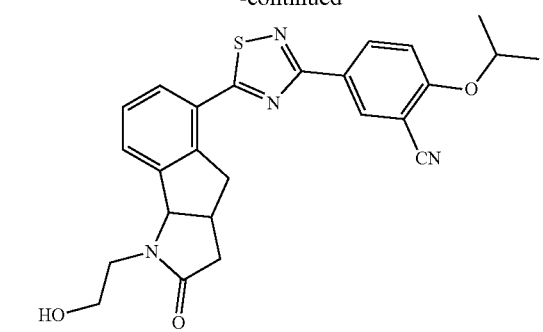
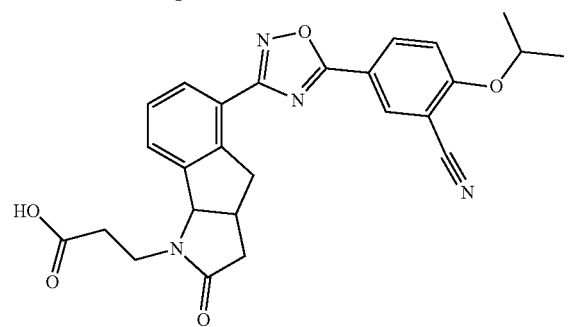
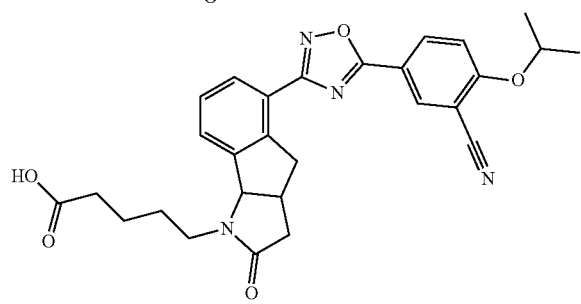
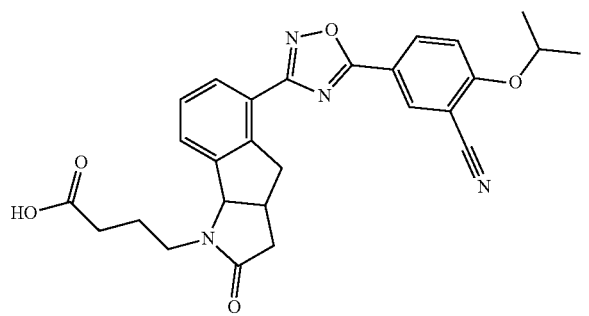
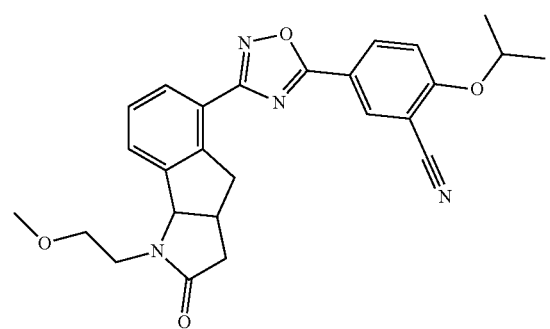
192
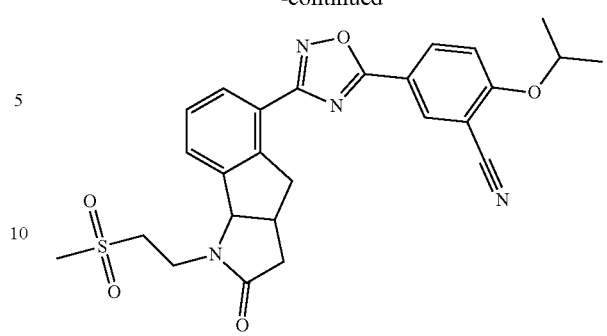
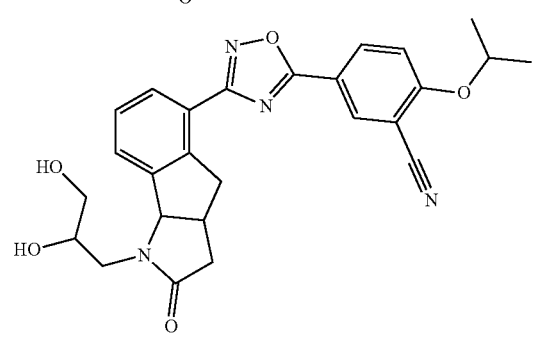
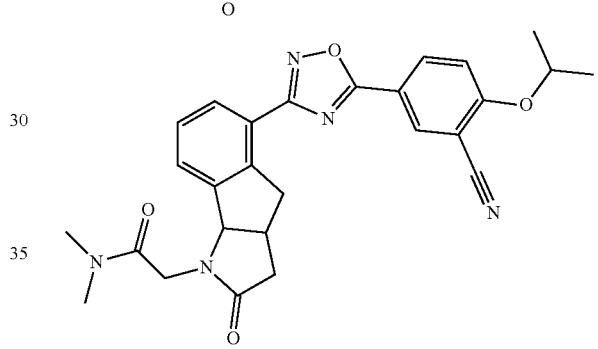
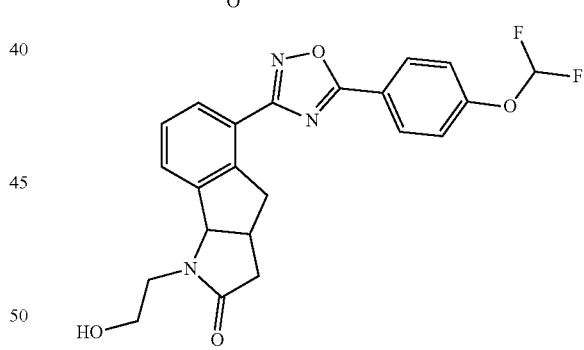
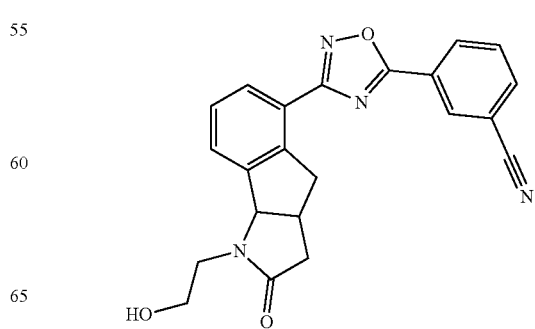

193
-continued
194
-continued
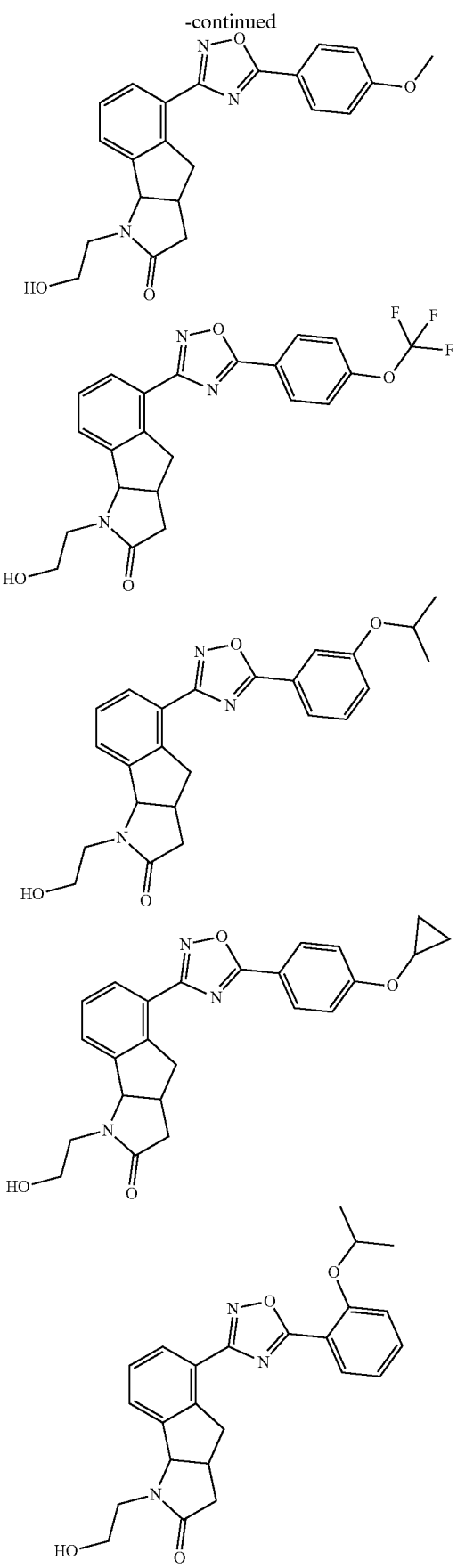
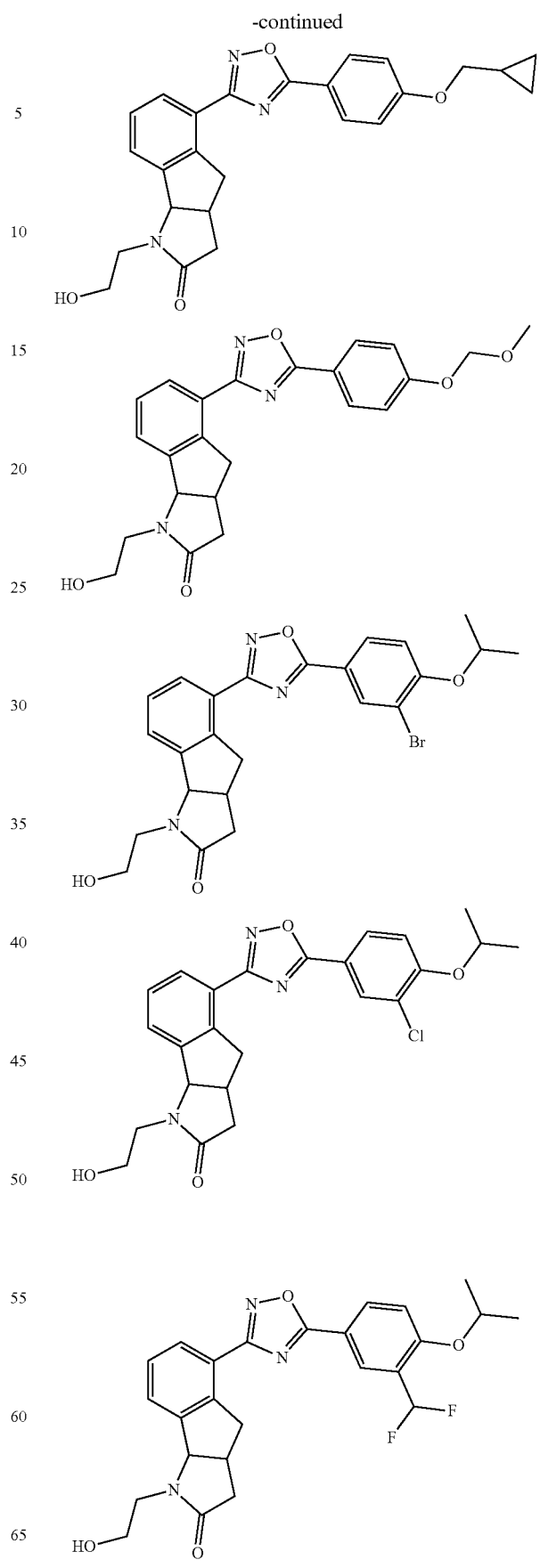

195
-continued
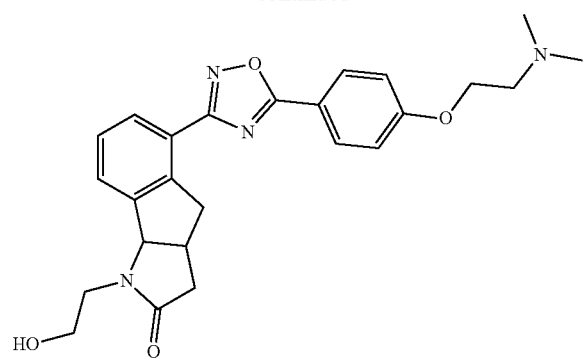
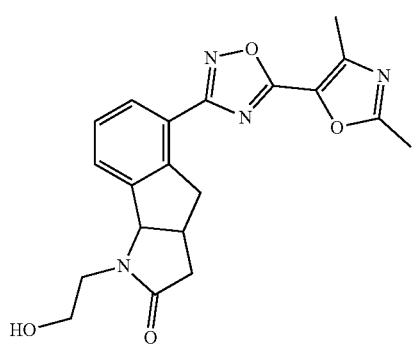
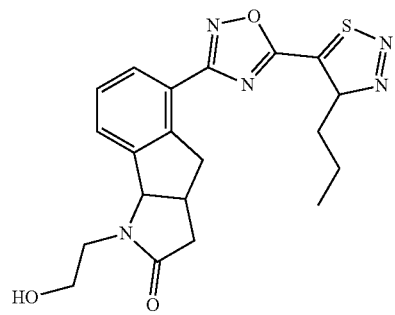
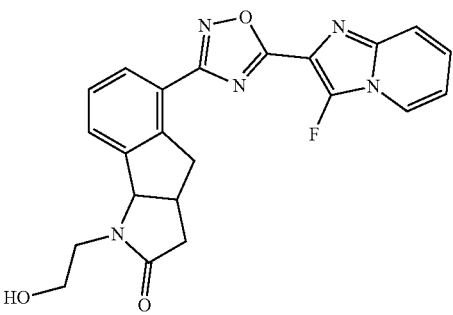
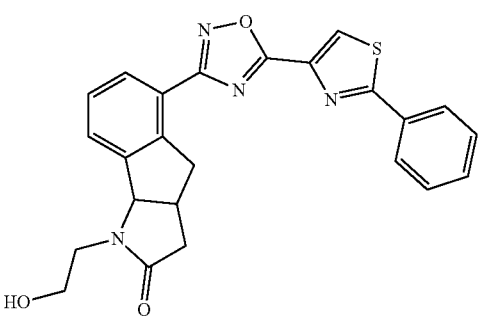
196
-continued
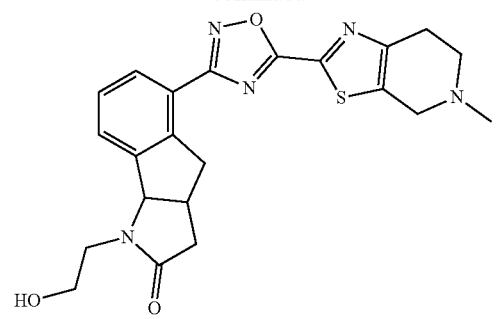
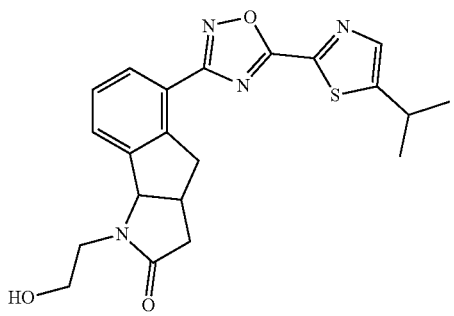
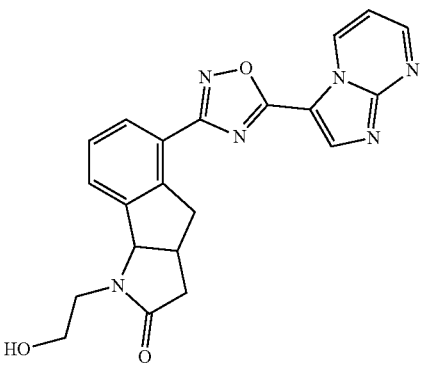
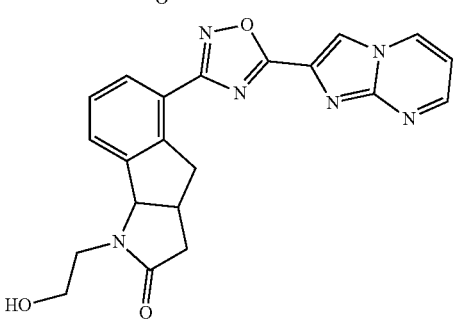
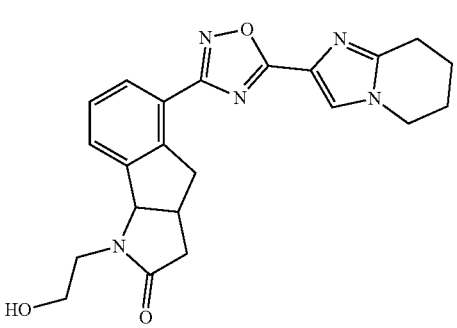

197
-continued
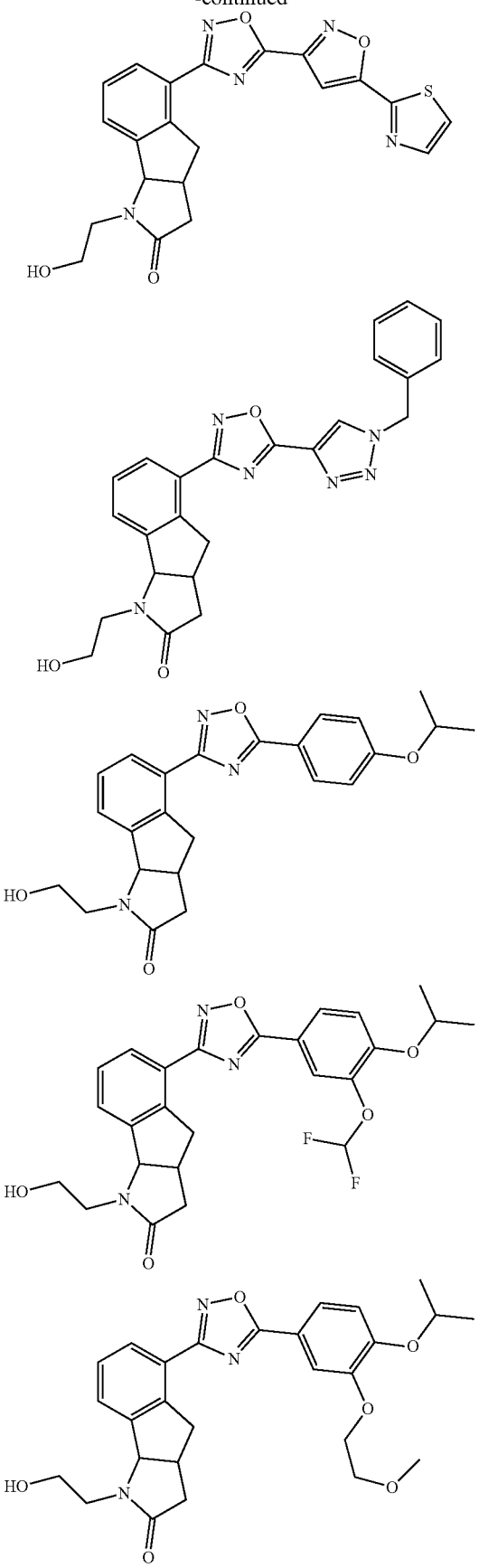
198
-continued
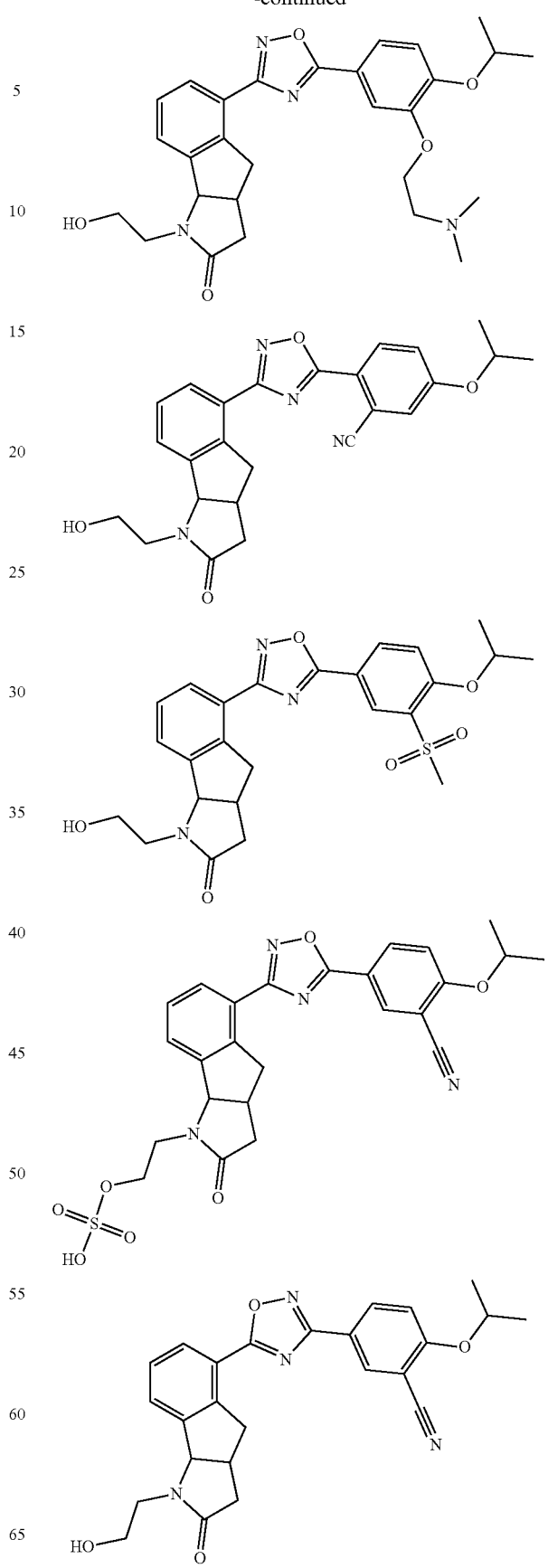

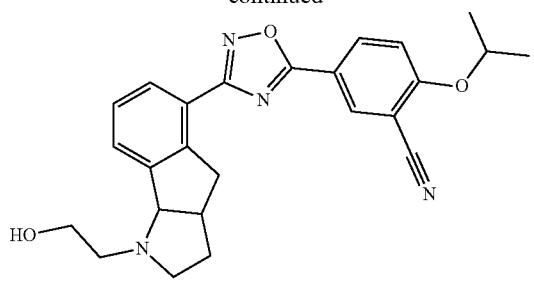
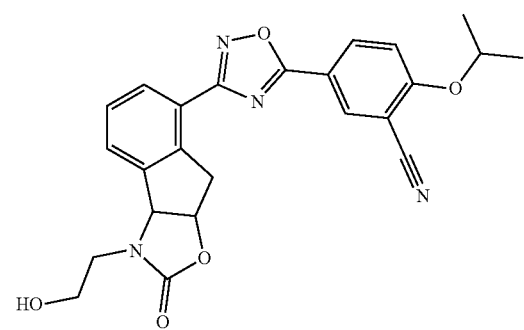
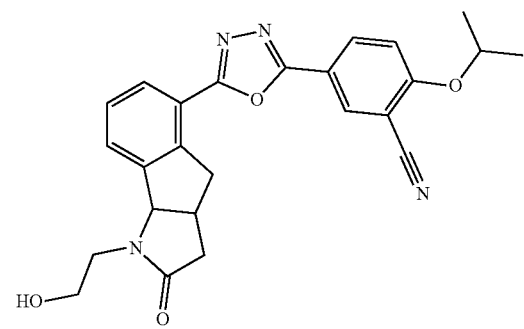
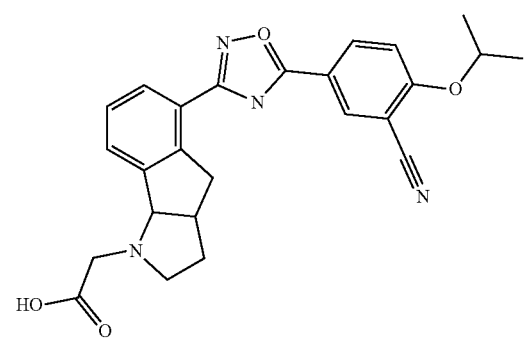
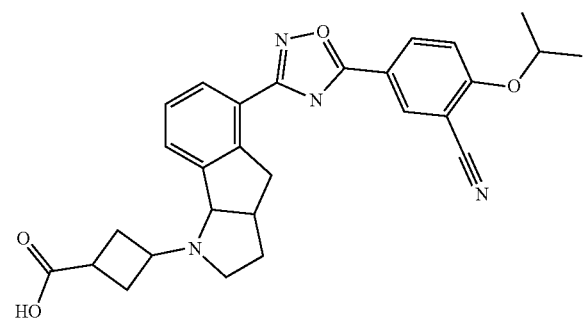
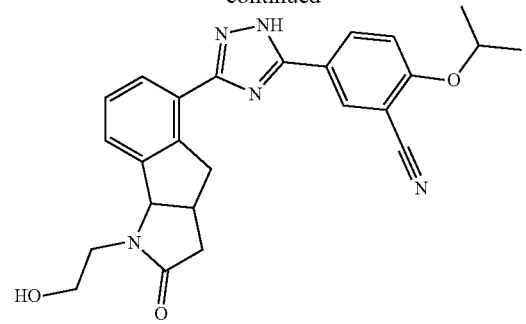
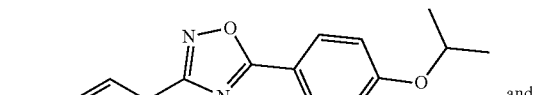
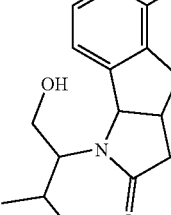
and
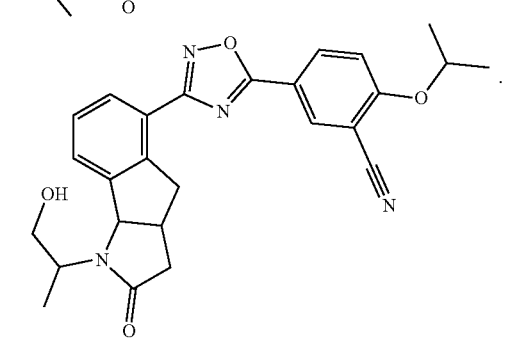
.
44. The compound or the pharmaceutically acceptable salt of the same according to claim 43, which is selected from the group consisting of
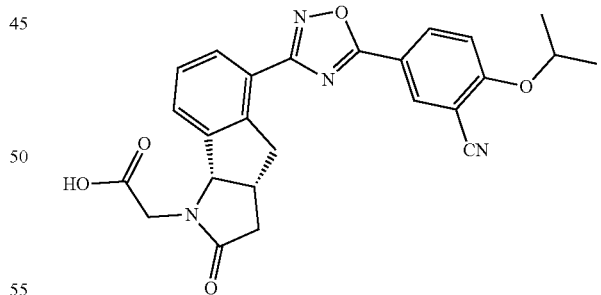
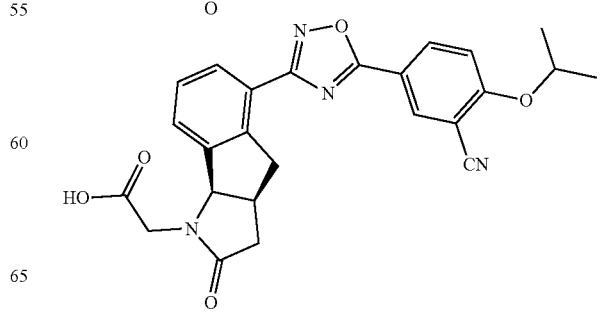

201
-continued
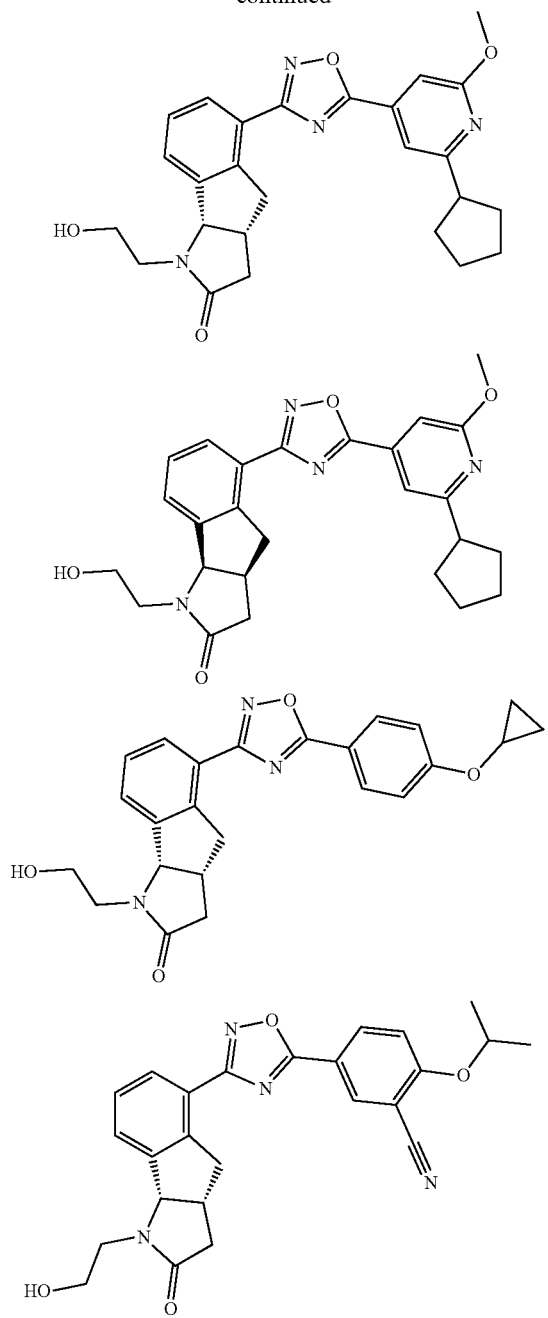
202
-continued
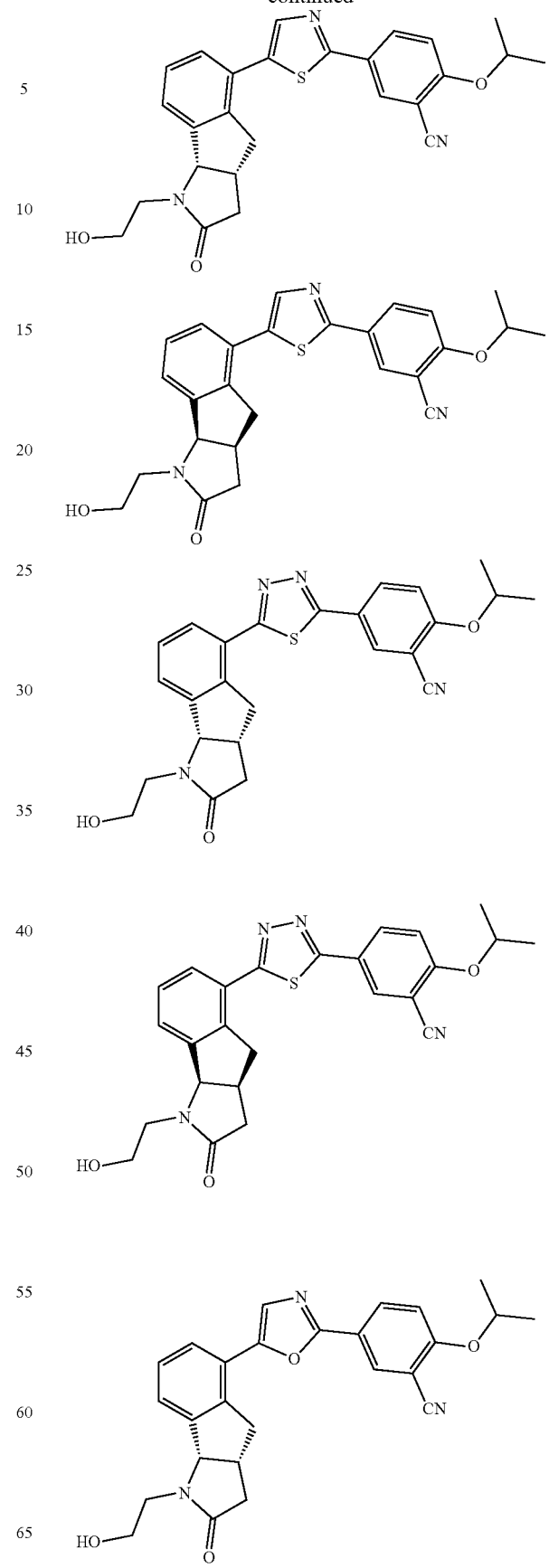

203
-continued
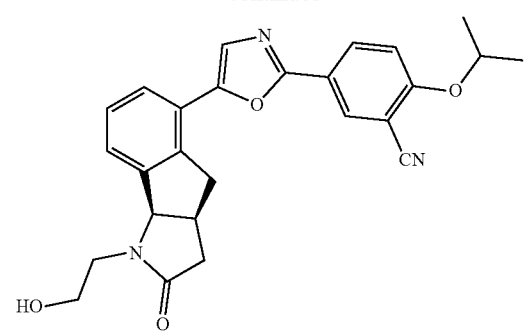
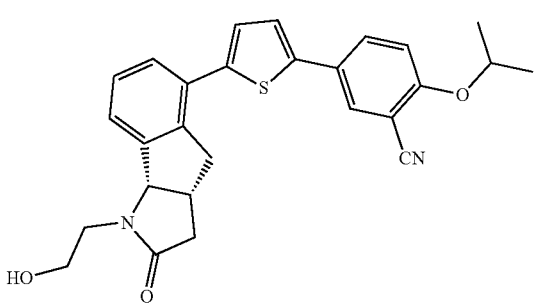 [SMILES: CC(C)Oc1ccc(-c2ccc(-c3cccc4c3C[C@@H]3CC(=O)N(CCO)[C@H]43)s2)cc1C#N]
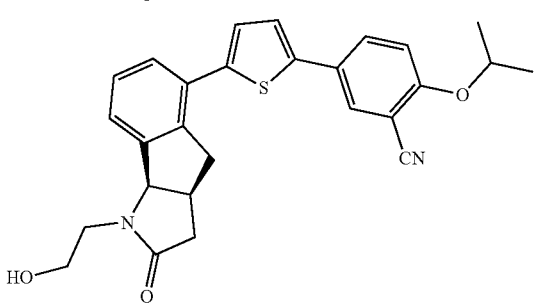
204
-continued
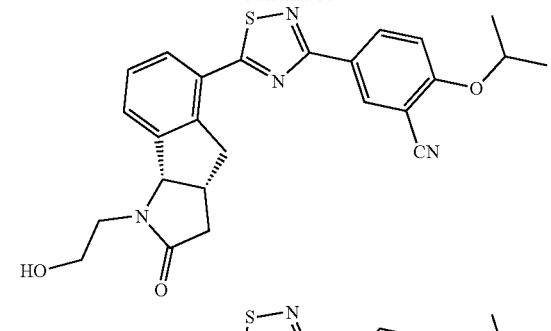
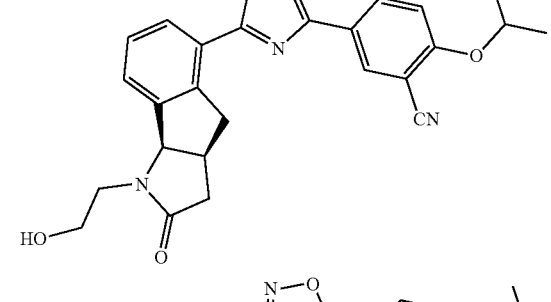
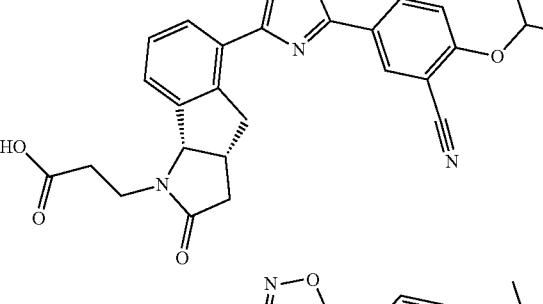

205
-continued
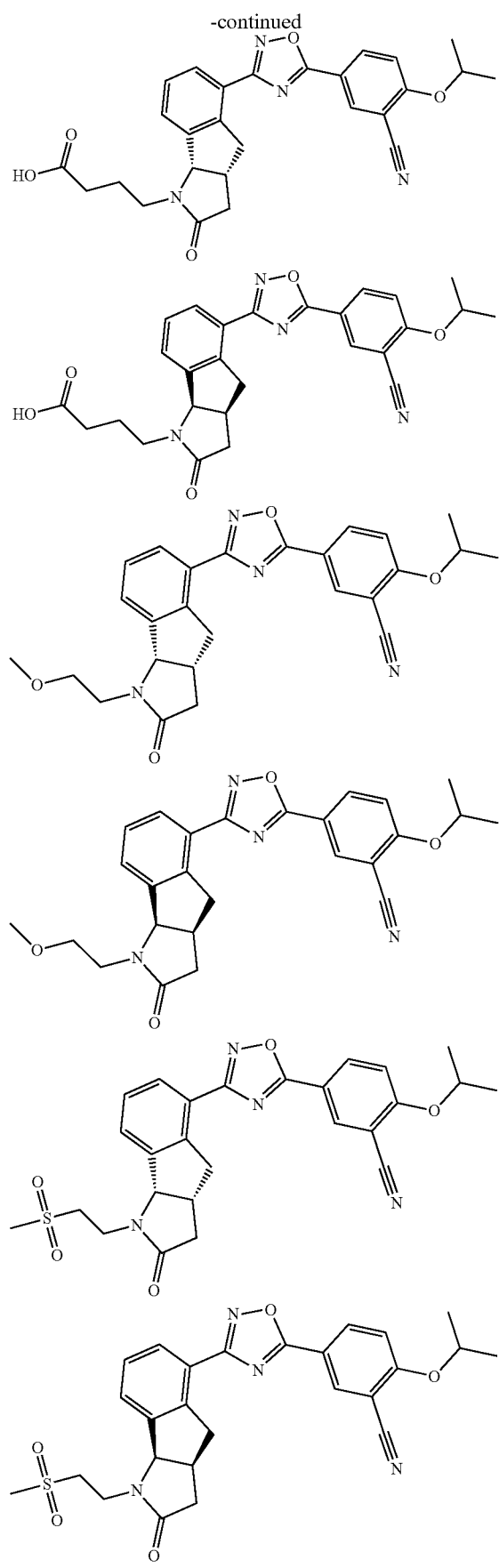
206
-continued
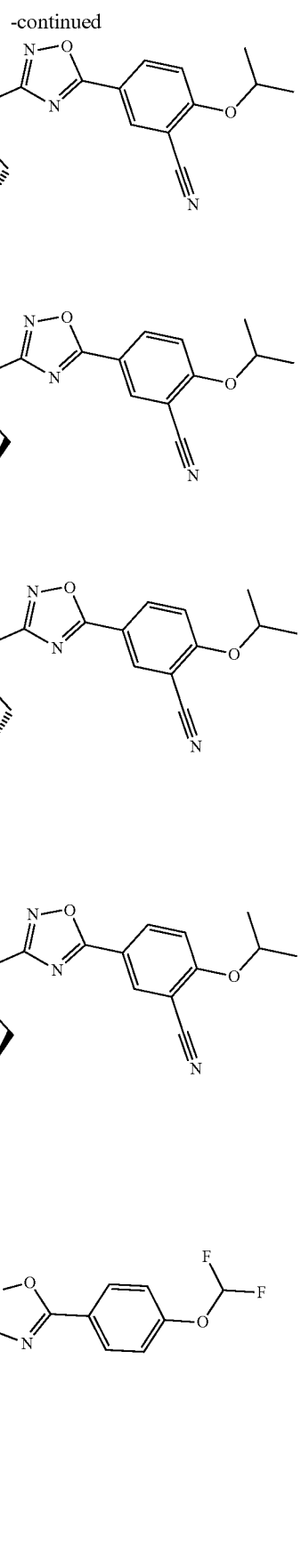

207
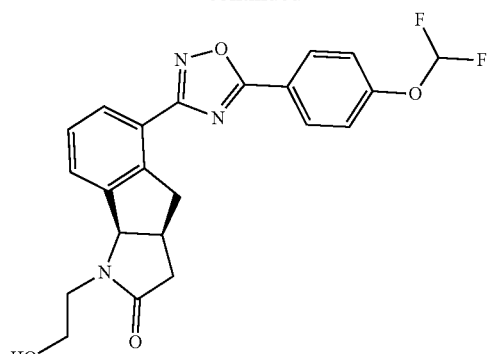
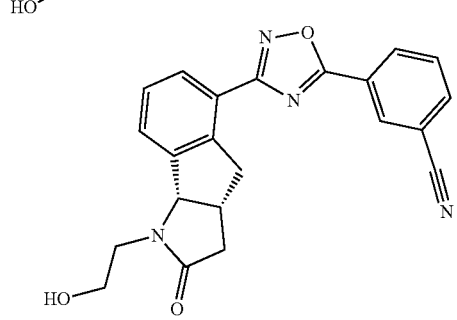
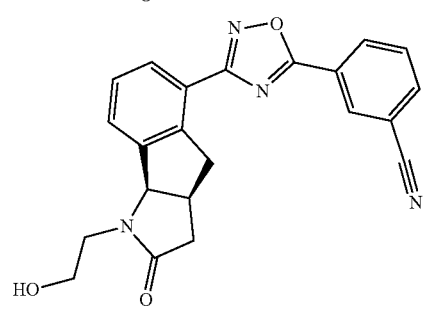
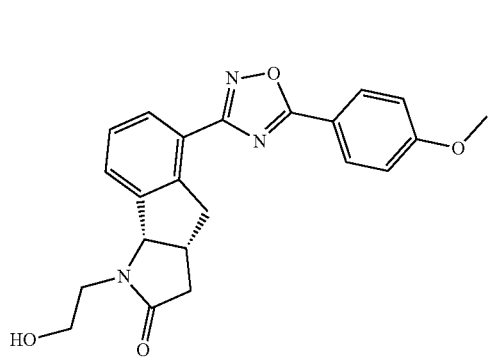
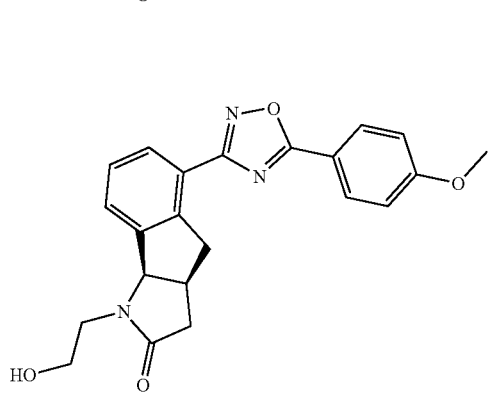
208
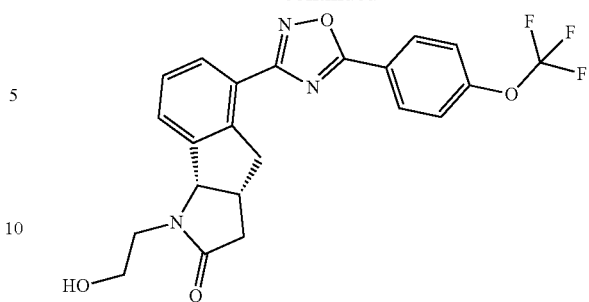
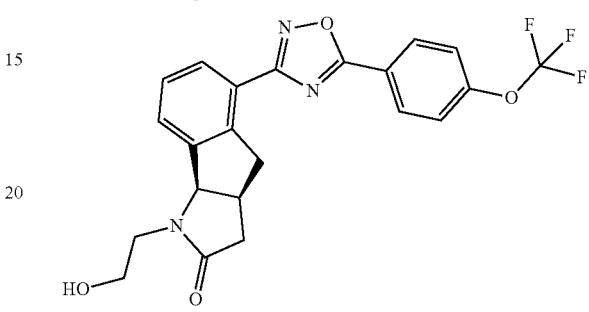
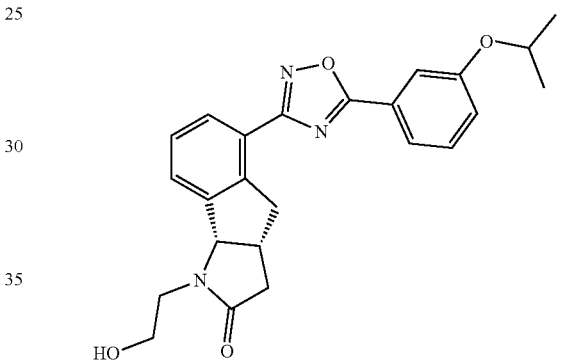
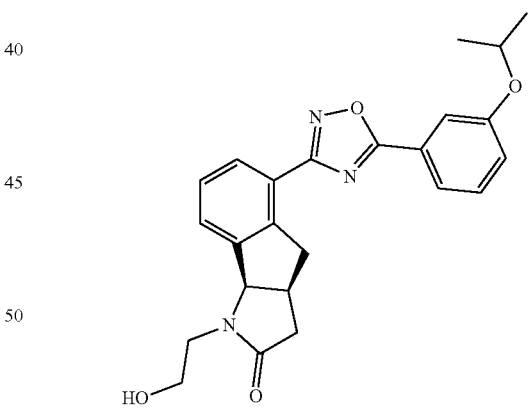
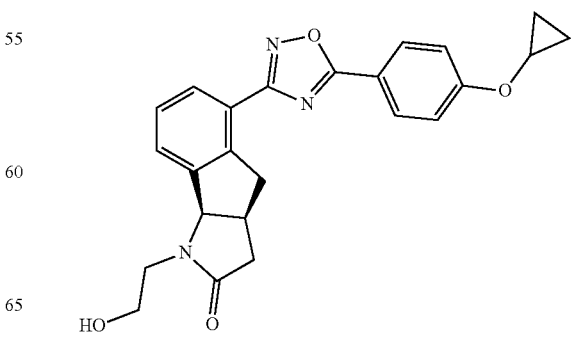

209
-continued
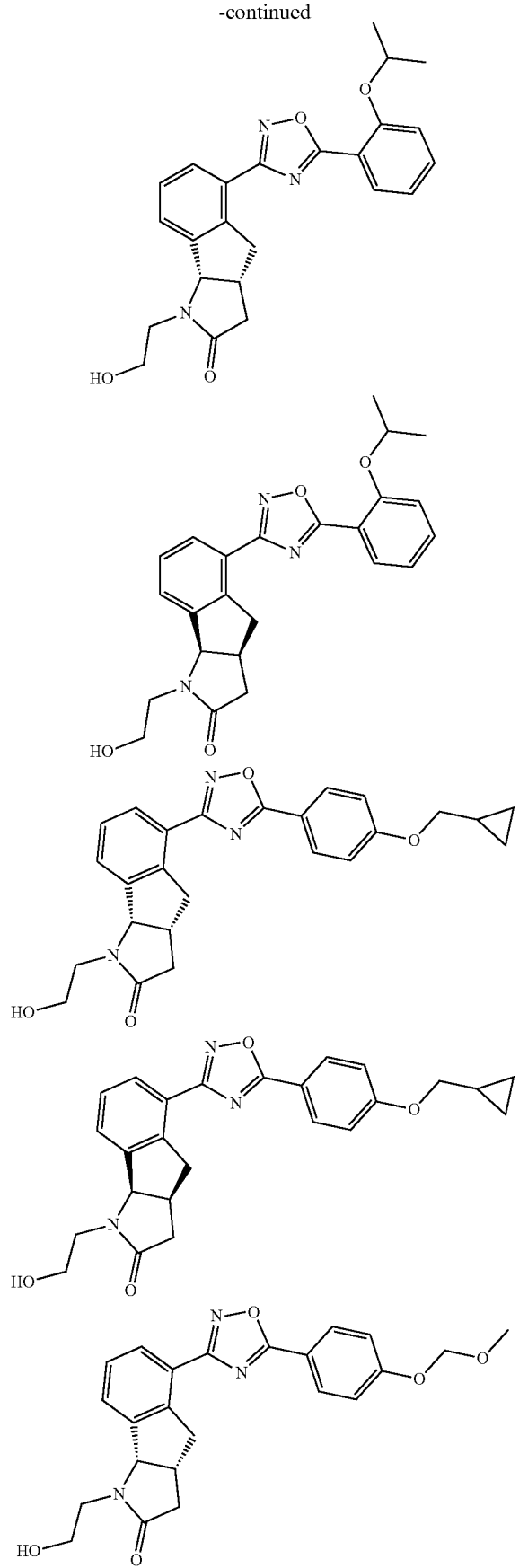
210
-continued
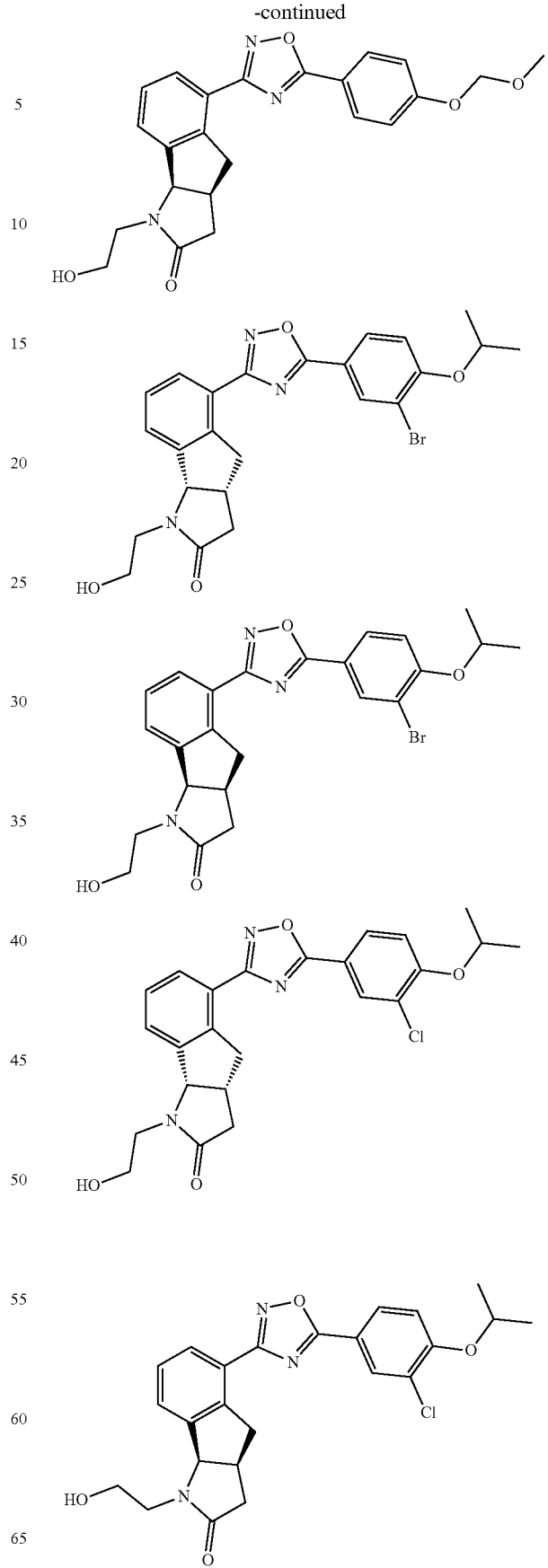

211
-continued
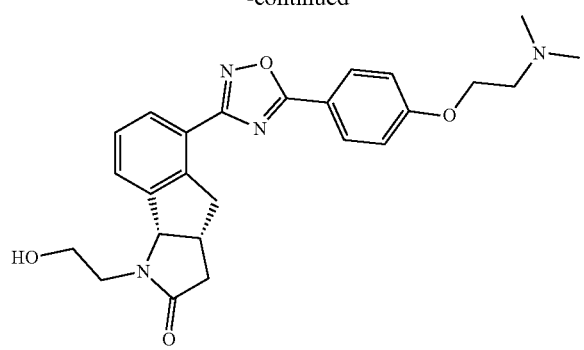
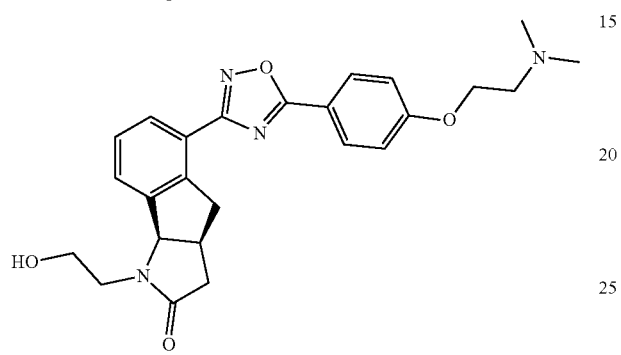
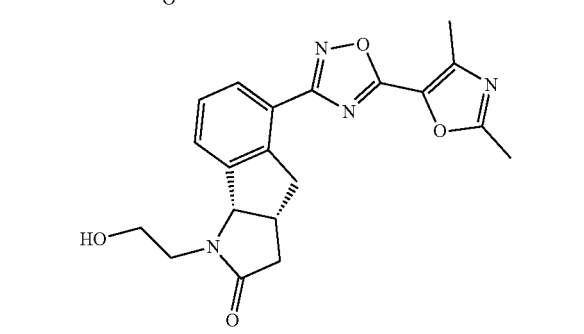
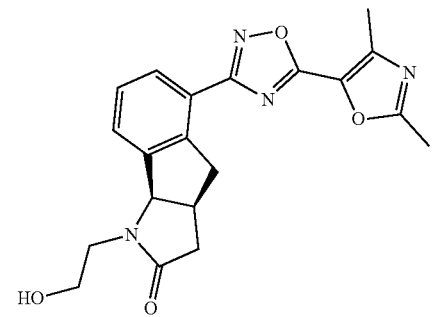
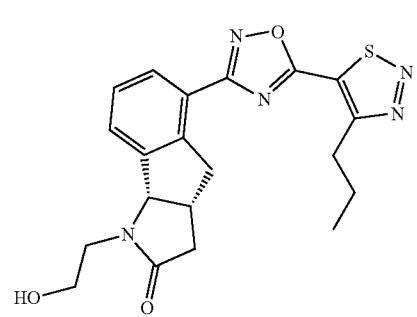
212
-continued
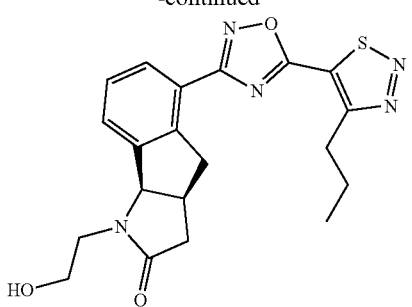
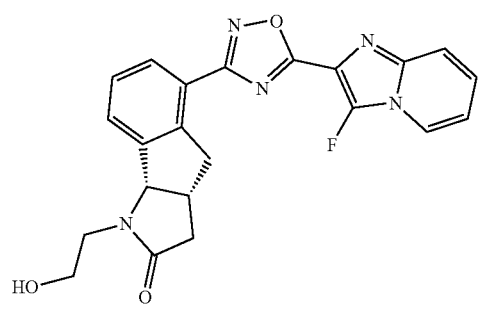
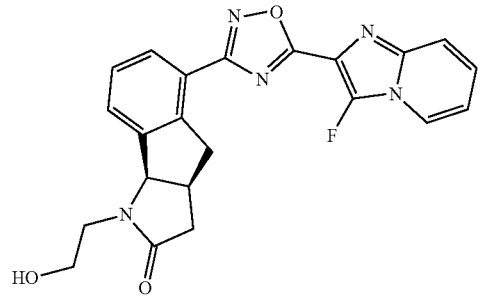
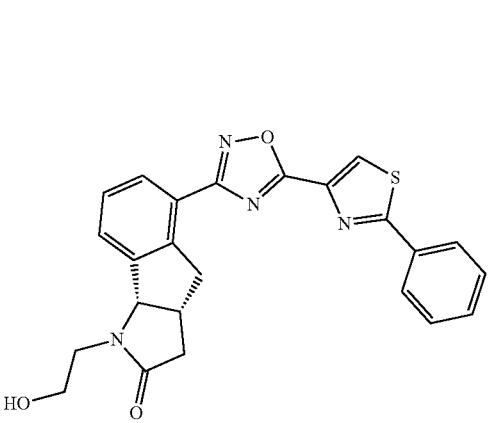
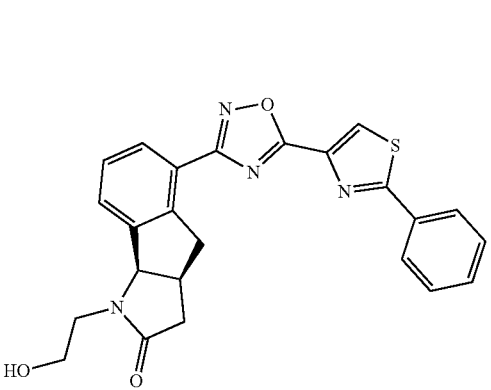

213
-continued
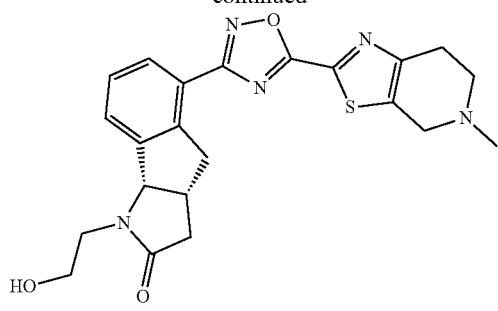
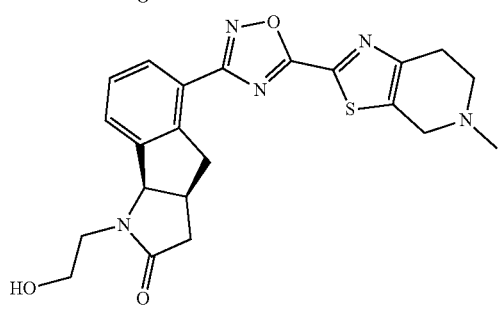
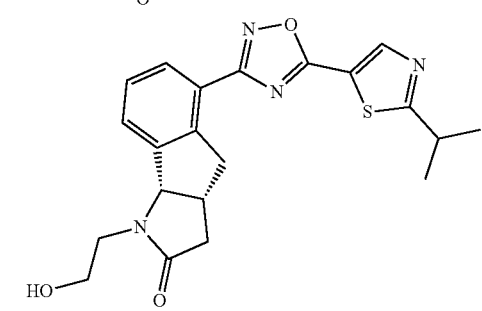
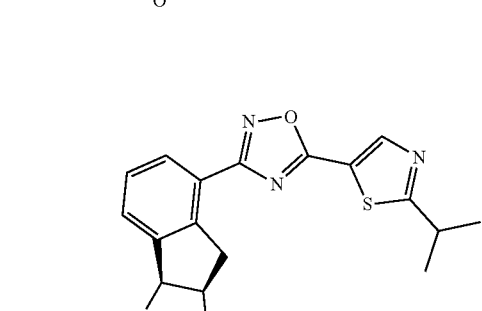
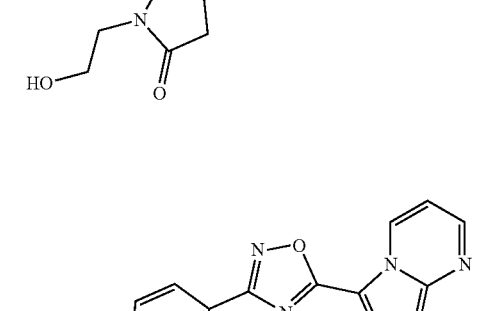
214
-continued
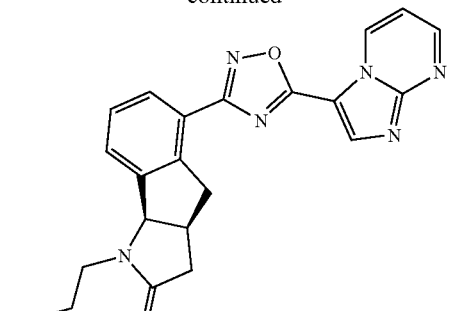
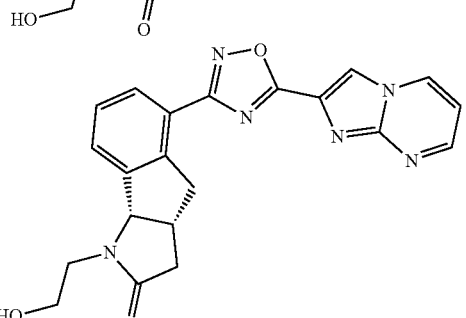
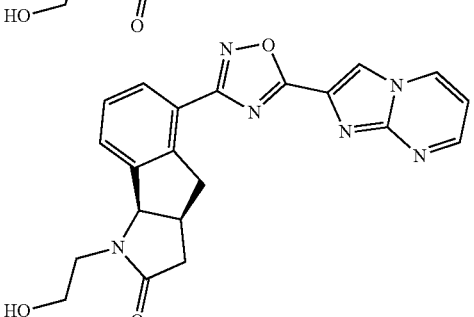
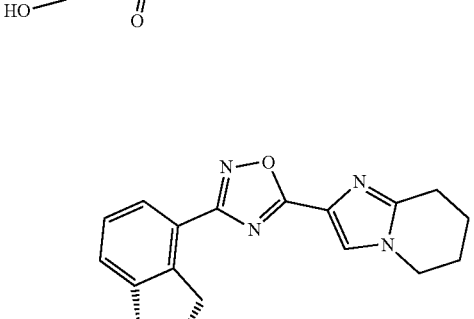
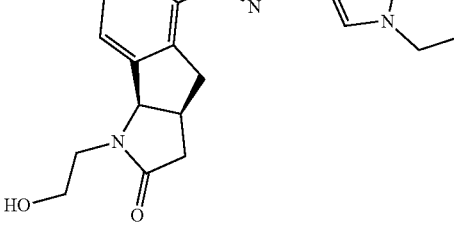

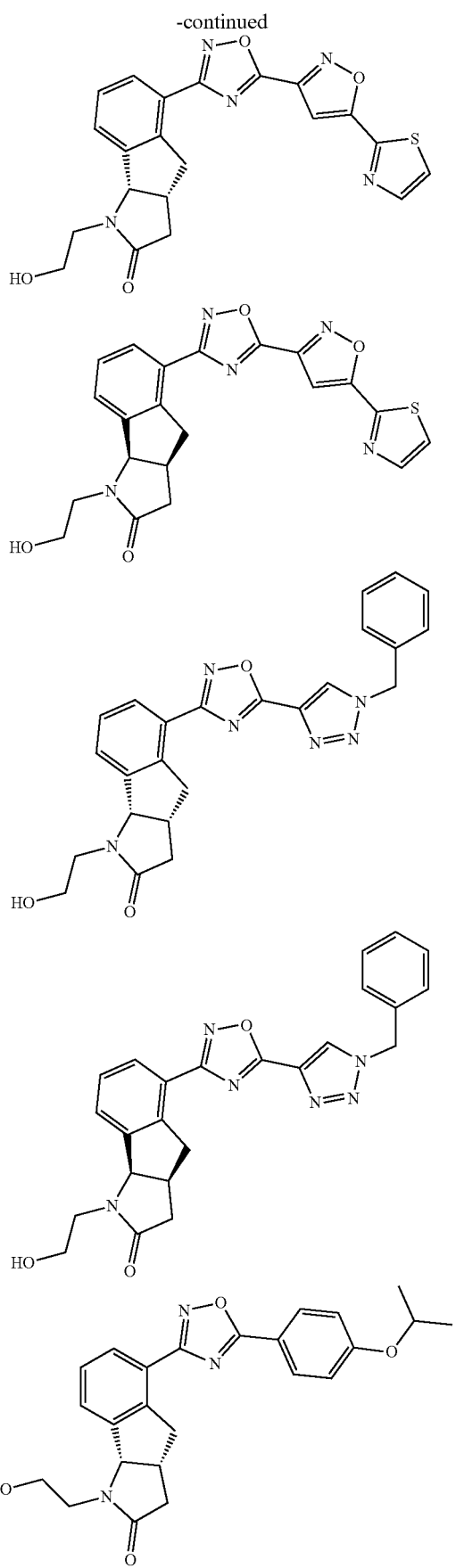
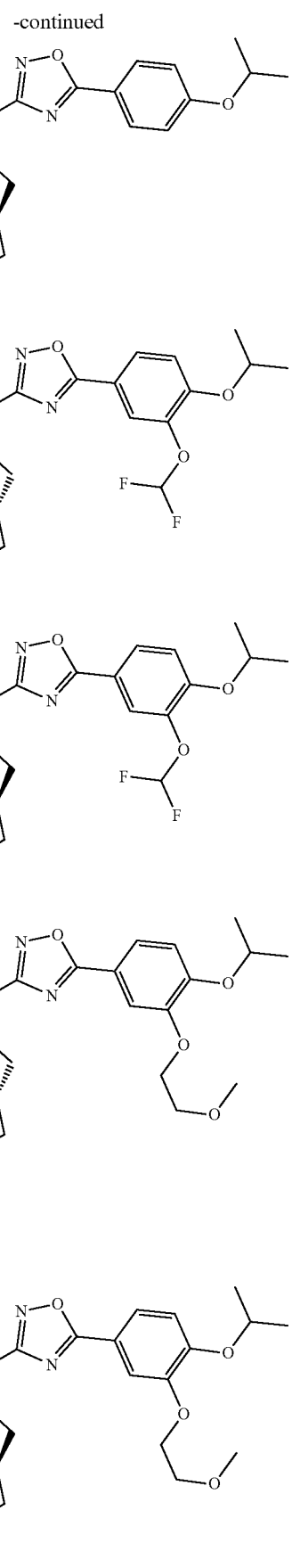

217
-continued
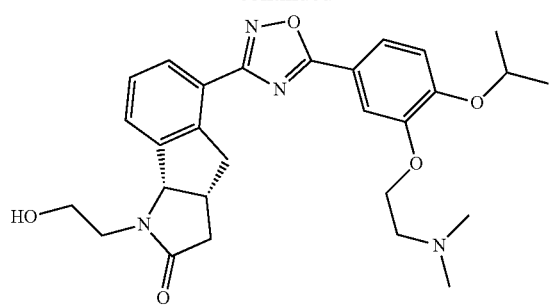
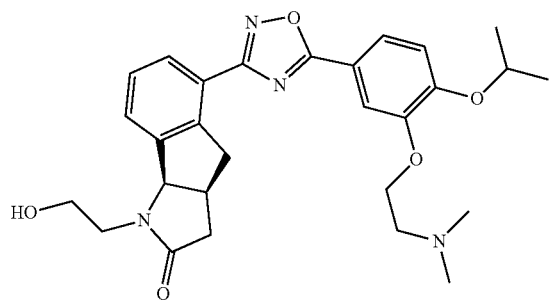
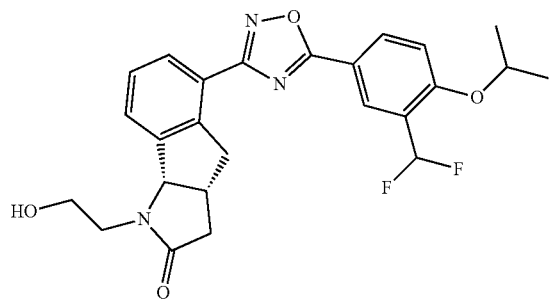
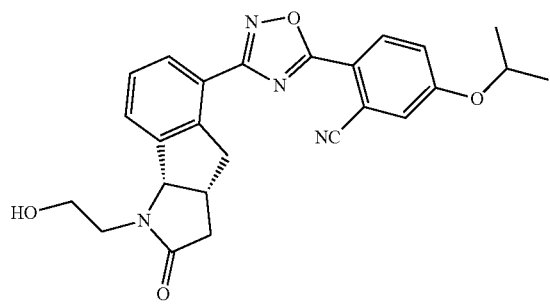
218
-continued
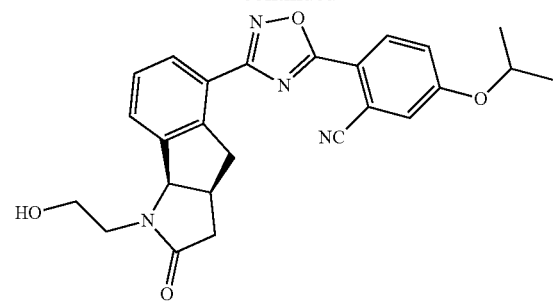
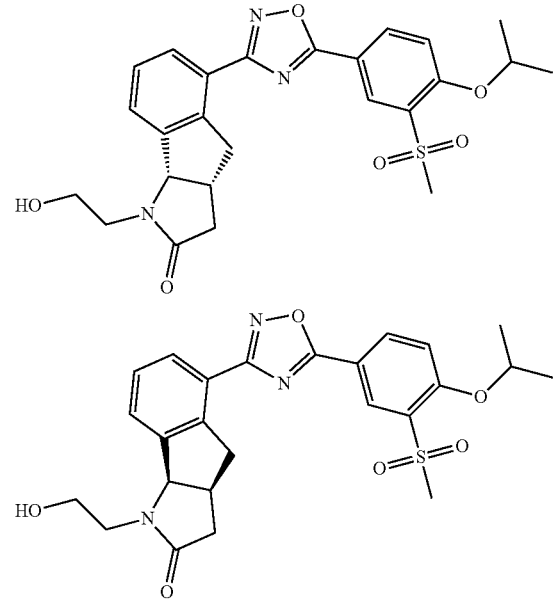
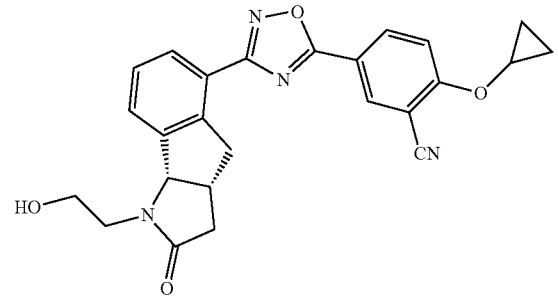
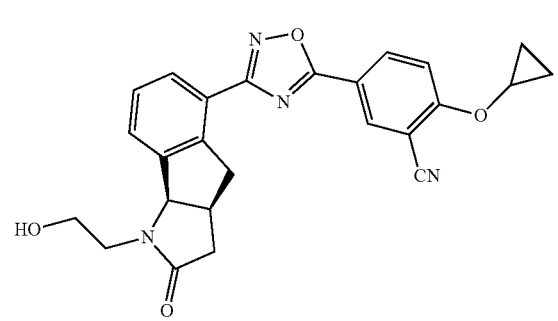

219
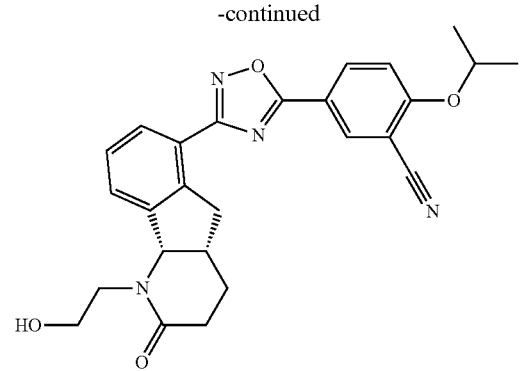
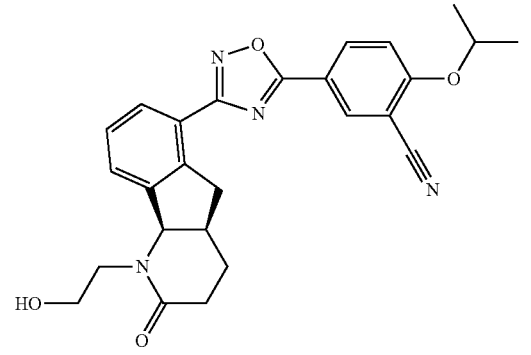
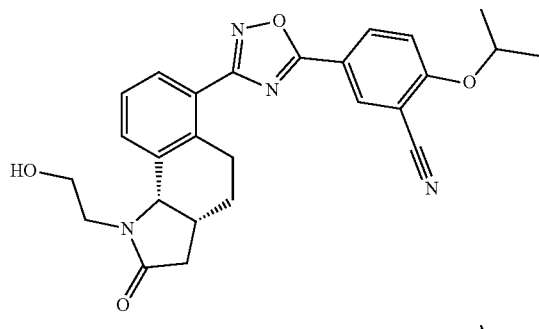
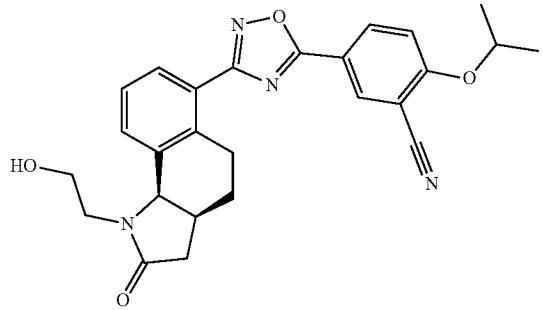
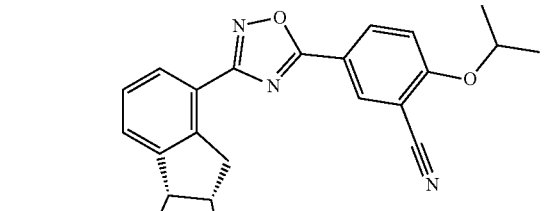
220
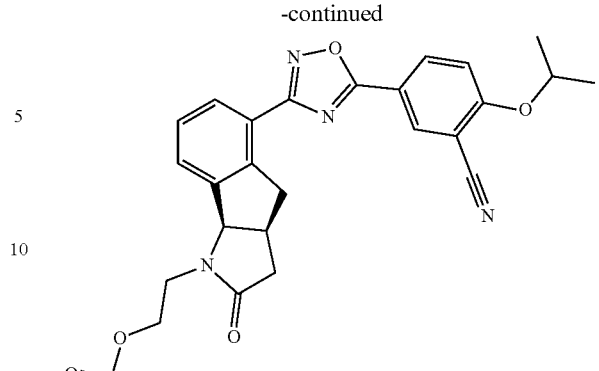
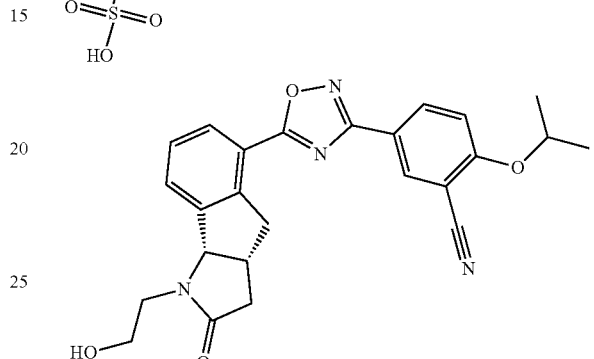
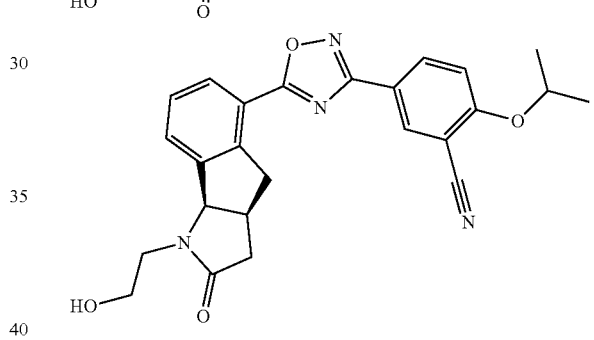
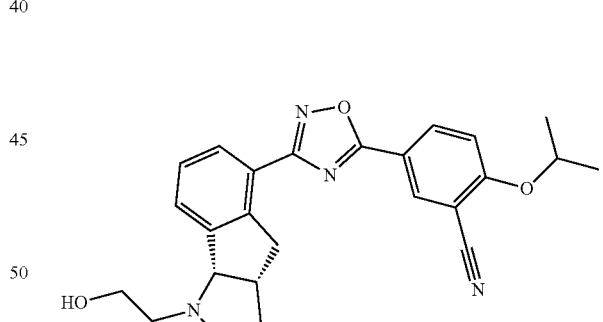
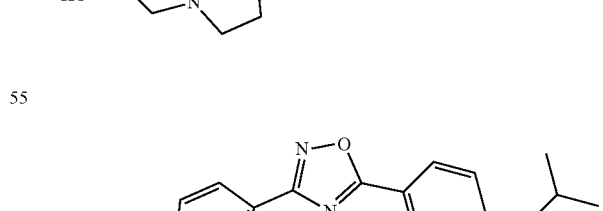
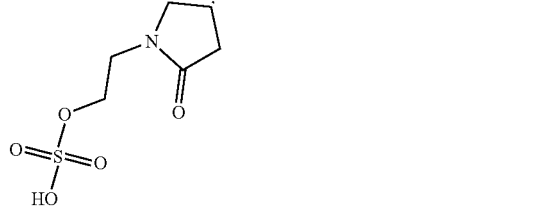
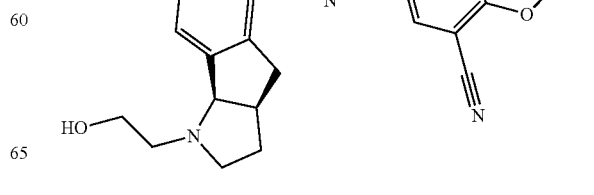

221
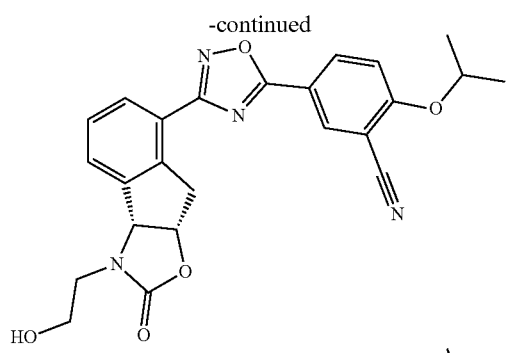
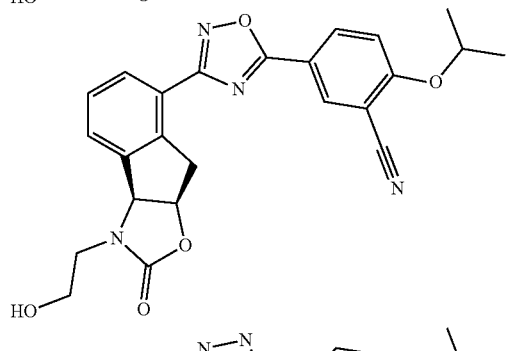
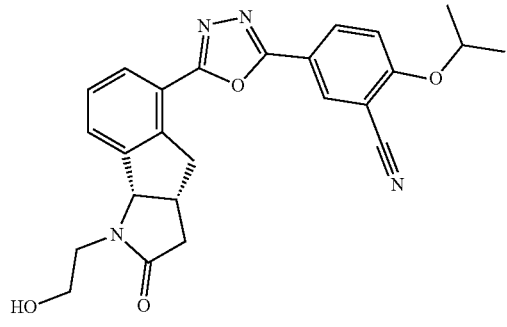
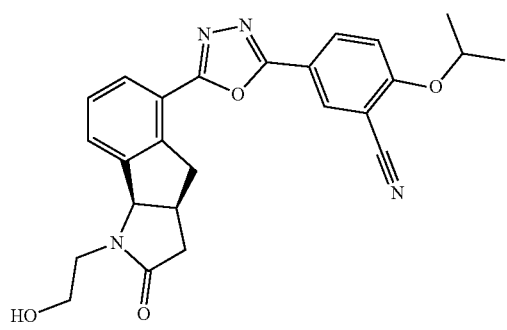
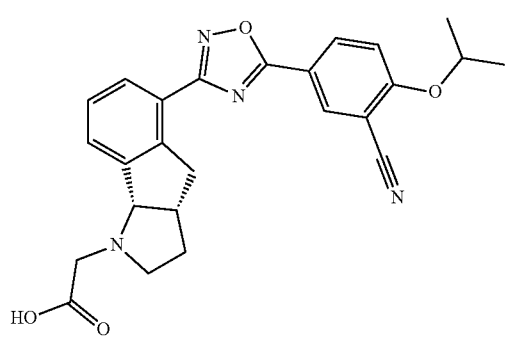
222
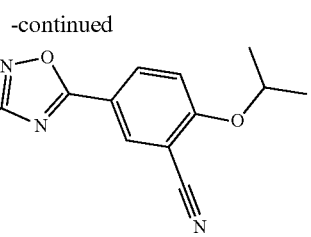
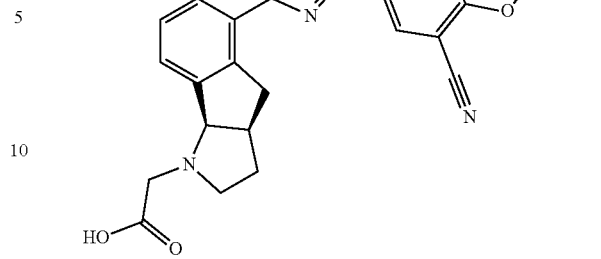
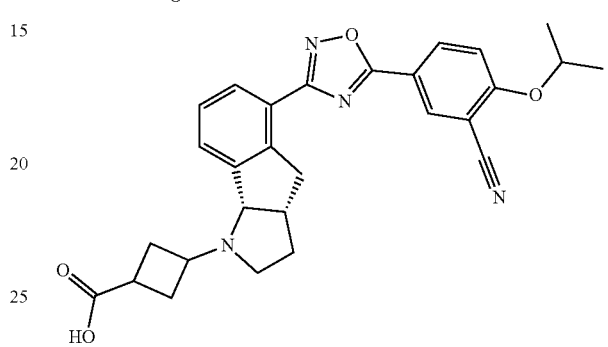
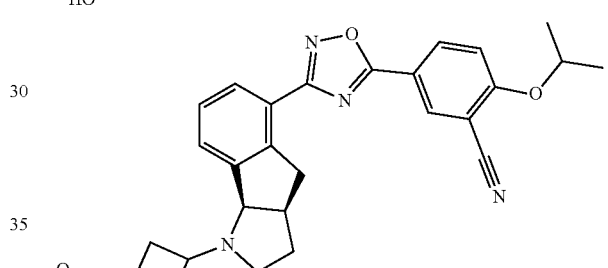
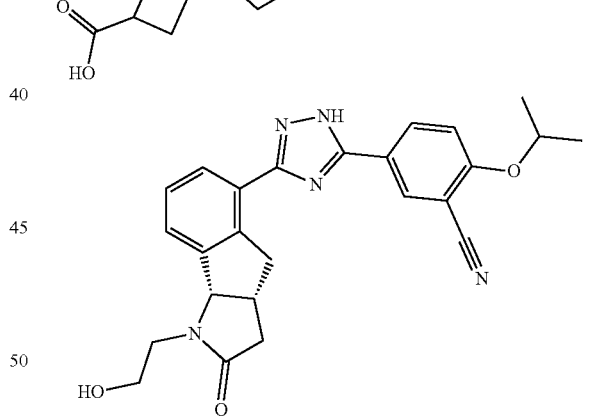
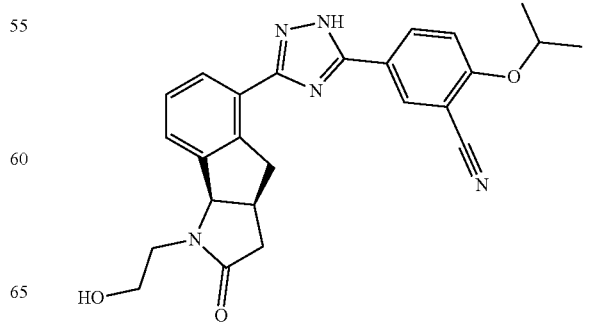

223

-continued

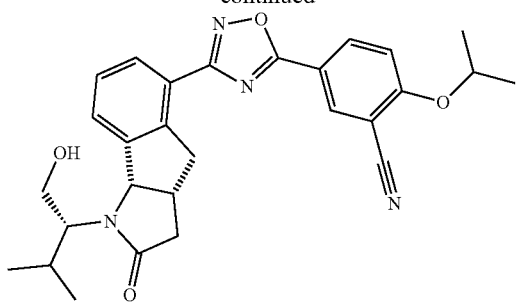

224

-continued

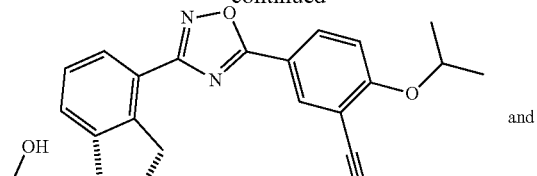

and

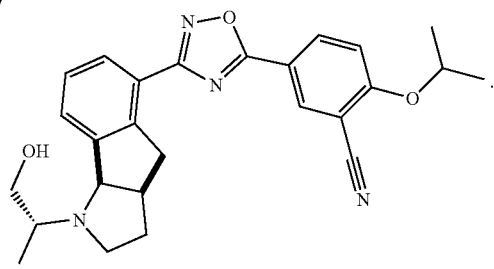

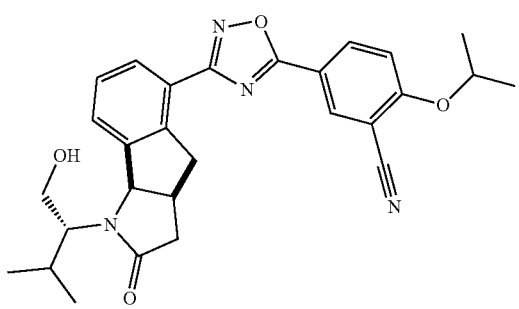

45. A method for treating S1P1 related disease in a subject in need thereof, comprising administering a pharmaceutically effective amount of the compound represented by formula (II) or the pharmaceutically acceptable salt of the same as defined in claim 1 to the subject, the S1P1 related disease is selected from IBD, autoimmune diseases, multiple sclerosis, disseminated sclerosis, amyotrophic lateral sclerosis, bronchial asthma and stroke.

* * * * *